US012459985B2

(12) United States Patent
Tian et al.

(10) Patent No.: US 12,459,985 B2
(45) Date of Patent: Nov. 4, 2025

(54) G-PROTEIN-COUPLED RECEPTOR INTERNAL SENSORS

(71) Applicant: THE REGENTS OF THE UNIVERSITY OF CALIFORNIA, Oakland, CA (US)

(72) Inventors: Lin Tian, Davis, CA (US); Tommaso Patriarchi, Davis, CA (US); Ruqiang Liang, Davis, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 1166 days.

(21) Appl. No.: 16/463,313

(22) PCT Filed: Nov. 22, 2017

(86) PCT No.: PCT/US2017/062993
§ 371 (c)(1),
(2) Date: May 22, 2019

(87) PCT Pub. No.: WO2018/098262
PCT Pub. Date: May 31, 2018

(65) Prior Publication Data
US 2021/0101960 A1 Apr. 8, 2021

Related U.S. Application Data

(60) Provisional application No. 62/513,991, filed on Jun. 1, 2017, provisional application No. 62/426,173, filed on Nov. 23, 2016.

(51) Int. Cl.
*C07K 14/71* (2006.01)
*A61K 49/00* (2006.01)
(Continued)

(52) U.S. Cl.
CPC ........ *C07K 14/723* (2013.01); *A61K 49/0008* (2013.01); *A61K 49/0056* (2013.01);
(Continued)

(58) Field of Classification Search
CPC .... C07K 2319/60; C07K 14/723; C12Q 1/66; C09K 11/06; G01N 21/6428; G01N 2333/726
See application file for complete search history.

(56) References Cited

U.S. PATENT DOCUMENTS 10,174,101 B2 * 1/2019 Jazayeri-Dezfuly ........................ C07K 14/723
2007/0161062 A1 7/2007 Tacke et al.
(Continued)

FOREIGN PATENT DOCUMENTS

WO 2015106067 A2 7/2015
WO 2019062744 4/2019
WO 2022081631 A1 4/2022

OTHER PUBLICATIONS

Duffet et al. A genetically encoded sensor for in vivo imaging of Orexin neuropeptides.(Nature Meth, 2022, 19:231-241 (Year: 2022).*
(Continued)

*Primary Examiner* — Arthur S Leonard
(74) *Attorney, Agent, or Firm* — Mintz Levin Cohn Ferris Glovsky and Popeo, P.C.

(57) ABSTRACT

Provided are circularly permuted fluorescent protein sensors useful to integrate into the third intracellular loop of a G protein-coupled receptor (GPCR). Also provided are GPCRs having a circularly permuted fluorescent protein sensor integrated into its third intracellular loop and methods of using such GPCRs, e.g., to screen for GPCR agonists and
(Continued)

antagonists and to monitor activation of GPCRs both in vitro and in vivo.

14 Claims, 46 Drawing Sheets

Specification includes a Sequence Listing.

(51) Int. Cl.

| | |
|---|---|
| ***C07K 14/72*** | (2006.01) |
| ***G01N 33/533*** | (2006.01) |
| ***G01N 33/542*** | (2006.01) |
| ***G01N 33/74*** | (2006.01) |

(52) U.S. Cl.

CPC ........... *G01N 33/542* (2013.01); *G01N 33/74* (2013.01); *C07K 2319/60* (2013.01); *G01N 2333/726* (2013.01)

(56) References Cited

U.S. PATENT DOCUMENTS

| | | | |
|---|---|---|---|
| 2012/0034691 | A1 | 2/2012 | Looger et al. |
| 2013/0332133 | A1 | 12/2013 | Horn et al. |
| 2015/0226755 | A1 | 8/2015 | Ai et al. |
| 2016/0229899 | A1 | 8/2016 | Auldridge et al. |
| 2023/0384333 | A1 | 11/2023 | Dong et al. |

OTHER PUBLICATIONS

Patriarchi et al. Ultrafast neuronal imaging of dopamine dynamics with designed genetically encoded sensors (Science, 2018, 360:1-8) (Year: 2018).*

Extended European Search Report in European Application No. 17873415.8 mailed Jun. 17, 2020, 7 pages.

International Search Report and Written Opinion corresponding to PCT/US2017/062993 mailed Apr. 5, 2018.

Alicea et al., "Structure of the *Escherichia coli* Phosphonate Binding Protein PhnD and Rationally Optimized Phosphonate Biosensors," J. Mol. Biol., 2011, 414, 356-369.

Dong, "Psychedelic-inspired drug discovery using an engineered biosensor", Cell, 2021, 184, 1-33.

Dunlap, "Identification of Psychoplastogenic N,N-Dimethylaminoisotryptamine (isoDMT) Analogs Through Structure-Activity Relationship Studies", J Med Chem 2020, 63, 3, 1142-1155.

Marvin et al. "A genetically encoded, high-signal-to-noise maltose sensor," Proteins 2011, 79, 3025-3036.

Marvin et al. "An optimized fluorescent probe for visualizing glutamate neurotransmission," Nat. Methods, 2013, 10, 2, 162-170.

Kostyuk, "Circularly Permuted Fluorescent Protein-Based Indicators: History, Principles, and Classification", International Journal of Molecular Sciences, 2019, 20, 4200, 1-37.

Patriarchi, "Ultrafast neuronal imaging of dopamine dynamics with designed genetically encoded sensors", Science 2019, 360, 6396, 1-22.

International Search Report and Written Opinion corresponding to PCT/US2021/054669 mailed Mar. 21, 2022, 15 pages.

Kim, "Structure of a Hallucinogen-Activated Gq-Coupled 5-HT2A Serotonin Receptor", Cell, 2020, 182, 6, 1574-1588.

López-Giménez, "Hallucinogens and Serotonin 5-HT2A Receptor-Mediated Signaling Pathways", in Inflammation-Associated Depression: Evidence, Mechansims and Implications:, 2017, Springer International Publishing, 36, 45-73.

Ly, "Psychedelics Promote Structural and Functional Neural Plasticity", Cell. Rep. 2018, 23, 3170-3182.

* cited by examiner

B

C

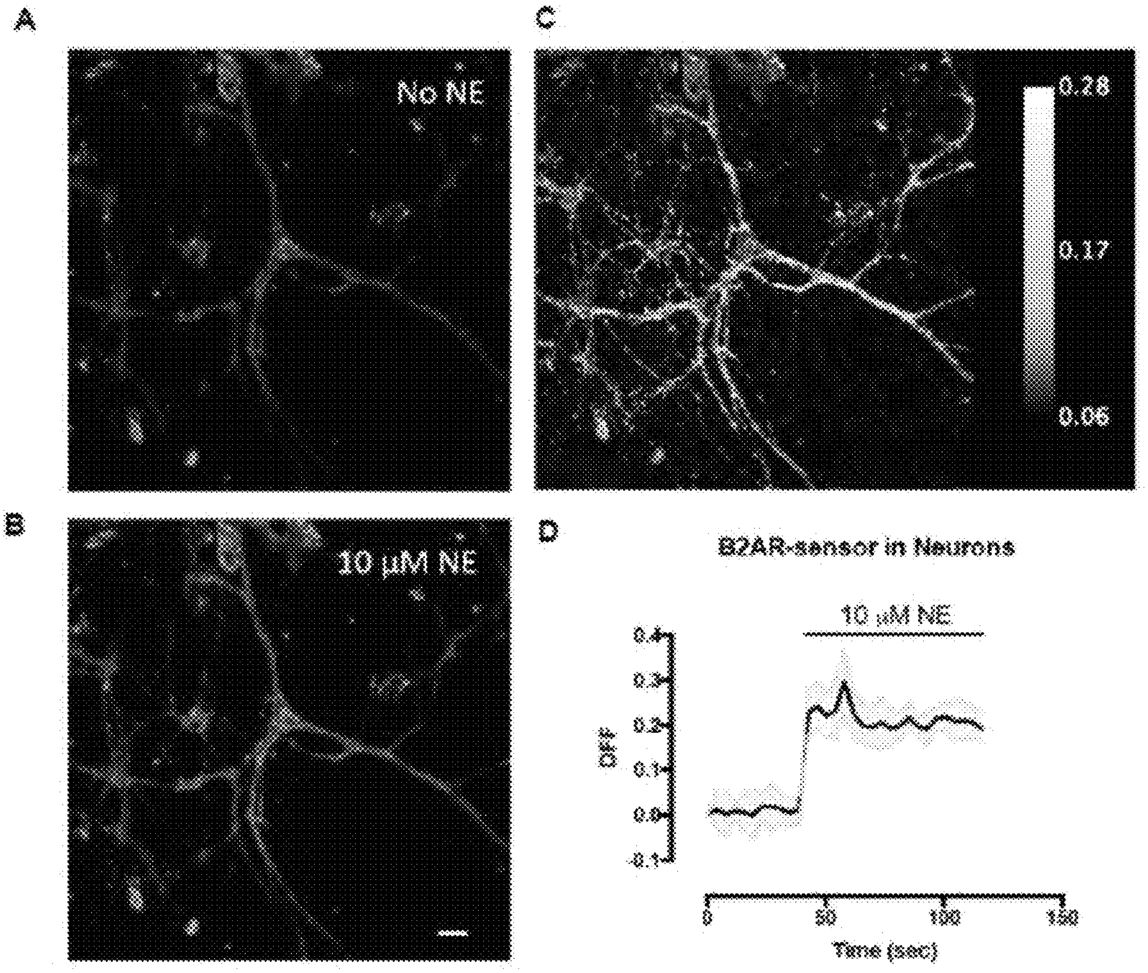
*Fig. 6A-D*

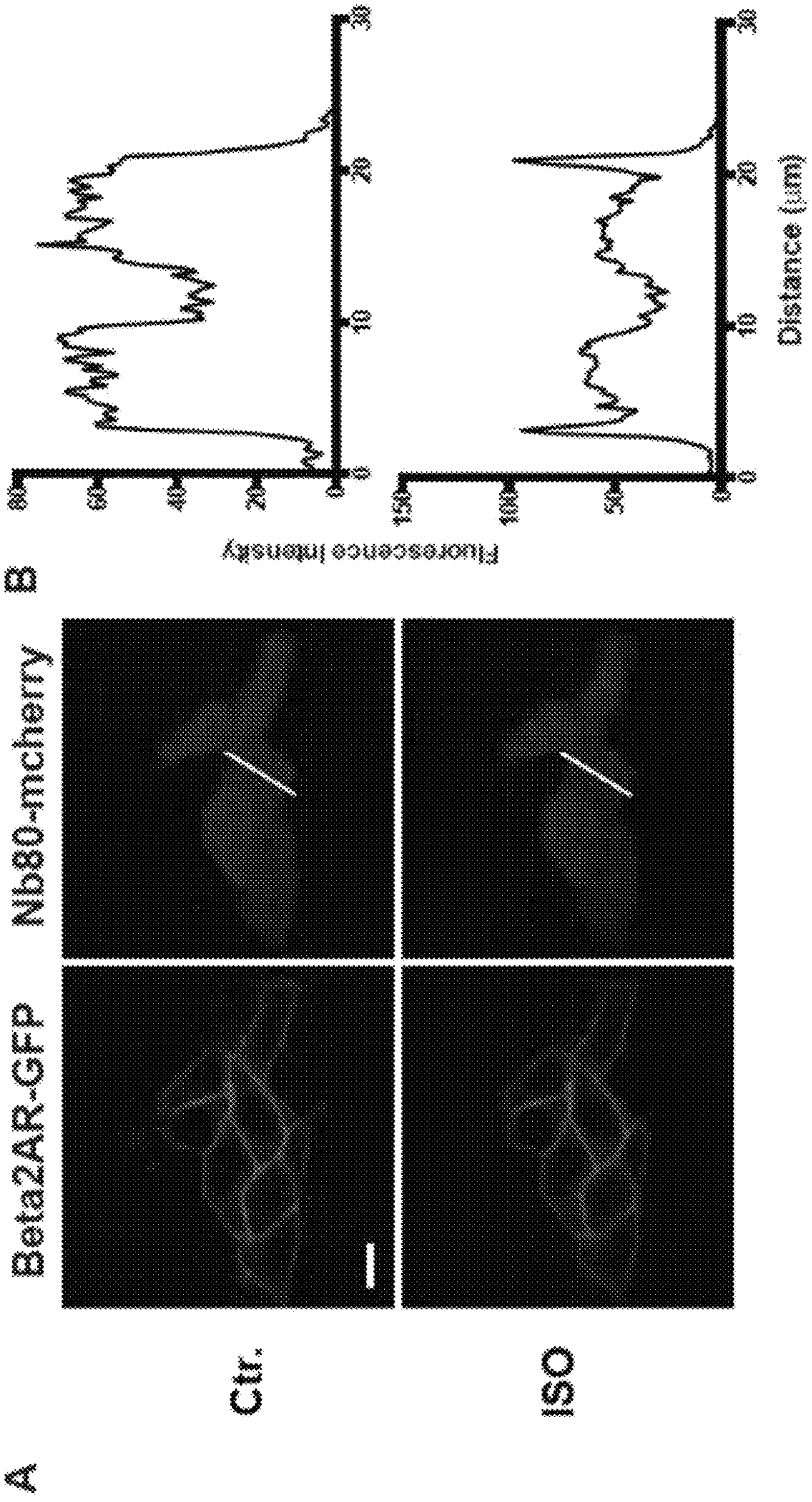
*Fig. 7A-B*

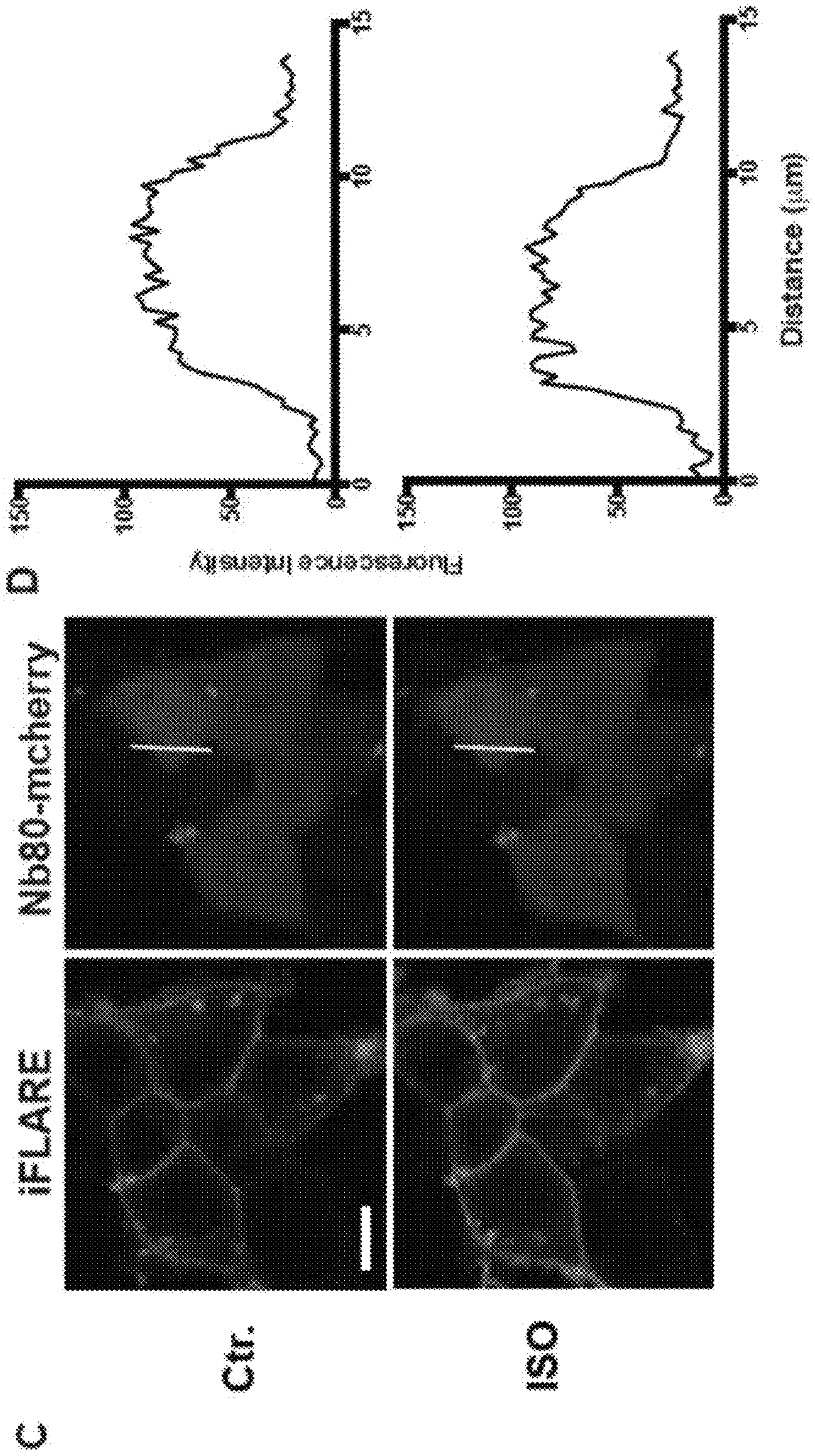
*Fig. 7C-D*

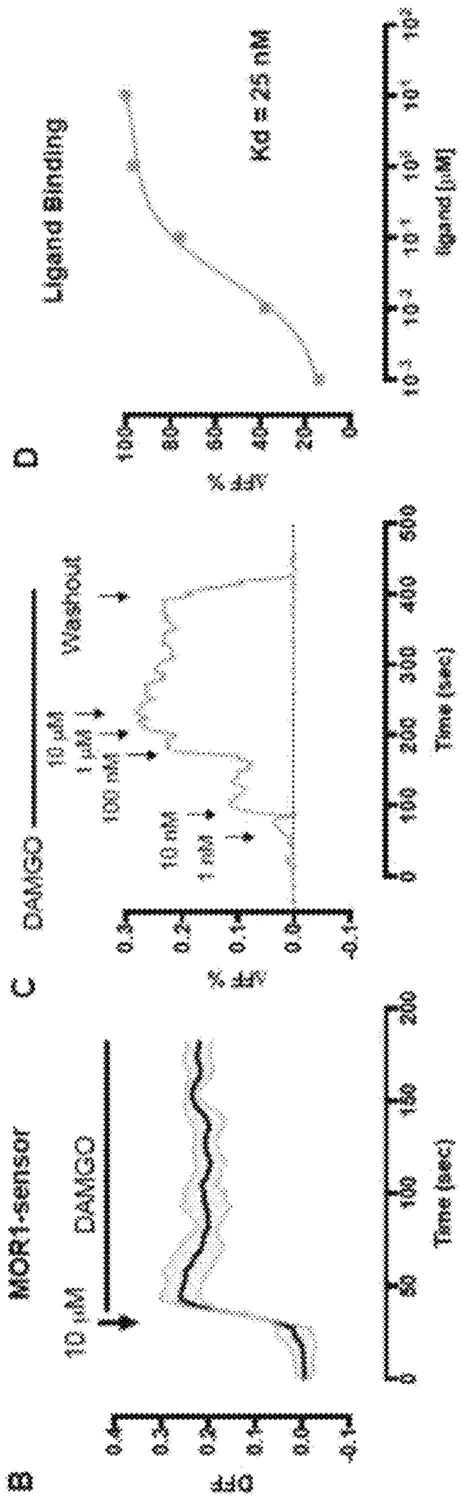
Fig. 8B-D

```
SEQ ID NO.: 128    eGFP        -----MVSKGEELFTGVVPILVELDGDVNGHKFSVSGEGEGDATYGKLTLKFICTTG-KLP
SEQ ID NO.: 129    eCFP        -----------GEELFTGVVPILVELDGDVNGHKFSVSGEGEGDATYGKLTLKFICTTG-KLP
SEQ ID NO.: 130    YFP         ----------KGEELFTGVVPILVELDGDVNGHKFSVSGEGEGDATYGKLTLKFICTTG-KLP
SEQ ID NO.: 131    paGFP       -----SMSKGEELFTGVVPILVELDGDVNGHKFSVSGEGEGDATYGKLTLKFICTTG-KLP
SEQ ID NO.: 132    sfGFP       ------MSKGEELFTGVVPILVELDGDVNGHKFSVRGEGEGDATNGKLTLKFICTTG-KLP
SEQ ID NO.: 133    pamCherry   MVSKGEEDNMAIIKEFMRFKVHMEGSVNGHVFEIEGEGEGRPYEGTQTAKLKVTKGGPLP
SEQ ID NO.: 134    mKate       --MHGSMS---ELITENMHMKLYMEGTVNNHHFKCTSEGEGKPYEGTQTMRIKVVEGGPLP
SEQ ID NO.: 135    mEos2       -------------MSAIKPDMKIKLRMEGNVNGHHFVIDGDGTGKPFEGKQSMDLEVKEGGPLP
                                      :.  : : : ::* **.* *    .:* * .  *. :  :      *  **

SEQ ID NO.: 128    eGFP        VPWPTLVTTLTVQCFSRYPDHMKQHDFFKSAMPEGYVQERTIFFKDDGNYKTRAEVKFEG
SEQ ID NO.: 129    eCFP        VPWPTLVTTLTVQCFSRYPDHMKQHDFFKSAMPEGYVQERTIFFKDDGNYKTRAEVKFEG
SEQ ID NO.: 130    YFP         VPWPTLVTTFTLQCFARYPDHMKRHDFFKSAMPEGYVQERTIFFKDDGNYKTRAEVKFEG
SEQ ID NO.: 131    paGFP       VPWPTLVTTFTVQCFSRYPDHMKRHDFFKSAMPEGYVQERTISFKDDGNYKTRAEVKFEG
SEQ ID NO.: 132    sfGFP       VPWPTLVTTLTVQCFSRYPDHMKRHDFFKSAMPEGYVQERTISFKDDGTYKTRAEVKFEG
SEQ ID NO.: 133    pamCherry   FTWDILSPQFMSNAYVKHPADIP---DYFKLSFPEGFKWERVMNFEDGGVVTVTQDSSLQD
SEQ ID NO.: 134    mKate       FAFDILATSFMSKTFINHTQGIP---DFFKQSFPEGFTWERVTTYEDGGVLTATQDTSLQD
SEQ ID NO.: 135    mEos2       FAFDILTTAFN-RVFAKYPDNIQ---DYFKQSFPKGYSWERSLTFEDGGICIARNDITMEG
                               ..:  * . :  . : .:. :    *:** ::*:*:  **   ::*.*    .  : .::.

SEQ ID NO.: 128    eGFP        DTLVNRIELKGIDFKEDGNILGHK-LEYNYNSHNVYIMADKQKNGIKVNFKIRHNIEDGS
SEQ ID NO.: 129    eCFP        DTLVNRIELKGIDFKEDGNILGHK-LEYNYISHNVYITADKQKNGIKANFKIRHNIEDGS
SEQ ID NO.: 130    YFP         DTLVNRIELKGIDFKEDGNILGHK-LEYNYNSHNVYIMADKQKNGIKVNFKIRHNIEDGS
SEQ ID NO.: 131    paGFP       DTLVNRIELKGIDFKEDGNILGHK-LEYNYNSHNVYITADKQKNGIKANFKIRHNIEDGS
SEQ ID NO.: 132    sfGFP       DTLVNRIELKGIDFKEDGNILGHK-LEYNFNSHNVYITADKQKNGIKANFKIRHNVEDGS
SEQ ID NO.: 133    pamCherry   GEFIYKVKLRGTNFPSDGPVMQKKTMGWEALSERMYPEDGALKGEVKPRVKLKDGGHYDA
SEQ ID NO.: 134    mKate       GCLIYNVKIRGVNFPSNGPVMQKKTLGWEASTEMLYPADGGLEGRSDMALKLVGGGHLIC
SEQ ID NO.: 135    mEos2       DTFYNKVRFYGTNFPANGPVMQKKTLKWEPSTEKMYVRDGVLTGDIHMALLLEGNAHYRC
                               . :  .:.: * :*  :* :: :* : ::  :. :*    .    .   .  . :  . .  .

SEQ ID NO.: 128    eGFP        VQLADHYQQNTPIGDGPVLLPDNHYLSTQSALSKDPNEKRDHMVLLEFVTAAGITLGMDE
SEQ ID NO.: 129    eCFP        VQLADHYQQNTPIGDGPVLLPDNHYLSTQSALSKDPNEKRDHMVLLEFVTAAGIT-------
SEQ ID NO.: 130    YFP         VQLADHYQQNTPIGDGPVLLPDNHYLSYQSALSKDPNEKRDHMVLLEFVTAAGI--------
SEQ ID NO.: 131    paGFP       VQLADHYQQNTPIGDGPVLLPDNHYLSHQSALSKDPNEKRDHMVLLEFVTAAGIT-------
SEQ ID NO.: 132    sfGFP       VQLADHYQQNTPIGDGPVLLPDNHYLSTQSVLSKDPNEKRDHMVLLEFVTAAGITHGMDE
SEQ ID NO.: 133    pamCherry   EVKTTYKAK-KPVQ--------LPGAYNVNRKLDITS-HNEDYTIVEQYERAEGRHSTGGMDE
SEQ ID NO.: 134    mKate       NLKTTYRSK-KPAKN----LKMPGVYYVDRRLERIK-EADKETYVEQHEVAVARYCDLPSKL
SEQ ID NO.: 135    mEos2       DFRTTYKAKEKGVK--------LPGYHFVDHCIEILS-HDKDYNKVKLYEHAVA-HSGLPDN-
                                  : :  : .          :*. : :.          .     ..    :     *  .  .

SEQ ID NO.: 128    eGFP        LYK---
SEQ ID NO.: 129    eCFP        ------
SEQ ID NO.: 130    YFP         ------
SEQ ID NO.: 131    paGFP       ------
SEQ ID NO.: 132    sfGFP       LYKGS
SEQ ID NO.: 133    pamCherry   LYK---
SEQ ID NO.: 134    mKate       GHKLN
SEQ ID NO.: 135    mEos2       ------
```

*Fig. 9*

| | | | |
|---|---|---|---|
| SEQ ID NO.: 136 | MGLUR3 | ------------------LVQIVMVSVWLILEAPG--TRRYTL----AEKRET------V | 726 |
| SEQ ID NO.: 137 | MGLUR5 | ------------------CIQLGIIVALFIMEPPD--IMHD------YPSIRE------V | 729 |
| SEQ ID NO.: 138 | GABAB1 | -----YA----TV----GLLVGMDVLTLAIWQIVDPLHRTIETFAKEEPKEDIDVSILPQ | 757 |
| SEQ ID NO.: 139 | GABAB2 | -----LV----IV----GGMLLIDLCILICWQAVDPLRRTVEKYSMEPDPAGRDISIRPL | 644 |
| SEQ ID NO.: 140 | CB1 | ----TYLMFWIGV----TSVLLLFIVYAY-MYILWKAHSHAVR---MI-QRGT------- | 313 |
| SEQ ID NO.: 141 | GNRHR | ----FYN-FFTFPSCLFIIPLFIMLICNAKIIFTLTRVLHQDPH---E------------ | 248 |
| SEQ ID NO.: 142 | V1A | ----AYV-TWMTGGIFVAPVVILGTCYGFICYNIWCNVRGKTA---SRQSKGA------- | 259 |
| SEQ ID NO.: 143 | OTR | ----AYI-TWITLAVYIVPVIVLAACYGLISFKIWQNLRLKTA---AAAAEA-------- | 243 |
| SEQ ID NO.: 144 | A2A | N---YMV-YFNFFACVLVPLLLMLGVYLRIFLAARRQLKQME----SQPLP--------- | 217 |
| SEQ ID NO.: 145 | B2AR | ----AYA-IASSIVSFYVPLVIMVFVYSRVFQEAKRQLQKID----KSEGR-F------- | 240 |
| SEQ ID NO.: 146 | DRD1 | ----TYA-ISSSVISFYIPVAIMIVTYTRIYRIAQKQIRRIA----ALERAAV------- | 236 |
| SEQ ID NO.: 147 | M2R | ----AVT-FGTAIAAFYLPVIIMTVLYWHISRASKSRIKKDK----KEPVANQ-DPVSP- | 233 |
| SEQ ID NO.: 148 | H1R | ----WFK-VMTAIINFYLPTLLMLWFYAKIYKAVRQHCQHRELINRSLPSFSE-IKLRP- | 241 |
| SEQ ID NO.: 149 | DRD2 | ----AFV-VYSSIVSFYVPFIVTLLVYIKIYIVLRRRRKRVN---TKRSSRAFRAHLRAP | 239 |
| SEQ ID NO.: 150 | 5HT2A | ----NFV-LIGSFVSFFIPLTIMVITYFLTIKSLQKEATLCV---SDLGTRAKLASFSFL | 284 |
| SEQ ID NO.: 151 | 5HT2B | ----DFM-LFGSLAAFFTPLAIMIVTYFLTIHALQKKAYLVK---NKPPQRLTWLTVSTV | 267 |
| SEQ ID NO.: 152 | NK1 | IYEKVYH-ICVTVLIYFLPLLVIGYAYTVVGITLWASEIPGD----SSDRY--------- | 236 |
| SEQ ID NO.: 153 | NK3 | HF--TYH-IIVIILVYCFPLLIMGITYTIVGITLWGGEIPGD----TCDKY--------- | 287 |
| SEQ ID NO.: 154 | NK2 | KTLLLYH-LVVIALIYFLPLAVMFVAYSVIGLTLWRRAVPGH----QAHGAN-------- | 238 |
| SEQ ID NO.: 155 | MT1 | ----QYT-AAVVVIHFLLPIAVVSFCYLRIWVLVLQARRKAK----PESR---------- | 239 |
| SEQ ID NO.: 156 | P2Y1 | RSYFIYS-MCTTVAMFCVPLVLILGCYGLIVRALIYKDLD---------N---------- | 251 |
| SEQ ID NO.: 157 | AT1 | TLPIGLG-LTKNILGFLFPFLIILTSYTLIWKALKKAYEIQK----NKPR---------- | 234 |
| SEQ ID NO.: 158 | KOR1 | WWDLFMK-ICVFIFAFVIPVLIIIVCYTLMILRLKSVRLLSG----SREK---------- | 265 |
| SEQ ID NO.: 159 | MOR1 | YWENLLK-ICVFIFAFIMPVLIITVCYGLMILRLKSVRMLSG----SKEK---------- | 273 |
| SEQ ID NO.: 160 | DOR1 | YWDTVTK-ICVFLFAFVVPILIITVCYGLMLLRLRSVRLLSG----SKEK---------- | 252 |

*Fig. 11A*

| | | | |
|---|---|---|---|
| SEQ ID NO.: 136 | MGLUR3 | I----------------------------------------------------------L | 728 |
| SEQ ID NO.: 137 | MGLUR5 | Y----------------------------------------------------------L | 731 |
| SEQ ID NO.: 138 | GABAB1 | LEHCSS-----RKHNTWLGIFY-------------------------------------- | 774 |
| SEQ ID NO.: 139 | GABAB2 | LEHCEN-----THNTIWLGIVY-------------------------------------- | 661 |
| SEQ ID NO.: 140 | CB1 | ---QKSI----------------------------------------------------- | 317 |
| SEQ ID NO.: 141 | GNRHR | ------------------------------------------------------------ | 248 |
| SEQ ID NO.: 142 | V1A | ---EQA------------------------------------------------------ | 262 |
| SEQ ID NO.: 143 | OTR | ---PEG------------------------------------------------------ | 246 |
| SEQ ID NO.: 144 | A2A | ------------------------------------------------------------ | 217 |
| SEQ ID NO.: 145 | B2AR | ---------HVQNLSQ-------------------------------------------- | 247 |
| SEQ ID NO.: 146 | DRD1 | ---------HAKNCQT-------------------------------------------- | 243 |
| SEQ ID NO.: 147 | M2R | -SLVQGRIVKPNNNNH-------PSSDDGL--EHNKIQNGKAPRDPVTE----------- | 272 |
| SEQ ID NO.: 148 | H1R | -ENPKGDAKKPGKESPWEVLKRKPKDAGGGSVLKSPSQTPKEMKSPVVFSQEDDREVDKL | 300 |
| SEQ ID NO.: 149 | DRD2 | L---KGNCTHPEDMKLCTVIMK---SNGSFPVNRRRVEAARRA---------QELEM--- | 281 |
| SEQ ID NO.: 150 | 5HT2A | ------PQSSLSSEKL-------------------------------------------- | 294 |
| SEQ ID NO.: 151 | 5HT2B | PQRDETPCSSPEKVAM-------------------------------------------- | 283 |
| SEQ ID NO.: 152 | NK1 | ------------------------------------------------------------ | 236 |
| SEQ ID NO.: 153 | NK3 | ------------------------------------------------------------ | 287 |
| SEQ ID NO.: 154 | NK2 | ------------------------------------------------------------ | 238 |
| SEQ ID NO.: 155 | MT1 | ------------------------------------------------------------ | 239 |
| SEQ ID NO.: 156 | P2Y1 | ------------------------------------------------------------ | 251 |
| SEQ ID NO.: 157 | AT1 | ------------------------------------------------------------ | 234 |
| SEQ ID NO.: 158 | KOR1 | ------------------------------------------------------------ | 265 |
| SEQ ID NO.: 159 | MOR1 | ------------------------------------------------------------ | 273 |

*Fig. 11B*

| | | | |
|---|---|---|---|
| SEQ ID NO.: 136 | MGLUR3 | KCNV----------------------------------KD-------------------- | 734 |
| SEQ ID NO.: 137 | MGLUR5 | ICNT----------------------------------TN-------------------- | 737 |
| SEQ ID NO.: 138 | GABAB1 | ------------------------------------------------------------ | 774 |
| SEQ ID NO.: 139 | GABAB2 | ------------------------------------------------------------ | 661 |
| SEQ ID NO.: 140 | CB1 | ------------------------------------------------------------ | 317 |
| SEQ ID NO.: 141 | GNRHR | ------------------------------------------------------------ | 248 |
| SEQ ID NO.: 142 | V1A | ------------------------------------------------------------ | 262 |
| SEQ ID NO.: 143 | OTR | ------------------------------------------------------------ | 246 |
| SEQ ID NO.: 144 | A2A | ------------------------------------------------------------ | 217 |
| SEQ ID NO.: 145 | B2AR | ------------------------------------------------------------ | 247 |
| SEQ ID NO.: 146 | DRD1 | ------------------------------------------------------------ | 243 |
| SEQ ID NO.: 147 | M2R | NCV-------QGEEKESSNDSTSVSAVASNMRDDEITQDENTVSTSLGHSKDENSKQTCI | 325 |
| SEQ ID NO.: 148 | H1R | YCFFLDIVHMQAAAEGSSRDY-----VAVNRSHGQLKTDEQGLNTH---GASEISEDQML | 352 |
| SEQ ID NO.: 149 | DRD2 | -----EML--SSTSPPERTRY-----SPIPPSHHQLTLPDPS-----HHGLHSTP----- | 319 |
| SEQ ID NO.: 150 | 5HT2A | -------F---------------------QR----------------------------- | 297 |
| SEQ ID NO.: 151 | 5HT2B | -------L---------------------DGSRKDKALFNSG-----D------------ | 298 |
| SEQ ID NO.: 152 | NK1 | ------------------------------------------------------------ | 236 |
| SEQ ID NO.: 153 | NK3 | ------------------------------------------------------------ | 287 |
| SEQ ID NO.: 154 | NK2 | ------------------------------------------------------------ | 238 |
| SEQ ID NO.: 155 | MT1 | ------------------------------------------------------------ | 239 |
| SEQ ID NO.: 156 | P2Y1 | ------------------------------------------------------------ | 251 |
| SEQ ID NO.: 157 | AT1 | ------------------------------------------------------------ | 234 |
| SEQ ID NO.: 158 | KOR1 | ------------------------------------------------------------ | 265 |
| SEQ ID NO.: 159 | MOR1 | ------------------------------------------------------------ | 273 |
| SEQ ID NO.: 160 | DOR1 | ------------------------------------------------------------ | 252 |

*Fig. 11C*

| | | | |
|---|---|---|---|
| SEQ ID NO.: 136 | MGLUR3 | --------------------SSMLI---SLTYDVILVILCTV----YAFKTRK--CPENF | 765 |
| SEQ ID NO.: 137 | MGLUR5 | --------------------LGVVT---PLGYNGLLILSCTF----YAFKTRN--VPANF | 768 |
| SEQ ID NO.: 138 | GABAB1 | ------------------------------GYKGLLLLLGIFL--AYETKSVSTEKINDH | 802 |
| SEQ ID NO.: 139 | GABAB2 | ------------------------------AYKGLLMLFGCFL--AWETRNVSIPALNDS | 689 |
| SEQ ID NO.: 140 | CB1 | -----------------------I---------IHTSEDGKV--QV----TRPDQARMDI | 339 |
| SEQ ID NO.: 141 | GNRHR | ---------------------------------------------LQLNQSKNNIPRARL | 263 |
| SEQ ID NO.: 142 | V1A | ---------------------------------GVAFQKGFL--LAPCVSSVKSISRAKI | 287 |
| SEQ ID NO.: 143 | OTR | ---------------------------------AAAGDGGRV--ALARVSSVKLISKAKI | 271 |
| SEQ ID NO.: 144 | A2A | ------------------------------------------------GERARSTLQKEV | 229 |
| SEQ ID NO.: 145 | B2AR | -----------------------------------VEQDGRTGHGLRRSSKF---CLKEH | 269 |
| SEQ ID NO.: 146 | DRD1 | -----------------------------------TTGNGKPVECSQPESSFKMSFKRET | 268 |
| SEQ ID NO.: 147 | M2R | RIGTKTPKSDSCTPTN--TTVEVVGSSGQNGDEKQNIVARKIVKMTKQPAKKKPPPSREK | 383 |
| SEQ ID NO.: 148 | H1R | GDSQSFSRTDSDTTTETAPGKGKLRSGSNTGLDYIKFTWKRL-RSHSRQYVSGLHMNRER | 411 |
| SEQ ID NO.: 149 | DRD2 | -DSPAKPEKNG--HAKDHPKIAKI-------FEIQTMPNGKTRTSLKTMSRRKLSQQKEK | 369 |
| SEQ ID NO.: 150 | 5HT2A | -------------S-------------------IH-REPG-----SYTGRRTMQSISNEQ | 319 |
| SEQ ID NO.: 151 | 5HT2B | -------------E-------------------TL-MRRT-----STIGKKSVQTISNEQ | 320 |
| SEQ ID NO.: 152 | NK1 | ----------------------------------------------------HEQVSAKR | 244 |
| SEQ ID NO.: 153 | NK3 | ----------------------------------------------------HEQLKAKR | 295 |
| SEQ ID NO.: 154 | NK2 | ----------------------------------------------------LRHLQAMK | 246 |
| SEQ ID NO.: 155 | MT1 | ----------------------------------------------------LCLKPSDL | 247 |
| SEQ ID NO.: 156 | P2Y1 | -------------------------------------------------------SPLRR | 256 |
| SEQ ID NO.: 157 | AT1 | -------------------------------------------------------ND--- | 236 |
| SEQ ID NO.: 158 | KOR1 | -------------------------------------------------------DRNLR | 270 |
| SEQ ID NO.: 159 | MOR1 | -------------------------------------------------------DRNLR | 278 |
| SEQ ID NO.: 160 | DOR1 | -------------------------------------------------------DRSLR | 257 |

*Fig. 11D*

| | | | |
|---|---|---|---|
| SEQ ID NO.: 140 | CB1 | RLAKTLVLILVVLIICWGPLLAIMVYDVFG-------KMNK---LIKTVFAFCSMLCLLN | 389 |
| SEQ ID NO.: 141 | GNRHR | KTLKMTVAFATSFTVCWTPYYVLGIWYWFD-------PEMLNR-LSDPVNHFFFLFAFLN | 315 |
| SEQ ID NO.: 142 | V1A | RTVKMTFVIVTAYIVCWAPFFIIQMWSVWD-------PMSVWTESENPTITITALLGSLN | 340 |
| SEQ ID NO.: 143 | OTR | RTVKMTFIIVLAFIVCWTPFFFVQMWSVWD-------ANAP---KEASAFIIVMLLASLN | 321 |
| SEQ ID NO.: 144 | A2A | HAAKSLAIIVGLFALCWLPLHIINCFTFFC-------PDCSHAP--LWLMYLAIVLSHTN | 280 |
| SEQ ID NO.: 145 | B2AR | KALKTLGIIMGTFTLCWLPFFIVNIVHVIQ-------DNLIRKE----VYILLNWIGYVN | 318 |
| SEQ ID NO.: 146 | DRD1 | KVLKTLSVIMGVFVCCWLPFFILNCILPFCGSGE-TQPFCIDSN----TFDVFVWFGWAN | 323 |
| SEQ ID NO.: 147 | M2R | KVTRTILAILLAFIITWAPYNVMVLINTFC-------APCIPNT----VWTIGYWLCYIN | 432 |
| SEQ ID NO.: 148 | H1R | KAAKQLGFIMAAFILCWIPYFIFFMVIAFC-------KNCCNEH----LHMFTIWLGYIN | 460 |
| SEQ ID NO.: 149 | DRD2 | KATQMLAIVLGVFIICWLPFFITHILNIHC-------D----CNIPPVLYSAFTWLGYVN | 418 |
| SEQ ID NO.: 150 | 5HT2A | KACKVLGIVFFLFVVMWCPFFITNIMAVIC-------KESCNEDVIGALLNVFVWIGYLS | 372 |
| SEQ ID NO.: 151 | 5HT2B | KASKVLGIVFFLFLLMWCPFFITNITLVLC-------D-SCNQTTLQMLLEIFVWIGYVS | 372 |
| SEQ ID NO.: 152 | NK1 | KVVKMMIVVVCTFAICWLPFHIFFLLPYINPDLYL-------KKFIQQVYLAIMWLAMSS | 297 |
| SEQ ID NO.: 153 | NK3 | KVVKMMIIVVMTFAICWLPYHIYFILTAIYQQLNR-------WKYIQQVYLASFWLAMSS | 348 |
| SEQ ID NO.: 154 | NK2 | KFVKTMVLVVLTFAICWLPYHLYFILGSFQEDIYC-------HKFIQQVYLALFWLAMSS | 299 |
| SEQ ID NO.: 155 | HT1 | RSFLTMFVVFVIFAICWAPLNCIGLAVAINPQEMA-------PQIPEGLFVTSYLLAYFN | 300 |
| SEQ ID NO.: 156 | P2Y1 | KSIYLVIIVLTVFAVSYIPFHVMKTMNLRARLDFQTPAMCAFNDKVYATYQVTRGLASLN | 316 |
| SEQ ID NO.: 157 | AT1 | DIFKIIMAIVLFFFFSWIPHQIFTFLDVLI--QLGIIRDCRIADIVDTAMPITICIAYFN | 294 |
| SEQ ID NO.: 158 | KOR1 | RITRLVLVVVAVFVVCWTPIHIFILVEALG--STSHS------TAALSSYYFCIALGYTN | 322 |
| SEQ ID NO.: 159 | MOR1 | RITRMVLVVVAVFIVCWTPIHIYVIIKALV--TIPET------TFQTVSWHFCIALGYTN | 330 |
| SEQ ID NO.: 160 | DOR1 | RITRMVLVVVGAFVVCWAPIHIFVIVWTLV--DIDRR-----DPLVVAALHLCIALGYAN | 310 |

*Fig. 11E*

```
SEQ ID NO.: 161  MT2R   ---------------------MSENGSFANCC------EA------GGWAVRPGWSGA--
SEQ ID NO.: 162  KOR    -------------MDSPIQIFRGEPG---PTCAPSACLPPNSSAWFPGWAEP-DSNGSAG
SEQ ID NO.: 163  5HT2A  MDILCEENTSLSSTTNSLMQLNDDTRLYSNDFNSG---EANTSDAFN-WTVD-SENRTNL
SEQ ID NO.: 164  A2AR   -------------------MFRQEQPLAEGSFAPMGSLQPDAGNA--------SWNGTEA
SEQ ID NO.: 165  B2AR   ----------------------------------MG--QPGNGSAFL----L-APNRSHA
SEQ ID NO.: 166  DRD1   ----------------------------------------------M----R-TLNTSAM
                                                                       . :

SEQ ID NO.: 161  MT2R   ---GSARPS-RTPRPPWVAPALSAVLIVTTAVDVVGNLLVILSVLRNRKLR-NAGNLFLV
SEQ ID NO.: 162  KOR    SEDAQLEPAHIS---PAIPVIITAVYSVVFVVGLVGNSLVMFVIIRYTKMK-TATNIYIF
SEQ ID NO.: 163  5HT2A  SCEGCLSPSCLSLLHLQEKNWSALLTAVVIILTIAGNILVIMAVSLEKKLQ-NATNYFLM
SEQ ID NO.: 164  A2AR   PGGGARA----TPYSLQVTLTLVCLAGLLMLLTVFGNVLVIIAVFTSRALK-APQNLFLV
SEQ ID NO.: 165  B2AR   PDHDV-T----QQRDEVWVVGMGIVMSLIVLAIVFGNVLVITAIAKFERLQ-TVTNYFIT
SEQ ID NO.: 166  DRD1   DGTGL-V----VERDFSVRILTACFLSLLILSTLLGNTLVCAAVIRFRHLRSKVTNFFVI
                                                .  :     : ** **   :     ::    * ::

SEQ ID NO.: 161  MT2R   SLALADLVVAFYPYPLILVAIFYDG-WALGEEHCKASAFVMGLSVIGSVFNITAIAINRY
SEQ ID NO.: 162  KOR    NLALADALVTT-TMPFQSTVYLMNS-WPFGDVLCKIVISIDYYNMFTSIFTLTMMSVDRY
SEQ ID NO.: 163  5HT2A  SLAIADMLLGFLVMPVSMLTILYGYRWPLPSKLCAVWIYLDVLFSTASIMHLCAISLDRY
SEQ ID NO.: 164  A2AR   SLASADILVATLVIPFSLANEVMGY-WYFGKAWCEIYLALDVLFCTSSIVHLCAISLDRY
SEQ ID NO.: 165  B2AR   SLACADLVMGLAVVPFGAAHILMKM-WTFGNFWCEFWTSIDVLCVTASIETLCVIAVDRY
SEQ ID NO.: 166  DRD1   SLAVSDLLVAVLVMPWKAVAEIAGF-WPFGSF-CNIWVAFDIMCSTASILNLCVISVDRY
                        .** :* ::     *      .    * : .  *     .       *:  :  ::::**
```

*Fig. 12A*

```
SEQ ID NO.: 161 MT2R   CYICHSMAYHRIYRRWHTPLHICLIWLLTVVALLPNFFVGSLEYDP--------------
SEQ ID NO.: 162 KOR    IAVCHPVKALDFRTPLKAKIINICIWLLSSSVGISAIVLGGTKVREDVDVIECS---LQF
SEQ ID NO.: 163 5HT2A  VAIQNPIHHSRFNSRTKAFLKIIAVWTISVGISMPIPVFGLQDDS------------KVF
SEQ ID NO.: 164 A2AR   WSITQAIEYNLKRTPRRIKAIIITVWVISAVISFPPLISIEKKGGG---------GGPQP
SEQ ID NO.: 165 B2AR   FAITSPFKYQSLLTKNKARVIILMVWIVSGLISFLPIQMHWYRATH-QEAINC-----YA
SEQ ID NO.: 166 DRD1   WAISSPFRYERKMTPKAAFILISVAWTLSVLISFIPVQLSWHKAKP-TSPSDGNATSLAE
                         :     .                    * ::      :

SEQ ID NO.: 161 MT2R   RIYSCTPIQTASTQYT----AAVVVIHFLLPIAVVSFCYLRIWVLVLQARRKAKP-----
SEQ ID NO.: 162 KOR    PD-----DD--YSWWDLFMKICVFIFAFVIPVLIIIVCYTLMILRLKSVRLLS-------
SEQ ID NO.: 163 5HT2A  KEGSCLLAD---DNFV----LIGSFVSPFIPLTIMVITYFLTIKSLQKEATLCVSDLGTR
SEQ ID NO.: 164 A2AR   AEPRCEIND--QKWYV----ISSCIGSFFAPCLIMILVYVRIYQIAKRRTRVPPSRRGPD
SEQ ID NO.: 165 B2AR   NETCCDFFT--NQAYA----IASSIVSFYVPLVIMVFVYSRVFQEAKRQLQKIDKSEGR-
SEQ ID NO.: 166 DRD1   TIDNCDSSL--SRTYA----ISSSVISFYIPVAIMIVTYTRIYRIAQKQIRRIAALERAA
                                   :         .  *  *  :: . *

SEQ ID NO.: 161 MT2R   ------------------------------------------------------------
SEQ ID NO.: 162 KOR    ------------------------------------------------------------
SEQ ID NO.: 163 5HT2A  AKLASP--------SFLPQ-------------------------------------SSLS
SEQ ID NO.: 164 A2AR   AVAAPPGGTERRPNGLGPERSAGPGGAEAEPLPTQLNGAPGEPAPAGPRDTDALDLEESS
SEQ ID NO.: 165 B2AR   FHVQ-----------------------------------------------------NLS
SEQ ID NO.: 166 DRD1   VHAK-----------------------------------------------------NCQ
```

Fig. 12B

```
SEQ ID NO.: 161   MT2R    ------------------------------------------------------------
SEQ ID NO.: 162   KOR     ---------------------------------------------------------GSR
SEQ ID NO.: 163   5HT2A   SEKLFQRS------------------IH---------R------------EP-----GSY
SEQ ID NO.: 164   A2AR    SSDHAERPPGPRRPERGPRGKGKARASQVKPGDSLPRRGPGATGIGTPAAGPGEERVGAA
SEQ ID NO.: 165   B2AR    Q------V-----------------------------------------EQDGRTGHGLR
SEQ ID NO.: 166   DRD1    T------T-----------------------------------------TGNGKPVECSQ

SEQ ID NO.: 161   MT2R    -ESRLCL-KPSDLRSFLTMFVVFVIFAICWAPLNCIGLAVAINPQEMA--PQIPEGLFVT
SEQ ID NO.: 162   KOR     ------EKDRNLRRITRLVLVVVAVFVVCWTPIHIFILVEALGSTSHS---TAALSSYYF
SEQ ID NO.: 163   5HT2A   TGRRTMQSISNEQKACKVLGIVFFLFVVMWCPFFITNIMAVICKESCN--EDVIGALLNV
SEQ ID NO.: 164   A2AR    KASRWRGRQNREKRFTFVLAVVIGVFVVCWFPFFFTYTLTAVG-------CSVPRTLFKF
SEQ ID NO.: 165   B2AR    RSSKF---CLKEHKALKTLGIIMGTFTLCWLPFFIVNIVHVIQ------DNLIRKEVYIL
SEQ ID NO.: 166   DRD1    PESSFKMSFKRETKVLKTLSVIMGVFVCCWLPFFILNCILPFCGSGETQPFCIDSNTFDV
                                       :    : ::.  *.   * *:          .

SEQ ID NO.: 161   MT2R    SYLLAYFNSCLNAIVYGLLNQNFRREYKRILLALWNPRHCIQD---------AS------
SEQ ID NO.: 162   KOR     CIALGYTNSSLNPILYAFLDENFKRCFRDFCFPLKMRMERQST---------SRVRNTV-

SEQ ID NO.: 163   5HT2A   FVWIGYLSSAVNPLVYTLFNKTYRSAFSRYIQCQYKENKKPLQLILVNTIPALAYKSSQ-
SEQ ID NO.: 164   A2AR    FFWFGYCNSSLNPVIYTIFNHDFRRAFKKILCRGDRKRI-V-------------------
SEQ ID NO.: 165   B2AR    LNWIGYVNSGFNPLIYC-RSPDFRIAFQELLCLRRSSLK-AYG------NGYSSNGNTG-
SEQ ID NO.: 166   DRD1    FVWFGWANSSLNPIIYA-FNADFRKAFSTLLGCYRLCPA-TNN-----AIETVSINNNGA
                            :.:  .*  .*  ::*    .   ::   :
```

*Fig. 12C*

```
SEQ ID NO.: 161   MT2R    --KGSHAEGLQSP----------APPIIGVQHQADAL-----------------------
SEQ ID NO.: 162   KOR     --------------------------------QDPAYLRDIDGMNKPV------------
SEQ ID NO.: 163   5HT2A   LQMGQKKNSKQDAKTTDNDCSMVAL---GKQHSEEASKDNSDGVNEKVSCV---------
SEQ ID NO.: 164   A2AR    ------------------------------------------------------------
SEQ ID NO.: 165   B2AR    EQSGYHV---EQEKENKLLCEDLPGTEDFVGHQGTVPSDNIDSQGRNCST---NDSLL--
SEQ ID NO.: 166   DRD1    AMFSSHH---EPRGSISKECNLVYLIPHAVGSSEDLKKEEAAGIARPLEKLSPALSVILD

SEQ ID NO.: 161   MT2R    ---------------------
SEQ ID NO.: 162   KOR     ---------------------
SEQ ID NO.: 163   5HT2A   ---------------------
SEQ ID NO.: 164   A2AR    ---------------------
SEQ ID NO.: 165   B2AR    ---------------------
SEQ ID NO.: 166   DRD1    YDTDVSLEKIQPITQNGQHPT
```

*Fig. 12D*

| | | | |
|---|---|---|---|
| DRD1 | RIYRIAQK<br>SEQ ID NO.: 52 | Universal Module | KRETKVLK<br>SEQ ID NO.: 53 |
| B1AR | RVFREAQK<br>SEQ ID NO.: 54 | Universal Module | REQKALKT<br>SEQ ID NO.: 55 |
| B2AR | RVFQEAKR<br>SEQ ID NO.: 56 | Universal Module | KEHKALKT<br>SEQ ID NO.: 57 |
| DRD2 | IVLRRRRK<br>SEQ ID NO.: 58 | Universal Module | QKEKKATQ<br>SEQ ID NO.: 59 |
| DRD4 | RGLQRWEV<br>SEQ ID NO.: 60 | Universal Module | GRERKAMR<br>SEQ ID NO.: 61 |
| KOR | LMILRLKS<br>SEQ ID NO.: 62 | Universal Module | REKDRNLR<br>SEQ ID NO.: 63 |
| MOR | LMILRLKS<br>SEQ ID NO.: 62 | Universal Module | KEKDRNLR<br>SEQ ID NO.: 64 |
| A2AR | RIYQIAKR<br>SEQ ID NO.: 65 | Universal Module | REKRFTFV<br>SEQ ID NO.: 66 |
| MT2 | VLVLQARR<br>SEQ ID NO.: 67 | Universal Module | KPSDLRSF<br>SEQ ID NO.: 68 |
| 5HT2A | LTIKSLQK<br>SEQ ID NO.: 69 | Universal Module | NEQKACKV<br>SEQ ID NO.: 70 |
| A1AR | RVYVVAKR<br>SEQ ID NO.: 71 | Universal Module | SREKKAAK<br>SEQ ID NO.: 72 |

*Fig. 17*

CONSENSUS GPCR SEQUENCE ABUTTING N-TERMINUS (L1) OF SENSOR

| | | |
|---|---|---|
| *DRD1/1-8* | (SEQ ID NO.: 52) | R I Y R I A Q K |
| *B1AR/1-16* | (SEQ ID NO.: 54) | R V F R E A Q K |
| *B2AR/9-17* | (SEQ ID NO.: 56) | R V F Q E A K R |
| *DRD2/10-17* | (SEQ ID NO.: 58) | I V L R R R R K |
| *DRD4/11-18* | (SEQ ID NO.: 60) | R G L Q R W E V |
| *KOR/12-19* | (SEQ ID NO.: 62) | L M I L R L K S |
| *MOR/13-20* | (SEQ ID NO.: 62) | L M I L R L K S |
| *A2AR/14-21* | (SEQ ID NO.: 65) | R I Y Q I A K R |
| *MT2/15-22* | (SEQ ID NO.: 67) | V L V L Q A R R |
| *5HT2A/16-23* | (SEQ ID NO.: 69) | L T I K S L Q K |
| *A1AR/17-24* | (SEQ ID NO.: 71) | R V Y V V A K R |

CONSENSUS GPCR SEQUENCE ABUTTING C-TERMINUS (L2) OF SENSOR

| | | |
|---|---|---|
| *DRD1/1-8* | (SEQ ID NO.: 53) | K R E T K V L K |
| *B1AR/1-16* | (SEQ ID NO.: 55) | R E Q K A L K T |
| *B2AR/9-17* | (SEQ ID NO.: 57) | K E H K A L K T |
| *DRD2/10-17* | (SEQ ID NO.: 59) | Q K E K K A T Q |
| *DRD4/11-18* | (SEQ ID NO.: 61) | G R E R K A M R |
| *KOR/12-19* | (SEQ ID NO.: 63) | R E K D R N L R |
| *MOR/13-20* | (SEQ ID NO.: 64) | K E K D R N L R |
| *A2AR/14-21* | (SEQ ID NO.: 66) | R E K R F T F V |
| *MT2/15-22* | (SEQ ID NO.: 68) | K P S D L R S F |
| *5HT2A/16-23* | (SEQ ID NO.: 70) | N E Q K A C K V |
| *A1AR/17-24* | (SEQ ID NO.: 72) | S R E K K A A K |

| DRD1 LSS-X1X2-cpGFP-X3X4-DQL | | |
|---|---|---|
| | | |
| DFF | $X_1X_2$ | $X_3X_4$ |
| 0.22 | AV | DH |
| 0.23 | RW | HY |
| 0.29 | GD | GG |
| 0.59 | AL | NH |
| 0.6 | PM | PH |
| 0.6 | PM | SS |
| 1 | GR | ST |
| 1.1 | GY | RS |
| 1.37 | IC | RH |
| 1.46 | GL | WP |

*Fig. 20*

| DF/F | Linker 1 | Linker 2 |
|---|---|---|
| 0.07873105 | LI | NHG |
| 0.394823032 | LII | NHN |
| 0.395419249 | LIW | NHM |
| 0.404941683 | LIV | NHR |
| 0.429789736 | LIL | NHT |
| 0.447368826 | LIF | NHS |
| 0.453278854 | LIW | NHT |
| 0.456238277 | LIP | NHK |
| 0.477873893 | LIN | NH |
| 0.478182402 | LIY | NHS |
| 0.515424797 | LIY | NHL |
| 0.517617964 | LIW | NHT |
| 0.538956305 | LIP | NHY |
| 0.54267596 | LIV | NHH |
| 0.595857785 | LIP | NHS |
| 0.60973342 | LIV | NHT |
| 0.727741703 | LII | NHS |
| 0.808182462 | LIW | NHF |
| 0.845519719 | LIW | NHE |
| 0.869164307 | LIW | NHI |
| 1.034953362 | LIW | NHM |
| 1.259123808 | LID | NHW |

*Fig. 21*

SEQUENCE LISTING

<160> NUMBER OF SEQ ID NOS: 176

<210> SEQ ID NO 1
<211> LENGTH: 241
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 1

```
Met Ser Arg Val Ser Lys Gly Glu Glu Leu Phe Thr Gly Val Val Pro
1               5                   10                  15

Ile Leu Val Glu Leu Asp Gly Asp Val Asn Gly His Lys Phe Ser Val
            20                  25                  30

Ser Gly Glu Gly Glu Gly Asp Ala Thr Tyr Gly Lys Leu Thr Leu Lys
        35                  40                  45

Phe Ile Cys Thr Thr Gly Lys Leu Pro Val Pro Trp Pro Thr Leu Val
    50                  55                  60

Thr Thr Leu Thr Tyr Gly Val Gln Cys Phe Ser Arg Tyr Pro Asp His
65                  70                  75                  80

Met Lys Gln His Asp Phe Phe Lys Ser Ala Met Pro Glu Gly Tyr Val
                85                  90                  95

Gln Glu Arg Thr Ile Phe Phe Lys Asp Asp Gly Asn Tyr Lys Thr Arg
            100                 105                 110

Ala Glu Val Lys Phe Glu Gly Asp Thr Leu Val Asn Arg Ile Glu Leu
        115                 120                 125

Lys Gly Ile Asp Phe Lys Glu Asp Gly Asn Ile Leu Gly His Lys Leu
    130                 135                 140

Glu Tyr Asn Tyr Asn Ser His Asn Val Tyr Ile Met Ala Asp Lys Gln
145                 150                 155                 160

Lys Asn Gly Ile Lys Val Asn Phe Lys Ile Arg His Asn Ile Glu Asp
                165                 170                 175

Gly Ser Val Gln Leu Ala Asp His Tyr Gln Gln Asn Thr Pro Ile Gly
            180                 185                 190

Asp Gly Pro Val Leu Leu Pro Asp Asn His Tyr Leu Ser Thr Gln Ser
        195                 200                 205

Ala Leu Ser Lys Asp Pro Asn Glu Lys Arg Asp His Met Val Leu Leu
    210                 215                 220

Glu Phe Val Thr Ala Ala Gly Ile Thr Leu Gly Met Asp Glu Leu Tyr
225                 230                 235                 240

Lys
```

<210> SEQ ID NO 2
<211> LENGTH: 239
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 2

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Trp Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Ile Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 3
<211> LENGTH: 239
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 3

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Gly Tyr Gly Leu Gln Cys Phe Ala Arg Tyr Pro Asp His Met Lys
65                  70                  75                  80

Leu His Asp Phe Phe Lys Ser Ala Met Pro Glu Gly Tyr Val Gln Glu
                85                  90                  95
```

```
Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235


<210> SEQ ID NO 4
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Ser Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser His Gln Ser Ala Leu
        195                 200                 205

Ser Lys Asp Pro Asn Glu Lys Arg Asp His Met Val Leu Leu Glu Phe
```

```
    210                 215                 220

Val Thr Ala Ala Gly Ile Thr Leu Gly Met Asp Glu Leu Tyr Lys
225                 230                 235


<210> SEQ ID NO 5
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
            20                  25                  30

Gly Glu Gly Asp Ala Thr Asn Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Thr Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Phe Asn Ser His Asn Val Tyr Ile Thr Ala Asp Lys Gln Lys Asn Gly
145                 150                 155                 160

Ile Lys Ala Asn Phe Lys Ile Arg His Asn Val Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Val Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235


<210> SEQ ID NO 6
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Gly Thr Gln Thr
```

```
        35                  40                  45

Ala Lys Leu Lys Val Thr Lys Gly Gly Pro Leu Pro Phe Ala Trp Asp
    50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
            180                 185                 190

Gln Leu Pro Gly Ala Tyr Asn Val Asn Ile Lys Leu Asp Ile Thr Ser
        195                 200                 205

His Asn Glu Asp Tyr Thr Ile Val Glu Gln Tyr Glu Arg Ala Glu Gly
    210                 215                 220

Arg His Ser Thr
225


<210> SEQ ID NO 7
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Val Phe
            20                  25                  30

Glu Ile Glu Gly Glu Gly Glu Gly Arg Pro Tyr Glu Gly Thr Gln Thr
        35                  40                  45

Ala Lys Leu Lys Val Thr Lys Gly Gly Pro Leu Pro Phe Thr Trp Asp
    50                  55                  60

Ile Leu Ser Pro Gln Phe Met Tyr Gly Ser Asn Ala Tyr Val Lys His
65                  70                  75                  80

Pro Ala Asp Ile Pro Asp Tyr Phe Lys Leu Ser Phe Pro Glu Gly Phe
                85                  90                  95

Lys Trp Glu Arg Val Met Lys Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Leu Ser Glu Arg Met Tyr Pro Glu Asp Gly
145                 150                 155                 160
```

```
Ala Leu Lys Gly Glu Val Lys Pro Arg Val Lys Leu Lys Asp Gly Gly
                165                 170                 175

His Tyr Asp Ala Glu Val Lys Thr Thr Tyr Lys Ala Lys Lys Pro Val
            180                 185                 190

Gln Leu Pro Gly Ala Tyr Asn Val Asn Arg Lys Leu Asp Ile Thr Ser
        195                 200                 205

His Asn Glu Asp Tyr Thr Ile Val Glu Gln Tyr Glu Arg Ala Glu Gly
    210                 215                 220

Arg His Ser Thr Gly Gly Met Asp Glu Leu Tyr Lys
225                 230                 235


<210> SEQ ID NO 8
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Val Ser Lys Gly Glu Glu Asn Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Ala Phe Gln Thr
        35                  40                  45

Ala Lys Leu Lys Val Thr Lys Gly Gly Pro Leu Pro Phe Ala Trp Asp
    50                  55                  60

Ile Leu Ser Pro Gln Phe Met Tyr Gly Ser Lys Val Tyr Ile Lys His
65                  70                  75                  80

Pro Ala Asp Ile Pro Asp Tyr Phe Lys Leu Ser Phe Pro Glu Gly Phe
                85                  90                  95

Arg Trp Glu Arg Val Met Asn Phe Glu Asp Gly Gly Ile Ile His Val
            100                 105                 110

Asn Gln Asp Ser Ser Leu Gln Asp Gly Val Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Glu Glu Arg Met Tyr Pro Glu Asp Gly
145                 150                 155                 160

Ala Leu Lys Ser Glu Ile Lys Lys Arg Leu Lys Leu Lys Asp Gly Gly
                165                 170                 175

His Tyr Ala Ala Glu Val Lys Thr Thr Tyr Lys Ala Lys Lys Pro Val
            180                 185                 190

Gln Leu Pro Gly Ala Tyr Ile Val Asp Ile Lys Leu Asp Ile Val Ser
        195                 200                 205

His Asn Glu Asp Tyr Thr Ile Val Glu Gln Tyr Glu Arg Ala Glu Gly
    210                 215                 220

Arg His Ser Thr Gly Gly Met Asp Glu Leu Tyr Lys
225                 230                 235


<210> SEQ ID NO 9
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 9

Met Val Ser Lys Gly Glu Glu Leu Ile Lys Glu Asn Met Arg Met Lys
1               5                   10                  15

Val Val Met Glu Gly Ser Val Asn Gly His Gln Phe Lys Cys Thr Gly
            20                  25                  30

Glu Gly Glu Gly Asn Pro Tyr Met Gly Thr Gln Thr Met Arg Ile Lys
        35                  40                  45

Val Ile Glu Gly Gly Pro Leu Pro Phe Ala Phe Asp Ile Leu Ala Thr
    50                  55                  60

Ser Phe Met Tyr Gly Ser Arg Thr Phe Ile Lys Tyr Pro Lys Gly Ile
65                  70                  75                  80

Pro Asp Phe Phe Lys Gln Ser Phe Pro Glu Gly Phe Thr Trp Glu Arg
                85                  90                  95

Val Thr Arg Tyr Glu Asp Gly Gly Val Val Thr Val Met Gln Asp Thr
            100                 105                 110

Ser Leu Glu Asp Gly Cys Leu Val Tyr His Val Gln Val Arg Gly Val
        115                 120                 125

Asn Phe Pro Ser Asn Gly Pro Val Met Gln Lys Lys Thr Lys Gly Trp
    130                 135                 140

Glu Pro Asn Thr Glu Met Met Tyr Pro Ala Asp Gly Gly Leu Arg Gly
145                 150                 155                 160

Tyr Thr His Met Ala Leu Lys Val Asp Gly Gly Gly His Leu Ser Cys
                165                 170                 175

Ser Phe Val Thr Thr Tyr Arg Ser Lys Lys Thr Val Gly Asn Ile Lys
            180                 185                 190

Met Pro Gly Ile His Ala Val Asp His Arg Leu Glu Arg Leu Glu Glu
        195                 200                 205

Ser Asp Asn Glu Met Phe Val Val Gln Arg Glu His Ala Val Ala Lys
    210                 215                 220

Phe Ala Gly Leu Gly Gly Gly Met Asp Glu Leu Tyr Lys
225                 230                 235

<210> SEQ ID NO 10
<211> LENGTH: 232
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Val Ser Glu Leu Ile Lys Glu Asn Met His Met Lys Leu Tyr Met
1               5                   10                  15

Glu Gly Thr Val Asn Asn His His Phe Lys Cys Thr Ser Glu Gly Glu
            20                  25                  30

Gly Lys Pro Tyr Glu Gly Thr Gln Thr Met Arg Ile Lys Ala Val Glu
        35                  40                  45

Gly Gly Pro Leu Pro Phe Ala Phe Asp Ile Leu Ala Thr Ser Phe Met
    50                  55                  60

Tyr Gly Ser Lys Thr Phe Ile Asn His Thr Gln Gly Ile Pro Asp Phe
65                  70                  75                  80

Phe Lys Gln Ser Phe Pro Glu Gly Phe Thr Trp Glu Arg Val Thr Thr
                85                  90                  95

Tyr Glu Asp Gly Gly Val Leu Thr Ala Thr Gln Asp Thr Ser Leu Gln
            100                 105                 110

Asp Gly Cys Leu Ile Tyr Asn Val Lys Ile Arg Gly Val Asn Phe Pro
115 120 125

Ser Asn Gly Pro Val Met Gln Lys Lys Thr Leu Gly Trp Glu Ala Ser
130 135 140

Thr Glu Thr Leu Tyr Pro Ala Asp Gly Gly Leu Glu Gly Arg Ala Asp
145 150 155 160

Met Ala Leu Lys Leu Val Gly Gly Gly His Leu Ile Cys Asn Leu Lys
165 170 175

Thr Thr Tyr Arg Ser Lys Lys Pro Ala Lys Asn Leu Lys Met Pro Gly
180 185 190

Val Tyr Tyr Val Asp Arg Arg Leu Glu Arg Ile Lys Glu Ala Asp Lys
195 200 205

Glu Thr Tyr Val Glu Gln His Glu Val Ala Val Ala Arg Tyr Cys Asp
210 215 220

Leu Pro Ser Lys Leu Gly His Arg
225 230

<210> SEQ ID NO 11
<211> LENGTH: 226
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 11

Met Ser Ala Ile Lys Pro Asp Met Lys Ile Lys Leu Arg Met Glu Gly
1 5 10 15

Asn Val Asn Gly His His Phe Val Ile Asp Gly Asp Gly Thr Gly Lys
20 25 30

Pro Phe Glu Gly Lys Gln Ser Met Asp Leu Glu Val Lys Glu Gly Gly
35 40 45

Pro Leu Pro Phe Ala Phe Asp Ile Leu Thr Thr Ala Phe His Tyr Gly
50 55 60

Asn Arg Val Phe Ala Lys Tyr Pro Asp Asn Ile Gln Asp Tyr Phe Lys
65 70 75 80

Gln Ser Phe Pro Lys Gly Tyr Ser Trp Glu Arg Ser Leu Thr Phe Glu
85 90 95

Asp Gly Gly Ile Cys Ile Ala Arg Asn Asp Ile Thr Met Glu Gly Asp
100 105 110

Thr Phe Tyr Asn Lys Val Arg Phe Tyr Gly Thr Asn Phe Pro Ala Asn
115 120 125

Gly Pro Val Met Gln Lys Lys Thr Leu Lys Trp Glu Pro Ser Thr Glu
130 135 140

Lys Met Tyr Val Arg Asp Gly Val Leu Thr Gly Asp Ile His Met Ala
145 150 155 160

Leu Leu Leu Glu Gly Asn Ala His Tyr Arg Cys Asp Phe Arg Thr Thr
165 170 175

Tyr Lys Ala Lys Glu Lys Gly Val Lys Leu Pro Gly Tyr His Phe Val
180 185 190

Asp His Cys Ile Glu Ile Leu Ser His Asp Lys Asp Tyr Asn Lys Val
195 200 205

Lys Leu Tyr Glu His Ala Val Ala His Ser Gly Leu Pro Asp Asn Ala
210 215 220

Arg Arg

225

<210> SEQ ID NO 12
<211> LENGTH: 237
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 12

```
Met Val Ser Lys Gly Glu Glu Thr Ile Met Ser Val Ile Lys Pro Asp
1               5                   10                  15

Met Lys Ile Lys Leu Arg Met Glu Gly Asn Val Asn Gly His Ala Phe
            20                  25                  30

Val Ile Glu Gly Glu Gly Ser Gly Lys Pro Phe Glu Gly Ile Gln Thr
        35                  40                  45

Ile Asp Leu Glu Val Lys Glu Gly Ala Pro Leu Pro Phe Ala Tyr Asp
    50                  55                  60

Ile Leu Thr Thr Ala Phe His Tyr Gly Asn Arg Val Phe Thr Lys Tyr
65                  70                  75                  80

Pro Glu Asp Ile Pro Asp Tyr Phe Lys Gln Ser Phe Pro Glu Gly Tyr
                85                  90                  95

Ser Trp Glu Arg Ser Met Thr Tyr Glu Asp Gly Gly Ile Cys Ile Ala
            100                 105                 110

Thr Asn Asp Ile Thr Met Glu Glu Asp Ser Phe Ile Asn Lys Ile His
        115                 120                 125

Phe Lys Gly Thr Asn Phe Pro Pro Asn Gly Pro Val Met Gln Lys Arg
    130                 135                 140

Thr Val Gly Trp Glu Val Ser Thr Glu Lys Met Tyr Val Arg Asp Gly
145                 150                 155                 160

Val Leu Lys Gly Asp Val Lys Met Lys Leu Leu Leu Lys Gly Gly Ser
                165                 170                 175

His Tyr Arg Cys Asp Phe Arg Thr Thr Tyr Lys Val Lys Gln Lys Ala
            180                 185                 190

Val Lys Leu Pro Asp Tyr His Phe Val Asp His Arg Ile Glu Ile Leu
        195                 200                 205

Ser His Asp Lys Asp Tyr Asn Lys Val Lys Leu Tyr Glu His Ala Val
    210                 215                 220

Ala Arg Asn Ser Thr Asp Ser Met Asp Glu Leu Tyr Lys
225                 230                 235
```

<210> SEQ ID NO 13
<211> LENGTH: 244
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 13

```
Met Val Ser Lys Gly Glu Glu Leu Ile Lys Glu Asn Met His Met Lys
1               5                   10                  15

Leu Tyr Met Glu Gly Thr Val Asn Asn His His Phe Lys Cys Thr Thr
            20                  25                  30

Glu Gly Glu Gly Lys Pro Tyr Glu Gly Thr Gln Thr Gln Arg Ile Lys
        35                  40                  45

Val Val Glu Gly Gly Pro Leu Pro Phe Ala Phe Asp Ile Leu Ala Thr
```

```
    50                  55                  60

Cys Phe Met Tyr Gly Ser Lys Thr Phe Ile Asn His Thr Gln Gly Ile
65                  70                  75                  80

Pro Asp Phe Phe Lys Gln Ser Phe Pro Glu Gly Phe Thr Trp Glu Arg
                85                  90                  95

Val Thr Thr Tyr Glu Asp Gly Gly Val Leu Thr Val Thr Gln Asp Thr
            100                 105                 110

Ser Leu Gln Asp Gly Cys Leu Ile Tyr Asn Val Lys Leu Arg Gly Val
        115                 120                 125

Asn Phe Pro Ser Asn Gly Pro Val Met Gln Lys Lys Thr Leu Gly Trp
    130                 135                 140

Glu Ala Thr Thr Glu Thr Leu Tyr Pro Ala Asp Gly Gly Leu Glu Gly
145                 150                 155                 160

Arg Cys Asp Met Ala Leu Lys Leu Val Gly Gly Gly His Leu His Cys
                165                 170                 175

Asn Leu Lys Thr Thr Tyr Arg Ser Lys Lys Pro Ala Lys Asn Leu Lys
            180                 185                 190

Met Pro Gly Val Tyr Phe Val Asp Arg Arg Leu Glu Arg Ile Lys Glu
        195                 200                 205

Ala Asp Asn Glu Thr Tyr Val Glu Gln His Glu Val Ala Val Ala Arg
    210                 215                 220

Tyr Cys Asp Leu Pro Ser Lys Leu Gly His Lys Leu Asn Gly Met Asp
225                 230                 235                 240

Glu Leu Tyr Lys


<210> SEQ ID NO 14
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Val Ser Lys Gly Glu Glu Leu Ile Lys Glu Asn Met His Met Lys
1               5                   10                  15

Leu Tyr Met Glu Gly Thr Val Asn Asn His His Phe Lys Cys Thr Ser
            20                  25                  30

Glu Gly Glu Gly Lys Pro Tyr Glu Gly Thr Gln Thr Gly Arg Ile Lys
        35                  40                  45

Val Val Glu Gly Gly Pro Leu Pro Phe Ala Phe Asp Ile Leu Ala Thr
    50                  55                  60

Cys Phe Met Tyr Gly Ser Lys Thr Phe Ile Asn His Thr Gln Gly Ile
65                  70                  75                  80

Pro Asp Phe Phe Lys Gln Ser Phe Pro Glu Gly Phe Thr Trp Glu Arg
                85                  90                  95

Val Thr Thr Tyr Glu Asp Gly Gly Val Leu Thr Ala Thr Gln Asp Thr
            100                 105                 110

Ser Leu Gln Asp Gly Cys Leu Ile Tyr Asn Val Lys Ile Arg Gly Val
        115                 120                 125

Asn Phe Pro Ser Asn Gly Pro Val Met Gln Lys Lys Thr Leu Gly Trp
    130                 135                 140

Glu Ala Ser Thr Glu Thr Leu Tyr Pro Ala Asp Gly Gly Leu Glu Gly
145                 150                 155                 160

Arg Cys Asp Met Ala Leu Lys Leu Val Gly Gly Gly His Leu Ile Cys
```

```
                165                 170                 175

Asn Leu Lys Thr Thr Tyr Arg Ser Lys Lys Pro Ala Lys Asn Leu Lys
            180                 185                 190

Met Pro Gly Val Tyr Phe Val Asp Arg Arg Leu Glu Arg Ile Lys Glu
        195                 200                 205

Ala Asp Asn Glu Thr Tyr Val Glu Gln His Glu Val Ala Val Ala Arg
    210                 215                 220

Tyr Cys Asp Leu Pro Ser Lys Leu Gly His Lys Leu Asn Gly Met Asp
225                 230                 235                 240

Glu Leu Tyr Lys


<210> SEQ ID NO 15
<211> LENGTH: 204
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Asn Val Tyr Ile Lys Ala Asp Lys Gln Lys Asn Gly Ile Lys Ala Asn
1               5                   10                  15

Phe Lys Ile Arg His Asn Ile Glu Asp Gly Gly Val Gln Leu Ala Tyr
            20                  25                  30

His Tyr Gln Gln Asn Thr Pro Ile Gly Asp Gly Pro Val Leu Leu Pro
        35                  40                  45

Asp Asn His Tyr Leu Ser Val Gln Ser Lys Leu Ser Lys Asp Pro Asn
    50                  55                  60

Glu Lys Arg Asp His Met Val Leu Leu Glu Phe Val Thr Ala Ala Gly
65                  70                  75                  80

Ile Thr Leu Gly Met Asp Glu Leu Tyr Lys Gly Gly Thr Gly Gly Ser
                85                  90                  95

Met Val Ser Lys Gly Glu Glu Leu Phe Thr Gly Val Val Pro Ile Leu
            100                 105                 110

Val Glu Leu Asp Gly Asp Val Asn Gly His Lys Phe Ser Val Ser Gly
        115                 120                 125

Glu Gly Glu Gly Asp Ala Thr Tyr Gly Lys Leu Thr Leu Lys Phe Ile
    130                 135                 140

Cys Thr Thr Gly Lys Leu Pro Val Pro Trp Pro Thr Leu Val Thr Thr
145                 150                 155                 160

Leu Thr Tyr Gly Val Gln Cys Phe Ser Arg Tyr Pro Asp His Met Lys
                165                 170                 175

Gln His Asp Phe Phe Lys Ser Ala Met Pro Glu Gly Tyr Ile Gln Glu
            180                 185                 190

Arg Thr Ile Phe Phe Lys Asp Asp Gly Asn Tyr Lys
        195                 200


<210> SEQ ID NO 16
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Asn Thr Glu Met Met Tyr Pro Ala Asp Gly Gly Leu Arg Gly Tyr Thr
1               5                   10                  15
```

```
His Met Ala Leu Lys Val Asp Gly Gly Gly His Leu Ser Cys Ser Phe
            20                  25                  30

Val Thr Thr Tyr Arg Ser Lys Lys Thr Val Gly Asn Ile Lys Met Pro
        35                  40                  45

Gly Ile His Tyr Val Ser His Arg Leu Glu Arg Leu Glu Glu Ser Asp
    50                  55                  60

Asn Glu Met Phe Val Val Gln Arg Glu His Ala Val Ala Lys Phe Val
65                  70                  75                  80

Gly Leu Gly Gly Gly Gly Gly Thr Gly Gly Ser Met Asn Ser Leu Ile
                85                  90                  95

Lys Glu Asn Met Arg Met Lys Val Val Leu Glu Gly Ser Val Asn Gly
            100                 105                 110

His Gln Phe Lys Cys Thr Gly Glu Gly Glu Gly Asn Pro Tyr Met Gly
        115                 120                 125

Thr Gln Thr Met Arg Ile Lys Val Ile Glu Gly Gly Pro Leu Pro Phe
    130                 135                 140

Ala Phe Asp Ile Leu Ala Thr Ser Phe Met Ser Arg Thr Phe Ile Lys
145                 150                 155                 160

Tyr Pro Lys Gly Ile Pro Asp Phe Phe Lys Gln Ser Phe Pro Glu Gly
                165                 170                 175

Phe Thr Trp Glu Arg Val Thr Arg Tyr Glu Asp Gly Gly Val Ile Thr
            180                 185                 190

Val Met Gln Asp Thr Ser Leu Glu Asp Gly Cys Leu Val Tyr His Ala
        195                 200                 205

Gln Val Arg Gly Val Asn Phe Pro Ser Asn Gly Ala Val Met Gln Lys
    210                 215                 220

Lys Thr Lys Gly Trp Glu Pro Thr Arg Asp Gln Leu Thr
225                 230                 235


<210> SEQ ID NO 17
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Val Val Ser Glu Arg Met Tyr Pro Glu Asp Gly Ala Leu Lys Ser Glu
1               5                   10                  15

Ile Lys Lys Gly Leu Arg Leu Lys Asp Gly Gly His Tyr Ala Ala Glu
            20                  25                  30

Val Lys Thr Thr Tyr Lys Ala Lys Lys Pro Val Gln Leu Pro Gly Ala
        35                  40                  45

Tyr Ile Val Asp Ile Lys Leu Asp Ile Val Ser His Asn Glu Asp Tyr
    50                  55                  60

Thr Ile Val Glu Gln Cys Glu Arg Ala Glu Gly Arg His Ser Thr Gly
65                  70                  75                  80

Gly Met Asp Glu Leu Tyr Lys Gly Gly Thr Gly Gly Ser Leu Val Ser
                85                  90                  95

Lys Gly Glu Glu Asp Asn Met Ala Ile Ile Lys Glu Phe Met Arg Phe
            100                 105                 110

Lys Val His Met Glu Gly Ser Val Asn Gly His Glu Phe Glu Ile Glu
        115                 120                 125

Gly Glu Gly Glu Gly Arg Pro Tyr Glu Ala Phe Gln Thr Ala Lys Leu
```

```
    130                 135                 140

Lys Val Thr Lys Gly Gly Pro Leu Pro Phe Ala Trp Asp Ile Leu Ser
145                 150                 155                 160

Pro Gln Phe Met Ser Lys Ala Tyr Ile Lys His Pro Ala Asp Ile Pro
                165                 170                 175

Asp Tyr Phe Lys Leu Ser Phe Pro Glu Gly Phe Arg Trp Glu Arg Val
            180                 185                 190

Met Asn Phe Glu Asp Gly Gly Ile Ile His Val Asn Gln Asp Ser Ser
        195                 200                 205

Leu Gln Asp Gly Val Phe Ile Tyr Lys Val Lys Leu Arg Gly Thr Asn
    210                 215                 220

Phe Pro Pro Asp Gly Pro Val Met Gln Lys Lys Thr Met Gly Trp Glu
225                 230                 235                 240

Ala


<210> SEQ ID NO 18
<211> LENGTH: 230
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Leu Glu Cys Glu Lys Met Tyr Val Arg Asp Gly Val Leu Thr Gly Asp
1               5                   10                  15

Ile His Met Ala Leu Leu Leu Glu Gly Asn Ala His Tyr Arg Cys Asp
            20                  25                  30

Phe Arg Thr Thr Tyr Lys Ala Lys Glu Lys Gly Val Lys Leu Pro Gly
        35                  40                  45

Tyr His Phe Val Asp His Cys Ile Glu Ile Leu Ser His Asp Lys Asp
    50                  55                  60

Tyr Asn Lys Val Lys Leu Tyr Glu His Ala Val Ala His Ser Gly Leu
65                  70                  75                  80

Pro Asp Asn Ala Arg Arg Gly Gly Thr Gly Gly Ser Met Val Ser Ala
                85                  90                  95

Ile Lys Pro Asp Met Lys Ile Lys Leu Arg Met Glu Gly Asn Val Asn
            100                 105                 110

Gly His His Phe Val Ile Asp Gly Asp Gly Thr Gly Lys Pro Tyr Glu
        115                 120                 125

Gly Lys Gln Thr Met Asp Leu Glu Val Lys Glu Gly Gly Pro Leu Pro
    130                 135                 140

Phe Ala Phe Asp Ile Leu Thr Thr Ala Phe His Asn Arg Val Phe Val
145                 150                 155                 160

Lys Tyr Pro Asp Asn Ile Gln Asp Tyr Phe Lys Gln Ser Phe Pro Lys
                165                 170                 175

Gly Tyr Ser Trp Glu Arg Ser Met Thr Phe Glu Asp Gly Gly Ile Cys
            180                 185                 190

Tyr Ala Arg Asn Asp Ile Thr Met Glu Gly Asp Thr Phe Tyr Asn Lys
        195                 200                 205

Val Arg Phe Tyr Gly Thr Asn Phe Pro Ala Asn Gly Pro Val Met Gln
    210                 215                 220

Lys Lys Thr Leu Lys Trp
225                 230
```

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (3)..(3)
<223> OTHER INFORMATION: Tyr or Phe
<220> FEATURE:
<221> NAME/KEY: MOD_RES
<222> LOCATION: (4)..(4)
<223> OTHER INFORMATION: Asn or Ile

<400> SEQUENCE: 19

Tyr Asn Xaa Xaa Ser His Asn Val
1 5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (3)..(3)
<223> OTHER INFORMATION: Ala, Pro, or Val
<220> FEATURE:
<221> NAME/KEY: MOD_RES
<222> LOCATION: (4)..(4)
<223> OTHER INFORMATION: Ser, Leu, Asn, or Thr
<220> FEATURE:
<221> NAME/KEY: MOD_RES
<222> LOCATION: (5)..(5)
<223> OTHER INFORMATION: Ser, Glu, or Thr
<220> FEATURE:
<221> NAME/KEY: MOD_RES
<222> LOCATION: (7)..(7)
<223> OTHER INFORMATION: Arg, Met, Thr, or Lys
<220> FEATURE:
<221> NAME/KEY: MOD_RES
<222> LOCATION: (8)..(8)
<223> OTHER INFORMATION: Met or Leu

<400> SEQUENCE: 20

Trp Glu Xaa Xaa Xaa Glu Xaa Xaa
1 5

<210> SEQ ID NO 21
<211> LENGTH: 2049
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 21
atgaagacga tcatcgccct gagctacatc ttctgcctgg tgttcgccga ctacaaggac 60
gatgatgacg ccatggggca gccaggtaat ggctctgcgt tcttgttggc cccgaacagg 120
agccatgctc ccgaccatga cgtcacccaa cagagagatg aggtctgggt agtaggcatg 180
ggtattgtca tgtctctgat agtcttggca atcgtgtttg gaaatgtgct cgttatcacg 240
gcaatagcta agtttgagcg acttcaaacg gtaacaaatt atttcataac atctctcgcg 300
tgtgcagatc tcgtaatggg actcgctgtg gtcccctttg gcgcggccca tatcctgatg 360
aagatgtgga cttttggtaa tttctggtgt gaattttgga ccagcataga tgtactctgt 420

```
gttacagctt caattgaaac tctctgtgtg atagccgttg atcgctattt cgccattacg    480
tcccctgcca agtatcaatc attgcttacc aagaataaag cccgagtaat aattctcatg    540
gtgtggatcg taagcgggct cacatctttt ttgccgattc agatgcactg gtatagagca    600
acgcaccaag aagccataaa ctgctacgca aatgaaactt gctgtgactt ctttacaaat    660
caggcttacg ctattgcctc ttcaatagtc agtttttacg ttcctctggt tattatggtg    720
tttgtatact cacgggtatt ccaggaggct aagcggcagc tccagaaaat agacaagagt    780
gagggacgct ttcatgtgca gaatctttca gccgtcaacg tctatatcaa ggccgacaag    840
cagaagaacg gcatcaaggc gaacttcaag atccgccaca acatcgagga cggcggcgtg    900
cagctcgcct accactacca gcagaacacc cccatcggcg acggccccgt gctgctgccc    960
gacaaccact acctgagcgt gcagtccaaa ctttcgaaag accccaacga gaagcgcgat   1020
cacatggtcc tgctggagtt cgtgaccgcc gccgggatca ctctcggcat ggacgagctg   1080
tacaagggcg gtaccggagg gagcatggtg agcaagggcg aggagctgtt caccggggtg   1140
gtgcccatcc tggtcgagct ggacggcgac gtaaacggcc acaagttcag cgtgtccggc   1200
gagggtgagg gcgatgccac ctacggcaag ctgaccctga agttcatctg caccaccggc   1260
aagctgcccg tgccctggcc caccctcgtg accaccctga cctacggcgt gcagtgcttc   1320
agccgctacc ccgaccacat gaagcagcac gacttcttca agtccgccat gcccgaaggc   1380
tacatccagg agcgcaccat cttcttcaag gacgacggca actacaagac ccgcgccgag   1440
gtgaagttcg agggcgacac cctggtgaac cgcatcgagc tgaagggcat cgacttcaag   1500
gaggacggca acatcctggg gcacaagctg gagtacaaca ccagacaagt tgaacaggac   1560
ggacgcacag gtcatggcct caggaggagt tctaagttct gcttgaagga gcacaaagcg   1620
ctgaagacgc ttggaattat catggggacg tttactctct gctggcttcc tttcttcata   1680
gtaaacattg ttcacgtaat ccaagacaat ctgattcgaa aggaggtgta tattctcctc   1740
aattggattg ggtacgtaaa cagcggattt aatcctctta tctattgccg aagccctgat   1800
ttccgcatag cctttcagga actgctttgt cttcgccgaa gcagccttaa agcgtacgga   1860
aatggttacg ctgcaaatgg gaatacaggc gagcaaagcg ggtatcacgt cgagcaagag   1920
aaggagaaca aacttctgtg cgaagacctg cctggcacgg aagattttgt cggacaccaa   1980
gggacggtac cgagtgacaa tatcgacagt caaggccgaa actgctcaac taatgattca   2040
ctcctgtag                                                           2049
```

```
<210> SEQ ID NO 22
<211> LENGTH: 682
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (163)..(163)
<223> OTHER INFORMATION: Phe, Ala, Gly, Val, Ile, Leu, Met, Ser, or Thr

<400> SEQUENCE: 22

Met Lys Thr Ile Ile Ala Leu Ser Tyr Ile Phe Cys Leu Val Phe Ala
1               5                   10                  15

Asp Tyr Lys Asp Asp Asp Asp Ala Met Gly Gln Pro Gly Asn Gly Ser
            20                  25                  30

Ala Phe Leu Leu Ala Pro Asn Arg Ser His Ala Pro Asp His Asp Val
```

```
        35                  40                  45

Thr Gln Gln Arg Asp Glu Val Trp Val Val Gly Met Gly Ile Val Met
    50                  55                  60

Ser Leu Ile Val Leu Ala Ile Val Phe Gly Asn Val Leu Val Ile Thr
65                  70                  75                  80

Ala Ile Ala Lys Phe Glu Arg Leu Gln Thr Val Thr Asn Tyr Phe Ile
                85                  90                  95

Thr Ser Leu Ala Cys Ala Asp Leu Val Met Gly Leu Ala Val Val Pro
            100                 105                 110

Phe Gly Ala Ala His Ile Leu Met Lys Met Trp Thr Phe Gly Asn Phe
        115                 120                 125

Trp Cys Glu Phe Trp Thr Ser Ile Asp Val Leu Cys Val Thr Ala Ser
    130                 135                 140

Ile Glu Thr Leu Cys Val Ile Ala Val Asp Arg Tyr Phe Ala Ile Thr
145                 150                 155                 160

Ser Pro Xaa Lys Tyr Gln Ser Leu Leu Thr Lys Asn Lys Ala Arg Val
                165                 170                 175

Ile Ile Leu Met Val Trp Ile Val Ser Gly Leu Thr Ser Phe Leu Pro
            180                 185                 190

Ile Gln Met His Trp Tyr Arg Ala Thr His Gln Glu Ala Ile Asn Cys
        195                 200                 205

Tyr Ala Asn Glu Thr Cys Cys Asp Phe Phe Thr Asn Gln Ala Tyr Ala
    210                 215                 220

Ile Ala Ser Ser Ile Val Ser Phe Tyr Val Pro Leu Val Ile Met Val
225                 230                 235                 240

Phe Val Tyr Ser Arg Val Phe Gln Glu Ala Lys Arg Gln Leu Gln Lys
                245                 250                 255

Ile Asp Lys Ser Glu Gly Arg Phe His Val Gln Asn Leu Ser Ala Val
            260                 265                 270

Asn Val Tyr Ile Lys Ala Asp Lys Gln Lys Asn Gly Ile Lys Ala Asn
        275                 280                 285

Phe Lys Ile Arg His Asn Ile Glu Asp Gly Gly Val Gln Leu Ala Tyr
    290                 295                 300

His Tyr Gln Gln Asn Thr Pro Ile Gly Asp Gly Pro Val Leu Leu Pro
305                 310                 315                 320

Asp Asn His Tyr Leu Ser Val Gln Ser Lys Leu Ser Lys Asp Pro Asn
                325                 330                 335

Glu Lys Arg Asp His Met Val Leu Leu Glu Phe Val Thr Ala Ala Gly
            340                 345                 350

Ile Thr Leu Gly Met Asp Glu Leu Tyr Lys Gly Gly Thr Gly Gly Ser
        355                 360                 365

Met Val Ser Lys Gly Glu Glu Leu Phe Thr Gly Val Val Pro Ile Leu
    370                 375                 380

Val Glu Leu Asp Gly Asp Val Asn Gly His Lys Phe Ser Val Ser Gly
385                 390                 395                 400

Glu Gly Glu Gly Asp Ala Thr Tyr Gly Lys Leu Thr Leu Lys Phe Ile
                405                 410                 415

Cys Thr Thr Gly Lys Leu Pro Val Pro Trp Pro Thr Leu Val Thr Thr
            420                 425                 430

Leu Thr Tyr Gly Val Gln Cys Phe Ser Arg Tyr Pro Asp His Met Lys
        435                 440                 445

Gln His Asp Phe Phe Lys Ser Ala Met Pro Glu Gly Tyr Ile Gln Glu
    450                 455                 460
```

```
Arg Thr Ile Phe Phe Lys Asp Asp Gly Asn Tyr Lys Thr Arg Ala Glu
465                 470                 475                 480

Val Lys Phe Glu Gly Asp Thr Leu Val Asn Arg Ile Glu Leu Lys Gly
                485                 490                 495

Ile Asp Phe Lys Glu Asp Gly Asn Ile Leu Gly His Lys Leu Glu Tyr
            500                 505                 510

Asn Thr Arg Gln Val Glu Gln Asp Gly Arg Thr Gly His Gly Leu Arg
        515                 520                 525

Arg Ser Ser Lys Phe Cys Leu Lys Glu His Lys Ala Leu Lys Thr Leu
    530                 535                 540

Gly Ile Ile Met Gly Thr Phe Thr Leu Cys Trp Leu Pro Phe Phe Ile
545                 550                 555                 560

Val Asn Ile Val His Val Ile Gln Asp Asn Leu Ile Arg Lys Glu Val
                565                 570                 575

Tyr Ile Leu Leu Asn Trp Ile Gly Tyr Val Asn Ser Gly Phe Asn Pro
            580                 585                 590

Leu Ile Tyr Cys Arg Ser Pro Asp Phe Arg Ile Ala Phe Gln Glu Leu
        595                 600                 605

Leu Cys Leu Arg Arg Ser Ser Leu Lys Ala Tyr Gly Asn Gly Tyr Ala
    610                 615                 620

Ala Asn Gly Asn Thr Gly Glu Gln Ser Gly Tyr His Val Glu Gln Glu
625                 630                 635                 640

Lys Glu Asn Lys Leu Leu Cys Glu Asp Leu Pro Gly Thr Glu Asp Phe
                645                 650                 655

Val Gly His Gln Gly Thr Val Pro Ser Asp Asn Ile Asp Ser Gln Gly
            660                 665                 670

Arg Asn Cys Ser Thr Asn Asp Ser Leu Leu
        675                 680
```

<210> SEQ ID NO 23
<211> LENGTH: 2010
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 23

```
atgaagacga tcatcgccct gagctacatc ttctgcctgg tgttcgccga ctacaaggac     60

gatgatgacg ccatggatag tagcgctgcg cctaccaacg cgtcaaactg caccgatgct    120

cttgcgtact cctcctgctc cccggcacct agtcccggtt cttgggtcaa tttgtcccat    180

ctggacggaa acctctctga tccctgtggg cctaacagga cggacctcgg tgggagggac    240

tccctttgcc cgccgaccgg atctccgtcc atgataacgg ccattacaat tatggcgttg    300

tatagcatcg tatgcgttgt aggtcttttt gggaatttcc tggtgatgta cgtcatcgtc    360

aggtacacaa agatgaaaac agctactaac atttatatat ttaacctggc gctcgcggac    420

gctctcgcaa cgtcaacgct cccgtttcag tccgtgaatt atctcatggg tacttggcct    480

ttcggaacaa tactgtgtaa aattgttata agcatagatt attataatat gttcacgtcc    540

atcttcacac tctgcacaat gtctgtggat aggtacattg ctgtatgtca cccagctaag    600

gcgcttgact ttagaactcc acgcaatgca aagattataa atgtgtgcaa ctggatcttg    660

tcctctgcaa tagggcttcc tgtgatgttc atggcgacta ctaagtacag acagggcagc    720

atagattgca cactcacctt ctcacaccca acttggtact gggaaaatct gctcaagatc    780
```

```
tgcgtcttca tttttgcttt tatcatgcca gtattgataa tcacggtctg ttacgggttg    840

atgattttgc ggctcaaatc agttcgaatg ctcagtatca aaaacgtcta tatcaaggcc    900

gacaagcaga agaacggcat caaggcgaac ttcaagatcc gccacaacat cgaggacggc    960

ggcgtgcagc tcgcctacca ctaccagcag aacacccccca tcggcgacgg ccccgtgctg   1020

ctgcccgaca accactacct gagcgtgcag tccaaacttt cgaaagaccc caacgagaag   1080

cgcgatcaca tggtcctgct ggagttcgtg accgccgccg ggatcactct cggcatggac   1140

gagctgtaca agggcggtac cggagggagc atggtgagca agggcgagga gctgttcacc   1200

ggggtggtgc ccatcctggt cgagctggac ggcgacgtaa acggccacaa gttcagcgtg   1260

tccggcgagg gtgagggcga tgccacctac ggcaagctga ccctgaagtt catctgcacc   1320

accggcaagc tgcccgtgcc ctggcccacc ctcgtgacca ccctgaccta cggcgtgcag   1380

tgcttcagcc gctaccccga ccacatgaag cagcacgact tcttcaagtc cgccatgccc   1440

gaaggctaca tccaggagcg caccatcttc ttcaaggacg acggcaacta caagacccgc   1500

gccgaggtga agttcgaggg cgacaccctg gtgaaccgca tcgagctgaa gggcatcgac   1560

ttcaaggagg acggcaacat cctggggcac aagctggagt acaacattat cggcagcaag   1620

gagaaggacc gcaacctcag aaggataacg agaatggtgc tggtcgtagt ggcggttttc   1680

attgtttgtt ggacgccaat acacatatac gtgattataa aggctctggt gacaattccc   1740

gaaacaacgt ttcagacggt ctcttggcat ttctgtattg cattggggta cactaattcc   1800

tgccttaatc ctgtattgta cgcctttctg gatgaaaact ttaaaagatg tttccgcgag   1860

ttctgcatac cgaccagcag caacattgaa caacaaaact ccacgcgcat acggcaaaat   1920

actagggatc acccgtccac tgcgaatact gtagaccgaa cgaaccatca gttggagaat   1980

ttggaagcgg aaactgctcc tctgccatga                                     2010
```

```
<210> SEQ ID NO 24
<211> LENGTH: 669
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (199)..(199)
<223> OTHER INFORMATION: Phe, Ala, Gly, Val, Ile, Leu, Met, Ser, or Thr

<400> SEQUENCE: 24

Met Lys Thr Ile Ile Ala Leu Ser Tyr Ile Phe Cys Leu Val Phe Ala
1               5                   10                  15

Asp Tyr Lys Asp Asp Asp Asp Ala Met Asp Ser Ser Ala Ala Pro Thr
            20                  25                  30

Asn Ala Ser Asn Cys Thr Asp Ala Leu Ala Tyr Ser Ser Cys Ser Pro
        35                  40                  45

Ala Pro Ser Pro Gly Ser Trp Val Asn Leu Ser His Leu Asp Gly Asn
    50                  55                  60

Leu Ser Asp Pro Cys Gly Pro Asn Arg Thr Asp Leu Gly Gly Arg Asp
65                  70                  75                  80

Ser Leu Cys Pro Pro Thr Gly Ser Pro Ser Met Ile Thr Ala Ile Thr
                85                  90                  95

Ile Met Ala Leu Tyr Ser Ile Val Cys Val Val Gly Leu Phe Gly Asn
            100                 105                 110
```

```
Phe Leu Val Met Tyr Val Ile Val Arg Tyr Thr Lys Met Lys Thr Ala
        115                 120                 125

Thr Asn Ile Tyr Ile Phe Asn Leu Ala Leu Ala Asp Ala Leu Ala Thr
    130                 135                 140

Ser Thr Leu Pro Phe Gln Ser Val Asn Tyr Leu Met Gly Thr Trp Pro
145                 150                 155                 160

Phe Gly Thr Ile Leu Cys Lys Ile Val Ile Ser Ile Asp Tyr Tyr Asn
                165                 170                 175

Met Phe Thr Ser Ile Phe Thr Leu Cys Thr Met Ser Val Asp Arg Tyr
            180                 185                 190

Ile Ala Val Cys His Pro Xaa Lys Ala Leu Asp Phe Arg Thr Pro Arg
        195                 200                 205

Asn Ala Lys Ile Ile Asn Val Cys Asn Trp Ile Leu Ser Ser Ala Ile
    210                 215                 220

Gly Leu Pro Val Met Phe Met Ala Thr Thr Lys Tyr Arg Gln Gly Ser
225                 230                 235                 240

Ile Asp Cys Thr Leu Thr Phe Ser His Pro Thr Trp Tyr Trp Glu Asn
                245                 250                 255

Leu Leu Lys Ile Cys Val Phe Ile Phe Ala Phe Ile Met Pro Val Leu
            260                 265                 270

Ile Ile Thr Val Cys Tyr Gly Leu Met Ile Leu Arg Leu Lys Ser Val
        275                 280                 285

Arg Met Leu Ser Ile Lys Asn Val Tyr Ile Lys Ala Asp Lys Gln Lys
    290                 295                 300

Asn Gly Ile Lys Ala Asn Phe Lys Ile Arg His Asn Ile Glu Asp Gly
305                 310                 315                 320

Gly Val Gln Leu Ala Tyr His Tyr Gln Gln Asn Thr Pro Ile Gly Asp
                325                 330                 335

Gly Pro Val Leu Leu Pro Asp Asn His Tyr Leu Ser Val Gln Ser Lys
            340                 345                 350

Leu Ser Lys Asp Pro Asn Glu Lys Arg Asp His Met Val Leu Leu Glu
        355                 360                 365

Phe Val Thr Ala Ala Gly Ile Thr Leu Gly Met Asp Glu Leu Tyr Lys
    370                 375                 380

Gly Gly Thr Gly Gly Ser Met Val Ser Lys Gly Glu Glu Leu Phe Thr
385                 390                 395                 400

Gly Val Val Pro Ile Leu Val Glu Leu Asp Gly Asp Val Asn Gly His
                405                 410                 415

Lys Phe Ser Val Ser Gly Glu Gly Glu Gly Asp Ala Thr Tyr Gly Lys
            420                 425                 430

Leu Thr Leu Lys Phe Ile Cys Thr Thr Gly Lys Leu Pro Val Pro Trp
        435                 440                 445

Pro Thr Leu Val Thr Thr Leu Thr Tyr Gly Val Gln Cys Phe Ser Arg
    450                 455                 460

Tyr Pro Asp His Met Lys Gln His Asp Phe Phe Lys Ser Ala Met Pro
465                 470                 475                 480

Glu Gly Tyr Ile Gln Glu Arg Thr Ile Phe Phe Lys Asp Asp Gly Asn
                485                 490                 495

Tyr Lys Thr Arg Ala Glu Val Lys Phe Glu Gly Asp Thr Leu Val Asn
            500                 505                 510

Arg Ile Glu Leu Lys Gly Ile Asp Phe Lys Glu Asp Gly Asn Ile Leu
        515                 520                 525

Gly His Lys Leu Glu Tyr Asn Ile Ile Gly Ser Lys Glu Lys Asp Arg
```

```
    530                 535                 540

Asn Leu Arg Arg Ile Thr Arg Met Val Leu Val Val Val Ala Val Phe
545                 550                 555                 560

Ile Val Cys Trp Thr Pro Ile His Ile Tyr Val Ile Ile Lys Ala Leu
                565                 570                 575

Val Thr Ile Pro Glu Thr Thr Phe Gln Thr Val Ser Trp His Phe Cys
            580                 585                 590

Ile Ala Leu Gly Tyr Thr Asn Ser Cys Leu Asn Pro Val Leu Tyr Ala
        595                 600                 605

Phe Leu Asp Glu Asn Phe Lys Arg Cys Phe Arg Glu Phe Cys Ile Pro
    610                 615                 620

Thr Ser Ser Asn Ile Glu Gln Gln Asn Ser Thr Arg Ile Arg Gln Asn
625                 630                 635                 640

Thr Arg Asp His Pro Ser Thr Ala Asn Thr Val Asp Arg Thr Asn His
                645                 650                 655

Gln Leu Glu Asn Leu Glu Ala Glu Thr Ala Pro Leu Pro
            660                 665


<210> SEQ ID NO 25
<211> LENGTH: 1962
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25

atgaagacga tcatcgccct gagctacatc ttctgcctgg tgttcgccga ctacaaggac     60

gatgatgacg ccatgaggac tctgaacacc tctgccatgg acgggactgg gctggtggtg    120

gagagggact tctctgttcg tatcctcact gcctgtttcc tgtcgctgct catcctgtcc    180

acgctcctgg ggaacacgct ggtctgtgct gccgttatca ggttccgaca cctgcggtcc    240

aaggtgacca acttctttgt catctccttg gctgtgtcag atctcttggt ggccgtcctg    300

gtcatgccct ggaaggcagt ggctgagatt gctggcttct ggccctttgg gtccttctgt    360

aacatctggg tggcctttga catcatgtgc tccactgcat ccatcctcaa cctctgtgtg    420

atcagcgtgg acaggtattg ggctatctcc agccctgccc ggtatgagag aaagatgacc    480

cccaaggcag ccttcatcct gatcagtgtg gcatggacct tgtctgtact catctccttc    540

atcccagtgc agctcagctg gcacaaggca aaacccacaa gcccctctga tggaaatgcc    600

acttccctgg ctgagaccat agacaactgt gactccagcc tcagcaggac atatgccatc    660

tcatcctctg taatcagctt ttacatccct gtggccatca tgattgtcac ctacaccagg    720

atctacagga ttgctcagaa acaaatacgg cgcattgcgg ccttggagag ggcagcagtc    780

cacgccaaga attgctctcg gaacgtgtat atcaaggctg ataaacaaaa gaatggtatc    840

aaagctaatt tcaaaatccg ccacaatatc gaagatggcg gcgtccagct cgcttatcat    900

tatcagcaga atacacctat cggtgacggg ccggtgcttt tgcctgataa ccattacctg    960

agtgttcaaa gtaaactgag caaggatcca aatgaaaaaa gggaccacat ggtgcttctc   1020

gaatttgtaa cggctgcagg cattactctc gggatggacg aactttacaa aggagggacc   1080

ggaggcagca tggtgtccaa gggggaggaa cttttcactg gcgtcgtgcc gatactcgtc   1140

gaactcgatg gagatgttaa tggacacaaa ttttcagtca gtggcgaagg ggaaggggat   1200

gctacttacg ggaaactcac actgaagttt atttgtacga caggcaaact cccggtacct   1260
```

```
tggccgacct tggtgaccac gttgacgtat ggagtacagt gcttctccag gtacccggac   1320

cacatgaagc aacatgactt tttcaaaagc gctatgcccg agggctacat tcaagaacgg   1380

actattttct ttaaggacga tggaaactat aaaaccagag ctgaggtgaa attcgagggt   1440

gacactcttg taaaccggat agaactcaaa ggtatagatt tcaaagaaga cggaaacatc   1500

ttggggcata aactcgagta taatcctcct cagaccacca caggtaatgg aaagcctgtc   1560

gaatgttctc aaccggaaag ttctttttaag atgtccttca aaagagaaac taaagtcctg   1620

aagactctgt cggtgatcat gggtgtgttt gtgtgctgtt ggctaccttt cttcatcttg   1680

aactgcattt tgcccttctg tgggtctggg gagacgcagc ccttctgcat tgattccaac   1740

acctttgacg tgtttgtgtg gtttgggtgg gctaattcat ccttgaaccc catcatttat   1800

gcctttaatg ctgattttcg gaaggcattt tcaaccctct taggatgcta cagactttgc   1860

cctgcgacga ataatgccat agagacggtg agtatcaata acaatggggc cgcgatgttt   1920

tccagccatc atgagccatt ctgctacgag aatgaagtct ga                       1962


<210> SEQ ID NO 26
<211> LENGTH: 653
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (153)..(153)
<223> OTHER INFORMATION: Phe, Ala, Gly, Val, Ile, Leu, Met, Ser, or Thr

<400> SEQUENCE: 26

Met Lys Thr Ile Ile Ala Leu Ser Tyr Ile Phe Cys Leu Val Phe Ala
1               5                   10                  15

Asp Tyr Lys Asp Asp Asp Asp Ala Met Arg Thr Leu Asn Thr Ser Ala
            20                  25                  30

Met Asp Gly Thr Gly Leu Val Val Glu Arg Asp Phe Ser Val Arg Ile
        35                  40                  45

Leu Thr Ala Cys Phe Leu Ser Leu Leu Ile Leu Ser Thr Leu Leu Gly
    50                  55                  60

Asn Thr Leu Val Cys Ala Ala Val Ile Arg Phe Arg His Leu Arg Ser
65                  70                  75                  80

Lys Val Thr Asn Phe Phe Val Ile Ser Leu Ala Val Ser Asp Leu Leu
                85                  90                  95

Val Ala Val Leu Val Met Pro Trp Lys Ala Val Ala Glu Ile Ala Gly
            100                 105                 110

Phe Trp Pro Phe Gly Ser Phe Cys Asn Ile Trp Val Ala Phe Asp Ile
        115                 120                 125

Met Cys Ser Thr Ala Ser Ile Leu Asn Leu Cys Val Ile Ser Val Asp
    130                 135                 140

Arg Tyr Trp Ala Ile Ser Ser Pro Xaa Arg Tyr Glu Arg Lys Met Thr
145                 150                 155                 160

Pro Lys Ala Ala Phe Ile Leu Ile Ser Val Ala Trp Thr Leu Ser Val
                165                 170                 175

Leu Ile Ser Phe Ile Pro Val Gln Leu Ser Trp His Lys Ala Lys Pro
            180                 185                 190

Thr Ser Pro Ser Asp Gly Asn Ala Thr Ser Leu Ala Glu Thr Ile Asp
        195                 200                 205

Asn Cys Asp Ser Ser Leu Ser Arg Thr Tyr Ala Ile Ser Ser Ser Val
```

```
    210                 215                 220

Ile Ser Phe Tyr Ile Pro Val Ala Ile Met Ile Val Thr Tyr Thr Arg
225                 230                 235                 240

Ile Tyr Arg Ile Ala Gln Lys Gln Ile Arg Arg Ile Ala Ala Leu Glu
                245                 250                 255

Arg Ala Ala Val His Ala Lys Asn Cys Ser Arg Asn Val Tyr Ile Lys
            260                 265                 270

Ala Asp Lys Gln Lys Asn Gly Ile Lys Ala Asn Phe Lys Ile Arg His
        275                 280                 285

Asn Ile Glu Asp Gly Gly Val Gln Leu Ala Tyr His Tyr Gln Gln Asn
    290                 295                 300

Thr Pro Ile Gly Asp Gly Pro Val Leu Leu Pro Asp Asn His Tyr Leu
305                 310                 315                 320

Ser Val Gln Ser Lys Leu Ser Lys Asp Pro Asn Glu Lys Arg Asp His
                325                 330                 335

Met Val Leu Leu Glu Phe Val Thr Ala Ala Gly Ile Thr Leu Gly Met
            340                 345                 350

Asp Glu Leu Tyr Lys Gly Gly Thr Gly Gly Ser Met Val Ser Lys Gly
        355                 360                 365

Glu Glu Leu Phe Thr Gly Val Val Pro Ile Leu Val Glu Leu Asp Gly
    370                 375                 380

Asp Val Asn Gly His Lys Phe Ser Val Ser Gly Glu Gly Glu Gly Asp
385                 390                 395                 400

Ala Thr Tyr Gly Lys Leu Thr Leu Lys Phe Ile Cys Thr Thr Gly Lys
                405                 410                 415

Leu Pro Val Pro Trp Pro Thr Leu Val Thr Thr Leu Thr Tyr Gly Val
            420                 425                 430

Gln Cys Phe Ser Arg Tyr Pro Asp His Met Lys Gln His Asp Phe Phe
        435                 440                 445

Lys Ser Ala Met Pro Glu Gly Tyr Ile Gln Glu Arg Thr Ile Phe Phe
    450                 455                 460

Lys Asp Asp Gly Asn Tyr Lys Thr Arg Ala Glu Val Lys Phe Glu Gly
465                 470                 475                 480

Asp Thr Leu Val Asn Arg Ile Glu Leu Lys Gly Ile Asp Phe Lys Glu
                485                 490                 495

Asp Gly Asn Ile Leu Gly His Lys Leu Glu Tyr Asn Pro Pro Gln Thr
            500                 505                 510

Thr Thr Gly Asn Gly Lys Pro Val Glu Cys Ser Gln Pro Glu Ser Ser
        515                 520                 525

Phe Lys Met Ser Phe Lys Arg Glu Thr Lys Val Leu Lys Thr Leu Ser
    530                 535                 540

Val Ile Met Gly Val Phe Val Cys Cys Trp Leu Pro Phe Phe Ile Leu
545                 550                 555                 560

Asn Cys Ile Leu Pro Phe Cys Gly Ser Gly Glu Thr Gln Pro Phe Cys
                565                 570                 575

Ile Asp Ser Asn Thr Phe Asp Val Phe Val Trp Phe Gly Trp Ala Asn
            580                 585                 590

Ser Ser Leu Asn Pro Ile Ile Tyr Ala Phe Asn Ala Asp Phe Arg Lys
        595                 600                 605

Ala Phe Ser Thr Leu Leu Gly Cys Tyr Arg Leu Cys Pro Ala Thr Asn
    610                 615                 620

Asn Ala Ile Glu Thr Val Ser Ile Asn Asn Asn Gly Ala Ala Met Phe
625                 630                 635                 640
```

Ser Ser His His Glu Pro Phe Cys Tyr Glu Asn Glu Val
645 650

<210> SEQ ID NO 27
<211> LENGTH: 2223
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 27
atgaagacga tcatcgccct gagctacatc ttctgcctgg tgttcgccga ctacaaggac 60
gatgatgacg ccatggacat actttgtgaa gagaatactt cactctcttc tactactaac 120
tctcttatgc aactgaacga tgatacccga ttgtactcaa acgacttcaa ttccggcgaa 180
gcgaacacca gtgacgcatt caactggact gtcgattctg aaaacagaac taatctgtca 240
tgcgagggtt gtcttagtcc ctcttgtctc agcctgttgc acctccagga aaagaactgg 300
tcagcactgc tcactgcggt agtgataata ctcactattg ctggcaatat tctcgtaatt 360
atggcagtct ccttggagaa gaaactccaa aacgccacaa attattttct tatgagcctt 420
gccatcgcag atatgctctt gggatttttg gtgatgcctg tgagtatgct cacgatactg 480
tatggatatc gctggcctct gccgtctaaa ctttgcgctg tgtggattta cttggatgtc 540 ctttttttcaa ctgcgagtat tatgcatctt tgcgccatta gtcttgatag gtatgtggct 600
atccaaaatc ctgcccacca ttcccgcttt aatagtagaa ctaaggcttt tctgaaaata 660
atagcagtgt ggaccatatc tgtcggcata agcatgccta tccccgtatt tggacttcaa 720
gatgactcaa aggtattcaa agaagggtca tgtctgctgg ccgatgacaa tttcgtgctt 780
attggatcct tcgtcagttt cttcattcct ttgacaatca tggtgattac ctactttctt 840
acgattaaat ctttgcaaaa ggaggctact ctgtgcgtca gcgacctcgg cactcgggcc 900
aaatctcgga acgtctatat caaggccgac aagcagaaga acggcatcaa ggcgaacttc 960
aagatccgcc acaacatcga ggacggcggc gtgcagctcg cctaccacta ccagcagaac 1020
acccccatcg gcgacggccc cgtgctgctg cccgacaacc actacctgag cgtgcagtcc 1080
aaactttcga aagaccccaa cgagaagcgc gatcacatgg tcctgctgga gttcgtgacc 1140
gccgccggga tcactctcgg catggacgag ctgtacaagg gcggtaccgg agggagcatg 1200
gtgagcaagg gcgaggagct gttcaccggg gtggtgccca tcctggtcga gctggacggc 1260
gacgtaaacg gccacaagtt cagcgtgtcc ggcgagggtg agggcgatgc cacctacggc 1320
aagctgaccc tgaagttcat ctgcaccacc ggcaagctgc ccgtgccctg gcccaccctc 1380
gtgaccaccc tgacctacgg cgtgcagtgc ttcagccgct accccgacca catgaagcag 1440
cacgacttct tcaagtccgc catgcccgaa ggctacatcc aggagcgcac catcttcttc 1500
aaggacgacg gcaactacaa gacccgcgcc gaggtgaagt tcgagggcga caccctggtg 1560
aaccgcatcg agctgaaggg catcgacttc aaggaggacg gcaacatcct ggggcacaag 1620
ctggagtaca accttttcct tgccagcttc tcattccttc cccagtcctc tctttccagt 1680
gagaaacttt tccaacgatc catacatagg gagccgggta gttatacagg acggcggacg 1740
atgcaatcaa ttagtaatga gcaaaaggct tgtaaggtac tcggcatagt cttctttctg 1800
tttgtggtga tgtggtgtcc cttctttata acgaatatca tggcagtgat ctgcaaggaa 1860
tcatgcaatg aggatgtgat cggggcactt ctgaacgttt tcgtgtggat agggtatctg 1920

```
tcaagtgctg tgaacccact ggtctatacc ttgtttaata agacataccg ctcagccttt   1980

tcacggtata ttcaatgtca gtataaggaa aacaagaaac ctctgcaact tattcttgtg   2040

aacactatcc ctgccctggc ttataagtca tcacagttgc agatgggcca gaaaaaaaat   2100

tccaagcagg acgcgaagac aacagacaac gattgtagta tggttgccct cggcaagcag   2160

cacagtgaag aagcgagcaa agacaatagt gatggcgtaa acgaaaaagt cagttgtgta   2220

taa                                                                 2223


<210> SEQ ID NO 28
<211> LENGTH: 740
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (205)..(205)
<223> OTHER INFORMATION: Phe, Ala, Gly, Val, Ile, Leu, Met, Ser, or Thr

<400> SEQUENCE: 28

Met Lys Thr Ile Ile Ala Leu Ser Tyr Ile Phe Cys Leu Val Phe Ala
1               5                   10                  15

Asp Tyr Lys Asp Asp Asp Asp Ala Met Asp Ile Leu Cys Glu Glu Asn
            20                  25                  30

Thr Ser Leu Ser Ser Thr Thr Asn Ser Leu Met Gln Leu Asn Asp Asp
        35                  40                  45

Thr Arg Leu Tyr Ser Asn Asp Phe Asn Ser Gly Glu Ala Asn Thr Ser
    50                  55                  60

Asp Ala Phe Asn Trp Thr Val Asp Ser Glu Asn Arg Thr Asn Leu Ser
65                  70                  75                  80

Cys Glu Gly Cys Leu Ser Pro Ser Cys Leu Ser Leu Leu His Leu Gln
                85                  90                  95

Glu Lys Asn Trp Ser Ala Leu Leu Thr Ala Val Val Ile Ile Leu Thr
            100                 105                 110

Ile Ala Gly Asn Ile Leu Val Ile Met Ala Val Ser Leu Glu Lys Lys
        115                 120                 125

Leu Gln Asn Ala Thr Asn Tyr Phe Leu Met Ser Leu Ala Ile Ala Asp
    130                 135                 140

Met Leu Leu Gly Phe Leu Val Met Pro Val Ser Met Leu Thr Ile Leu
145                 150                 155                 160

Tyr Gly Tyr Arg Trp Pro Leu Pro Ser Lys Leu Cys Ala Val Trp Ile
                165                 170                 175

Tyr Leu Asp Val Leu Phe Ser Thr Ala Ser Ile Met His Leu Cys Ala
            180                 185                 190

Ile Ser Leu Asp Arg Tyr Val Ala Ile Gln Asn Pro Xaa His His Ser
        195                 200                 205

Arg Phe Asn Ser Arg Thr Lys Ala Phe Leu Lys Ile Ile Ala Val Trp
    210                 215                 220

Thr Ile Ser Val Gly Ile Ser Met Pro Ile Pro Val Phe Gly Leu Gln
225                 230                 235                 240

Asp Asp Ser Lys Val Phe Lys Glu Gly Ser Cys Leu Leu Ala Asp Asp
                245                 250                 255

Asn Phe Val Leu Ile Gly Ser Phe Val Ser Phe Phe Ile Pro Leu Thr
            260                 265                 270

Ile Met Val Ile Thr Tyr Phe Leu Thr Ile Lys Ser Leu Gln Lys Glu
```

```
        275                 280                 285

Ala Thr Leu Cys Val Ser Asp Leu Gly Thr Arg Ala Lys Ser Arg Asn
    290                 295                 300

Val Tyr Ile Lys Ala Asp Lys Gln Lys Asn Gly Ile Lys Ala Asn Phe
305                 310                 315                 320

Lys Ile Arg His Asn Ile Glu Asp Gly Gly Val Gln Leu Ala Tyr His
                325                 330                 335

Tyr Gln Gln Asn Thr Pro Ile Gly Asp Gly Pro Val Leu Leu Pro Asp
            340                 345                 350

Asn His Tyr Leu Ser Val Gln Ser Lys Leu Ser Lys Asp Pro Asn Glu
        355                 360                 365

Lys Arg Asp His Met Val Leu Leu Glu Phe Val Thr Ala Ala Gly Ile
    370                 375                 380

Thr Leu Gly Met Asp Glu Leu Tyr Lys Gly Gly Thr Gly Gly Ser Met
385                 390                 395                 400

Val Ser Lys Gly Glu Glu Leu Phe Thr Gly Val Val Pro Ile Leu Val
                405                 410                 415

Glu Leu Asp Gly Asp Val Asn Gly His Lys Phe Ser Val Ser Gly Glu
            420                 425                 430

Gly Glu Gly Asp Ala Thr Tyr Gly Lys Leu Thr Leu Lys Phe Ile Cys
        435                 440                 445

Thr Thr Gly Lys Leu Pro Val Pro Trp Pro Thr Leu Val Thr Thr Leu
    450                 455                 460

Thr Tyr Gly Val Gln Cys Phe Ser Arg Tyr Pro Asp His Met Lys Gln
465                 470                 475                 480

His Asp Phe Phe Lys Ser Ala Met Pro Glu Gly Tyr Ile Gln Glu Arg
                485                 490                 495

Thr Ile Phe Phe Lys Asp Asp Gly Asn Tyr Lys Thr Arg Ala Glu Val
            500                 505                 510

Lys Phe Glu Gly Asp Thr Leu Val Asn Arg Ile Glu Leu Lys Gly Ile
        515                 520                 525

Asp Phe Lys Glu Asp Gly Asn Ile Leu Gly His Lys Leu Glu Tyr Asn
    530                 535                 540

Leu Phe Leu Ala Ser Phe Ser Phe Leu Pro Gln Ser Ser Leu Ser Ser
545                 550                 555                 560

Glu Lys Leu Phe Gln Arg Ser Ile His Arg Glu Pro Gly Ser Tyr Thr
                565                 570                 575

Gly Arg Arg Thr Met Gln Ser Ile Ser Asn Glu Gln Lys Ala Cys Lys
            580                 585                 590

Val Leu Gly Ile Val Phe Phe Leu Phe Val Val Met Trp Cys Pro Phe
        595                 600                 605

Phe Ile Thr Asn Ile Met Ala Val Ile Cys Lys Glu Ser Cys Asn Glu
    610                 615                 620

Asp Val Ile Gly Ala Leu Leu Asn Val Phe Val Trp Ile Gly Tyr Leu
625                 630                 635                 640

Ser Ser Ala Val Asn Pro Leu Val Tyr Thr Leu Phe Asn Lys Thr Tyr
                645                 650                 655

Arg Ser Ala Phe Ser Arg Tyr Ile Gln Cys Gln Tyr Lys Glu Asn Lys
            660                 665                 670

Lys Pro Leu Gln Leu Ile Leu Val Asn Thr Ile Pro Ala Leu Ala Tyr
        675                 680                 685

Lys Ser Ser Gln Leu Gln Met Gly Gln Lys Lys Asn Ser Lys Gln Asp
    690                 695                 700
```

Ala Lys Thr Thr Asp Asn Asp Cys Ser Met Val Ala Leu Gly Lys Gln
705 710 715 720

His Ser Glu Glu Ala Ser Lys Asp Asn Ser Asp Gly Val Asn Glu Lys
725 730 735

Val Ser Cys Val
740

<210> SEQ ID NO 29
<211> LENGTH: 612
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 29
aacgtctata tcaaggccga caagcagaag aacggcatca aggcgaactt caagatccgc 60
cacaacatcg aggacggcgg cgtgcagctc gcctaccact accagcagaa cacccccatc 120
ggcgacggcc ccgtgctgct gcccgacaac cactacctga gcgtgcagtc caaactttcg 180
aaagacccca acgagaagcg cgatcacatg gtcctgctgg agttcgtgac cgccgccggg 240
atcactctcg gcatggacga gctgtacaag ggcggtaccg gagggagcat ggtgagcaag 300
ggcgaggagc tgttcaccgg ggtggtgccc atcctggtcg agctggacgg cgacgtaaac 360
ggccacaagt tcagcgtgtc cggcgagggt gagggcgatg ccacctacgg caagctgacc 420
ctgaagttca tctgcaccac cggcaagctg cccgtgccct ggcccaccct cgtgaccacc 480
ctgacctacg gcgtgcagtg cttcagccgc taccccgacc acatgaagca gcacgacttc 540
ttcaagtccg ccatgcccga aggctacatc caggagcgca ccatcttctt caaggacgac 600
ggcaactaca as 612

<210> SEQ ID NO 30
<211> LENGTH: 662
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (129)..(129)
<223> OTHER INFORMATION: Phe, Ala, Gly, Val, Ile, Leu, Met, Ser, or Thr
<220> FEATURE:
<221> NAME/KEY: MOD_RES
<222> LOCATION: (648)..(648)
<223> OTHER INFORMATION: Leu or Met

<400> SEQUENCE: 30

Met Arg Thr Leu Asn Thr Ser Ala Met Asp Gly Thr Gly Leu Val Val
1 5 10 15

Glu Arg Asp Phe Ser Val Arg Ile Leu Thr Ala Cys Phe Leu Ser Leu
20 25 30

Leu Ile Leu Ser Thr Leu Leu Gly Asn Thr Leu Val Cys Ala Ala Val
35 40 45

Ile Arg Phe Arg His Leu Arg Ser Lys Val Thr Asn Phe Phe Val Ile
50 55 60

Ser Leu Ala Val Ser Asp Leu Leu Val Ala Val Leu Val Met Pro Trp
65 70 75 80

Lys Ala Val Ala Glu Ile Ala Gly Phe Trp Pro Phe Gly Ser Phe Cys
85 90 95

```
Asn Ile Trp Val Ala Phe Asp Ile Met Cys Ser Thr Ala Ser Ile Leu
            100                 105                 110

Asn Leu Cys Val Ile Ser Val Asp Arg Tyr Trp Ala Ile Ser Ser Pro
        115                 120                 125

Xaa Arg Tyr Glu Arg Lys Met Thr Pro Lys Ala Ala Phe Ile Leu Ile
    130                 135                 140

Ser Val Ala Trp Thr Leu Ser Val Leu Ile Ser Phe Ile Pro Val Gln
145                 150                 155                 160

Leu Ser Trp His Lys Ala Lys Pro Thr Ser Pro Ser Asp Gly Asn Ala
                165                 170                 175

Thr Ser Leu Ala Glu Thr Ile Asp Asn Cys Asp Ser Ser Leu Ser Arg
            180                 185                 190

Thr Tyr Ala Ile Ser Ser Ser Val Ile Ser Phe Tyr Ile Pro Val Ala
        195                 200                 205

Ile Met Ile Val Thr Tyr Thr Arg Ile Tyr Arg Ile Ala Gln Lys Gln
    210                 215                 220

Leu Gln Lys Ile Asp Leu Ser Ser Leu Ile Asn Val Tyr Ile Lys Ala
225                 230                 235                 240

Asp Lys Gln Lys Asn Gly Ile Lys Ala Asn Phe Lys Ile Arg His Asn
                245                 250                 255

Ile Glu Asp Gly Gly Val Gln Leu Ala Tyr His Tyr Gln Gln Asn Thr
            260                 265                 270

Pro Ile Gly Asp Gly Pro Val Leu Leu Pro Asp Asn His Tyr Leu Ser
        275                 280                 285

Val Gln Ser Lys Leu Ser Lys Asp Pro Asn Glu Lys Arg Asp His Met
    290                 295                 300

Val Leu Leu Glu Phe Val Thr Ala Ala Gly Ile Thr Leu Gly Met Asp
305                 310                 315                 320

Glu Leu Tyr Lys Gly Gly Thr Gly Gly Ser Met Val Ser Lys Gly Glu
                325                 330                 335

Glu Leu Phe Thr Gly Val Val Pro Ile Leu Val Glu Leu Asp Gly Asp
            340                 345                 350

Val Asn Gly His Lys Phe Ser Val Ser Gly Glu Gly Glu Gly Asp Ala
        355                 360                 365

Thr Tyr Gly Lys Leu Thr Leu Lys Phe Ile Cys Thr Thr Gly Lys Leu
    370                 375                 380

Pro Val Pro Trp Pro Thr Leu Val Thr Thr Leu Thr Tyr Gly Val Gln
385                 390                 395                 400

Cys Phe Ser Arg Tyr Pro Asp His Met Lys Gln His Asp Phe Phe Lys
                405                 410                 415

Ser Ala Met Pro Glu Gly Tyr Ile Gln Glu Arg Thr Ile Phe Phe Lys
            420                 425                 430

Asp Asp Gly Asn Tyr Lys Thr Arg Ala Glu Val Lys Phe Glu Gly Asp
        435                 440                 445

Thr Leu Val Asn Arg Ile Glu Leu Lys Gly Ile Asp Phe Lys Glu Asp
    450                 455                 460

Gly Asn Ile Leu Gly His Lys Leu Glu Tyr Asn Asn His Asp Gln Leu
465                 470                 475                 480

Lys Arg Glu Thr Lys Val Leu Lys Thr Leu Ser Val Ile Met Gly Val
                485                 490                 495

Phe Val Cys Cys Trp Leu Pro Phe Phe Ile Leu Asn Cys Ile Leu Pro
            500                 505                 510
```

```
Phe Cys Gly Ser Gly Glu Thr Gln Pro Phe Cys Ile Asp Ser Asn Thr
        515                 520                 525

Phe Asp Val Phe Val Trp Phe Gly Trp Ala Asn Ser Ser Leu Asn Pro
    530                 535                 540

Ile Ile Tyr Ala Phe Asn Ala Asp Phe Arg Lys Ala Phe Ser Thr Leu
545                 550                 555                 560

Leu Gly Cys Tyr Arg Leu Cys Pro Ala Thr Asn Asn Ala Ile Glu Thr
                565                 570                 575

Val Ser Ile Asn Asn Asn Gly Ala Ala Met Phe Ser Ser His His Glu
            580                 585                 590

Pro Arg Gly Ser Ile Ser Lys Glu Cys Asn Leu Val Tyr Leu Ile Pro
        595                 600                 605

His Ala Val Gly Ser Ser Glu Asp Leu Lys Lys Glu Glu Ala Ala Gly
    610                 615                 620

Ile Ala Arg Pro Leu Glu Lys Leu Ser Pro Ala Leu Ser Val Ile Leu
625                 630                 635                 640

Asp Tyr Asp Thr Asp Val Ser Xaa Glu Lys Ile Gln Pro Ile Thr Gln
                645                 650                 655

Asn Gly Gln His Pro Thr
            660


<210> SEQ ID NO 31
<211> LENGTH: 670
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (164)..(164)
<223> OTHER INFORMATION: Phe, Ala, Gly, Val, Ile, Leu, Met, Ser, or Thr

<400> SEQUENCE: 31

Met Gly Ala Gly Val Leu Val Leu Gly Ala Ser Glu Pro Gly Asn Leu
1               5                   10                  15

Ser Ser Ala Ala Pro Leu Pro Asp Gly Ala Ala Thr Ala Ala Arg Leu
            20                  25                  30

Leu Val Pro Ala Ser Pro Pro Ala Ser Leu Leu Pro Pro Ala Ser Glu
        35                  40                  45

Ser Pro Glu Pro Leu Ser Gln Gln Trp Thr Ala Gly Met Gly Leu Leu
    50                  55                  60

Met Ala Leu Ile Val Leu Leu Ile Val Ala Gly Asn Val Leu Val Ile
65                  70                  75                  80

Val Ala Ile Ala Lys Thr Pro Arg Leu Gln Thr Leu Thr Asn Leu Phe
                85                  90                  95

Ile Met Ser Leu Ala Ser Ala Asp Leu Val Met Gly Leu Leu Val Val
            100                 105                 110

Pro Phe Gly Ala Thr Ile Val Val Trp Gly Arg Trp Glu Tyr Gly Ser
        115                 120                 125

Phe Phe Cys Glu Leu Trp Thr Ser Val Asp Val Leu Cys Val Thr Ala
    130                 135                 140

Ser Ile Glu Thr Leu Cys Val Ile Ala Leu Asp Arg Tyr Leu Ala Ile
145                 150                 155                 160

Thr Ser Pro Xaa Arg Tyr Gln Ser Leu Leu Thr Arg Ala Arg Ala Arg
                165                 170                 175

Gly Leu Val Cys Thr Val Trp Ala Ile Ser Ala Leu Val Ser Phe Leu
```

```
            180                 185                 190

Pro Ile Leu Met His Trp Trp Arg Ala Glu Ser Asp Glu Ala Arg Arg
        195                 200                 205

Cys Tyr Asn Asp Pro Lys Cys Cys Asp Phe Val Thr Asn Arg Ala Tyr
    210                 215                 220

Ala Ile Ala Ser Ser Val Val Ser Phe Tyr Val Pro Leu Cys Ile Met
225                 230                 235                 240

Ala Phe Val Tyr Leu Arg Val Phe Arg Glu Ala Gln Lys Gln Leu Gln
                245                 250                 255

Lys Ile Asp Leu Ser Ser Leu Ile Asn Val Tyr Ile Lys Ala Asp Lys
            260                 265                 270

Gln Lys Asn Gly Ile Lys Ala Asn Phe Lys Ile Arg His Asn Ile Glu
        275                 280                 285

Asp Gly Gly Val Gln Leu Ala Tyr His Tyr Gln Gln Asn Thr Pro Ile
    290                 295                 300

Gly Asp Gly Pro Val Leu Leu Pro Asp Asn His Tyr Leu Ser Val Gln
305                 310                 315                 320

Ser Lys Leu Ser Lys Asp Pro Asn Glu Lys Arg Asp His Met Val Leu
                325                 330                 335

Leu Glu Phe Val Thr Ala Ala Gly Ile Thr Leu Gly Met Asp Glu Leu
            340                 345                 350

Tyr Lys Gly Gly Thr Gly Gly Ser Met Val Ser Lys Gly Glu Glu Leu
        355                 360                 365

Phe Thr Gly Val Val Pro Ile Leu Val Glu Leu Asp Gly Asp Val Asn
    370                 375                 380

Gly His Lys Phe Ser Val Ser Gly Glu Gly Glu Gly Asp Ala Thr Tyr
385                 390                 395                 400

Gly Lys Leu Thr Leu Lys Phe Ile Cys Thr Thr Gly Lys Leu Pro Val
                405                 410                 415

Pro Trp Pro Thr Leu Val Thr Thr Leu Thr Tyr Gly Val Gln Cys Phe
            420                 425                 430

Ser Arg Tyr Pro Asp His Met Lys Gln His Asp Phe Phe Lys Ser Ala
        435                 440                 445

Met Pro Glu Gly Tyr Ile Gln Glu Arg Thr Ile Phe Phe Lys Asp Asp
    450                 455                 460

Gly Asn Tyr Lys Thr Arg Ala Glu Val Lys Phe Glu Gly Asp Thr Leu
465                 470                 475                 480

Val Asn Arg Ile Glu Leu Lys Gly Ile Asp Phe Lys Glu Asp Gly Asn
                485                 490                 495

Ile Leu Gly His Lys Leu Glu Tyr Asn Asn His Asp Gln Leu Arg Glu
            500                 505                 510

Gln Lys Ala Leu Lys Thr Leu Gly Ile Ile Met Gly Val Phe Thr Leu
        515                 520                 525

Cys Trp Leu Pro Phe Phe Leu Ala Asn Val Val Lys Ala Phe His Arg
    530                 535                 540

Glu Leu Val Pro Asp Arg Leu Phe Val Phe Phe Asn Trp Leu Gly Tyr
545                 550                 555                 560

Ala Asn Ser Ala Phe Asn Pro Ile Ile Tyr Cys Arg Ser Pro Asp Phe
                565                 570                 575

Arg Lys Ala Phe Gln Gly Leu Leu Cys Cys Ala Arg Arg Ala Ala Arg
            580                 585                 590

Arg Arg His Ala Thr His Gly Asp Arg Pro Arg Ala Ser Gly Cys Leu
        595                 600                 605
```

```
Ala Arg Pro Gly Pro Pro Pro Ser Pro Gly Ala Ala Ser Asp Asp Asp
    610                 615                 620

Asp Asp Asp Val Val Gly Ala Thr Pro Pro Ala Arg Leu Leu Glu Pro
625                 630                 635                 640

Trp Ala Gly Cys Asn Gly Gly Ala Ala Ala Asp Ser Asp Ser Ser Leu
                645                 650                 655

Asp Glu Pro Cys Arg Pro Gly Phe Ala Ser Glu Ser Lys Val
            660                 665                 670


<210> SEQ ID NO 32
<211> LENGTH: 629
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (139)..(139)
<223> OTHER INFORMATION: Phe, Ala, Gly, Val, Ile, Leu, Met, Ser, or Thr

<400> SEQUENCE: 32

Met Gly Gln Pro Gly Asn Gly Ser Ala Phe Leu Leu Ala Pro Asn Arg
1               5                   10                  15

Ser His Ala Pro Asp His Asp Val Thr Gln Gln Arg Asp Glu Val Trp
            20                  25                  30

Val Val Gly Met Gly Ile Val Met Ser Leu Ile Val Leu Ala Ile Val
        35                  40                  45

Phe Gly Asn Val Leu Val Ile Thr Ala Ile Ala Lys Phe Glu Arg Leu
    50                  55                  60

Gln Thr Val Thr Asn Tyr Phe Ile Thr Ser Leu Ala Cys Ala Asp Leu
65                  70                  75                  80

Val Met Gly Leu Ala Val Val Pro Phe Gly Ala Ala His Ile Leu Met
                85                  90                  95

Lys Met Trp Thr Phe Gly Asn Phe Trp Cys Glu Phe Trp Thr Ser Ile
            100                 105                 110

Asp Val Leu Cys Val Thr Ala Ser Ile Glu Thr Leu Cys Val Ile Ala
        115                 120                 125

Val Asp Arg Tyr Phe Ala Ile Thr Ser Pro Xaa Lys Tyr Gln Ser Leu
    130                 135                 140

Leu Thr Lys Asn Lys Ala Arg Val Ile Ile Leu Met Val Trp Ile Val
145                 150                 155                 160

Ser Gly Leu Thr Ser Phe Leu Pro Ile Gln Met His Trp Tyr Arg Ala
                165                 170                 175

Thr His Gln Glu Ala Ile Asn Cys Tyr Ala Asn Glu Thr Cys Cys Asp
            180                 185                 190

Phe Phe Thr Asn Gln Ala Tyr Ala Ile Ala Ser Ser Ile Val Ser Phe
        195                 200                 205

Tyr Val Pro Leu Val Ile Met Val Phe Val Tyr Ser Arg Val Phe Gln
    210                 215                 220

Glu Ala Lys Arg Gln Leu Gln Lys Ile Asp Leu Ser Ser Leu Ile Asn
225                 230                 235                 240

Val Tyr Ile Lys Ala Asp Lys Gln Lys Asn Gly Ile Lys Ala Asn Phe
                245                 250                 255

Lys Ile Arg His Asn Ile Glu Asp Gly Gly Val Gln Leu Ala Tyr His
            260                 265                 270
```

```
Tyr Gln Gln Asn Thr Pro Ile Gly Asp Gly Pro Val Leu Leu Pro Asp
        275                 280                 285

Asn His Tyr Leu Ser Val Gln Ser Lys Leu Ser Lys Asp Pro Asn Glu
    290                 295                 300

Lys Arg Asp His Met Val Leu Leu Glu Phe Val Thr Ala Ala Gly Ile
305                 310                 315                 320

Thr Leu Gly Met Asp Glu Leu Tyr Lys Gly Gly Thr Gly Gly Ser Met
                325                 330                 335

Val Ser Lys Gly Glu Glu Leu Phe Thr Gly Val Val Pro Ile Leu Val
            340                 345                 350

Glu Leu Asp Gly Asp Val Asn Gly His Lys Phe Ser Val Ser Gly Glu
        355                 360                 365

Gly Glu Gly Asp Ala Thr Tyr Gly Lys Leu Thr Leu Lys Phe Ile Cys
    370                 375                 380

Thr Thr Gly Lys Leu Pro Val Pro Trp Pro Thr Leu Val Thr Thr Leu
385                 390                 395                 400

Thr Tyr Gly Val Gln Cys Phe Ser Arg Tyr Pro Asp His Met Lys Gln
                405                 410                 415

His Asp Phe Phe Lys Ser Ala Met Pro Glu Gly Tyr Ile Gln Glu Arg
            420                 425                 430

Thr Ile Phe Phe Lys Asp Asp Gly Asn Tyr Lys Thr Arg Ala Glu Val
        435                 440                 445

Lys Phe Glu Gly Asp Thr Leu Val Asn Arg Ile Glu Leu Lys Gly Ile
    450                 455                 460

Asp Phe Lys Glu Asp Gly Asn Ile Leu Gly His Lys Leu Glu Tyr Asn
465                 470                 475                 480

Asn His Asp Gln Leu Lys Glu His Lys Ala Leu Lys Thr Leu Gly Ile
                485                 490                 495

Ile Met Gly Thr Phe Thr Leu Cys Trp Leu Pro Phe Phe Ile Val Asn
            500                 505                 510

Ile Val His Val Ile Gln Asp Asn Leu Ile Arg Lys Glu Val Tyr Ile
        515                 520                 525

Leu Leu Asn Trp Ile Gly Tyr Val Asn Ser Gly Phe Asn Pro Leu Ile
    530                 535                 540

Tyr Cys Arg Ser Pro Asp Phe Arg Ile Ala Phe Gln Glu Leu Leu Cys
545                 550                 555                 560

Leu Arg Arg Ser Arg Tyr Pro Asn Val Arg Pro Asn Asn Gly Tyr Ile
                565                 570                 575

Tyr Asn Ala His Ser Trp Gln Ser Glu Asn Arg Glu Gln Ser Lys Gly
            580                 585                 590

Ser Ser Gly Asp Ser Asp His Ala Glu Gly Asn Leu Ala Lys Glu Glu
        595                 600                 605

Cys Leu Ser Ala Asp Lys Thr Asp Ser Asn Gly Asn Cys Ser Lys Ala
    610                 615                 620

Gln Met Arg Val Leu
625
```

<210> SEQ ID NO 33
<211> LENGTH: 675
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES

```
<222> LOCATION: (181)..(181)
<223> OTHER INFORMATION: Phe, Ala, Gly, Val, Ile, Leu, Met, Ser, or Thr

<400> SEQUENCE: 33

Met Asp Ile Leu Cys Glu Glu Asn Thr Ser Leu Ser Ser Thr Thr Asn
1               5                   10                  15

Ser Leu Met Gln Leu Asn Asp Asp Thr Arg Leu Tyr Ser Asn Asp Phe
            20                  25                  30

Asn Ser Gly Glu Ala Asn Thr Ser Asp Ala Phe Asn Trp Thr Val Asp
        35                  40                  45

Ser Glu Asn Arg Thr Asn Leu Ser Cys Glu Gly Cys Leu Ser Pro Ser
    50                  55                  60

Cys Leu Ser Leu Leu His Leu Gln Glu Lys Asn Trp Ser Ala Leu Leu
65                  70                  75                  80

Thr Ala Val Val Ile Ile Leu Thr Ile Ala Gly Asn Ile Leu Val Ile
                85                  90                  95

Met Ala Val Ser Leu Glu Lys Lys Leu Gln Asn Ala Thr Asn Tyr Phe
            100                 105                 110

Leu Met Ser Leu Ala Ile Ala Asp Met Leu Leu Gly Phe Leu Val Met
        115                 120                 125

Pro Val Ser Met Leu Thr Ile Leu Tyr Gly Tyr Arg Trp Pro Leu Pro
    130                 135                 140

Ser Lys Leu Cys Ala Val Trp Ile Tyr Leu Asp Val Leu Phe Ser Thr
145                 150                 155                 160

Ala Ser Ile Met His Leu Cys Ala Ile Ser Leu Asp Arg Tyr Val Ala
                165                 170                 175

Ile Gln Asn Pro Xaa His His Ser Arg Phe Asn Ser Arg Thr Lys Ala
            180                 185                 190

Phe Leu Lys Ile Ile Ala Val Trp Thr Ile Ser Val Gly Ile Ser Met
        195                 200                 205

Pro Ile Pro Val Phe Gly Leu Gln Asp Asp Ser Lys Val Phe Lys Glu
    210                 215                 220

Gly Ser Cys Leu Leu Ala Asp Asp Asn Phe Val Leu Ile Gly Ser Phe
225                 230                 235                 240

Val Ser Phe Phe Ile Pro Leu Thr Ile Met Val Ile Thr Tyr Phe Leu
                245                 250                 255

Thr Ile Lys Ser Leu Gln Lys Gln Leu Gln Lys Ile Asp Leu Ser Ser
            260                 265                 270

Leu Ile Asn Val Tyr Ile Lys Ala Asp Lys Gln Lys Asn Gly Ile Lys
        275                 280                 285

Ala Asn Phe Lys Ile Arg His Asn Ile Glu Asp Gly Gly Val Gln Leu
    290                 295                 300

Ala Tyr His Tyr Gln Gln Asn Thr Pro Ile Gly Asp Gly Pro Val Leu
305                 310                 315                 320

Leu Pro Asp Asn His Tyr Leu Ser Val Gln Ser Lys Leu Ser Lys Asp
                325                 330                 335

Pro Asn Glu Lys Arg Asp His Met Val Leu Leu Glu Phe Val Thr Ala
            340                 345                 350

Ala Gly Ile Thr Leu Gly Met Asp Glu Leu Tyr Lys Gly Gly Thr Gly
        355                 360                 365

Gly Ser Met Val Ser Lys Gly Glu Glu Leu Phe Thr Gly Val Val Pro
    370                 375                 380

Ile Leu Val Glu Leu Asp Gly Asp Val Asn Gly His Lys Phe Ser Val
385                 390                 395                 400
```

```
Ser Gly Glu Gly Glu Gly Asp Ala Thr Tyr Gly Lys Leu Thr Leu Lys
                405                 410                 415

Phe Ile Cys Thr Thr Gly Lys Leu Pro Val Pro Trp Pro Thr Leu Val
            420                 425                 430

Thr Thr Leu Thr Tyr Gly Val Gln Cys Phe Ser Arg Tyr Pro Asp His
        435                 440                 445

Met Lys Gln His Asp Phe Phe Lys Ser Ala Met Pro Glu Gly Tyr Ile
    450                 455                 460

Gln Glu Arg Thr Ile Phe Phe Lys Asp Asp Gly Asn Tyr Lys Thr Arg
465                 470                 475                 480

Ala Glu Val Lys Phe Glu Gly Asp Thr Leu Val Asn Arg Ile Glu Leu
                485                 490                 495

Lys Gly Ile Asp Phe Lys Glu Asp Gly Asn Ile Leu Gly His Lys Leu
            500                 505                 510

Glu Tyr Asn Asn His Asp Gln Leu Asn Glu Gln Lys Ala Cys Lys Val
        515                 520                 525

Leu Gly Ile Val Phe Phe Leu Phe Val Val Met Trp Cys Pro Phe Phe
    530                 535                 540

Ile Thr Asn Ile Met Ala Val Ile Cys Lys Glu Ser Cys Asn Glu Asp
545                 550                 555                 560

Val Ile Gly Ala Leu Leu Asn Val Phe Val Trp Ile Gly Tyr Leu Ser
                565                 570                 575

Ser Ala Val Asn Pro Leu Val Tyr Thr Leu Phe Asn Lys Thr Tyr Arg
            580                 585                 590

Ser Ala Phe Ser Arg Tyr Ile Gln Cys Gln Tyr Lys Glu Asn Lys Lys
        595                 600                 605

Pro Leu Gln Leu Ile Leu Val Asn Thr Ile Pro Ala Leu Ala Tyr Lys
    610                 615                 620

Ser Ser Gln Leu Gln Met Gly Gln Lys Lys Asn Ser Lys Gln Asp Ala
625                 630                 635                 640

Lys Thr Thr Asp Asn Asp Cys Ser Met Val Ala Leu Gly Lys Gln His
                645                 650                 655

Ser Glu Glu Ala Ser Lys Asp Asn Ser Asp Gly Val Asn Glu Lys Val
            660                 665                 670

Ser Cys Val
        675


<210> SEQ ID NO 34
<211> LENGTH: 649
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (110)..(110)
<223> OTHER INFORMATION: Phe, Ala, Gly, Val, Ile, Leu, Met, Ser, or Thr

<400> SEQUENCE: 34

Met Pro Ile Met Gly Ser Ser Val Tyr Ile Thr Val Glu Leu Ala Ile
1               5                   10                  15

Ala Val Leu Ala Ile Leu Gly Asn Val Leu Val Cys Trp Ala Val Trp
            20                  25                  30

Leu Asn Ser Asn Leu Gln Asn Val Thr Asn Tyr Phe Val Val Ser Leu
        35                  40                  45
```

```
Ala Ala Ala Asp Ile Ala Val Gly Val Leu Ala Ile Pro Phe Ala Ile
    50                  55                  60

Thr Ile Ser Thr Gly Phe Cys Ala Ala Cys His Gly Cys Leu Phe Ile
65                  70                  75                  80

Ala Cys Phe Val Leu Val Leu Thr Gln Ser Ser Ile Phe Ser Leu Leu
                85                  90                  95

Ala Ile Ala Ile Asp Arg Tyr Ile Ala Ile Arg Ile Pro Xaa Arg Tyr
            100                 105                 110

Asn Gly Leu Val Thr Gly Thr Arg Ala Lys Gly Ile Ile Ala Ile Cys
        115                 120                 125

Trp Val Leu Ser Phe Ala Ile Gly Leu Thr Pro Met Leu Gly Trp Asn
    130                 135                 140

Asn Cys Gly Gln Pro Lys Glu Gly Lys Asn His Ser Gln Gly Cys Gly
145                 150                 155                 160

Glu Gly Gln Val Ala Cys Leu Phe Glu Asp Val Val Pro Met Asn Tyr
                165                 170                 175

Met Val Tyr Phe Asn Phe Phe Ala Cys Val Leu Val Pro Leu Leu Leu
            180                 185                 190

Met Leu Gly Val Tyr Leu Arg Ile Phe Leu Ala Ala Arg Arg Gln Leu
        195                 200                 205

Gln Lys Ile Asp Leu Ser Ser Leu Ile Asn Val Tyr Ile Lys Ala Asp
    210                 215                 220

Lys Gln Lys Asn Gly Ile Lys Ala Asn Phe Lys Ile Arg His Asn Ile
225                 230                 235                 240

Glu Asp Gly Gly Val Gln Leu Ala Tyr His Tyr Gln Gln Asn Thr Pro
                245                 250                 255

Ile Gly Asp Gly Pro Val Leu Leu Pro Asp Asn His Tyr Leu Ser Val
            260                 265                 270

Gln Ser Lys Leu Ser Lys Asp Pro Asn Glu Lys Arg Asp His Met Val
        275                 280                 285

Leu Leu Glu Phe Val Thr Ala Ala Gly Ile Thr Leu Gly Met Asp Glu
    290                 295                 300

Leu Tyr Lys Gly Gly Thr Gly Gly Ser Met Val Ser Lys Gly Glu Glu
305                 310                 315                 320

Leu Phe Thr Gly Val Val Pro Ile Leu Val Glu Leu Asp Gly Asp Val
                325                 330                 335

Asn Gly His Lys Phe Ser Val Ser Gly Glu Gly Glu Gly Asp Ala Thr
            340                 345                 350

Tyr Gly Lys Leu Thr Leu Lys Phe Ile Cys Thr Thr Gly Lys Leu Pro
        355                 360                 365

Val Pro Trp Pro Thr Leu Val Thr Thr Leu Thr Tyr Gly Val Gln Cys
    370                 375                 380

Phe Ser Arg Tyr Pro Asp His Met Lys Gln His Asp Phe Phe Lys Ser
385                 390                 395                 400

Ala Met Pro Glu Gly Tyr Ile Gln Glu Arg Thr Ile Phe Phe Lys Asp
                405                 410                 415

Asp Gly Asn Tyr Lys Thr Arg Ala Glu Val Lys Phe Glu Gly Asp Thr
            420                 425                 430

Leu Val Asn Arg Ile Glu Leu Lys Gly Ile Asp Phe Lys Glu Asp Gly
        435                 440                 445

Asn Ile Leu Gly His Lys Leu Glu Tyr Asn Asn His Asp Gln Leu Lys
    450                 455                 460

Glu Val His Ala Ala Lys Ser Leu Ala Ile Ile Val Gly Leu Phe Ala
```

```
465                 470                 475                 480

Leu Cys Trp Leu Pro Leu His Ile Ile Asn Cys Phe Thr Phe Phe Cys
                485                 490                 495

Pro Asp Cys Ser His Ala Pro Leu Trp Leu Met Tyr Leu Ala Ile Val
            500                 505                 510

Leu Ser His Thr Asn Ser Val Val Asn Pro Phe Ile Tyr Ala Tyr Arg
        515                 520                 525

Ile Arg Glu Phe Arg Gln Thr Phe Arg Lys Ile Ile Arg Ser His Val
    530                 535                 540

Leu Arg Gln Gln Glu Pro Phe Lys Ala Ala Gly Thr Ser Ala Arg Val
545                 550                 555                 560

Leu Ala Ala His Gly Ser Asp Gly Glu Gln Val Ser Leu Arg Leu Asn
                565                 570                 575

Gly His Pro Pro Gly Val Trp Ala Asn Gly Ser Ala Pro His Pro Glu
            580                 585                 590

Arg Arg Pro Asn Gly Tyr Ala Leu Gly Leu Val Ser Gly Gly Ser Ala
        595                 600                 605

Gln Glu Ser Gln Gly Asn Thr Gly Leu Pro Asp Val Glu Leu Leu Ser
    610                 615                 620

His Glu Leu Lys Gly Val Cys Pro Glu Pro Pro Gly Leu Asp Asp Pro
625                 630                 635                 640

Leu Ala Gln Asp Gly Ala Gly Val Ser
                645


<210> SEQ ID NO 35
<211> LENGTH: 565
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (139)..(139)
<223> OTHER INFORMATION: Phe, Ala, Gly, Val, Ile, Leu, Met, Ser, or Thr

<400> SEQUENCE: 35

Met Gly Ser Leu Gln Pro Asp Ala Gly Asn Ala Ser Trp Asn Gly Thr
1               5                   10                  15

Glu Ala Pro Gly Gly Gly Ala Arg Ala Thr Pro Tyr Ser Leu Gln Val
            20                  25                  30

Thr Leu Thr Leu Val Cys Leu Ala Gly Leu Leu Met Leu Leu Thr Val
        35                  40                  45

Phe Gly Asn Val Leu Val Ile Ile Ala Val Phe Thr Ser Arg Ala Leu
    50                  55                  60

Lys Ala Pro Gln Asn Leu Phe Leu Val Ser Leu Ala Ser Ala Asp Ile
65                  70                  75                  80

Leu Val Ala Thr Leu Val Ile Pro Phe Ser Leu Ala Asn Glu Val Met
                85                  90                  95

Gly Tyr Trp Tyr Phe Gly Lys Ala Trp Cys Glu Ile Tyr Leu Ala Leu
            100                 105                 110

Asp Val Leu Phe Cys Thr Ser Ser Ile Val His Leu Cys Ala Ile Ser
        115                 120                 125

Leu Asp Arg Tyr Trp Ser Ile Thr Gln Ala Xaa Glu Tyr Asn Leu Lys
    130                 135                 140

Arg Thr Pro Arg Arg Ile Lys Ala Ile Ile Ile Thr Val Trp Val Ile
145                 150                 155                 160
```

```
Ser Ala Val Ile Ser Phe Pro Pro Leu Ile Ser Ile Glu Lys Lys Gly
                165                 170                 175

Gly Gly Gly Gly Pro Gln Pro Ala Glu Pro Arg Cys Glu Ile Asn Asp
            180                 185                 190

Gln Lys Trp Tyr Val Ile Ser Ser Cys Ile Gly Ser Phe Phe Ala Pro
        195                 200                 205

Cys Leu Ile Met Ile Leu Val Tyr Val Arg Ile Tyr Gln Ile Ala Lys
    210                 215                 220

Arg Gln Leu Gln Lys Ile Asp Leu Ser Ser Leu Ile Asn Val Tyr Ile
225                 230                 235                 240

Lys Ala Asp Lys Gln Lys Asn Gly Ile Lys Ala Asn Phe Lys Ile Arg
                245                 250                 255

His Asn Ile Glu Asp Gly Gly Val Gln Leu Ala Tyr His Tyr Gln Gln
            260                 265                 270

Asn Thr Pro Ile Gly Asp Gly Pro Val Leu Leu Pro Asp Asn His Tyr
        275                 280                 285

Leu Ser Val Gln Ser Lys Leu Ser Lys Asp Pro Asn Glu Lys Arg Asp
    290                 295                 300

His Met Val Leu Leu Glu Phe Val Thr Ala Ala Gly Ile Thr Leu Gly
305                 310                 315                 320

Met Asp Glu Leu Tyr Lys Gly Gly Thr Gly Gly Ser Met Val Ser Lys
                325                 330                 335

Gly Glu Glu Leu Phe Thr Gly Val Val Pro Ile Leu Val Glu Leu Asp
            340                 345                 350

Gly Asp Val Asn Gly His Lys Phe Ser Val Ser Gly Glu Gly Glu Gly
        355                 360                 365

Asp Ala Thr Tyr Gly Lys Leu Thr Leu Lys Phe Ile Cys Thr Thr Gly
    370                 375                 380

Lys Leu Pro Val Pro Trp Pro Thr Leu Val Thr Thr Leu Thr Tyr Gly
385                 390                 395                 400

Val Gln Cys Phe Ser Arg Tyr Pro Asp His Met Lys Gln His Asp Phe
                405                 410                 415

Phe Lys Ser Ala Met Pro Glu Gly Tyr Ile Gln Glu Arg Thr Ile Phe
            420                 425                 430

Phe Lys Asp Asp Gly Asn Tyr Lys Thr Arg Ala Glu Val Lys Phe Glu
        435                 440                 445

Gly Asp Thr Leu Val Asn Arg Ile Glu Leu Lys Gly Ile Asp Phe Lys
    450                 455                 460

Glu Asp Gly Asn Ile Leu Gly His Lys Leu Glu Tyr Asn Asn His Asp
465                 470                 475                 480

Gln Leu Arg Glu Lys Arg Phe Thr Phe Val Leu Ala Val Val Ile Gly
                485                 490                 495

Val Phe Val Val Cys Trp Phe Pro Phe Phe Phe Thr Tyr Thr Leu Thr
            500                 505                 510

Ala Val Gly Cys Ser Val Pro Arg Thr Leu Phe Lys Phe Phe Phe Trp
        515                 520                 525

Phe Gly Tyr Cys Asn Ser Ser Leu Asn Pro Val Ile Tyr Thr Ile Phe
    530                 535                 540

Asn His Asp Phe Arg Arg Ala Phe Lys Lys Ile Leu Cys Arg Gly Asp
545                 550                 555                 560

Arg Lys Arg Ile Val
                565
```

<210> SEQ ID NO 36
<211> LENGTH: 630
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (164)..(164)
<223> OTHER INFORMATION: Phe, Ala, Gly, Val, Ile, Leu, Met, Ser, or Thr

<400> SEQUENCE: 36

```
Met Asp Ser Pro Ile Gln Ile Phe Arg Gly Glu Pro Gly Pro Thr Cys
1               5                   10                  15

Ala Pro Ser Ala Cys Leu Pro Pro Asn Ser Ser Ala Trp Phe Pro Gly
            20                  25                  30

Trp Ala Glu Pro Asp Ser Asn Gly Ser Ala Gly Ser Glu Asp Ala Gln
        35                  40                  45

Leu Glu Pro Ala His Ile Ser Pro Ala Ile Pro Val Ile Ile Thr Ala
    50                  55                  60

Val Tyr Ser Val Val Phe Val Val Gly Leu Val Gly Asn Ser Leu Val
65                  70                  75                  80

Met Phe Val Ile Ile Arg Tyr Thr Lys Met Lys Thr Ala Thr Asn Ile
                85                  90                  95

Tyr Ile Phe Asn Leu Ala Leu Ala Asp Ala Leu Val Thr Thr Thr Met
            100                 105                 110

Pro Phe Gln Ser Thr Val Tyr Leu Met Asn Ser Trp Pro Phe Gly Asp
        115                 120                 125

Val Leu Cys Lys Ile Val Ile Ser Ile Asp Tyr Tyr Asn Met Phe Thr
    130                 135                 140

Ser Ile Phe Thr Leu Thr Met Met Ser Val Asp Arg Tyr Ile Ala Val
145                 150                 155                 160

Cys His Pro Xaa Lys Ala Leu Asp Phe Arg Thr Pro Leu Lys Ala Lys
                165                 170                 175

Ile Ile Asn Ile Cys Ile Trp Leu Leu Ser Ser Ser Val Gly Ile Ser
            180                 185                 190

Ala Ile Val Leu Gly Gly Thr Lys Val Arg Glu Asp Val Asp Val Ile
        195                 200                 205

Glu Cys Ser Leu Gln Phe Pro Asp Asp Asp Tyr Ser Trp Trp Asp Leu
    210                 215                 220

Phe Met Lys Ile Cys Val Phe Ile Phe Ala Phe Val Ile Pro Val Leu
225                 230                 235                 240

Ile Ile Ile Val Cys Tyr Thr Leu Met Ile Leu Arg Leu Lys Ser Gln
                245                 250                 255

Leu Gln Lys Ile Asp Leu Ser Ser Leu Ile Asn Val Tyr Ile Lys Ala
            260                 265                 270

Asp Lys Gln Lys Asn Gly Ile Lys Ala Asn Phe Lys Ile Arg His Asn
        275                 280                 285

Ile Glu Asp Gly Gly Val Gln Leu Ala Tyr His Tyr Gln Gln Asn Thr
    290                 295                 300

Pro Ile Gly Asp Gly Pro Val Leu Leu Pro Asp Asn His Tyr Leu Ser
305                 310                 315                 320

Val Gln Ser Lys Leu Ser Lys Asp Pro Asn Glu Lys Arg Asp His Met
                325                 330                 335

Val Leu Leu Glu Phe Val Thr Ala Ala Gly Ile Thr Leu Gly Met Asp
```

```
            340                 345                 350

Glu Leu Tyr Lys Gly Gly Thr Gly Gly Ser Met Val Ser Lys Gly Glu
        355                 360                 365

Glu Leu Phe Thr Gly Val Val Pro Ile Leu Val Glu Leu Asp Gly Asp
    370                 375                 380

Val Asn Gly His Lys Phe Ser Val Ser Gly Glu Gly Glu Gly Asp Ala
385                 390                 395                 400

Thr Tyr Gly Lys Leu Thr Leu Lys Phe Ile Cys Thr Thr Gly Lys Leu
                405                 410                 415

Pro Val Pro Trp Pro Thr Leu Val Thr Thr Leu Thr Tyr Gly Val Gln
            420                 425                 430

Cys Phe Ser Arg Tyr Pro Asp His Met Lys Gln His Asp Phe Phe Lys
        435                 440                 445

Ser Ala Met Pro Glu Gly Tyr Ile Gln Glu Arg Thr Ile Phe Phe Lys
    450                 455                 460

Asp Asp Gly Asn Tyr Lys Thr Arg Ala Glu Val Lys Phe Glu Gly Asp
465                 470                 475                 480

Thr Leu Val Asn Arg Ile Glu Leu Lys Gly Ile Asp Phe Lys Glu Asp
                485                 490                 495

Gly Asn Ile Leu Gly His Lys Leu Glu Tyr Asn Asn His Asp Gln Leu
            500                 505                 510

Arg Glu Lys Asp Arg Asn Leu Arg Arg Ile Thr Arg Leu Val Leu Val
        515                 520                 525

Val Val Ala Val Phe Val Val Cys Trp Thr Pro Ile His Ile Phe Ile
    530                 535                 540

Leu Val Glu Ala Leu Gly Ser Thr Ser His Ser Thr Ala Ala Leu Ala
545                 550                 555                 560

Ala Tyr Tyr Phe Cys Ile Ala Leu Gly Tyr Thr Asn Ala Ala Leu Asn
                565                 570                 575

Pro Ile Leu Tyr Ala Phe Leu Asp Glu Asn Phe Lys Arg Cys Phe Arg
            580                 585                 590

Asp Phe Cys Phe Pro Leu Lys Met Arg Met Glu Arg Gln Ala Thr Ala
        595                 600                 605

Arg Val Arg Asn Thr Val Gln Asp Pro Ala Tyr Leu Arg Asp Ile Asp
    610                 615                 620

Gly Met Asn Lys Pro Val
625                 630
```

<210> SEQ ID NO 37
<211> LENGTH: 650
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (175)..(175)
<223> OTHER INFORMATION: Phe, Ala, Gly, Val, Ile, Leu, Met, Ser, or Thr

<400> SEQUENCE: 37

```
Met Asp Ser Ser Ala Ala Pro Thr Asn Ala Ser Asn Cys Thr Asp Ala
1               5                   10                  15

Leu Ala Tyr Ser Ser Cys Ser Pro Ala Pro Ser Pro Gly Ser Trp Val
            20                  25                  30

Asn Leu Ser His Leu Asp Gly Asn Leu Ser Asp Pro Cys Gly Pro Asn
        35                  40                  45
```

```
Arg Thr Asp Leu Gly Gly Arg Asp Ser Leu Cys Pro Pro Thr Gly Ser
    50                  55                  60

Pro Ser Met Ile Thr Ala Ile Thr Ile Met Ala Leu Tyr Ser Ile Val
65                  70                  75                  80

Cys Val Val Gly Leu Phe Gly Asn Phe Leu Val Met Tyr Val Ile Val
                85                  90                  95

Arg Tyr Thr Lys Met Lys Thr Ala Thr Asn Ile Tyr Ile Phe Asn Leu
            100                 105                 110

Ala Leu Ala Asp Ala Leu Ala Thr Ser Thr Leu Pro Phe Gln Ser Val
        115                 120                 125

Asn Tyr Leu Met Gly Thr Trp Pro Phe Gly Thr Ile Leu Cys Lys Ile
    130                 135                 140

Val Ile Ser Ile Asp Tyr Tyr Asn Met Phe Thr Ser Ile Phe Thr Leu
145                 150                 155                 160

Cys Thr Met Ser Val Asp Arg Tyr Ile Ala Val Cys His Pro Xaa Lys
                165                 170                 175

Ala Leu Asp Phe Arg Thr Pro Arg Asn Ala Lys Ile Ile Asn Val Cys
            180                 185                 190

Asn Trp Ile Leu Ser Ser Ala Ile Gly Leu Pro Val Met Phe Met Ala
        195                 200                 205

Thr Thr Lys Tyr Arg Gln Gly Ser Ile Asp Cys Thr Leu Thr Phe Ser
    210                 215                 220

His Pro Thr Trp Tyr Trp Glu Asn Leu Leu Lys Ile Cys Val Phe Ile
225                 230                 235                 240

Phe Ala Phe Ile Met Pro Val Leu Ile Ile Thr Val Cys Tyr Gly Leu
                245                 250                 255

Met Ile Leu Arg Leu Lys Ser Gln Leu Gln Lys Ile Asp Leu Ser Ser
            260                 265                 270

Leu Ile Asn Val Tyr Ile Lys Ala Asp Lys Gln Lys Asn Gly Ile Lys
        275                 280                 285

Ala Asn Phe Lys Ile Arg His Asn Ile Glu Asp Gly Gly Val Gln Leu
    290                 295                 300

Ala Tyr His Tyr Gln Gln Asn Thr Pro Ile Gly Asp Gly Pro Val Leu
305                 310                 315                 320

Leu Pro Asp Asn His Tyr Leu Ser Val Gln Ser Lys Leu Ser Lys Asp
                325                 330                 335

Pro Asn Glu Lys Arg Asp His Met Val Leu Leu Glu Phe Val Thr Ala
            340                 345                 350

Ala Gly Ile Thr Leu Gly Met Asp Glu Leu Tyr Lys Gly Gly Thr Gly
        355                 360                 365

Gly Ser Met Val Ser Lys Gly Glu Glu Leu Phe Thr Gly Val Val Pro
    370                 375                 380

Ile Leu Val Glu Leu Asp Gly Asp Val Asn Gly His Lys Phe Ser Val
385                 390                 395                 400

Ser Gly Glu Gly Glu Gly Asp Ala Thr Tyr Gly Lys Leu Thr Leu Lys
                405                 410                 415

Phe Ile Cys Thr Thr Gly Lys Leu Pro Val Pro Trp Pro Thr Leu Val
            420                 425                 430

Thr Thr Leu Thr Tyr Gly Val Gln Cys Phe Ser Arg Tyr Pro Asp His
        435                 440                 445

Met Lys Gln His Asp Phe Phe Lys Ser Ala Met Pro Glu Gly Tyr Ile
    450                 455                 460
```

```
Gln Glu Arg Thr Ile Phe Phe Lys Asp Asp Gly Asn Tyr Lys Thr Arg
465                 470                 475                 480

Ala Glu Val Lys Phe Glu Gly Asp Thr Leu Val Asn Arg Ile Glu Leu
                485                 490                 495

Lys Gly Ile Asp Phe Lys Glu Asp Gly Asn Ile Leu Gly His Lys Leu
            500                 505                 510

Glu Tyr Asn Asn His Asp Gln Leu Lys Glu Lys Asp Arg Asn Leu Arg
        515                 520                 525

Arg Ile Thr Arg Met Val Leu Val Val Val Ala Val Phe Ile Val Cys
    530                 535                 540

Trp Thr Pro Ile His Ile Tyr Val Ile Ile Lys Ala Leu Val Thr Ile
545                 550                 555                 560

Pro Glu Thr Thr Phe Gln Thr Val Ser Trp His Phe Cys Ile Ala Leu
                565                 570                 575

Gly Tyr Thr Asn Ser Cys Leu Asn Pro Val Leu Tyr Ala Phe Leu Asp
            580                 585                 590

Glu Asn Phe Lys Arg Cys Phe Arg Glu Phe Cys Ile Pro Thr Ser Ser
        595                 600                 605

Asn Ile Glu Gln Gln Asn Ser Thr Arg Ile Arg Gln Asn Thr Arg Asp
    610                 615                 620

His Pro Ser Thr Ala Asn Thr Val Asp Arg Thr Asn His Gln Leu Glu
625                 630                 635                 640

Asn Leu Glu Ala Glu Thr Ala Pro Leu Pro
                645                 650
```

<210> SEQ ID NO 38
<211> LENGTH: 585
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (154)..(154)
<223> OTHER INFORMATION: Phe, Ala, Gly, Val, Ile, Leu, Met, Ser, or Thr

<400> SEQUENCE: 38

```
Met Glu Pro Ala Pro Ser Ala Gly Ala Glu Leu Gln Pro Pro Leu Phe
1               5                   10                  15

Ala Asn Ala Ser Asp Ala Tyr Pro Ser Ala Cys Pro Ser Ala Gly Ala
            20                  25                  30

Asn Ala Ser Gly Pro Pro Gly Ala Arg Ser Ala Ser Ser Leu Ala Leu
        35                  40                  45

Ala Ile Ala Ile Thr Ala Leu Tyr Ser Ala Val Cys Ala Val Gly Leu
    50                  55                  60

Leu Gly Asn Val Leu Val Met Phe Gly Ile Val Arg Tyr Thr Lys Met
65                  70                  75                  80

Lys Thr Ala Thr Asn Ile Tyr Ile Phe Asn Leu Ala Leu Ala Asp Ala
                85                  90                  95

Leu Ala Thr Ser Thr Leu Pro Phe Gln Ser Ala Lys Tyr Leu Met Glu
            100                 105                 110

Thr Trp Pro Phe Gly Glu Leu Leu Cys Lys Ala Val Leu Ser Ile Asp
        115                 120                 125

Tyr Tyr Asn Met Phe Thr Ser Ile Phe Thr Ala Thr Met Met Ser Val
    130                 135                 140

Asp Arg Tyr Ile Ala Val Cys His Pro Xaa Lys Ala Leu Asp Phe Arg
```

```
145                 150                 155                 160

Thr Pro Ala Lys Ala Lys Leu Ile Asn Ile Cys Ile Trp Val Leu Ala
                165                 170                 175

Ser Gly Val Gly Val Pro Ile Met Val Met Ala Val Thr Arg Pro Arg
            180                 185                 190

Asp Gly Ala Val Val Cys Met Leu Gln Phe Pro Ser Pro Ser Trp Tyr
        195                 200                 205

Trp Asp Thr Val Thr Lys Ile Cys Val Phe Leu Phe Ala Phe Val Val
    210                 215                 220

Pro Ile Leu Ile Ile Thr Val Cys Tyr Gly Leu Met Leu Leu Arg Leu
225                 230                 235                 240

Arg Ser Gln Leu Gln Lys Ile Asp Leu Ser Ser Leu Ile Asn Val Tyr
                245                 250                 255

Ile Lys Ala Asp Lys Gln Lys Asn Gly Ile Lys Ala Asn Phe Lys Ile
            260                 265                 270

Arg His Asn Ile Glu Asp Gly Gly Val Gln Leu Ala Tyr His Tyr Gln
        275                 280                 285

Gln Asn Thr Pro Ile Gly Asp Gly Pro Val Leu Leu Pro Asp Asn His
    290                 295                 300

Tyr Leu Ser Val Gln Ser Lys Leu Ser Lys Asp Pro Asn Glu Lys Arg
305                 310                 315                 320

Asp His Met Val Leu Leu Glu Phe Val Thr Ala Ala Gly Ile Thr Leu
                325                 330                 335

Gly Met Asp Glu Leu Tyr Lys Gly Gly Thr Gly Gly Ser Met Val Ser
            340                 345                 350

Lys Gly Glu Glu Leu Phe Thr Gly Val Val Pro Ile Leu Val Glu Leu
        355                 360                 365

Asp Gly Asp Val Asn Gly His Lys Phe Ser Val Ser Gly Glu Gly Glu
    370                 375                 380

Gly Asp Ala Thr Tyr Gly Lys Leu Thr Leu Lys Phe Ile Cys Thr Thr
385                 390                 395                 400

Gly Lys Leu Pro Val Pro Trp Pro Thr Leu Val Thr Thr Leu Thr Tyr
                405                 410                 415

Gly Val Gln Cys Phe Ser Arg Tyr Pro Asp His Met Lys Gln His Asp
            420                 425                 430

Phe Phe Lys Ser Ala Met Pro Glu Gly Tyr Ile Gln Glu Arg Thr Ile
        435                 440                 445

Phe Phe Lys Asp Asp Gly Asn Tyr Lys Thr Arg Ala Glu Val Lys Phe
    450                 455                 460

Glu Gly Asp Thr Leu Val Asn Arg Ile Glu Leu Lys Gly Ile Asp Phe
465                 470                 475                 480

Lys Glu Asp Gly Asn Ile Leu Gly His Lys Leu Glu Tyr Asn Asn His
                485                 490                 495

Asp Gln Leu Lys Glu Lys Asp Arg Ser Leu Arg Arg Ile Thr Arg Met
            500                 505                 510

Val Leu Val Val Val Gly Ala Phe Val Val Cys Trp Ala Pro Ile His
        515                 520                 525

Ile Phe Val Ile Val Trp Thr Leu Val Asp Ile Asp Arg Arg Asp Pro
    530                 535                 540

Leu Val Val Ala Ala Leu His Leu Cys Ile Ala Leu Gly Tyr Ala Asn
545                 550                 555                 560

Ser Ser Leu Asn Pro Val Leu Tyr Ala Phe Leu Asp Glu Asn Phe Lys
                565                 570                 575
```

```
Arg Cys Phe Arg Gln Leu Cys Arg Ala
            580                 585


<210> SEQ ID NO 39
<211> LENGTH: 609
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (146)..(146)
<223> OTHER INFORMATION: Phe, Ala, Gly, Val, Ile, Leu, Met, Ser, or Thr

<400> SEQUENCE: 39

Met Ser Glu Asn Gly Ser Phe Ala Asn Cys Cys Glu Ala Gly Gly Trp
1               5                   10                  15

Ala Val Arg Pro Gly Trp Ser Gly Ala Gly Ser Ala Arg Pro Ser Arg
            20                  25                  30

Thr Pro Arg Pro Pro Trp Val Ala Pro Ala Leu Ser Ala Val Leu Ile
        35                  40                  45

Val Thr Thr Ala Val Asp Val Val Gly Asn Leu Leu Val Ile Leu Ser
    50                  55                  60

Val Leu Arg Asn Arg Lys Leu Arg Asn Ala Gly Asn Leu Phe Leu Val
65                  70                  75                  80

Ser Leu Ala Leu Ala Asp Leu Val Val Ala Phe Tyr Pro Tyr Pro Leu
                85                  90                  95

Ile Leu Val Ala Ile Phe Tyr Asp Gly Trp Ala Leu Gly Glu Glu His
            100                 105                 110

Cys Lys Ala Ser Ala Phe Val Met Gly Leu Ser Val Ile Gly Ser Val
        115                 120                 125

Phe Asn Ile Thr Ala Ile Ala Ile Asn Arg Tyr Cys Tyr Ile Cys His
    130                 135                 140

Ser Xaa Ala Tyr His Arg Ile Tyr Arg Arg Trp His Thr Pro Leu His
145                 150                 155                 160

Ile Cys Leu Ile Trp Leu Leu Thr Val Val Ala Leu Leu Pro Asn Phe
                165                 170                 175

Phe Val Gly Ser Leu Glu Tyr Asp Pro Arg Ile Tyr Ser Cys Thr Phe
            180                 185                 190

Ile Gln Thr Ala Ser Thr Gln Tyr Thr Ala Ala Val Val Val Ile His
        195                 200                 205

Phe Leu Leu Pro Ile Ala Val Val Ser Phe Cys Tyr Leu Arg Ile Trp
    210                 215                 220

Val Leu Val Leu Gln Ala Arg Arg Gln Leu Gln Lys Ile Asp Leu Ser
225                 230                 235                 240

Ser Leu Ile Asn Val Tyr Ile Lys Ala Asp Lys Gln Lys Asn Gly Ile
                245                 250                 255

Lys Ala Asn Phe Lys Ile Arg His Asn Ile Glu Asp Gly Gly Val Gln
            260                 265                 270

Leu Ala Tyr His Tyr Gln Gln Asn Thr Pro Ile Gly Asp Gly Pro Val
        275                 280                 285

Leu Leu Pro Asp Asn His Tyr Leu Ser Val Gln Ser Lys Leu Ser Lys
    290                 295                 300

Asp Pro Asn Glu Lys Arg Asp His Met Val Leu Leu Glu Phe Val Thr
305                 310                 315                 320
```

```
Ala Ala Gly Ile Thr Leu Gly Met Asp Glu Leu Tyr Lys Gly Gly Thr
                325                 330                 335

Gly Gly Ser Met Val Ser Lys Gly Glu Glu Leu Phe Thr Gly Val Val
            340                 345                 350

Pro Ile Leu Val Glu Leu Asp Gly Asp Val Asn Gly His Lys Phe Ser
        355                 360                 365

Val Ser Gly Glu Gly Glu Gly Asp Ala Thr Tyr Gly Lys Leu Thr Leu
    370                 375                 380

Lys Phe Ile Cys Thr Thr Gly Lys Leu Pro Val Pro Trp Pro Thr Leu
385                 390                 395                 400

Val Thr Thr Leu Thr Tyr Gly Val Gln Cys Phe Ser Arg Tyr Pro Asp
                405                 410                 415

His Met Lys Gln His Asp Phe Phe Lys Ser Ala Met Pro Glu Gly Tyr
            420                 425                 430

Ile Gln Glu Arg Thr Ile Phe Phe Lys Asp Asp Gly Asn Tyr Lys Thr
        435                 440                 445

Arg Ala Glu Val Lys Phe Glu Gly Asp Thr Leu Val Asn Arg Ile Glu
    450                 455                 460

Leu Lys Gly Ile Asp Phe Lys Glu Asp Gly Asn Ile Leu Gly His Lys
465                 470                 475                 480

Leu Glu Tyr Asn Asn His Asp Gln Leu Lys Pro Ser Asp Leu Arg Ser
                485                 490                 495

Phe Leu Thr Met Phe Val Val Phe Val Ile Phe Ala Ile Cys Trp Ala
            500                 505                 510

Pro Leu Asn Cys Ile Gly Leu Ala Val Ala Ile Asn Pro Gln Glu Met
        515                 520                 525

Ala Pro Gln Ile Pro Glu Gly Leu Phe Val Thr Ser Tyr Leu Leu Ala
    530                 535                 540

Tyr Phe Asn Ser Cys Leu Asn Ala Ile Val Tyr Gly Leu Leu Asn Gln
545                 550                 555                 560

Asn Phe Arg Arg Glu Tyr Lys Arg Ile Leu Leu Ala Leu Trp Asn Pro
                565                 570                 575

Arg His Cys Ile Gln Asp Ala Ser Lys Gly Ser His Ala Glu Gly Leu
            580                 585                 590

Gln Ser Pro Ala Pro Pro Ile Ile Gly Val Gln His Gln Ala Asp Ala
        595                 600                 605

Leu


<210> SEQ ID NO 40
<211> LENGTH: 692
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (222)..(222)
<223> OTHER INFORMATION: Phe, Ala, Gly, Val, Ile, Leu, Met, Ser, or Thr

<400> SEQUENCE: 40

Met Lys Ser Ile Leu Asp Gly Leu Ala Asp Thr Thr Phe Arg Thr Ile
1               5                   10                  15

Thr Thr Asp Leu Leu Tyr Val Gly Ser Asn Asp Ile Gln Tyr Glu Asp
            20                  25                  30

Ile Lys Gly Asp Met Ala Ser Lys Leu Gly Tyr Phe Pro Gln Lys Phe
        35                  40                  45
```

```
Pro Leu Thr Ser Phe Arg Gly Ser Pro Phe Gln Glu Lys Met Thr Ala
    50                  55                  60

Gly Asp Asn Pro Gln Leu Val Pro Ala Asp Gln Val Asn Ile Thr Glu
65                  70                  75                  80

Phe Tyr Asn Lys Ser Leu Ser Ser Phe Lys Glu Asn Glu Glu Asn Ile
                85                  90                  95

Gln Cys Gly Glu Asn Phe Met Asp Ile Glu Cys Phe Met Val Leu Asn
            100                 105                 110

Pro Ser Gln Gln Leu Ala Ile Ala Val Leu Ser Leu Thr Leu Gly Thr
        115                 120                 125

Phe Thr Val Leu Glu Asn Leu Leu Val Leu Cys Val Ile Leu His Ser
    130                 135                 140

Arg Ser Leu Arg Cys Arg Pro Ser Tyr His Phe Ile Gly Ser Leu Ala
145                 150                 155                 160

Val Ala Asp Leu Leu Gly Ser Val Ile Phe Val Tyr Ser Phe Ile Asp
                165                 170                 175

Phe His Val Phe His Arg Lys Asp Ser Arg Asn Val Phe Leu Phe Lys
            180                 185                 190

Leu Gly Gly Val Thr Ala Ser Phe Thr Ala Ser Val Gly Ser Leu Phe
        195                 200                 205

Leu Thr Ala Ile Asp Arg Tyr Ile Ser Ile His Arg Pro Xaa Ala Tyr
    210                 215                 220

Lys Arg Ile Val Thr Arg Pro Lys Ala Val Val Ala Phe Cys Leu Met
225                 230                 235                 240

Trp Thr Ile Ala Ile Val Ile Ala Val Leu Pro Leu Leu Gly Trp Asn
                245                 250                 255

Cys Glu Lys Leu Gln Ser Val Cys Ser Asp Ile Phe Pro His Ile Asp
            260                 265                 270

Glu Thr Tyr Leu Met Phe Trp Ile Gly Val Thr Ser Val Leu Leu Leu
        275                 280                 285

Phe Ile Val Tyr Ala Tyr Met Tyr Ile Leu Trp Lys Ala His Ser His
    290                 295                 300

Ala Val Arg Met Ile Gln Arg Gln Leu Gln Lys Ile Asp Leu Ser Ser
305                 310                 315                 320

Leu Ile Asn Val Tyr Ile Lys Ala Asp Lys Gln Lys Asn Gly Ile Lys
                325                 330                 335

Ala Asn Phe Lys Ile Arg His Asn Ile Glu Asp Gly Gly Val Gln Leu
            340                 345                 350

Ala Tyr His Tyr Gln Gln Asn Thr Pro Ile Gly Asp Gly Pro Val Leu
        355                 360                 365

Leu Pro Asp Asn His Tyr Leu Ser Val Gln Ser Lys Leu Ser Lys Asp
    370                 375                 380

Pro Asn Glu Lys Arg Asp His Met Val Leu Leu Glu Phe Val Thr Ala
385                 390                 395                 400

Ala Gly Ile Thr Leu Gly Met Asp Glu Leu Tyr Lys Gly Gly Thr Gly
                405                 410                 415

Gly Ser Met Val Ser Lys Gly Glu Glu Leu Phe Thr Gly Val Val Pro
            420                 425                 430

Ile Leu Val Glu Leu Asp Gly Asp Val Asn Gly His Lys Phe Ser Val
        435                 440                 445

Ser Gly Glu Gly Glu Gly Asp Ala Thr Tyr Gly Lys Leu Thr Leu Lys
    450                 455                 460
```

Phe Ile Cys Thr Thr Gly Lys Leu Pro Val Pro Trp Pro Thr Leu Val
465 470 475 480

Thr Thr Leu Thr Tyr Gly Val Gln Cys Phe Ser Arg Tyr Pro Asp His
485 490 495

Met Lys Gln His Asp Phe Phe Lys Ser Ala Met Pro Glu Gly Tyr Ile
500 505 510

Gln Glu Arg Thr Ile Phe Phe Lys Asp Asp Gly Asn Tyr Lys Thr Arg
515 520 525

Ala Glu Val Lys Phe Glu Gly Asp Thr Leu Val Asn Arg Ile Glu Leu
530 535 540

Lys Gly Ile Asp Phe Lys Glu Asp Gly Asn Ile Leu Gly His Lys Leu
545 550 555 560

Glu Tyr Asn Asn His Asp Gln Leu Arg Met Asp Ile Arg Leu Ala Lys
565 570 575

Thr Leu Val Leu Ile Leu Val Val Leu Ile Ile Cys Trp Gly Pro Leu
580 585 590

Leu Ala Ile Met Val Tyr Asp Val Phe Gly Lys Met Asn Lys Leu Ile
595 600 605

Lys Thr Val Phe Ala Phe Cys Ser Met Leu Cys Leu Leu Asn Ser Thr
610 615 620

Val Asn Pro Ile Ile Tyr Ala Leu Arg Ser Lys Asp Leu Arg His Ala
625 630 635 640

Phe Arg Ser Met Phe Pro Ser Cys Glu Gly Thr Ala Gln Pro Leu Asp
645 650 655

Asn Ser Met Gly Asp Ser Asp Cys Leu His Lys His Ala Asn Asn Ala
660 665 670

Ala Ser Val His Arg Ala Ala Glu Ser Cys Ile Lys Ser Thr Val Lys
675 680 685

Ile Ala Lys Val
690

<210> SEQ ID NO 41
<211> LENGTH: 554
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (133)..(133)
<223> OTHER INFORMATION: Phe, Ala, Gly, Val, Ile, Leu, Met, Ser, or Thr

<400> SEQUENCE: 41

Met Ser Leu Pro Asn Ser Ser Cys Leu Leu Glu Asp Lys Met Cys Glu
1 5 10 15

Gly Asn Lys Thr Thr Met Ala Ser Pro Gln Leu Met Pro Leu Val Val
20 25 30

Val Leu Ser Thr Ile Cys Leu Val Thr Val Gly Leu Asn Leu Leu Val
35 40 45

Leu Tyr Ala Val Arg Ser Glu Arg Lys Leu His Thr Val Gly Asn Leu
50 55 60

Tyr Ile Val Ser Leu Ser Val Ala Asp Leu Ile Val Gly Ala Val Val
65 70 75 80

Met Pro Met Asn Ile Leu Tyr Leu Leu Met Ser Lys Trp Ser Leu Gly
85 90 95

Arg Pro Leu Cys Leu Phe Trp Leu Ser Met Asp Tyr Val Ala Ser Thr

```
                100                 105                 110

Ala Ser Ile Phe Ser Val Phe Ile Leu Cys Ile Asp Arg Tyr Arg Ser
        115                 120                 125

Val Gln Gln Pro Xaa Arg Tyr Leu Lys Tyr Arg Thr Lys Thr Arg Ala
    130                 135                 140

Ser Ala Thr Ile Leu Gly Ala Trp Phe Leu Ser Phe Leu Trp Val Ile
145                 150                 155                 160

Pro Ile Leu Gly Trp Asn His Phe Met Gln Gln Thr Ser Val Arg Arg
                165                 170                 175

Glu Asp Lys Cys Glu Thr Asp Phe Tyr Asp Val Thr Trp Phe Lys Val
            180                 185                 190

Met Thr Ala Ile Ile Asn Phe Tyr Leu Pro Thr Leu Leu Met Leu Trp
        195                 200                 205

Phe Tyr Ala Lys Ile Tyr Lys Ala Val Arg Gln Leu Gln Lys Ile Asp
    210                 215                 220

Leu Ser Ser Leu Ile Asn Val Tyr Ile Lys Ala Asp Lys Gln Lys Asn
225                 230                 235                 240

Gly Ile Lys Ala Asn Phe Lys Ile Arg His Asn Ile Glu Asp Gly Gly
                245                 250                 255

Val Gln Leu Ala Tyr His Tyr Gln Gln Asn Thr Pro Ile Gly Asp Gly
            260                 265                 270

Pro Val Leu Leu Pro Asp Asn His Tyr Leu Ser Val Gln Ser Lys Leu
        275                 280                 285

Ser Lys Asp Pro Asn Glu Lys Arg Asp His Met Val Leu Leu Glu Phe
    290                 295                 300

Val Thr Ala Ala Gly Ile Thr Leu Gly Met Asp Glu Leu Tyr Lys Gly
305                 310                 315                 320

Gly Thr Gly Gly Ser Met Val Ser Lys Gly Glu Glu Leu Phe Thr Gly
                325                 330                 335

Val Val Pro Ile Leu Val Glu Leu Asp Gly Asp Val Asn Gly His Lys
            340                 345                 350

Phe Ser Val Ser Gly Glu Gly Glu Gly Asp Ala Thr Tyr Gly Lys Leu
        355                 360                 365

Thr Leu Lys Phe Ile Cys Thr Thr Gly Lys Leu Pro Val Pro Trp Pro
    370                 375                 380

Thr Leu Val Thr Thr Leu Thr Tyr Gly Val Gln Cys Phe Ser Arg Tyr
385                 390                 395                 400

Pro Asp His Met Lys Gln His Asp Phe Phe Lys Ser Ala Met Pro Glu
                405                 410                 415

Gly Tyr Ile Gln Glu Arg Thr Ile Phe Phe Lys Asp Asp Gly Asn Tyr
            420                 425                 430

Lys Thr Arg Ala Glu Val Lys Phe Glu Gly Asp Thr Leu Val Asn Arg
        435                 440                 445

Ile Glu Leu Lys Gly Ile Asp Phe Lys Glu Asp Gly Asn Ile Leu Gly
    450                 455                 460

His Lys Leu Glu Tyr Asn Asn His Asp Gln Leu Arg Glu Arg Lys Ala
465                 470                 475                 480

Ala Lys Gln Leu Gly Phe Ile Met Ala Ala Phe Ile Leu Cys Trp Ile
                485                 490                 495

Pro Tyr Phe Ile Phe Phe Met Val Ile Ala Phe Cys Lys Asn Cys Cys
            500                 505                 510

Asn Glu His Leu His Met Phe Thr Ile Trp Leu Gly Tyr Ile Asn Ser
        515                 520                 525
```

Thr Leu Asn Pro Leu Ile Tyr Pro Leu Cys Asn Glu Asn Phe Lys Lys
    530                 535                 540

Thr Phe Lys Arg Ile Leu His Ile Arg Ser
545                 550

<210> SEQ ID NO 42
<211> LENGTH: 627
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Met Asn Ser Thr Leu Phe Ser Gln Val Glu Asn His Ser Val His Ser
1               5                   10                  15

Asn Phe Ser Glu Lys Asn Ala Gln Leu Leu Ala Phe Glu Asn Asp Asp
            20                  25                  30

Cys His Leu Pro Leu Ala Met Ile Phe Thr Leu Ala Leu Ala Tyr Gly
        35                  40                  45

Ala Val Ile Ile Leu Gly Val Ser Gly Asn Leu Ala Leu Ile Ile Ile
    50                  55                  60

Ile Leu Lys Gln Lys Glu Met Arg Asn Val Thr Asn Ile Leu Ile Val
65                  70                  75                  80

Asn Leu Ser Phe Ser Asp Leu Leu Val Ala Ile Met Cys Leu Pro Phe
                85                  90                  95

Thr Phe Val Tyr Thr Leu Met Asp His Trp Val Phe Gly Glu Ala Met
            100                 105                 110

Cys Lys Leu Asn Pro Phe Val Gln Cys Val Ser Ile Thr Val Ser Ile
        115                 120                 125

Phe Ser Leu Val Leu Ile Ala Val Glu Arg His Gln Leu Ile Ile Asn
    130                 135                 140

Pro Arg Gly Trp Arg Pro Asn Asn Arg His Ala Tyr Val Gly Ile Ala
145                 150                 155                 160

Val Ile Trp Val Leu Ala Val Ala Ser Ser Leu Pro Phe Leu Ile Tyr
                165                 170                 175

Gln Val Met Thr Asp Glu Pro Phe Gln Asn Val Thr Leu Asp Ala Tyr
            180                 185                 190

Lys Asp Lys Tyr Val Cys Phe Asp Gln Phe Pro Ser Asp Ser His Arg
        195                 200                 205

Leu Ser Tyr Thr Thr Leu Leu Leu Val Leu Gln Tyr Phe Gly Pro Leu
    210                 215                 220

Cys Phe Ile Phe Ile Cys Tyr Phe Lys Ile Tyr Ile Arg Leu Lys Arg
225                 230                 235                 240

Arg Gln Leu Gln Lys Ile Asp Leu Ser Ser Leu Ile Asn Val Tyr Ile
                245                 250                 255

Lys Ala Asp Lys Gln Lys Asn Gly Ile Lys Ala Asn Phe Lys Ile Arg
            260                 265                 270

His Asn Ile Glu Asp Gly Gly Val Gln Leu Ala Tyr His Tyr Gln Gln
        275                 280                 285

Asn Thr Pro Ile Gly Asp Gly Pro Val Leu Leu Pro Asp Asn His Tyr
    290                 295                 300

Leu Ser Val Gln Ser Lys Leu Ser Lys Asp Pro Asn Glu Lys Arg Asp
305                 310                 315                 320

His Met Val Leu Leu Glu Phe Val Thr Ala Ala Gly Ile Thr Leu Gly

```
                325                 330                 335

Met Asp Glu Leu Tyr Lys Gly Gly Thr Gly Gly Ser Met Val Ser Lys
            340                 345                 350

Gly Glu Glu Leu Phe Thr Gly Val Val Pro Ile Leu Val Glu Leu Asp
        355                 360                 365

Gly Asp Val Asn Gly His Lys Phe Ser Val Ser Gly Glu Gly Glu Gly
    370                 375                 380

Asp Ala Thr Tyr Gly Lys Leu Thr Leu Lys Phe Ile Cys Thr Thr Gly
385                 390                 395                 400

Lys Leu Pro Val Pro Trp Pro Thr Leu Val Thr Thr Leu Thr Tyr Gly
                405                 410                 415

Val Gln Cys Phe Ser Arg Tyr Pro Asp His Met Lys Gln His Asp Phe
            420                 425                 430

Phe Lys Ser Ala Met Pro Glu Gly Tyr Ile Gln Glu Arg Thr Ile Phe
        435                 440                 445

Phe Lys Asp Asp Gly Asn Tyr Lys Thr Arg Ala Glu Val Lys Phe Glu
    450                 455                 460

Gly Asp Thr Leu Val Asn Arg Ile Glu Leu Lys Gly Ile Asp Phe Lys
465                 470                 475                 480

Glu Asp Gly Asn Ile Leu Gly His Lys Leu Glu Tyr Asn Asn His Asp
                485                 490                 495

Gln Leu Ser Glu Thr Lys Arg Ile Asn Ile Met Leu Leu Ser Ile Val
            500                 505                 510

Val Ala Phe Ala Val Cys Trp Leu Pro Leu Thr Ile Phe Asn Thr Val
        515                 520                 525

Phe Asp Trp Asn His Gln Ile Ile Ala Thr Cys Asn His Asn Leu Leu
    530                 535                 540

Phe Leu Leu Cys His Leu Thr Ala Met Ile Ser Thr Cys Val Asn Pro
545                 550                 555                 560

Ile Phe Tyr Gly Phe Leu Asn Lys Asn Phe Gln Arg Asp Leu Gln Phe
                565                 570                 575

Phe Phe Asn Phe Cys Asp Phe Arg Ser Arg Asp Asp Asp Tyr Glu Thr
            580                 585                 590

Ile Ala Met Ser Thr Met His Thr Asp Val Ser Lys Thr Ser Leu Lys
        595                 600                 605

Gln Ala Ser Pro Val Ala Phe Lys Lys Ile Asn Asn Asn Asp Asp Asn
    610                 615                 620

Glu Lys Ile
625


<210> SEQ ID NO 43
<211> LENGTH: 558
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (129)..(129)
<223> OTHER INFORMATION: Phe, Ala, Gly, Val, Ile, Leu, Met, Ser, or Thr

<400> SEQUENCE: 43

Met Asn Asn Ser Thr Asn Ser Ser Asn Asn Ser Leu Ala Leu Thr Ser
1               5                   10                  15

Pro Tyr Lys Thr Phe Glu Val Val Phe Ile Val Leu Val Ala Gly Ser
            20                  25                  30
```

```
Leu Ser Leu Val Thr Ile Ile Gly Asn Ile Leu Val Met Val Ser Ile
        35                  40                  45

Lys Val Asn Arg His Leu Gln Thr Val Asn Asn Tyr Phe Leu Phe Ser
    50                  55                  60

Leu Ala Cys Ala Asp Leu Ile Ile Gly Val Phe Ser Met Asn Leu Tyr
65                  70                  75                  80

Thr Leu Tyr Thr Val Ile Gly Tyr Trp Pro Leu Gly Pro Val Val Cys
                85                  90                  95

Asp Leu Trp Leu Ala Leu Asp Tyr Val Val Ser Asn Ala Ser Val Met
            100                 105                 110

Asn Leu Leu Ile Ile Ser Phe Asp Arg Tyr Phe Cys Val Thr Lys Pro
        115                 120                 125

Xaa Thr Tyr Pro Val Lys Arg Thr Thr Lys Met Ala Gly Met Met Ile
    130                 135                 140

Ala Ala Ala Trp Val Leu Ser Phe Ile Leu Trp Ala Pro Ala Ile Leu
145                 150                 155                 160

Phe Trp Gln Phe Ile Val Gly Val Arg Thr Val Glu Asp Gly Glu Cys
                165                 170                 175

Tyr Ile Gln Phe Phe Ser Asn Ala Ala Val Thr Phe Gly Thr Ala Ile
            180                 185                 190

Ala Ala Phe Tyr Leu Pro Val Ile Ile Met Thr Val Leu Tyr Trp His
        195                 200                 205

Ile Ser Arg Ala Ser Lys Ser Gln Leu Gln Lys Ile Asp Leu Ser Ser
    210                 215                 220

Leu Ile Asn Val Tyr Ile Lys Ala Asp Lys Gln Lys Asn Gly Ile Lys
225                 230                 235                 240

Ala Asn Phe Lys Ile Arg His Asn Ile Glu Asp Gly Gly Val Gln Leu
                245                 250                 255

Ala Tyr His Tyr Gln Gln Asn Thr Pro Ile Gly Asp Gly Pro Val Leu
            260                 265                 270

Leu Pro Asp Asn His Tyr Leu Ser Val Gln Ser Lys Leu Ser Lys Asp
        275                 280                 285

Pro Asn Glu Lys Arg Asp His Met Val Leu Leu Glu Phe Val Thr Ala
    290                 295                 300

Ala Gly Ile Thr Leu Gly Met Asp Glu Leu Tyr Lys Gly Gly Thr Gly
305                 310                 315                 320

Gly Ser Met Val Ser Lys Gly Glu Glu Leu Phe Thr Gly Val Val Pro
                325                 330                 335

Ile Leu Val Glu Leu Asp Gly Asp Val Asn Gly His Lys Phe Ser Val
            340                 345                 350

Ser Gly Glu Gly Glu Gly Asp Ala Thr Tyr Gly Lys Leu Thr Leu Lys
        355                 360                 365

Phe Ile Cys Thr Thr Gly Lys Leu Pro Val Pro Trp Pro Thr Leu Val
    370                 375                 380

Thr Thr Leu Thr Tyr Gly Val Gln Cys Phe Ser Arg Tyr Pro Asp His
385                 390                 395                 400

Met Lys Gln His Asp Phe Phe Lys Ser Ala Met Pro Glu Gly Tyr Ile
                405                 410                 415

Gln Glu Arg Thr Ile Phe Phe Lys Asp Asp Gly Asn Tyr Lys Thr Arg
            420                 425                 430

Ala Glu Val Lys Phe Glu Gly Asp Thr Leu Val Asn Arg Ile Glu Leu
        435                 440                 445
```

```
Lys Gly Ile Asp Phe Lys Glu Asp Gly Asn Ile Leu Gly His Lys Leu
    450                 455                 460

Glu Tyr Asn Asn His Asp Gln Leu Arg Glu Lys Lys Val Thr Arg Thr
465                 470                 475                 480

Ile Leu Ala Ile Leu Leu Ala Phe Ile Ile Thr Trp Ala Pro Tyr Asn
                485                 490                 495

Val Met Val Leu Ile Asn Thr Phe Cys Ala Pro Cys Ile Pro Asn Thr
            500                 505                 510

Val Trp Thr Ile Gly Tyr Trp Leu Cys Tyr Ile Asn Ser Thr Ile Asn
        515                 520                 525

Pro Ala Cys Tyr Ala Leu Cys Asn Ala Thr Phe Lys Lys Thr Phe Lys
    530                 535                 540

His Leu Leu Met Cys His Tyr Lys Asn Ile Gly Ala Thr Arg
545                 550                 555


<210> SEQ ID NO 44
<211> LENGTH: 637
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (152)..(152)
<223> OTHER INFORMATION: Phe, Ala, Gly, Val, Ile, Leu, Met, Ser, or Thr

<400> SEQUENCE: 44

Met Glu Pro Ser Ala Thr Pro Gly Ala Gln Met Gly Val Pro Pro Gly
1               5                   10                  15

Ser Arg Glu Pro Ser Pro Val Pro Pro Asp Tyr Glu Asp Glu Phe Leu
            20                  25                  30

Arg Tyr Leu Trp Arg Asp Tyr Leu Tyr Pro Lys Gln Tyr Glu Trp Val
        35                  40                  45

Leu Ile Ala Ala Tyr Val Ala Val Phe Val Val Ala Leu Val Gly Asn
    50                  55                  60

Thr Leu Val Cys Leu Ala Val Trp Arg Asn His His Met Arg Thr Val
65                  70                  75                  80

Thr Asn Tyr Phe Ile Val Asn Leu Ser Leu Ala Asp Val Leu Val Thr
                85                  90                  95

Ala Ile Cys Leu Pro Ala Ser Leu Leu Val Asp Ile Thr Glu Ser Trp
            100                 105                 110

Leu Phe Gly His Ala Leu Cys Lys Val Ile Pro Tyr Leu Gln Ala Val
        115                 120                 125

Ser Val Ser Val Ala Val Leu Thr Leu Ser Phe Ile Ala Leu Asp Arg
    130                 135                 140

Trp Tyr Ala Ile Cys His Pro Xaa Leu Phe Lys Ser Thr Ala Arg Arg
145                 150                 155                 160

Ala Arg Gly Ser Ile Leu Gly Ile Trp Ala Val Ser Leu Ala Ile Met
                165                 170                 175

Val Pro Gln Ala Ala Val Met Glu Cys Ser Ser Val Leu Pro Glu Leu
            180                 185                 190

Ala Asn Arg Thr Arg Leu Phe Ser Val Cys Asp Glu Arg Trp Ala Asp
        195                 200                 205

Asp Leu Tyr Pro Lys Ile Tyr His Ser Cys Phe Phe Ile Val Thr Tyr
    210                 215                 220

Leu Ala Pro Leu Gly Leu Met Ala Met Ala Tyr Phe Gln Ile Phe Arg
```

```
225                 230                 235                 240

Lys Leu Trp Gly Arg Gln Leu Gln Lys Ile Asp Leu Ser Ser Leu Ile
                245                 250                 255

Asn Val Tyr Ile Lys Ala Asp Lys Gln Lys Asn Gly Ile Lys Ala Asn
            260                 265                 270

Phe Lys Ile Arg His Asn Ile Glu Asp Gly Gly Val Gln Leu Ala Tyr
        275                 280                 285

His Tyr Gln Gln Asn Thr Pro Ile Gly Asp Gly Pro Val Leu Leu Pro
    290                 295                 300

Asp Asn His Tyr Leu Ser Val Gln Ser Lys Leu Ser Lys Asp Pro Asn
305                 310                 315                 320

Glu Lys Arg Asp His Met Val Leu Leu Glu Phe Val Thr Ala Ala Gly
                325                 330                 335

Ile Thr Leu Gly Met Asp Glu Leu Tyr Lys Gly Gly Thr Gly Gly Ser
            340                 345                 350

Met Val Ser Lys Gly Glu Glu Leu Phe Thr Gly Val Val Pro Ile Leu
        355                 360                 365

Val Glu Leu Asp Gly Asp Val Asn Gly His Lys Phe Ser Val Ser Gly
    370                 375                 380

Glu Gly Glu Gly Asp Ala Thr Tyr Gly Lys Leu Thr Leu Lys Phe Ile
385                 390                 395                 400

Cys Thr Thr Gly Lys Leu Pro Val Pro Trp Pro Thr Leu Val Thr Thr
                405                 410                 415

Leu Thr Tyr Gly Val Gln Cys Phe Ser Arg Tyr Pro Asp His Met Lys
            420                 425                 430

Gln His Asp Phe Phe Lys Ser Ala Met Pro Glu Gly Tyr Ile Gln Glu
        435                 440                 445

Arg Thr Ile Phe Phe Lys Asp Asp Gly Asn Tyr Lys Thr Arg Ala Glu
    450                 455                 460

Val Lys Phe Glu Gly Asp Thr Leu Val Asn Arg Ile Glu Leu Lys Gly
465                 470                 475                 480

Ile Asp Phe Lys Glu Asp Gly Asn Ile Leu Gly His Lys Leu Glu Tyr
                485                 490                 495

Asn Asn His Asp Gln Leu Arg Ala Arg Arg Lys Thr Ala Lys Met Leu
            500                 505                 510

Met Val Val Leu Leu Val Phe Ala Leu Cys Tyr Leu Pro Ile Ser Val
        515                 520                 525

Leu Asn Val Leu Lys Arg Val Phe Gly Met Phe Arg Gln Ala Ser Asp
    530                 535                 540

Arg Glu Ala Val Tyr Ala Cys Phe Thr Phe Ser His Trp Leu Val Tyr
545                 550                 555                 560

Ala Asn Ser Ala Ala Asn Pro Ile Ile Tyr Asn Phe Leu Ser Gly Lys
                565                 570                 575

Phe Arg Glu Gln Phe Lys Ala Ala Phe Ser Cys Cys Leu Pro Gly Leu
            580                 585                 590

Gly Pro Cys Gly Ser Leu Lys Ala Pro Ser Pro Arg Ser Ser Ala Ser
        595                 600                 605

His Lys Ser Leu Ser Leu Gln Ser Arg Cys Ser Ile Ser Lys Ile Ser
    610                 615                 620

Glu His Val Val Leu Thr Ser Val Thr Thr Val Leu Pro
625                 630                 635
```

<210> SEQ ID NO 45

<211> LENGTH: 1677
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 45
atggaccccc ttaacctctc atggtacgac gatgatcttg agaggcagaa ctggtcccga 60
ccattcaatg ggtctgatgg taaggctgac cggcctcatt acaattatta tgcgaccctg 120
cttactcttc ttatcgctgt gatcgtattc ggcaacgtct tggtttgcat ggcagtctct 180
agggaaaaag cgctccagac gacaactaat tacttgattg tgagtctggc tgtagctgac 240
ttgcttgtgg cgaccctggt gatgccatgg gtcgtatact tggaagtcgt tggcgagtgg 300
aagttttcta ggattcattg cgacatattt gtaactctgg acgtaatgat gtgtactgct 360
tccattttga acctctgcgc tatatccatt gacaggtaca cggcggttgc tatgccgatg 420
ctttataata cccggtattc aagcaaaagg cgagtaactg tgatgataag cattgtatgg 480
gtgctcagtt tcacaattag ctgccctctg ctcttcggcc ttaacaacgc ggatcaaaat 540
gaatgcatca tcgcaaaccc ggcttttgtg gtttatagca gcattgttag cttctatgtg 600
ccattcatag ttacgctcct tgtttatata aaaatttata tcgtgcttag gcgccgccga 660
aaacgagtta acaccaagcg gagcagcctg agctcactca ttaatgtata tatcaaagct 720
gataagcaaa aaaacggtat caaggctaat tttaagatca gacataatat agaggatgga 780
ggcgttcaac tggcctacca ctaccagcaa aacacgccga tcggggatgg gccagtactt 840
ctgccagata accattatct ctcagttcaa agcaaactct ctaaggaccc taatgagaaa 900
cgagatcata tggttctgct cgaattcgtt acagccgccg gtatcacact tgggatggac 960
gagttgtata agggtggaac aggagggtca atggtaagca aaggcgagga gctgtttacg 1020
ggggtcgtcc cgatacttgt tgaactcgac ggcgatgtca acgggcacaa attctcagtg 1080
agtggcgagg gggaaggaga cgccacttat ggaaaactga cattgaaatt catatgtacg 1140
actgggaagt tgcctgtgcc ttggcctacg ctcgttacta cacttactta cggggtacag 1200
tgtttcagta ggtatccaga tcacatgaaa cagcacgatt ttttcaagag tgcaatgccg 1260
gaaggatata tacaagaaag aactattttc tttaaagatg acggcaacta taaaacgcga 1320
gcagaggtga agtttgaggg cgataccttg gttaatagga tcgaactcaa aggcatagac 1380
ttcaaagaag acggaaacat tctgggtcac aaactggaat acaacaatca tgaccaactg 1440
cagaaggaaa agaaggccac gcaaatgttg gcaatcgtgc tcggcgtgtt cataatctgc 1500
tggcttccat tttttataac gcatatattg aacatacact gtgattgcaa tattccacca 1560
gtcctgtata gtgcgtttac gtggttgggt tatgtgaatt ctgcggttaa cccgatcatt 1620
tacaccacgt tcaacataga attccgaaag gcattcctca aaatattgca ttgttag 1677

<210> SEQ ID NO 46
<211> LENGTH: 550
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (140)..(140)
<223> OTHER INFORMATION: Phe, Ala, Gly, Val, Ile, Leu, Met, Ser, or Thr

<400> SEQUENCE: 46

```
Met Asp Pro Leu Asn Leu Ser Trp Tyr Asp Asp Asp Leu Glu Arg Gln
1               5                   10                  15

Asn Trp Ser Arg Pro Phe Asn Gly Ser Asp Gly Lys Ala Asp Arg Pro
            20                  25                  30

His Tyr Asn Tyr Tyr Ala Thr Leu Leu Thr Leu Leu Ile Ala Val Ile
        35                  40                  45

Val Phe Gly Asn Val Leu Val Cys Met Ala Val Ser Arg Glu Lys Ala
    50                  55                  60

Leu Gln Thr Thr Thr Asn Tyr Leu Ile Val Ser Leu Ala Val Ala Asp
65                  70                  75                  80

Leu Leu Val Ala Thr Leu Val Met Pro Trp Val Val Tyr Leu Glu Val
                85                  90                  95

Val Gly Glu Trp Lys Phe Ser Arg Ile His Cys Asp Ile Phe Val Thr
            100                 105                 110

Leu Asp Val Met Met Cys Thr Ala Ser Ile Leu Asn Leu Cys Ala Ile
        115                 120                 125

Ser Ile Asp Arg Tyr Thr Ala Val Ala Met Pro Xaa Leu Tyr Asn Thr
    130                 135                 140

Arg Tyr Ser Ser Lys Arg Arg Val Thr Val Met Ile Ser Ile Val Trp
145                 150                 155                 160

Val Leu Ser Phe Thr Ile Ser Cys Pro Leu Leu Phe Gly Leu Asn Asn
                165                 170                 175

Ala Asp Gln Asn Glu Cys Ile Ile Ala Asn Pro Ala Phe Val Val Tyr
            180                 185                 190

Ser Ser Ile Val Ser Phe Tyr Val Pro Phe Ile Val Thr Leu Leu Val
        195                 200                 205

Tyr Ile Lys Ile Tyr Ile Val Leu Arg Arg Arg Arg Lys Leu Ser Ser
    210                 215                 220

Leu Ile Asn Val Tyr Ile Lys Ala Asp Lys Gln Lys Asn Gly Ile Lys
225                 230                 235                 240

Ala Asn Phe Lys Ile Arg His Asn Ile Glu Asp Gly Gly Val Gln Leu
                245                 250                 255

Ala Tyr His Tyr Gln Gln Asn Thr Pro Ile Gly Asp Gly Pro Val Leu
            260                 265                 270

Leu Pro Asp Asn His Tyr Leu Ser Val Gln Ser Lys Leu Ser Lys Asp
        275                 280                 285

Pro Asn Glu Lys Arg Asp His Met Val Leu Leu Glu Phe Val Thr Ala
    290                 295                 300

Ala Gly Ile Thr Leu Gly Met Asp Glu Leu Tyr Lys Gly Gly Thr Gly
305                 310                 315                 320

Gly Ser Met Val Ser Lys Gly Glu Glu Leu Phe Thr Gly Val Val Pro
                325                 330                 335

Ile Leu Val Glu Leu Asp Gly Asp Val Asn Gly His Lys Phe Ser Val
            340                 345                 350

Ser Gly Glu Gly Glu Gly Asp Ala Thr Tyr Gly Lys Leu Thr Leu Lys
        355                 360                 365

Phe Ile Cys Thr Thr Gly Lys Leu Pro Val Pro Trp Pro Thr Leu Val
    370                 375                 380

Thr Thr Leu Thr Tyr Gly Val Gln Cys Phe Ser Arg Tyr Pro Asp His
385                 390                 395                 400

Met Lys Gln His Asp Phe Phe Lys Ser Ala Met Pro Glu Gly Tyr Ile
                405                 410                 415
```

```
Gln Glu Arg Thr Ile Phe Phe Lys Asp Asp Gly Asn Tyr Lys Thr Arg
            420                 425                 430

Ala Glu Val Lys Phe Glu Gly Asp Thr Leu Val Asn Arg Ile Glu Leu
        435                 440                 445

Lys Gly Ile Asp Phe Lys Glu Asp Gly Asn Ile Leu Gly His Lys Leu
    450                 455                 460

Glu Tyr Asn Asn His Asp Gln Leu Gln Lys Glu Lys Lys Ala Thr Gln
465                 470                 475                 480

Met Leu Ala Ile Val Leu Gly Val Phe Ile Ile Cys Trp Leu Pro Phe
                485                 490                 495

Phe Ile Thr His Ile Leu Asn Ile His Cys Asp Cys Asn Ile Pro Pro
            500                 505                 510

Val Leu Tyr Ser Ala Phe Thr Trp Leu Gly Tyr Val Asn Ser Ala Val
        515                 520                 525

Asn Pro Ile Ile Tyr Thr Thr Phe Asn Ile Glu Phe Arg Lys Ala Phe
    530                 535                 540

Leu Lys Ile Leu His Cys
545                 550
```

<210> SEQ ID NO 47
<211> LENGTH: 1671
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 47

```
atggggaaca gatccactgc agatgcagac ggtcttctcg caggccgggg acctgctgcc     60

ggagcgagcg ctggggcttc cgcaggtctt gctgggcagg gggccgcggc cttggttgga    120

ggcgttttgc ttataggggc cgttcttgct ggcaatagtt tggtatgtgt ttcagttgcg    180

acagagcgcg cacttcagac gccgactaac tcctttatag tgagtttggc tgctgcagat    240

ctcttgttgg cattgttggt actcccactg ttcgtttatt cagaagtaca gggtggcgca    300

tggctcctgt cacccaggtt gtgtgatgcc ttgatggcca tggatgttat gctgtgtacc    360

gcttctatct ttaacctttg tgctatcagt gttgacagat tcgtcgcggt cgcggtccct    420

ctgaggtata accggcaagg aggcagcagg aggcaactgc tgctgatcgg cgcaacttgg    480

ctcctctccg cagcagtggc cgcgcctgtt ctgtgtggtc tcaacgacgt tcgcggcaga    540

gacccggctg tatgtcgcct cgaggataga gattatgtcg tatactcaag tgtgtgttcc    600

tttttcttc cttgcccact gatgcttctg ttgtattggg ctacctttag aggactgcaa    660

cgctgggaag tcctgagctc actcattaat gtatatatca aagctgataa gcaaaaaaac    720

ggtatcaagg ctaattttaa gatcagacat aatatagagg atggaggcgt tcaactggcc    780

taccactacc agcaaaacac gccgatcggg gatgggccag tacttctgcc agataaccat    840

tatctctcag ttcaaagcaa actctctaag gaccctaatg agaaacgaga tcatatggtt    900

ctgctcgaat tcgttacagc cgccggtatc acacttggga tggacgagtt gtataagggt    960

ggaacaggag ggtcaatggt aagcaaaggc gaggagctgt ttacgggggt cgtcccgata   1020

cttgttgaac tcgacggcga tgtcaacggg cacaaattct cagtgagtgg cgagggggaa   1080

ggagacgcca cttatggaaa actgacattg aaattcatat gtacgactgg gaagttgcct   1140

gtgccttggc ctacgctcgt tactacactt acttacgggg tacagtgttt cagtaggtat   1200

ccagatcaca tgaaacagca cgattttttc aagagtgcaa tgccggaagg atatatacaa   1260
```

```
gaaagaacta ttttctttaa agatgacggc aactataaaa cgcgagcaga ggtgaagttt   1320

gagggcgata ccttggttaa taggatcgaa ctcaaaggca tagacttcaa agaagacgga   1380

aacattctgg gtcacaaact ggaatacaac aatcatgacc aactgggccg cgaacggaaa   1440

gccatgcgag ttttgccggt ggtagtaggg gcattccttc tttgttggac ccctttttt   1500

gtggtgcata taacgcaggc tctgtgcccg gcctgttctg tcccaccccg cctcgtgtca   1560

gctgtcactt ggttgggtta cgtaaactca gccctcaatc cagttatcta tacggttttc   1620

aatgccgagt tcaggaatgt ttttaggaag gcccttagag cctgttgtta g            1671
```

```
<210> SEQ ID NO 48
<211> LENGTH: 556
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (141)..(141)
<223> OTHER INFORMATION: Phe, Ala, Gly, Val, Ile, Leu, Met, Ser, or Thr

<400> SEQUENCE: 48

Met Gly Asn Arg Ser Thr Ala Asp Ala Asp Gly Leu Leu Ala Gly Arg
1               5                   10                  15

Gly Pro Ala Ala Gly Ala Ser Ala Gly Ala Ser Ala Gly Leu Ala Gly
            20                  25                  30

Gln Gly Ala Ala Ala Leu Val Gly Gly Val Leu Leu Ile Gly Ala Val
        35                  40                  45

Leu Ala Gly Asn Ser Leu Val Cys Val Ser Val Ala Thr Glu Arg Ala
    50                  55                  60

Leu Gln Thr Pro Thr Asn Ser Phe Ile Val Ser Leu Ala Ala Ala Asp
65                  70                  75                  80

Leu Leu Leu Ala Leu Leu Val Leu Pro Leu Phe Val Tyr Ser Glu Val
                85                  90                  95

Gln Gly Gly Ala Trp Leu Leu Ser Pro Arg Leu Cys Asp Ala Leu Met
            100                 105                 110

Ala Met Asp Val Met Leu Cys Thr Ala Ser Ile Phe Asn Leu Cys Ala
        115                 120                 125

Ile Ser Val Asp Arg Phe Val Ala Val Ala Val Pro Xaa Arg Tyr Asn
    130                 135                 140

Arg Gln Gly Gly Ser Arg Arg Gln Leu Leu Leu Ile Gly Ala Thr Trp
145                 150                 155                 160

Leu Leu Ser Ala Ala Val Ala Ala Pro Val Leu Cys Gly Leu Asn Asp
                165                 170                 175

Val Arg Gly Arg Asp Pro Ala Val Cys Arg Leu Glu Asp Arg Asp Tyr
            180                 185                 190

Val Val Tyr Ser Ser Val Cys Ser Phe Phe Leu Pro Cys Pro Leu Met
        195                 200                 205

Leu Leu Leu Tyr Trp Ala Thr Phe Arg Gly Leu Gln Arg Trp Glu Val
    210                 215                 220

Leu Ser Ser Leu Ile Asn Val Tyr Ile Lys Ala Asp Lys Gln Lys Asn
225                 230                 235                 240

Gly Ile Lys Ala Asn Phe Lys Ile Arg His Asn Ile Glu Asp Gly Gly
                245                 250                 255

Val Gln Leu Ala Tyr His Tyr Gln Gln Asn Thr Pro Ile Gly Asp Gly
```

```
            260                 265                 270

Pro Val Leu Leu Pro Asp Asn His Tyr Leu Ser Val Gln Ser Lys Leu
        275                 280                 285

Ser Lys Asp Pro Asn Glu Lys Arg Asp His Met Val Leu Leu Glu Phe
    290                 295                 300

Val Thr Ala Ala Gly Ile Thr Leu Gly Met Asp Glu Leu Tyr Lys Gly
305                 310                 315                 320

Gly Thr Gly Gly Ser Met Val Ser Lys Gly Glu Glu Leu Phe Thr Gly
                325                 330                 335

Val Val Pro Ile Leu Val Glu Leu Asp Gly Asp Val Asn Gly His Lys
            340                 345                 350

Phe Ser Val Ser Gly Glu Gly Glu Gly Asp Ala Thr Tyr Gly Lys Leu
        355                 360                 365

Thr Leu Lys Phe Ile Cys Thr Thr Gly Lys Leu Pro Val Pro Trp Pro
    370                 375                 380

Thr Leu Val Thr Thr Leu Thr Tyr Gly Val Gln Cys Phe Ser Arg Tyr
385                 390                 395                 400

Pro Asp His Met Lys Gln His Asp Phe Phe Lys Ser Ala Met Pro Glu
                405                 410                 415

Gly Tyr Ile Gln Glu Arg Thr Ile Phe Phe Lys Asp Asp Gly Asn Tyr
            420                 425                 430

Lys Thr Arg Ala Glu Val Lys Phe Glu Gly Asp Thr Leu Val Asn Arg
        435                 440                 445

Ile Glu Leu Lys Gly Ile Asp Phe Lys Glu Asp Gly Asn Ile Leu Gly
    450                 455                 460

His Lys Leu Glu Tyr Asn Asn His Asp Gln Leu Gly Arg Glu Arg Lys
465                 470                 475                 480

Ala Met Arg Val Leu Pro Val Val Val Gly Ala Phe Leu Leu Cys Trp
                485                 490                 495

Thr Pro Phe Phe Val Val His Ile Thr Gln Ala Leu Cys Pro Ala Cys
            500                 505                 510

Ser Val Pro Pro Arg Leu Val Ser Ala Val Thr Trp Leu Gly Tyr Val
        515                 520                 525

Asn Ser Ala Leu Asn Pro Val Ile Tyr Thr Val Phe Asn Ala Glu Phe
    530                 535                 540

Arg Asn Val Phe Arg Lys Ala Leu Arg Ala Cys Cys
545                 550                 555


<210> SEQ ID NO 49
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(11)
<223> OTHER INFORMATION: Any amino acid

<400> SEQUENCE: 49

Gln Leu Gln Lys Ile Asp Leu Ser Ser Xaa Xaa
1               5                   10


<210> SEQ ID NO 50
<211> LENGTH: 6
<212> TYPE: PRT
<213> ORGANISM: Artificial Sequence
```

<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any amino acid

<400> SEQUENCE: 50

Leu Ser Ser Leu Ile Xaa
1               5

<210> SEQ ID NO 51
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid

<400> SEQUENCE: 51

Xaa Asn His Asp Gln Leu
1               5

<210> SEQ ID NO 52
<211> LENGTH: 8
<212> TYPE: PRT
<213> ORGANISM: Homo sapiens

<400> SEQUENCE: 52

Arg Ile Tyr Arg Ile Ala Gln Lys
1               5

<210> SEQ ID NO 53
<211> LENGTH: 8
<212> TYPE: PRT
<213> ORGANISM: Homo sapiens

<400> SEQUENCE: 53

Lys Arg Glu Thr Lys Val Leu Lys
1               5

<210> SEQ ID NO 54
<211> LENGTH: 8
<212> TYPE: PRT
<213> ORGANISM: Homo sapiens

<400> SEQUENCE: 54

Arg Val Phe Arg Glu Ala Gln Lys
1               5

<210> SEQ ID NO 55
<211> LENGTH: 8
<212> TYPE: PRT
<213> ORGANISM: Homo sapiens

<400> SEQUENCE: 55

Arg Glu Gln Lys Ala Leu Lys Thr
1               5

<210> SEQ ID NO 56
<211> LENGTH: 8
<212> TYPE: PRT

<213> ORGANISM: Homo sapiens

<400> SEQUENCE: 56

Arg Val Phe Gln Glu Ala Lys Arg
1               5

<210> SEQ ID NO 57
<211> LENGTH: 8
<212> TYPE: PRT
<213> ORGANISM: Homo sapiens

<400> SEQUENCE: 57

Lys Glu His Lys Ala Leu Lys Thr
1               5

<210> SEQ ID NO 58
<211> LENGTH: 8
<212> TYPE: PRT
<213> ORGANISM: Homo sapiens

<400> SEQUENCE: 58

Ile Val Leu Arg Arg Arg Arg Lys
1               5

<210> SEQ ID NO 59
<211> LENGTH: 8
<212> TYPE: PRT
<213> ORGANISM: Homo sapiens

<400> SEQUENCE: 59

Gln Lys Glu Lys Lys Ala Thr Gln
1               5

<210> SEQ ID NO 60
<211> LENGTH: 8
<212> TYPE: PRT
<213> ORGANISM: Homo sapiens

<400> SEQUENCE: 60

Arg Gly Leu Gln Arg Trp Glu Val
1               5

<210> SEQ ID NO 61
<211> LENGTH: 8
<212> TYPE: PRT
<213> ORGANISM: Homo sapiens

<400> SEQUENCE: 61

Gly Arg Glu Arg Lys Ala Met Arg
1               5

<210> SEQ ID NO 62
<211> LENGTH: 8
<212> TYPE: PRT
<213> ORGANISM: Homo sapiens

<400> SEQUENCE: 62

Leu Met Ile Leu Arg Leu Lys Ser
1               5

<210> SEQ ID NO 63
<211> LENGTH: 8
<212> TYPE: PRT
<213> ORGANISM: Homo sapiens

<400> SEQUENCE: 63

Arg Glu Lys Asp Arg Asn Leu Arg
1 5

<210> SEQ ID NO 64
<211> LENGTH: 8
<212> TYPE: PRT
<213> ORGANISM: Homo sapiens

<400> SEQUENCE: 64

Lys Glu Lys Asp Arg Asn Leu Arg
1 5

<210> SEQ ID NO 65
<211> LENGTH: 8
<212> TYPE: PRT
<213> ORGANISM: Homo sapiens

<400> SEQUENCE: 65

Arg Ile Tyr Gln Ile Ala Lys Arg
1 5

<210> SEQ ID NO 66
<211> LENGTH: 8
<212> TYPE: PRT
<213> ORGANISM: Homo sapiens

<400> SEQUENCE: 66

Arg Glu Lys Arg Phe Thr Phe Val
1 5

<210> SEQ ID NO 67
<211> LENGTH: 8
<212> TYPE: PRT
<213> ORGANISM: Homo sapiens

<400> SEQUENCE: 67

Val Leu Val Leu Gln Ala Arg Arg
1 5

<210> SEQ ID NO 68
<211> LENGTH: 8
<212> TYPE: PRT
<213> ORGANISM: Homo sapiens

<400> SEQUENCE: 68

Lys Pro Ser Asp Leu Arg Ser Phe
1 5

<210> SEQ ID NO 69
<211> LENGTH: 8
<212> TYPE: PRT
<213> ORGANISM: Homo sapiens

<400> SEQUENCE: 69

Leu Thr Ile Lys Ser Leu Gln Lys
1 5

<210> SEQ ID NO 70
<211> LENGTH: 8
<212> TYPE: PRT
<213> ORGANISM: Homo sapiens

<400> SEQUENCE: 70

Asn Glu Gln Lys Ala Cys Lys Val
1               5

<210> SEQ ID NO 71
<211> LENGTH: 8
<212> TYPE: PRT
<213> ORGANISM: Homo sapiens

<400> SEQUENCE: 71

Arg Val Tyr Val Val Ala Lys Arg
1               5

<210> SEQ ID NO 72
<211> LENGTH: 8
<212> TYPE: PRT
<213> ORGANISM: Homo sapiens

<400> SEQUENCE: 72

Ser Arg Glu Lys Lys Ala Ala Lys
1               5

<210> SEQ ID NO 73
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Leu Ser Ser Leu Ile
1               5

<210> SEQ ID NO 74
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Asn His Asp Gln Leu
1               5

<210> SEQ ID NO 75
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gln Leu Gln Lys Ile Asp Leu Ser Ser Leu Ile
1               5                   10

<210> SEQ ID NO 76
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Arg Gln Leu Gln

1

<210> SEQ ID NO 77
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 77

Cys Trp Leu Pro
1

<210> SEQ ID NO 78
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 78

Gln Leu Gln Lys Ile Asp Lys Ser Glu Gly Arg Phe His Val Gln Asn
1 5 10 15

Leu Ser

<210> SEQ ID NO 79
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 79

Lys Glu His Lys
1

<210> SEQ ID NO 80
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 80

Phe Cys Leu Lys
1

<210> SEQ ID NO 81
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 81

Ala Lys Arg Gln
1

<210> SEQ ID NO 82
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 82

Leu Gln Lys Ile
1

<210> SEQ ID NO 83
<211> LENGTH: 23
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 83

Lys Ser Glu Gly Arg Phe His Val Gln Leu Ser Gln Val Glu Gln Asp
1 5 10 15

Gly Arg Thr Gly His Gly Leu
20

<210> SEQ ID NO 84
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 84

Gln Asn Leu Ser
1

<210> SEQ ID NO 85
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 85

Ala Glu Val Lys
1

<210> SEQ ID NO 86
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 86

Glu Ala Lys Arg
1

<210> SEQ ID NO 87
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 87

Gln Leu Gln Lys
1

<210> SEQ ID NO 88
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 88

Lys Arg Gln Leu
1

<210> SEQ ID NO 89
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 89

Gln Lys Ile Asp
1

<210> SEQ ID NO 90
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 90

Arg Met Leu Ser
1

<210> SEQ ID NO 91
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 91

Ile Ala Gln Lys
1

<210> SEQ ID NO 92
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 92

Lys Arg Glu Thr
1

<210> SEQ ID NO 93
<211> LENGTH: 4
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 93

Ala Lys Asn Cys
1

<210> SEQ ID NO 94
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gln Thr Thr Thr
1

<210> SEQ ID NO 95
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Ser Leu Gln Lys
1

<210> SEQ ID NO 96
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Asn Glu Gln Lys
1

<210> SEQ ID NO 97
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Thr Arg Ala Lys
1

<210> SEQ ID NO 98
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Leu Ala Ser Phe
1

<210> SEQ ID NO 99
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 99

Phe Cys Glu Asn Glu Val
1 5

<210> SEQ ID NO 100
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 100
gtcagttttt acgttcctct ggttattatg 30

<210> SEQ ID NO 101
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 101
catgataatt ccaagcgtct tcagcg 26

<210> SEQ ID NO 102
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 102
ggcagcaagg agaaggaccg c 21

<210> SEQ ID NO 103
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 103
actgagcatt cgaactgatt tgagcc 26

<210> SEQ ID NO 104
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 104
cagaccacca caggtaatgg aaagcctg 28

<210> SEQ ID NO 105
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 105
gcaattcttg gcgtggactg ctgc 24

<210> SEQ ID NO 106
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 106
cttgccagct tctcattcct tcccc 25

<210> SEQ ID NO 107
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 107
tttggcccga gtgccgaggt c 21

<210> SEQ ID NO 108
<211> LENGTH: 59
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (28)..(29)
<223> OTHER INFORMATION: a, c, t, g, unknown or other
<220> FEATURE:
<221> NAME/KEY: modified_base
<222> LOCATION: (31)..(32)
<223> OTHER INFORMATION: a, c, t, g, unknown or other

<400> SEQUENCE: 108
ggacgctttc atgtgcagaa tctttcannk nnkaacgtct atatcaaggc cgacaagca 59

<210> SEQ ID NO 109
<211> LENGTH: 55
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (27)..(28)
<223> OTHER INFORMATION: a, c, t, g, unknown or other
<220> FEATURE:
<221> NAME/KEY: modified_base
<222> LOCATION: (30)..(31)
<223> OTHER INFORMATION: a, c, t, g, unknown or other

<400> SEQUENCE: 109
ctgtgcgtcc gtcctgttca acttgmnnmn ngttgtactc cagcttgtgc cccag 55

<210> SEQ ID NO 110
<211> LENGTH: 54
<212> TYPE: DNA
<213> ORGANISM: Artificial Sequence
<220> FEATURE:
<223> OTHER INFORMATION: Description of Artificial Sequence: Synthetic
primer
<220> FEATURE:
<221> NAME/KEY: modified_base
<222> LOCATION: (28)..(29)
<223> OTHER INFORMATION: a, c, t, g, unknown or other
<220> FEATURE:
<221> NAME/KEY: modified_base
<222> LOCATION: (31)..(32)
<223> OTHER INFORMATION: a, c, t, g, unknown or other

<400> SEQUENCE: 110
ttggaagcgg aaactgctcc tctgccannk nnkaacgtct atatcaaggc cgac 54

<210> SEQ ID NO 111
<211> LENGTH: 49
<212> TYPE: DNA
<213> ORGANISM: Artificial Sequence
<220> FEATURE:
<223> OTHER INFORMATION: Description of Artificial Sequence: Synthetic
primer
<220> FEATURE:
<221> NAME/KEY: modified_base
<222> LOCATION: (27)..(28)
<223> OTHER INFORMATION: a, c, t, g, unknown or other
<220> FEATURE:
<221> NAME/KEY: modified_base
<222> LOCATION: (30)..(31)
<223> OTHER INFORMATION: a, c, t, g, unknown or other

<400> SEQUENCE: 111
gcggccgctg tacatcaggt tgtcamnnmn ngttgtactc cagcttgtg 49

<210> SEQ ID NO 112
<211> LENGTH: 55
<212> TYPE: DNA
<213> ORGANISM: Artificial Sequence
<220> FEATURE:
<223> OTHER INFORMATION: Description of Artificial Sequence: Synthetic
primer
<220> FEATURE:
<221> NAME/KEY: modified_base
<222> LOCATION: (25)..(26)
<223> OTHER INFORMATION: a, c, t, g, unknown or other
<220> FEATURE:
<221> NAME/KEY: modified_base
<222> LOCATION: (28)..(29)
<223> OTHER INFORMATION: a, c, t, g, unknown or other

<400> SEQUENCE: 112
gcagcagtcc acgccaagaa ttgcnnknnk aacgtctata tcaaggccga caagc 55

<210> SEQ ID NO 113
<211> LENGTH: 58
<212> TYPE: DNA
<213> ORGANISM: Artificial Sequence
<220> FEATURE:
<223> OTHER INFORMATION: Description of Artificial Sequence: Synthetic
primer
<220> FEATURE:
<221> NAME/KEY: modified_base
<222> LOCATION: (30)..(31)
<223> OTHER INFORMATION: a, c, t, g, unknown or other
<220> FEATURE:
<221> NAME/KEY: modified_base
<222> LOCATION: (33)..(34)

<223> OTHER INFORMATION: a, c, t, g, unknown or other

<400> SEQUENCE: 113
caggctttcc attacctgtg gtggtctgmn nmnngttgta ctccagcttg tgccccag 58

<210> SEQ ID NO 114
<211> LENGTH: 54
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (22)..(23)
<223> OTHER INFORMATION: a, c, t, g, unknown or other
<220> FEATURE:
<221> NAME/KEY: modified_base
<222> LOCATION: (25)..(26)
<223> OTHER INFORMATION: a, c, t, g, unknown or other

<400> SEQUENCE: 114
gacctcggca ctcgggccaa annknnkaac gtctatatca aggccgacaa gcag 54

<210> SEQ ID NO 115
<211> LENGTH: 59
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (27)..(28)
<223> OTHER INFORMATION: a, c, t, g, unknown or other
<220> FEATURE:
<221> NAME/KEY: modified_base
<222> LOCATION: (30)..(31)
<223> OTHER INFORMATION: a, c, t, g, unknown or other

<400> SEQUENCE: 115
ggggaaggaa tgagaagctg gcaagmnnmn ngttgtactc cagcttgtgc cccaggatg 59

<210> SEQ ID NO 116
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 116

Ala Lys Arg Gln Leu Gln Lys Ile
1               5

<210> SEQ ID NO 117
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 117

Gln Asn Leu Ser Gln Val Glu Gln
1               5

<210> SEQ ID NO 118
<211> LENGTH: 8

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 118

Glu Ala Lys Arg Lys Glu His Lys
1 5

<210> SEQ ID NO 119
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 119

Lys Arg Gln Leu Phe Cys Leu Lys
1 5

<210> SEQ ID NO 120
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 120

Ile Ala Gln Lys Lys Arg Glu Thr
1 5

<210> SEQ ID NO 121
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 121

Ser Leu Gln Lys Asn Glu Gln Lys
1 5

<210> SEQ ID NO 122
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 122

Arg Leu Lys Ser Arg Glu Lys Asp
1 5

<210> SEQ ID NO 123
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 123

Ile Ala Lys Arg Arg Glu Lys Arg 1 5

<210> SEQ ID NO 124
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 124

Gln Ala Arg Arg Lys Pro Ser Asp
1 5

<210> SEQ ID NO 125
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 125

Gln Leu Gln Lys Ile Asp Lys Ser Glu Gly Arg Phe His Val Gln Asn
1 5 10 15

Leu Ser Lys Glu His Lys
20

<210> SEQ ID NO 126
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 126

Gln Leu Gln Lys Ile Asp Lys Ser Glu Gly Arg Phe His Val Gln Asn
1 5 10 15

Leu Ser Phe Cys Leu Lys
20

<210> SEQ ID NO 127
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 127

Gly Gly Thr Gly Gly Ser
1 5

<210> SEQ ID NO 128
<211> LENGTH: 237
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 128

Met Val Ser Lys Gly Glu Glu Leu Phe Thr Gly Val Val Pro Ile Leu
1 5 10 15

Val Glu Leu Asp Gly Asp Val Asn Gly His Lys Phe Ser Val Ser Gly

```
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Val Gln Cys Phe Ser Arg Tyr Pro Asp His Met Lys Gln His
65                  70                  75                  80

Asp Phe Phe Lys Ser Ala Met Pro Glu Gly Tyr Val Gln Glu Arg Thr
                85                  90                  95

Ile Phe Phe Lys Asp Asp Gly Asn Tyr Lys Thr Arg Ala Glu Val Lys
            100                 105                 110

Phe Glu Gly Asp Thr Leu Val Asn Arg Ile Glu Leu Lys Gly Ile Asp
        115                 120                 125

Phe Lys Glu Asp Gly Asn Ile Leu Gly His Lys Leu Glu Tyr Asn Tyr
    130                 135                 140

Asn Ser His Asn Val Tyr Ile Met Ala Asp Lys Gln Lys Asn Gly Ile
145                 150                 155                 160

Lys Val Asn Phe Lys Ile Arg His Asn Ile Glu Asp Gly Ser Val Gln
                165                 170                 175

Leu Ala Asp His Tyr Gln Gln Asn Thr Pro Ile Gly Asp Gly Pro Val
            180                 185                 190

Leu Leu Pro Asp Asn His Tyr Leu Ser Thr Gln Ser Ala Leu Ser Lys
        195                 200                 205

Asp Pro Asn Glu Lys Arg Asp His Met Val Leu Leu Glu Phe Val Thr
    210                 215                 220

Ala Ala Gly Ile Thr Leu Gly Met Asp Glu Leu Tyr Lys
225                 230                 235


<210> SEQ ID NO 129
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Gly Glu Glu Leu Phe Thr Gly Val Val Pro Ile Leu Val Glu Leu Asp
1               5                   10                  15

Gly Asp Val Asn Gly His Lys Phe Ser Val Ser Gly Glu Gly Glu Gly
            20                  25                  30

Asp Ala Thr Tyr Gly Lys Leu Thr Leu Lys Phe Ile Cys Thr Thr Gly
        35                  40                  45

Lys Leu Pro Val Pro Trp Pro Thr Leu Val Thr Thr Leu Thr Val Gln
    50                  55                  60

Cys Phe Ser Arg Tyr Pro Asp His Met Lys Gln His Asp Phe Phe Lys
65                  70                  75                  80

Ser Ala Met Pro Glu Gly Tyr Val Gln Glu Arg Thr Ile Phe Phe Lys
                85                  90                  95

Asp Asp Gly Asn Tyr Lys Thr Arg Ala Glu Val Lys Phe Glu Gly Asp
            100                 105                 110

Thr Leu Val Asn Arg Ile Glu Leu Lys Gly Ile Asp Phe Lys Glu Asp
        115                 120                 125

Gly Asn Ile Leu Gly His Lys Leu Glu Tyr Asn Tyr Ile Ser His Asn
    130                 135                 140
```

Val Tyr Ile Thr Ala Asp Lys Gln Lys Asn Gly Ile Lys Ala Asn Phe
145 150 155 160

Lys Ile Arg His Asn Ile Glu Asp Gly Ser Val Gln Leu Ala Asp His
165 170 175

Tyr Gln Gln Asn Thr Pro Ile Gly Asp Gly Pro Val Leu Leu Pro Asp
180 185 190

Asn His Tyr Leu Ser Thr Gln Ser Ala Leu Ser Lys Asp Pro Asn Glu
195 200 205

Lys Arg Asp His Met Val Leu Leu Glu Phe Val Thr Ala Ala Gly Ile
210 215 220

Thr
225

<210> SEQ ID NO 130
<211> LENGTH: 225
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 130

Lys Gly Glu Glu Leu Phe Thr Gly Val Val Pro Ile Leu Val Glu Leu
1 5 10 15

Asp Gly Asp Val Asn Gly His Lys Phe Ser Val Ser Gly Glu Gly Glu
20 25 30

Gly Asp Ala Thr Tyr Gly Lys Leu Thr Leu Lys Phe Ile Cys Thr Thr
35 40 45

Gly Lys Leu Pro Val Pro Trp Pro Thr Leu Val Thr Thr Phe Thr Leu
50 55 60

Gln Cys Phe Ala Arg Tyr Pro Asp His Met Lys Arg His Asp Phe Phe
65 70 75 80

Lys Ser Ala Met Pro Glu Gly Tyr Val Gln Glu Arg Thr Ile Phe Phe
85 90 95

Lys Asp Asp Gly Asn Tyr Lys Thr Arg Ala Glu Val Lys Phe Glu Gly
100 105 110

Asp Thr Leu Val Asn Arg Ile Glu Leu Lys Gly Ile Asp Phe Lys Glu
115 120 125

Asp Gly Asn Ile Leu Gly His Lys Leu Glu Tyr Asn Tyr Asn Ser His
130 135 140

Asn Val Tyr Ile Met Ala Asp Lys Gln Lys Asn Gly Ile Lys Val Asn
145 150 155 160

Phe Lys Ile Arg His Asn Ile Glu Asp Gly Ser Val Gln Leu Ala Asp
165 170 175

His Tyr Gln Gln Asn Thr Pro Ile Gly Asp Gly Pro Val Leu Leu Pro
180 185 190

Asp Asn His Tyr Leu Ser Tyr Gln Ser Ala Leu Ser Lys Asp Pro Asn
195 200 205

Glu Lys Arg Asp His Met Val Leu Leu Glu Phe Val Thr Ala Ala Gly
210 215 220

Ile
225

<210> SEQ ID NO 131
<211> LENGTH: 229
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 131

Ser Met Ser Lys Gly Glu Glu Leu Phe Thr Gly Val Val Pro Ile Leu
1 5 10 15

Val Glu Leu Asp Gly Asp Val Asn Gly His Lys Phe Ser Val Ser Gly
20 25 30

Glu Gly Glu Gly Asp Ala Thr Tyr Gly Lys Leu Thr Leu Lys Phe Ile
35 40 45

Cys Thr Thr Gly Lys Leu Pro Val Pro Trp Pro Thr Leu Val Thr Thr
50 55 60

Phe Thr Val Gln Cys Phe Ser Arg Tyr Pro Asp His Met Lys Arg His
65 70 75 80

Asp Phe Phe Lys Ser Ala Met Pro Glu Gly Tyr Val Gln Glu Arg Thr
85 90 95

Ile Ser Phe Lys Asp Asp Gly Asn Tyr Lys Thr Arg Ala Glu Val Lys
100 105 110

Phe Glu Gly Asp Thr Leu Val Asn Arg Ile Glu Leu Lys Gly Ile Asp
115 120 125

Phe Lys Glu Asp Gly Asn Ile Leu Gly His Lys Leu Glu Tyr Asn Tyr
130 135 140

Asn Ser His Asn Val Tyr Ile Thr Ala Asp Lys Gln Lys Asn Gly Ile
145 150 155 160

Lys Ala Asn Phe Lys Ile Arg His Asn Ile Glu Asp Gly Ser Val Gln
165 170 175

Leu Ala Asp His Tyr Gln Gln Asn Thr Pro Ile Gly Asp Gly Pro Val
180 185 190

Leu Leu Pro Asp Asn His Tyr Leu Ser His Gln Ser Ala Leu Ser Lys
195 200 205

Asp Pro Asn Glu Lys Arg Asp His Met Val Leu Leu Glu Phe Val Thr
210 215 220

Ala Ala Gly Ile Thr
225

<210> SEQ ID NO 132
<211> LENGTH: 238
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 132

Met Ser Lys Gly Glu Glu Leu Phe Thr Gly Val Val Pro Ile Leu Val
1 5 10 15

Glu Leu Asp Gly Asp Val Asn Gly His Lys Phe Ser Val Arg Gly Glu
20 25 30

Gly Glu Gly Asp Ala Thr Asn Gly Lys Leu Thr Leu Lys Phe Ile Cys
35 40 45

Thr Thr Gly Lys Leu Pro Val Pro Trp Pro Thr Leu Val Thr Thr Leu
50 55 60

Thr Val Gln Cys Phe Ser Arg Tyr Pro Asp His Met Lys Arg His Asp
65 70 75 80

Phe Phe Lys Ser Ala Met Pro Glu Gly Tyr Val Gln Glu Arg Thr Ile
85 90 95

Ser Phe Lys Asp Asp Gly Thr Tyr Lys Thr Arg Ala Glu Val Lys Phe
100 105 110

Glu Gly Asp Thr Leu Val Asn Arg Ile Glu Leu Lys Gly Ile Asp Phe
115 120 125

Lys Glu Asp Gly Asn Ile Leu Gly His Lys Leu Glu Tyr Asn Phe Asn
130 135 140

Ser His Asn Val Tyr Ile Thr Ala Asp Lys Gln Lys Asn Gly Ile Lys
145 150 155 160

Ala Asn Phe Lys Ile Arg His Asn Val Glu Asp Gly Ser Val Gln Leu
165 170 175

Ala Asp His Tyr Gln Gln Asn Thr Pro Ile Gly Asp Gly Pro Val Leu
180 185 190

Leu Pro Asp Asn His Tyr Leu Ser Thr Gln Ser Val Leu Ser Lys Asp
195 200 205

Pro Asn Glu Lys Arg Asp His Met Val Leu Leu Glu Phe Val Thr Ala
210 215 220

Ala Gly Ile Thr His Gly Met Asp Glu Leu Tyr Lys Gly Ser
225 230 235

<210> SEQ ID NO 133
<211> LENGTH: 234
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 133

Met Val Ser Lys Gly Glu Glu Asp Asn Met Ala Ile Ile Lys Glu Phe
1 5 10 15

Met Arg Phe Lys Val His Met Glu Gly Ser Val Asn Gly His Val Phe
20 25 30

Glu Ile Glu Gly Glu Gly Glu Gly Arg Pro Tyr Glu Gly Thr Gln Thr
35 40 45

Ala Lys Leu Lys Val Thr Lys Gly Gly Pro Leu Pro Phe Thr Trp Asp
50 55 60

Ile Leu Ser Pro Gln Phe Met Ser Asn Ala Tyr Val Lys His Pro Ala
65 70 75 80

Asp Ile Pro Asp Tyr Phe Lys Leu Ser Phe Pro Glu Gly Phe Lys Trp
85 90 95

Glu Arg Val Met Lys Phe Glu Asp Gly Gly Val Val Thr Val Thr Gln
100 105 110

Asp Ser Ser Leu Gln Asp Gly Glu Phe Ile Tyr Lys Val Lys Leu Arg
115 120 125

Gly Thr Asn Phe Pro Ser Asp Gly Pro Val Met Gln Lys Lys Thr Met
130 135 140

Gly Trp Glu Ala Leu Ser Glu Arg Met Tyr Pro Glu Asp Gly Ala Leu
145 150 155 160

Lys Gly Glu Val Lys Pro Arg Val Lys Leu Lys Asp Gly Gly His Tyr
165 170 175

Asp Ala Glu Val Lys Thr Thr Tyr Lys Ala Lys Lys Pro Val Gln Leu
180 185 190

Pro Gly Ala Tyr Asn Val Asn Arg Lys Leu Asp Ile Thr Ser His Asn
195 200 205

Glu Asp Tyr Thr Ile Val Glu Gln Tyr Glu Arg Ala Glu Gly Arg His 210 215 220

Ser Thr Gly Gly Met Asp Glu Leu Tyr Lys
225 230

<210> SEQ ID NO 134
<211> LENGTH: 235
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 134

Met His Gly Ser Met Ser Glu Leu Ile Thr Glu Asn Met His Met Lys
1 5 10 15

Leu Tyr Met Glu Gly Thr Val Asn Asn His His Phe Lys Cys Thr Ser
20 25 30

Glu Gly Glu Gly Lys Pro Tyr Glu Gly Thr Gln Thr Met Arg Ile Lys
35 40 45

Val Val Glu Gly Gly Pro Leu Pro Phe Ala Phe Asp Ile Leu Ala Thr
50 55 60

Ser Phe Met Ser Lys Thr Phe Ile Asn His Thr Gln Gly Ile Pro Asp
65 70 75 80

Phe Phe Lys Gln Ser Phe Pro Glu Gly Phe Thr Trp Glu Arg Val Thr
85 90 95

Thr Tyr Glu Asp Gly Gly Val Leu Thr Ala Thr Gln Asp Thr Ser Leu
100 105 110

Gln Asp Gly Cys Leu Ile Tyr Asn Val Lys Ile Arg Gly Val Asn Phe
115 120 125

Pro Ser Asn Gly Pro Val Met Gln Lys Lys Thr Leu Gly Trp Glu Ala
130 135 140

Ser Thr Glu Met Leu Tyr Pro Ala Asp Gly Gly Leu Glu Gly Arg Ser
145 150 155 160

Asp Met Ala Leu Lys Leu Val Gly Gly Gly His Leu Ile Cys Asn Leu
165 170 175

Lys Thr Thr Tyr Arg Ser Lys Lys Pro Ala Lys Asn Leu Lys Met Pro
180 185 190

Gly Val Tyr Tyr Val Asp Arg Arg Leu Glu Arg Ile Lys Glu Ala Asp
195 200 205

Lys Glu Thr Tyr Val Glu Gln His Glu Val Ala Val Ala Arg Tyr Cys
210 215 220

Asp Leu Pro Ser Lys Leu Gly His Lys Leu Asn
225 230 235

<210> SEQ ID NO 135
<211> LENGTH: 220
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 135

Met Ser Ala Ile Lys Pro Asp Met Lys Ile Lys Leu Arg Met Glu Gly
1 5 10 15

Asn Val Asn Gly His His Phe Val Ile Asp Gly Asp Gly Thr Gly Lys
20 25 30

Pro Phe Glu Gly Lys Gln Ser Met Asp Leu Glu Val Lys Glu Gly Gly

```
        35                  40                  45

Pro Leu Pro Phe Ala Phe Asp Ile Leu Thr Thr Ala Phe Asn Arg Val
    50                  55                  60

Phe Ala Lys Tyr Pro Asp Asn Ile Gln Asp Tyr Phe Lys Gln Ser Phe
65                  70                  75                  80

Pro Lys Gly Tyr Ser Trp Glu Arg Ser Leu Thr Phe Glu Asp Gly Gly
                85                  90                  95

Ile Cys Ile Ala Arg Asn Asp Ile Thr Met Glu Gly Asp Thr Phe Tyr
            100                 105                 110

Asn Lys Val Arg Phe Tyr Gly Thr Asn Phe Pro Ala Asn Gly Pro Val
        115                 120                 125

Met Gln Lys Lys Thr Leu Lys Trp Glu Pro Ser Thr Glu Lys Met Tyr
    130                 135                 140

Val Arg Asp Gly Val Leu Thr Gly Asp Ile His Met Ala Leu Leu Leu
145                 150                 155                 160

Glu Gly Asn Ala His Tyr Arg Cys Asp Phe Arg Thr Thr Tyr Lys Ala
                165                 170                 175

Lys Glu Lys Gly Val Lys Leu Pro Gly Tyr His Phe Val Asp His Cys
            180                 185                 190

Ile Glu Ile Leu Ser His Asp Lys Asp Tyr Asn Lys Val Lys Leu Tyr
        195                 200                 205

Glu His Ala Val Ala His Ser Gly Leu Pro Asp Asn
    210                 215                 220


<210> SEQ ID NO 136
<211> LENGTH: 69
<212> TYPE: PRT
<213> ORGANISM: Unknown
<220> FEATURE:
<223> OTHER INFORMATION: Description of Unknown:
      Metabotropic Glutamate Receptor type-3 sequence

<400> SEQUENCE: 136

Leu Val Gln Ile Val Met Val Ser Val Trp Leu Ile Leu Glu Ala Pro
1               5                   10                  15

Gly Thr Arg Arg Tyr Thr Leu Ala Glu Lys Arg Glu Thr Val Ile Leu
            20                  25                  30

Lys Cys Asn Val Lys Asp Ser Ser Met Leu Ile Ser Leu Thr Tyr Asp
        35                  40                  45

Val Ile Leu Val Ile Leu Cys Thr Val Tyr Ala Phe Lys Thr Arg Lys
    50                  55                  60

Cys Pro Glu Asn Phe
65


<210> SEQ ID NO 137
<211> LENGTH: 67
<212> TYPE: PRT
<213> ORGANISM: Unknown
<220> FEATURE:
<223> OTHER INFORMATION: Description of Unknown:
      Metabotropic Glutamate Receptor type-5 sequence

<400> SEQUENCE: 137

Cys Ile Gln Leu Gly Ile Ile Val Ala Leu Phe Ile Met Glu Pro Pro
1               5                   10                  15

Asp Ile Met His Asp Tyr Pro Ser Ile Arg Glu Val Tyr Leu Ile Cys
            20                  25                  30

Asn Thr Thr Asn Leu Gly Val Val Thr Pro Leu Gly Tyr Asn Gly Leu
```

35 40 45

Leu Ile Leu Ser Cys Thr Phe Tyr Ala Phe Lys Thr Arg Asn Val Pro
50 55 60

Ala Asn Phe
65

<210> SEQ ID NO 138
<211> LENGTH: 92
<212> TYPE: PRT
<213> ORGANISM: Unknown
<220> FEATURE:
<223> OTHER INFORMATION: Description of Unknown:
Gamma-aminobutyric acid Receptor type-2 sequence

<400> SEQUENCE: 138

Tyr Ala Thr Val Gly Leu Leu Val Gly Met Asp Val Leu Thr Leu Ala
1 5 10 15

Ile Trp Gln Ile Val Asp Pro Leu His Arg Thr Ile Glu Thr Phe Ala
20 25 30

Lys Glu Glu Pro Lys Glu Asp Ile Asp Val Ser Ile Leu Pro Gln Leu
35 40 45

Glu His Cys Ser Ser Arg Lys Met Asn Thr Trp Leu Gly Ile Phe Tyr
50 55 60

Gly Tyr Lys Gly Leu Leu Leu Leu Leu Gly Ile Phe Leu Ala Tyr Glu
65 70 75 80

Thr Lys Ser Val Ser Thr Glu Lys Ile Asn Asp His
85 90

<210> SEQ ID NO 139
<211> LENGTH: 92
<212> TYPE: PRT
<213> ORGANISM: Unknown
<220> FEATURE:
<223> OTHER INFORMATION: Description of Unknown:
Gamma-aminobutyric acid Receptor type-2 sequence

<400> SEQUENCE: 139

Leu Val Ile Val Gly Gly Met Leu Leu Ile Asp Leu Cys Ile Leu Ile
1 5 10 15

Cys Trp Gln Ala Val Asp Pro Leu Arg Arg Thr Val Glu Lys Tyr Ser
20 25 30

Met Glu Pro Asp Pro Ala Gly Arg Asp Ile Ser Ile Arg Pro Leu Leu
35 40 45

Glu His Cys Glu Asn Thr His Met Thr Ile Trp Leu Gly Ile Val Tyr
50 55 60

Ala Tyr Lys Gly Leu Leu Met Leu Phe Gly Cys Phe Leu Ala Trp Glu
65 70 75 80

Thr Arg Asn Val Ser Ile Pro Ala Leu Asn Asp Ser
85 90

<210> SEQ ID NO 140
<211> LENGTH: 116
<212> TYPE: PRT
<213> ORGANISM: Unknown
<220> FEATURE:
<223> OTHER INFORMATION: Description of Unknown:
Cannabinoid Receptor type-1 sequence

<400> SEQUENCE: 140

Thr Tyr Leu Met Phe Trp Ile Gly Val Thr Ser Val Leu Leu Leu Phe
1 5 10 15

Ile Val Tyr Ala Tyr Met Tyr Ile Leu Trp Lys Ala His Ser His Ala
20 25 30

Val Arg Met Ile Gln Arg Gly Thr Gln Lys Ser Ile Ile Ile His Thr
35 40 45

Ser Glu Asp Gly Lys Val Gln Val Thr Arg Pro Asp Gln Ala Arg Met
50 55 60

Asp Ile Arg Leu Ala Lys Thr Leu Val Leu Ile Leu Val Val Leu Ile
65 70 75 80

Ile Cys Trp Gly Pro Leu Leu Ala Ile Met Val Tyr Asp Val Phe Gly
85 90 95

Lys Met Asn Lys Leu Ile Lys Thr Val Phe Ala Phe Cys Ser Met Leu
100 105 110

Cys Leu Leu Asn
115

<210> SEQ ID NO 141
<211> LENGTH: 106
<212> TYPE: PRT
<213> ORGANISM: Unknown
<220> FEATURE:
<223> OTHER INFORMATION: Description of Unknown:
Gonadotropin-Releasing Hormone Receptor sequence

<400> SEQUENCE: 141

Phe Tyr Asn Phe Phe Thr Phe Ser Cys Leu Phe Ile Ile Pro Leu Phe
1 5 10 15

Ile Met Leu Ile Cys Asn Ala Lys Ile Ile Phe Thr Leu Thr Arg Val
20 25 30

Leu His Gln Asp Pro His Glu Leu Gln Leu Asn Gln Ser Lys Asn Asn
35 40 45

Ile Pro Arg Ala Arg Leu Lys Thr Leu Lys Met Thr Val Ala Phe Ala
50 55 60

Thr Ser Phe Thr Val Cys Trp Thr Pro Tyr Tyr Val Leu Gly Ile Trp
65 70 75 80

Tyr Trp Phe Asp Pro Glu Met Leu Asn Arg Leu Ser Asp Pro Val Asn
85 90 95

His Phe Phe Phe Leu Phe Ala Phe Leu Asn
100 105

<210> SEQ ID NO 142
<211> LENGTH: 126
<212> TYPE: PRT
<213> ORGANISM: Unknown
<220> FEATURE:
<223> OTHER INFORMATION: Description of Unknown:
Vasopressin Receptor type-1 sequence

<400> SEQUENCE: 142

Ala Tyr Val Thr Trp Met Thr Gly Gly Ile Phe Val Ala Pro Val Val
1 5 10 15

Ile Leu Gly Thr Cys Tyr Gly Phe Ile Cys Tyr Asn Ile Trp Cys Asn
20 25 30

Val Arg Gly Lys Thr Ala Ser Arg Gln Ser Lys Gly Ala Glu Gln Ala
35 40 45

Gly Val Ala Phe Gln Lys Gly Phe Leu Leu Ala Pro Cys Val Ser Ser
50 55 60

Val Lys Ser Ile Ser Arg Ala Lys Ile Arg Thr Val Lys Met Thr Phe
65 70 75 80

```
Val Ile Val Thr Ala Tyr Ile Val Cys Trp Ala Pro Phe Phe Ile Ile
                85                  90                  95

Gln Met Trp Ser Val Trp Asp Pro Met Ser Val Trp Thr Glu Ser Glu
            100                 105                 110

Asn Pro Thr Ile Thr Ile Thr Ala Leu Leu Gly Ser Leu Asn
        115                 120                 125
```

<210> SEQ ID NO 143
<211> LENGTH: 123
<212> TYPE: PRT
<213> ORGANISM: Unknown
<220> FEATURE:
<223> OTHER INFORMATION: Description of Unknown:
Oxytocin Receptor sequence

<400> SEQUENCE: 143

```
Ala Tyr Ile Thr Trp Ile Thr Leu Ala Val Tyr Ile Val Pro Val Ile
1               5                   10                  15

Val Leu Ala Ala Cys Tyr Gly Leu Ile Ser Phe Lys Ile Trp Gln Asn
            20                  25                  30

Leu Arg Leu Lys Thr Ala Ala Ala Ala Ala Ala Glu Ala Pro Glu Gly
        35                  40                  45

Ala Ala Ala Gly Asp Gly Gly Arg Val Ala Leu Ala Arg Val Ser Ser
    50                  55                  60

Val Lys Leu Ile Ser Lys Ala Lys Ile Arg Thr Val Lys Met Thr Phe
65                  70                  75                  80

Ile Ile Val Leu Ala Phe Ile Val Cys Trp Thr Pro Phe Phe Phe Val
                85                  90                  95

Gln Met Trp Ser Val Trp Asp Ala Asn Ala Pro Lys Glu Ala Ser Ala
            100                 105                 110

Phe Ile Ile Val Met Leu Leu Ala Ser Leu Asn
        115                 120
```

<210> SEQ ID NO 144
<211> LENGTH: 106
<212> TYPE: PRT
<213> ORGANISM: Unknown
<220> FEATURE:
<223> OTHER INFORMATION: Description of Unknown:
Adenosine Receptor type-2 sequence

<400> SEQUENCE: 144

```
Asn Tyr Met Val Tyr Phe Asn Phe Phe Ala Cys Val Leu Val Pro Leu
1               5                   10                  15

Leu Leu Met Leu Gly Val Tyr Leu Arg Ile Phe Leu Ala Ala Arg Arg
            20                  25                  30

Gln Leu Lys Gln Met Glu Ser Gln Pro Leu Pro Gly Glu Arg Ala Arg
        35                  40                  45

Ser Thr Leu Gln Lys Glu Val His Ala Ala Lys Ser Leu Ala Ile Ile
    50                  55                  60

Val Gly Leu Phe Ala Leu Cys Trp Leu Pro Leu His Ile Ile Asn Cys
65                  70                  75                  80

Phe Thr Phe Phe Cys Pro Asp Cys Ser His Ala Pro Leu Trp Leu Met
                85                  90                  95

Tyr Leu Ala Ile Val Leu Ser His Thr Asn
            100                 105
```

<210> SEQ ID NO 145

<211> LENGTH: 121
<212> TYPE: PRT
<213> ORGANISM: Homo sapiens

<400> SEQUENCE: 145

Ala Tyr Ala Ile Ala Ser Ser Ile Val Ser Phe Tyr Val Pro Leu Val
1               5                   10                  15

Ile Met Val Phe Val Tyr Ser Arg Val Phe Gln Glu Ala Lys Arg Gln
            20                  25                  30

Leu Gln Lys Ile Asp Lys Ser Glu Gly Arg Phe His Val Gln Asn Leu
        35                  40                  45

Ser Gln Val Glu Gln Asp Gly Arg Thr Gly His Gly Leu Arg Arg Ser
    50                  55                  60

Ser Lys Phe Cys Leu Lys Glu His Lys Ala Leu Lys Thr Leu Gly Ile
65                  70                  75                  80

Ile Met Gly Thr Phe Thr Leu Cys Trp Leu Pro Phe Phe Ile Val Asn
                85                  90                  95

Ile Val His Val Ile Gln Asp Asn Leu Ile Arg Lys Glu Val Tyr Ile
            100                 105                 110

Leu Leu Asn Trp Ile Gly Tyr Val Asn
        115                 120

<210> SEQ ID NO 146
<211> LENGTH: 131
<212> TYPE: PRT
<213> ORGANISM: Homo sapiens

<400> SEQUENCE: 146

Thr Tyr Ala Ile Ser Ser Ser Val Ile Ser Phe Tyr Ile Pro Val Ala
1               5                   10                  15

Ile Met Ile Val Thr Tyr Thr Arg Ile Tyr Arg Ile Ala Gln Lys Gln
            20                  25                  30

Ile Arg Arg Ile Ala Ala Leu Glu Arg Ala Ala Val His Ala Lys Asn
        35                  40                  45

Cys Gln Thr Thr Thr Gly Asn Gly Lys Pro Val Glu Cys Ser Gln Pro
    50                  55                  60

Glu Ser Ser Phe Lys Met Ser Phe Lys Arg Glu Thr Lys Val Leu Lys
65                  70                  75                  80

Thr Leu Ser Val Ile Met Gly Val Phe Val Cys Cys Trp Leu Pro Phe
                85                  90                  95

Phe Ile Leu Asn Cys Ile Leu Pro Phe Cys Gly Ser Gly Glu Thr Gln
            100                 105                 110

Pro Phe Cys Ile Asp Ser Asn Thr Phe Asp Val Phe Val Trp Phe Gly
        115                 120                 125

Trp Ala Asn
    130

<210> SEQ ID NO 147
<211> LENGTH: 248
<212> TYPE: PRT
<213> ORGANISM: Unknown
<220> FEATURE:
<223> OTHER INFORMATION: Description of Unknown:
      Acetylcholine Muscarinic Receptor type-2 sequence

<400> SEQUENCE: 147

Ala Val Thr Phe Gly Thr Ala Ile Ala Ala Phe Tyr Leu Pro Val Ile
1               5                   10                  15

```
Ile Met Thr Val Leu Tyr Trp His Ile Ser Arg Ala Ser Lys Ser Arg
            20                  25                  30

Ile Lys Lys Asp Lys Lys Glu Pro Val Ala Asn Gln Asp Pro Val Ser
        35                  40                  45

Pro Ser Leu Val Gln Gly Arg Ile Val Lys Pro Asn Asn Asn Asn Met
    50                  55                  60

Pro Ser Ser Asp Asp Gly Leu Glu His Asn Lys Ile Gln Asn Gly Lys
65                  70                  75                  80

Ala Pro Arg Asp Pro Val Thr Glu Asn Cys Val Gln Gly Glu Glu Lys
                85                  90                  95

Glu Ser Ser Asn Asp Ser Thr Ser Val Ser Ala Val Ala Ser Asn Met
            100                 105                 110

Arg Asp Asp Glu Ile Thr Gln Asp Glu Asn Thr Val Ser Thr Ser Leu
        115                 120                 125

Gly His Ser Lys Asp Glu Asn Ser Lys Gln Thr Cys Ile Arg Ile Gly
    130                 135                 140

Thr Lys Thr Pro Lys Ser Asp Ser Cys Thr Pro Thr Asn Thr Thr Val
145                 150                 155                 160

Glu Val Val Gly Ser Ser Gly Gln Asn Gly Asp Glu Lys Gln Asn Ile
                165                 170                 175

Val Ala Arg Lys Ile Val Lys Met Thr Lys Gln Pro Ala Lys Lys Lys
            180                 185                 190

Pro Pro Pro Ser Arg Glu Lys Lys Val Thr Arg Thr Ile Leu Ala Ile
        195                 200                 205

Leu Leu Ala Phe Ile Ile Thr Trp Ala Pro Tyr Asn Val Met Val Leu
    210                 215                 220

Ile Asn Thr Phe Cys Ala Pro Cys Ile Pro Asn Thr Val Trp Thr Ile
225                 230                 235                 240

Gly Tyr Trp Leu Cys Tyr Ile Asn
                245


<210> SEQ ID NO 148
<211> LENGTH: 272
<212> TYPE: PRT
<213> ORGANISM: Unknown
<220> FEATURE:
<223> OTHER INFORMATION: Description of Unknown:
      Histamine Receptor type-1 sequence

<400> SEQUENCE: 148

Trp Phe Lys Val Met Thr Ala Ile Ile Asn Phe Tyr Leu Pro Thr Leu
1               5                   10                  15

Leu Met Leu Trp Phe Tyr Ala Lys Ile Tyr Lys Ala Val Arg Gln His
            20                  25                  30

Cys Gln His Arg Glu Leu Ile Asn Arg Ser Leu Pro Ser Phe Ser Glu
        35                  40                  45

Ile Lys Leu Arg Pro Glu Asn Pro Lys Gly Asp Ala Lys Lys Pro Gly
    50                  55                  60

Lys Glu Ser Pro Trp Glu Val Leu Lys Arg Lys Pro Lys Asp Ala Gly
65                  70                  75                  80

Gly Gly Ser Val Leu Lys Ser Pro Ser Gln Thr Pro Lys Glu Met Lys
                85                  90                  95

Ser Pro Val Val Phe Ser Gln Glu Asp Asp Arg Glu Val Asp Lys Leu
            100                 105                 110

Tyr Cys Phe Pro Leu Asp Ile Val His Met Gln Ala Ala Ala Glu Gly
        115                 120                 125
```

```
Ser Ser Arg Asp Tyr Val Ala Val Asn Arg Ser His Gly Gln Leu Lys
    130                 135                 140

Thr Asp Glu Gln Gly Leu Asn Thr His Gly Ala Ser Glu Ile Ser Glu
145                 150                 155                 160

Asp Gln Met Leu Gly Asp Ser Gln Ser Phe Ser Arg Thr Asp Ser Asp
                165                 170                 175

Thr Thr Thr Glu Thr Ala Pro Gly Lys Gly Lys Leu Arg Ser Gly Ser
            180                 185                 190

Asn Thr Gly Leu Asp Tyr Ile Lys Phe Thr Trp Lys Arg Leu Arg Ser
        195                 200                 205

His Ser Arg Gln Tyr Val Ser Gly Leu His Met Asn Arg Glu Arg Lys
    210                 215                 220

Ala Ala Lys Gln Leu Gly Phe Ile Met Ala Ala Phe Ile Leu Cys Trp
225                 230                 235                 240

Ile Pro Tyr Phe Ile Phe Phe Met Val Ile Ala Phe Cys Lys Asn Cys
                245                 250                 255

Cys Asn Glu His Leu His Met Phe Thr Ile Trp Leu Gly Tyr Ile Asn
            260                 265                 270


<210> SEQ ID NO 149
<211> LENGTH: 231
<212> TYPE: PRT
<213> ORGANISM: Unknown
<220> FEATURE:
<223> OTHER INFORMATION: Description of Unknown:
      Dopamine Receptor type-2 sequence

<400> SEQUENCE: 149

Ala Phe Val Val Tyr Ser Ser Ile Val Ser Phe Tyr Val Pro Phe Ile
1               5                   10                  15

Val Thr Leu Leu Val Tyr Ile Lys Ile Tyr Ile Val Leu Arg Arg Arg
            20                  25                  30

Arg Lys Arg Val Asn Thr Lys Arg Ser Ser Arg Ala Phe Arg Ala His
        35                  40                  45

Leu Arg Ala Pro Leu Lys Gly Asn Cys Thr His Pro Glu Asp Met Lys
    50                  55                  60

Leu Cys Thr Val Ile Met Lys Ser Asn Gly Ser Phe Pro Val Asn Arg
65                  70                  75                  80

Arg Arg Val Glu Ala Ala Arg Arg Ala Gln Glu Leu Glu Met Glu Met
                85                  90                  95

Leu Ser Ser Thr Ser Pro Pro Glu Arg Thr Arg Tyr Ser Pro Ile Pro
            100                 105                 110

Pro Ser His His Gln Leu Thr Leu Pro Asp Pro Ser His His Gly Leu
        115                 120                 125

His Ser Thr Pro Asp Ser Pro Ala Lys Pro Glu Lys Asn Gly His Ala
    130                 135                 140

Lys Asp His Pro Lys Ile Ala Lys Ile Phe Glu Ile Gln Thr Met Pro
145                 150                 155                 160

Asn Gly Lys Thr Arg Thr Ser Leu Lys Thr Met Ser Arg Arg Lys Leu
                165                 170                 175

Ser Gln Gln Lys Glu Lys Lys Ala Thr Gln Met Leu Ala Ile Val Leu
            180                 185                 190

Gly Val Phe Ile Ile Cys Trp Leu Pro Phe Phe Ile Thr His Ile Leu
        195                 200                 205

Asn Ile His Cys Asp Cys Asn Ile Pro Pro Val Leu Tyr Ser Ala Phe
```

```
    210                 215                 220

Thr Trp Leu Gly Tyr Val Asn
225                 230


<210> SEQ ID NO 150
<211> LENGTH: 140
<212> TYPE: PRT
<213> ORGANISM: Homo sapiens

<400> SEQUENCE: 150

Asn Phe Val Leu Ile Gly Ser Phe Val Ser Phe Phe Ile Pro Leu Thr
1               5                   10                  15

Ile Met Val Ile Thr Tyr Phe Leu Thr Ile Lys Ser Leu Gln Lys Glu
            20                  25                  30

Ala Thr Leu Cys Val Ser Asp Leu Gly Thr Arg Ala Lys Leu Ala Ser
        35                  40                  45

Phe Ser Phe Leu Pro Gln Ser Ser Leu Ser Ser Glu Lys Leu Phe Gln
    50                  55                  60

Arg Ser Ile His Arg Glu Pro Gly Ser Tyr Thr Gly Arg Arg Thr Met
65                  70                  75                  80

Gln Ser Ile Ser Asn Glu Gln Lys Ala Cys Lys Val Leu Gly Ile Val
                85                  90                  95

Phe Phe Leu Phe Val Val Met Trp Cys Pro Phe Phe Ile Thr Asn Ile
            100                 105                 110

Met Ala Val Ile Cys Lys Glu Ser Cys Asn Glu Asp Val Ile Gly Ala
        115                 120                 125

Leu Leu Asn Val Phe Val Trp Ile Gly Tyr Leu Ser
    130                 135                 140


<210> SEQ ID NO 151
<211> LENGTH: 157
<212> TYPE: PRT
<213> ORGANISM: Unknown
<220> FEATURE:
<223> OTHER INFORMATION: Description of Unknown:
      Serotonin Receptor type-2B sequence

<400> SEQUENCE: 151

Asp Phe Met Leu Phe Gly Ser Leu Ala Ala Phe Phe Thr Pro Leu Ala
1               5                   10                  15

Ile Met Ile Val Thr Tyr Phe Leu Thr Ile His Ala Leu Gln Lys Lys
            20                  25                  30

Ala Tyr Leu Val Lys Asn Lys Pro Pro Gln Arg Leu Thr Trp Leu Thr
        35                  40                  45

Val Ser Thr Val Phe Gln Arg Asp Glu Thr Pro Cys Ser Ser Pro Glu
    50                  55                  60

Lys Val Ala Met Leu Asp Gly Ser Arg Lys Asp Lys Ala Leu Pro Asn
65                  70                  75                  80

Ser Gly Asp Glu Thr Leu Met Arg Arg Thr Ser Thr Ile Gly Lys Lys
                85                  90                  95

Ser Val Gln Thr Ile Ser Asn Glu Gln Arg Ala Ser Lys Val Leu Gly
            100                 105                 110

Ile Val Phe Phe Leu Phe Leu Leu Met Trp Cys Pro Phe Phe Ile Thr
        115                 120                 125

Asn Ile Thr Leu Val Leu Cys Asp Ser Cys Asn Gln Thr Thr Leu Gln
    130                 135                 140

Met Leu Leu Glu Ile Phe Val Trp Ile Gly Tyr Val Ser
```

145 150 155

<210> SEQ ID NO 152
<211> LENGTH: 107
<212> TYPE: PRT
<213> ORGANISM: Unknown
<220> FEATURE:
<223> OTHER INFORMATION: Description of Unknown:
Tachykinin Receptor type-1 sequence

<400> SEQUENCE: 152

```
Ile Tyr Glu Lys Val Tyr His Ile Cys Val Thr Val Leu Ile Tyr Phe
1               5                   10                  15

Leu Pro Leu Leu Val Ile Gly Tyr Ala Tyr Thr Val Val Gly Ile Thr
            20                  25                  30

Leu Trp Ala Ser Glu Ile Pro Gly Asp Ser Ser Asp Arg Tyr His Glu
        35                  40                  45

Gln Val Ser Ala Lys Arg Lys Val Val Lys Met Met Ile Val Val Val
    50                  55                  60

Cys Thr Phe Ala Ile Cys Trp Leu Pro Phe His Ile Phe Phe Leu Leu
65                  70                  75                  80

Pro Tyr Ile Asn Pro Asp Leu Tyr Leu Lys Lys Phe Ile Gln Gln Val
                85                  90                  95

Tyr Leu Ala Ile Met Trp Leu Ala Met Ser Ser
            100                 105
```

<210> SEQ ID NO 153
<211> LENGTH: 105
<212> TYPE: PRT
<213> ORGANISM: Unknown
<220> FEATURE:
<223> OTHER INFORMATION: Description of Unknown:
Tachykinin Receptor type-3 sequence

<400> SEQUENCE: 153

```
His Phe Thr Tyr His Ile Ile Val Ile Ile Leu Val Tyr Cys Phe Pro
1               5                   10                  15

Leu Leu Ile Met Gly Ile Thr Tyr Thr Ile Val Gly Ile Thr Leu Trp
            20                  25                  30

Gly Gly Glu Ile Pro Gly Asp Thr Cys Asp Lys Tyr His Glu Gln Leu
        35                  40                  45

Lys Ala Lys Arg Lys Val Val Lys Met Met Ile Ile Val Val Met Thr
    50                  55                  60

Phe Ala Ile Cys Trp Leu Pro Tyr His Ile Tyr Phe Ile Leu Thr Ala
65                  70                  75                  80

Ile Tyr Gln Gln Leu Asn Arg Trp Lys Tyr Ile Gln Gln Val Tyr Leu
                85                  90                  95

Ala Ser Phe Trp Leu Ala Met Ser Ser
            100                 105
```

<210> SEQ ID NO 154
<211> LENGTH: 108
<212> TYPE: PRT
<213> ORGANISM: Unknown
<220> FEATURE:
<223> OTHER INFORMATION: Description of Unknown:
Tachykinin Receptor type-2 sequence

<400> SEQUENCE: 154

```
Lys Thr Leu Leu Leu Tyr His Leu Val Val Ile Ala Leu Ile Tyr Phe
1               5                   10                  15
```

```
Leu Pro Leu Ala Val Met Phe Val Ala Tyr Ser Val Ile Gly Leu Thr
            20                  25                  30

Leu Trp Arg Arg Ala Val Pro Gly His Gln Ala His Gly Ala Asn Leu
        35                  40                  45

Arg His Leu Gln Ala Met Lys Lys Phe Val Lys Thr Met Val Leu Val
    50                  55                  60

Val Leu Thr Phe Ala Ile Cys Trp Leu Pro Tyr His Leu Tyr Phe Ile
65                  70                  75                  80

Leu Gly Ser Phe Gln Glu Asp Ile Tyr Cys His Lys Phe Ile Gln Gln
                85                  90                  95

Val Tyr Leu Ala Leu Phe Trp Leu Ala Met Ser Ser
            100                 105


<210> SEQ ID NO 155
<211> LENGTH: 102
<212> TYPE: PRT
<213> ORGANISM: Unknown
<220> FEATURE:
<223> OTHER INFORMATION: Description of Unknown:
      Melatonin Receptor type-1B sequence

<400> SEQUENCE: 155

Gln Tyr Thr Ala Ala Val Val Val Ile His Phe Leu Leu Pro Ile Ala
1               5                   10                  15

Val Val Ser Phe Cys Tyr Leu Arg Ile Trp Val Leu Val Leu Gln Ala
            20                  25                  30

Arg Arg Lys Ala Lys Pro Glu Ser Arg Leu Cys Leu Lys Pro Ser Asp
        35                  40                  45

Leu Arg Ser Phe Leu Thr Met Phe Val Val Phe Val Ile Phe Ala Ile
    50                  55                  60

Cys Trp Ala Pro Leu Asn Cys Ile Gly Leu Ala Val Ala Ile Asn Pro
65                  70                  75                  80

Gln Glu Met Ala Pro Gln Ile Pro Glu Gly Leu Phe Val Thr Ser Tyr
                85                  90                  95

Leu Leu Ala Tyr Phe Asn
            100


<210> SEQ ID NO 156
<211> LENGTH: 105
<212> TYPE: PRT
<213> ORGANISM: Unknown
<220> FEATURE:
<223> OTHER INFORMATION: Description of Unknown:
      P2 purinoceptor type Y1 sequence

<400> SEQUENCE: 156

Arg Ser Tyr Phe Ile Tyr Ser Met Cys Thr Thr Val Ala Met Phe Cys
1               5                   10                  15

Val Pro Leu Val Leu Ile Leu Gly Cys Tyr Gly Leu Ile Val Arg Ala
            20                  25                  30

Leu Ile Tyr Lys Asp Leu Asp Asn Ser Pro Leu Arg Arg Lys Ser Ile
        35                  40                  45

Tyr Leu Val Ile Ile Val Leu Thr Val Phe Ala Val Ser Tyr Ile Pro
    50                  55                  60

Phe His Val Met Lys Thr Met Asn Leu Arg Ala Arg Leu Asp Phe Gln
65                  70                  75                  80

Thr Pro Ala Met Cys Ala Phe Asn Asp Arg Val Tyr Ala Thr Tyr Gln
                85                  90                  95
```

Val Thr Arg Gly Leu Ala Ser Leu Asn
100 105

<210> SEQ ID NO 157
<211> LENGTH: 105
<212> TYPE: PRT
<213> ORGANISM: Unknown
<220> FEATURE:
<223> OTHER INFORMATION: Description of Unknown:
Angiotensin-II Receptor type-1 sequence

<400> SEQUENCE: 157

Thr Leu Pro Ile Gly Leu Gly Leu Thr Lys Asn Ile Leu Gly Phe Leu
1 5 10 15

Phe Pro Phe Leu Ile Ile Leu Thr Ser Tyr Thr Leu Ile Trp Lys Ala
20 25 30

Leu Lys Lys Ala Tyr Glu Ile Gln Lys Asn Lys Pro Arg Asn Asp Asp
35 40 45

Ile Phe Lys Ile Ile Met Ala Ile Val Leu Phe Phe Phe Phe Ser Trp
50 55 60

Ile Pro His Gln Ile Phe Thr Phe Leu Asp Val Leu Ile Gln Leu Gly
65 70 75 80

Ile Ile Arg Asp Cys Arg Ile Ala Asp Ile Val Asp Thr Ala Met Pro
85 90 95

Ile Thr Ile Cys Ile Ala Tyr Phe Asn
100 105

<210> SEQ ID NO 158
<211> LENGTH: 102
<212> TYPE: PRT
<213> ORGANISM: Unknown
<220> FEATURE:
<223> OTHER INFORMATION: Description of Unknown:
Kappa Opioid Receptor type-1 sequence

<400> SEQUENCE: 158

Trp Trp Asp Leu Phe Met Lys Ile Cys Val Phe Ile Phe Ala Phe Val
1 5 10 15

Ile Pro Val Leu Ile Ile Ile Val Cys Tyr Thr Leu Met Ile Leu Arg
20 25 30

Leu Lys Ser Val Arg Leu Leu Ser Gly Ser Arg Glu Lys Asp Arg Asn
35 40 45

Leu Arg Arg Ile Thr Arg Leu Val Leu Val Val Val Ala Val Phe Val
50 55 60

Val Cys Trp Thr Pro Ile His Ile Phe Ile Leu Val Glu Ala Leu Gly
65 70 75 80

Ser Thr Ser His Ser Thr Ala Ala Leu Ser Ser Tyr Tyr Phe Cys Ile
85 90 95

Ala Leu Gly Tyr Thr Asn
100

<210> SEQ ID NO 159
<211> LENGTH: 102
<212> TYPE: PRT
<213> ORGANISM: Unknown
<220> FEATURE:
<223> OTHER INFORMATION: Description of Unknown:
Mu Opioid Receptor type-1 sequence

<400> SEQUENCE: 159

```
Tyr Trp Glu Asn Leu Leu Lys Ile Cys Val Phe Ile Phe Ala Phe Ile
1               5                   10                  15

Met Pro Val Leu Ile Ile Thr Val Cys Tyr Gly Leu Met Ile Leu Arg
            20                  25                  30

Leu Lys Ser Val Arg Met Leu Ser Gly Ser Lys Glu Lys Asp Arg Asn
        35                  40                  45

Leu Arg Arg Ile Thr Arg Met Val Leu Val Val Val Ala Val Phe Ile
    50                  55                  60

Val Cys Trp Thr Pro Ile His Ile Tyr Val Ile Ile Lys Ala Leu Val
65                  70                  75                  80

Thr Ile Pro Glu Thr Thr Phe Gln Thr Val Ser Trp His Phe Cys Ile
                85                  90                  95

Ala Leu Gly Tyr Thr Asn
            100


<210> SEQ ID NO 160
<211> LENGTH: 103
<212> TYPE: PRT
<213> ORGANISM: Unknown
<220> FEATURE:
<223> OTHER INFORMATION: Description of Unknown:
      Delta Opioid Receptor type-1 sequence

<400> SEQUENCE: 160

Tyr Trp Asp Thr Val Thr Lys Ile Cys Val Phe Leu Phe Ala Phe Val
1               5                   10                  15

Val Pro Ile Leu Ile Ile Thr Val Cys Tyr Gly Leu Met Leu Leu Arg
            20                  25                  30

Leu Arg Ser Val Arg Leu Leu Ser Gly Ser Lys Glu Lys Asp Arg Ser
        35                  40                  45

Leu Arg Arg Ile Thr Arg Met Val Leu Val Val Val Gly Ala Phe Val
    50                  55                  60

Val Cys Trp Ala Pro Ile His Ile Phe Val Ile Val Trp Thr Leu Val
65                  70                  75                  80

Asp Ile Asp Arg Arg Asp Pro Leu Val Val Ala Ala Leu His Leu Cys
                85                  90                  95

Ile Ala Leu Gly Tyr Ala Asn
            100


<210> SEQ ID NO 161
<211> LENGTH: 362
<212> TYPE: PRT
<213> ORGANISM: Homo sapiens

<400> SEQUENCE: 161

Met Ser Glu Asn Gly Ser Phe Ala Asn Cys Cys Glu Ala Gly Gly Trp
1               5                   10                  15

Ala Val Arg Pro Gly Trp Ser Gly Ala Gly Ser Ala Arg Pro Ser Arg
            20                  25                  30

Thr Pro Arg Pro Pro Trp Val Ala Pro Ala Leu Ser Ala Val Leu Ile
        35                  40                  45

Val Thr Thr Ala Val Asp Val Val Gly Asn Leu Leu Val Ile Leu Ser
    50                  55                  60

Val Leu Arg Asn Arg Lys Leu Arg Asn Ala Gly Asn Leu Phe Leu Val
65                  70                  75                  80

Ser Leu Ala Leu Ala Asp Leu Val Val Ala Phe Tyr Pro Tyr Pro Leu
                85                  90                  95
```

Ile Leu Val Ala Ile Phe Tyr Asp Gly Trp Ala Leu Gly Glu Glu His
100 105 110

Cys Lys Ala Ser Ala Phe Val Met Gly Leu Ser Val Ile Gly Ser Val
115 120 125

Phe Asn Ile Thr Ala Ile Ala Ile Asn Arg Tyr Cys Tyr Ile Cys His
130 135 140

Ser Met Ala Tyr His Arg Ile Tyr Arg Arg Trp His Thr Pro Leu His
145 150 155 160

Ile Cys Leu Ile Trp Leu Leu Thr Val Val Ala Leu Leu Pro Asn Phe
165 170 175

Phe Val Gly Ser Leu Glu Tyr Asp Pro Arg Ile Tyr Ser Cys Thr Phe
180 185 190

Ile Gln Thr Ala Ser Thr Gln Tyr Thr Ala Ala Val Val Val Ile His
195 200 205

Phe Leu Leu Pro Ile Ala Val Val Ser Phe Cys Tyr Leu Arg Ile Trp
210 215 220

Val Leu Val Leu Gln Ala Arg Arg Lys Ala Lys Pro Glu Ser Arg Leu
225 230 235 240

Cys Leu Lys Pro Ser Asp Leu Arg Ser Phe Leu Thr Met Phe Val Val
245 250 255

Phe Val Ile Phe Ala Ile Cys Trp Ala Pro Leu Asn Cys Ile Gly Leu
260 265 270

Ala Val Ala Ile Asn Pro Gln Glu Met Ala Pro Gln Ile Pro Glu Gly
275 280 285

Leu Phe Val Thr Ser Tyr Leu Leu Ala Tyr Phe Asn Ser Cys Leu Asn
290 295 300

Ala Ile Val Tyr Gly Leu Leu Asn Gln Asn Phe Arg Arg Glu Tyr Lys
305 310 315 320

Arg Ile Leu Leu Ala Leu Trp Asn Pro Arg His Cys Ile Gln Asp Ala
325 330 335

Ser Lys Gly Ser His Ala Glu Gly Leu Gln Ser Pro Ala Pro Pro Ile
340 345 350

Ile Gly Val Gln His Gln Ala Asp Ala Leu
355 360

<210> SEQ ID NO 162
<211> LENGTH: 380
<212> TYPE: PRT
<213> ORGANISM: Homo sapiens

<400> SEQUENCE: 162

Met Asp Ser Pro Ile Gln Ile Phe Arg Gly Glu Pro Gly Pro Thr Cys
1 5 10 15

Ala Pro Ser Ala Cys Leu Pro Pro Asn Ser Ser Ala Trp Phe Pro Gly
20 25 30

Trp Ala Glu Pro Asp Ser Asn Gly Ser Ala Gly Ser Glu Asp Ala Gln
35 40 45

Leu Glu Pro Ala His Ile Ser Pro Ala Ile Pro Val Ile Ile Thr Ala
50 55 60

Val Tyr Ser Val Val Phe Val Val Gly Leu Val Gly Asn Ser Leu Val
65 70 75 80

Met Phe Val Ile Ile Arg Tyr Thr Lys Met Lys Thr Ala Thr Asn Ile
85 90 95

Tyr Ile Phe Asn Leu Ala Leu Ala Asp Ala Leu Val Thr Thr Thr Met
100 105 110

```
Pro Phe Gln Ser Thr Val Tyr Leu Met Asn Ser Trp Pro Phe Gly Asp
        115                 120                 125

Val Leu Cys Lys Ile Val Ile Ser Ile Asp Tyr Tyr Asn Met Phe Thr
    130                 135                 140

Ser Ile Phe Thr Leu Thr Met Met Ser Val Asp Arg Tyr Ile Ala Val
145                 150                 155                 160

Cys His Pro Val Lys Ala Leu Asp Phe Arg Thr Pro Leu Lys Ala Lys
                165                 170                 175

Ile Ile Asn Ile Cys Ile Trp Leu Leu Ser Ser Ser Val Gly Ile Ser
            180                 185                 190

Ala Ile Val Leu Gly Gly Thr Lys Val Arg Glu Asp Val Asp Val Ile
        195                 200                 205

Glu Cys Ser Leu Gln Phe Pro Asp Asp Asp Tyr Ser Trp Trp Asp Leu
    210                 215                 220

Phe Met Lys Ile Cys Val Phe Ile Phe Ala Phe Val Ile Pro Val Leu
225                 230                 235                 240

Ile Ile Ile Val Cys Tyr Thr Leu Met Ile Leu Arg Leu Lys Ser Val
                245                 250                 255

Arg Leu Leu Ser Gly Ser Arg Glu Lys Asp Arg Asn Leu Arg Arg Ile
            260                 265                 270

Thr Arg Leu Val Leu Val Val Val Ala Val Phe Val Val Cys Trp Thr
        275                 280                 285

Pro Ile His Ile Phe Ile Leu Val Glu Ala Leu Gly Ser Thr Ser His
    290                 295                 300

Ser Thr Ala Ala Leu Ser Ser Tyr Tyr Phe Cys Ile Ala Leu Gly Tyr
305                 310                 315                 320

Thr Asn Ser Ser Leu Asn Pro Ile Leu Tyr Ala Phe Leu Asp Glu Asn
                325                 330                 335

Phe Lys Arg Cys Phe Arg Asp Phe Cys Phe Pro Leu Lys Met Arg Met
            340                 345                 350

Glu Arg Gln Ser Thr Ser Arg Val Arg Asn Thr Val Gln Asp Pro Ala
        355                 360                 365

Tyr Leu Arg Asp Ile Asp Gly Met Asn Lys Pro Val
    370                 375                 380


<210> SEQ ID NO 163
<211> LENGTH: 471
<212> TYPE: PRT
<213> ORGANISM: Homo sapiens

<400> SEQUENCE: 163

Met Asp Ile Leu Cys Glu Glu Asn Thr Ser Leu Ser Ser Thr Thr Asn
1               5                   10                  15

Ser Leu Met Gln Leu Asn Asp Asp Thr Arg Leu Tyr Ser Asn Asp Phe
            20                  25                  30

Asn Ser Gly Glu Ala Asn Thr Ser Asp Ala Phe Asn Trp Thr Val Asp
        35                  40                  45

Ser Glu Asn Arg Thr Asn Leu Ser Cys Glu Gly Cys Leu Ser Pro Ser
    50                  55                  60

Cys Leu Ser Leu Leu His Leu Gln Glu Lys Asn Trp Ser Ala Leu Leu
65                  70                  75                  80

Thr Ala Val Val Ile Ile Leu Thr Ile Ala Gly Asn Ile Leu Val Ile
                85                  90                  95

Met Ala Val Ser Leu Glu Lys Lys Leu Gln Asn Ala Thr Asn Tyr Phe
```

```
            100                 105                 110

Leu Met Ser Leu Ala Ile Ala Asp Met Leu Leu Gly Phe Leu Val Met
        115                 120                 125

Pro Val Ser Met Leu Thr Ile Leu Tyr Gly Tyr Arg Trp Pro Leu Pro
    130                 135                 140

Ser Lys Leu Cys Ala Val Trp Ile Tyr Leu Asp Val Leu Phe Ser Thr
145                 150                 155                 160

Ala Ser Ile Met His Leu Cys Ala Ile Ser Leu Asp Arg Tyr Val Ala
                165                 170                 175

Ile Gln Asn Pro Ile His His Ser Arg Phe Asn Ser Arg Thr Lys Ala
            180                 185                 190

Phe Leu Lys Ile Ile Ala Val Trp Thr Ile Ser Val Gly Ile Ser Met
        195                 200                 205

Pro Ile Pro Val Phe Gly Leu Gln Asp Asp Ser Lys Val Phe Lys Glu
    210                 215                 220

Gly Ser Cys Leu Leu Ala Asp Asp Asn Phe Val Leu Ile Gly Ser Phe
225                 230                 235                 240

Val Ser Phe Phe Ile Pro Leu Thr Ile Met Val Ile Thr Tyr Phe Leu
                245                 250                 255

Thr Ile Lys Ser Leu Gln Lys Glu Ala Thr Leu Cys Val Ser Asp Leu
            260                 265                 270

Gly Thr Arg Ala Lys Leu Ala Ser Phe Ser Phe Leu Pro Gln Ser Ser
        275                 280                 285

Leu Ser Ser Glu Lys Leu Phe Gln Arg Ser Ile His Arg Glu Pro Gly
    290                 295                 300

Ser Tyr Thr Gly Arg Arg Thr Met Gln Ser Ile Ser Asn Glu Gln Lys
305                 310                 315                 320

Ala Cys Lys Val Leu Gly Ile Val Phe Phe Leu Phe Val Val Met Trp
                325                 330                 335

Cys Pro Phe Phe Ile Thr Asn Ile Met Ala Val Ile Cys Lys Glu Ser
            340                 345                 350

Cys Asn Glu Asp Val Ile Gly Ala Leu Leu Asn Val Phe Val Trp Ile
        355                 360                 365

Gly Tyr Leu Ser Ser Ala Val Asn Pro Leu Val Tyr Thr Leu Phe Asn
    370                 375                 380

Lys Thr Tyr Arg Ser Ala Phe Ser Arg Tyr Ile Gln Cys Gln Tyr Lys
385                 390                 395                 400

Glu Asn Lys Lys Pro Leu Gln Leu Ile Leu Val Asn Thr Ile Pro Ala
                405                 410                 415

Leu Ala Tyr Lys Ser Ser Gln Leu Gln Met Gly Gln Lys Lys Asn Ser
            420                 425                 430

Lys Gln Asp Ala Lys Thr Thr Asp Asn Asp Cys Ser Met Val Ala Leu
        435                 440                 445

Gly Lys Gln His Ser Glu Glu Ala Ser Lys Asp Asn Ser Asp Gly Val
    450                 455                 460

Asn Glu Lys Val Ser Cys Val
465                 470


<210> SEQ ID NO 164
<211> LENGTH: 465
<212> TYPE: PRT
<213> ORGANISM: Homo sapiens

<400> SEQUENCE: 164
```

```
Met Phe Arg Gln Glu Gln Pro Leu Ala Glu Gly Ser Phe Ala Pro Met
1               5                   10                  15

Gly Ser Leu Gln Pro Asp Ala Gly Asn Ala Ser Trp Asn Gly Thr Glu
            20                  25                  30

Ala Pro Gly Gly Gly Ala Arg Ala Thr Pro Tyr Ser Leu Gln Val Thr
        35                  40                  45

Leu Thr Leu Val Cys Leu Ala Gly Leu Leu Met Leu Leu Thr Val Phe
    50                  55                  60

Gly Asn Val Leu Val Ile Ile Ala Val Phe Thr Ser Arg Ala Leu Lys
65                  70                  75                  80

Ala Pro Gln Asn Leu Phe Leu Val Ser Leu Ala Ser Ala Asp Ile Leu
                85                  90                  95

Val Ala Thr Leu Val Ile Pro Phe Ser Leu Ala Asn Glu Val Met Gly
            100                 105                 110

Tyr Trp Tyr Phe Gly Lys Ala Trp Cys Glu Ile Tyr Leu Ala Leu Asp
        115                 120                 125

Val Leu Phe Cys Thr Ser Ser Ile Val His Leu Cys Ala Ile Ser Leu
    130                 135                 140

Asp Arg Tyr Trp Ser Ile Thr Gln Ala Ile Glu Tyr Asn Leu Lys Arg
145                 150                 155                 160

Thr Pro Arg Arg Ile Lys Ala Ile Ile Ile Thr Val Trp Val Ile Ser
                165                 170                 175

Ala Val Ile Ser Phe Pro Pro Leu Ile Ser Ile Glu Lys Lys Gly Gly
            180                 185                 190

Gly Gly Gly Pro Gln Pro Ala Glu Pro Arg Cys Glu Ile Asn Asp Gln
        195                 200                 205

Lys Trp Tyr Val Ile Ser Ser Cys Ile Gly Ser Phe Phe Ala Pro Cys
    210                 215                 220

Leu Ile Met Ile Leu Val Tyr Val Arg Ile Tyr Gln Ile Ala Lys Arg
225                 230                 235                 240

Arg Thr Arg Val Pro Pro Ser Arg Arg Gly Pro Asp Ala Val Ala Ala
                245                 250                 255

Pro Pro Gly Gly Thr Glu Arg Arg Pro Asn Gly Leu Gly Pro Glu Arg
            260                 265                 270

Ser Ala Gly Pro Gly Gly Ala Glu Ala Glu Pro Leu Pro Thr Gln Leu
        275                 280                 285

Asn Gly Ala Pro Gly Glu Pro Ala Pro Ala Gly Pro Arg Asp Thr Asp
    290                 295                 300

Ala Leu Asp Leu Glu Glu Ser Ser Ser Ser Asp His Ala Glu Arg Pro
305                 310                 315                 320

Pro Gly Pro Arg Arg Pro Glu Arg Gly Pro Arg Gly Lys Gly Lys Ala
                325                 330                 335

Arg Ala Ser Gln Val Lys Pro Gly Asp Ser Leu Pro Arg Arg Gly Pro
            340                 345                 350

Gly Ala Thr Gly Ile Gly Thr Pro Ala Ala Gly Pro Gly Glu Glu Arg
        355                 360                 365

Val Gly Ala Ala Lys Ala Ser Arg Trp Arg Gly Arg Gln Asn Arg Glu
    370                 375                 380

Lys Arg Phe Thr Phe Val Leu Ala Val Val Ile Gly Val Phe Val Val
385                 390                 395                 400

Cys Trp Phe Pro Phe Phe Phe Thr Tyr Thr Leu Thr Ala Val Gly Cys
                405                 410                 415

Ser Val Pro Arg Thr Leu Phe Lys Phe Phe Phe Trp Phe Gly Tyr Cys
```

```
            420                 425                 430

Asn Ser Ser Leu Asn Pro Val Ile Tyr Thr Ile Phe Asn His Asp Phe
        435                 440                 445

Arg Arg Ala Phe Lys Lys Ile Leu Cys Arg Gly Asp Arg Lys Arg Ile
    450                 455                 460

Val
465


<210> SEQ ID NO 165
<211> LENGTH: 413
<212> TYPE: PRT
<213> ORGANISM: Homo sapiens

<400> SEQUENCE: 165

Met Gly Gln Pro Gly Asn Gly Ser Ala Phe Leu Leu Ala Pro Asn Arg
1               5                   10                  15

Ser His Ala Pro Asp His Asp Val Thr Gln Gln Arg Asp Glu Val Trp
            20                  25                  30

Val Val Gly Met Gly Ile Val Met Ser Leu Ile Val Leu Ala Ile Val
        35                  40                  45

Phe Gly Asn Val Leu Val Ile Thr Ala Ile Ala Lys Phe Glu Arg Leu
    50                  55                  60

Gln Thr Val Thr Asn Tyr Phe Ile Thr Ser Leu Ala Cys Ala Asp Leu
65                  70                  75                  80

Val Met Gly Leu Ala Val Val Pro Phe Gly Ala Ala His Ile Leu Met
                85                  90                  95

Lys Met Trp Thr Phe Gly Asn Phe Trp Cys Glu Phe Trp Thr Ser Ile
            100                 105                 110

Asp Val Leu Cys Val Thr Ala Ser Ile Glu Thr Leu Cys Val Ile Ala
        115                 120                 125

Val Asp Arg Tyr Phe Ala Ile Thr Ser Pro Phe Lys Tyr Gln Ser Leu
    130                 135                 140

Leu Thr Lys Asn Lys Ala Arg Val Ile Ile Leu Met Val Trp Ile Val
145                 150                 155                 160

Ser Gly Leu Ile Ser Phe Leu Pro Ile Gln Met His Trp Tyr Arg Ala
                165                 170                 175

Thr His Gln Glu Ala Ile Asn Cys Tyr Ala Asn Glu Thr Cys Cys Asp
            180                 185                 190

Phe Phe Thr Asn Gln Ala Tyr Ala Ile Ala Ser Ser Ile Val Ser Phe
        195                 200                 205

Tyr Val Pro Leu Val Ile Met Val Phe Val Tyr Ser Arg Val Phe Gln
    210                 215                 220

Glu Ala Lys Arg Gln Leu Gln Lys Ile Asp Lys Ser Glu Gly Arg Phe
225                 230                 235                 240

His Val Gln Asn Leu Ser Gln Val Glu Gln Asp Gly Arg Thr Gly His
                245                 250                 255

Gly Leu Arg Arg Ser Ser Lys Phe Cys Leu Lys Glu His Lys Ala Leu
            260                 265                 270

Lys Thr Leu Gly Ile Ile Met Gly Thr Phe Thr Leu Cys Trp Leu Pro
        275                 280                 285

Phe Phe Ile Val Asn Ile Val His Val Ile Gln Asp Asn Leu Ile Arg
    290                 295                 300

Lys Glu Val Tyr Ile Leu Leu Asn Trp Ile Gly Tyr Val Asn Ser Gly
305                 310                 315                 320
```

```
Phe Asn Pro Leu Ile Tyr Cys Arg Ser Pro Asp Phe Arg Ile Ala Phe
                325                 330                 335

Gln Glu Leu Leu Cys Leu Arg Arg Ser Ser Leu Lys Ala Tyr Gly Asn
            340                 345                 350

Gly Tyr Ser Ser Asn Gly Asn Thr Gly Glu Gln Ser Gly Tyr His Val
        355                 360                 365

Glu Gln Glu Lys Glu Asn Lys Leu Leu Cys Glu Asp Leu Pro Gly Thr
    370                 375                 380

Glu Asp Phe Val Gly His Gln Gly Thr Val Pro Ser Asp Asn Ile Asp
385                 390                 395                 400

Ser Gln Gly Arg Asn Cys Ser Thr Asn Asp Ser Leu Leu
                405                 410


<210> SEQ ID NO 166
<211> LENGTH: 446
<212> TYPE: PRT
<213> ORGANISM: Homo sapiens

<400> SEQUENCE: 166

Met Arg Thr Leu Asn Thr Ser Ala Met Asp Gly Thr Gly Leu Val Val
1               5                   10                  15

Glu Arg Asp Phe Ser Val Arg Ile Leu Thr Ala Cys Phe Leu Ser Leu
            20                  25                  30

Leu Ile Leu Ser Thr Leu Leu Gly Asn Thr Leu Val Cys Ala Ala Val
        35                  40                  45

Ile Arg Phe Arg His Leu Arg Ser Lys Val Thr Asn Phe Phe Val Ile
    50                  55                  60

Ser Leu Ala Val Ser Asp Leu Leu Val Ala Val Leu Val Met Pro Trp
65                  70                  75                  80

Lys Ala Val Ala Glu Ile Ala Gly Phe Trp Pro Phe Gly Ser Phe Cys
                85                  90                  95

Asn Ile Trp Val Ala Phe Asp Ile Met Cys Ser Thr Ala Ser Ile Leu
            100                 105                 110

Asn Leu Cys Val Ile Ser Val Asp Arg Tyr Trp Ala Ile Ser Ser Pro
        115                 120                 125

Phe Arg Tyr Glu Arg Lys Met Thr Pro Lys Ala Ala Phe Ile Leu Ile
    130                 135                 140

Ser Val Ala Trp Thr Leu Ser Val Leu Ile Ser Phe Ile Pro Val Gln
145                 150                 155                 160

Leu Ser Trp His Lys Ala Lys Pro Thr Ser Pro Ser Asp Gly Asn Ala
                165                 170                 175

Thr Ser Leu Ala Glu Thr Ile Asp Asn Cys Asp Ser Ser Leu Ser Arg
            180                 185                 190

Thr Tyr Ala Ile Ser Ser Ser Val Ile Ser Phe Tyr Ile Pro Val Ala
        195                 200                 205

Ile Met Ile Val Thr Tyr Thr Arg Ile Tyr Arg Ile Ala Gln Lys Gln
    210                 215                 220

Ile Arg Arg Ile Ala Ala Leu Glu Arg Ala Ala Val His Ala Lys Asn
225                 230                 235                 240

Cys Gln Thr Thr Thr Gly Asn Gly Lys Pro Val Glu Cys Ser Gln Pro
                245                 250                 255

Glu Ser Ser Phe Lys Met Ser Phe Lys Arg Glu Thr Lys Val Leu Lys
            260                 265                 270

Thr Leu Ser Val Ile Met Gly Val Phe Val Cys Cys Trp Leu Pro Phe
        275                 280                 285
```

Phe Ile Leu Asn Cys Ile Leu Pro Phe Cys Gly Ser Gly Glu Thr Gln
    290                 295                 300

Pro Phe Cys Ile Asp Ser Asn Thr Phe Asp Val Phe Val Trp Phe Gly
305                 310                 315                 320

Trp Ala Asn Ser Ser Leu Asn Pro Ile Ile Tyr Ala Phe Asn Ala Asp
                325                 330                 335

Phe Arg Lys Ala Phe Ser Thr Leu Leu Gly Cys Tyr Arg Leu Cys Pro
            340                 345                 350

Ala Thr Asn Asn Ala Ile Glu Thr Val Ser Ile Asn Asn Asn Gly Ala
        355                 360                 365

Ala Met Phe Ser Ser His His Glu Pro Arg Gly Ser Ile Ser Lys Glu
    370                 375                 380

Cys Asn Leu Val Tyr Leu Ile Pro His Ala Val Gly Ser Ser Glu Asp
385                 390                 395                 400

Leu Lys Lys Glu Glu Ala Ala Gly Ile Ala Arg Pro Leu Glu Lys Leu
                405                 410                 415

Ser Pro Ala Leu Ser Val Ile Leu Asp Tyr Asp Thr Asp Val Ser Leu
            420                 425                 430

Glu Lys Ile Gln Pro Ile Thr Gln Asn Gly Gln His Pro Thr
        435                 440                 445

<210> SEQ ID NO 167
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Arg Ile Ala Gln
1

<210> SEQ ID NO 168
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Arg Ile Ala Gln Lys
1               5

<210> SEQ ID NO 169
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Ser Phe Lys Arg Glu Thr
1               5

<210> SEQ ID NO 170
<211> LENGTH: 4
<212> TYPE: PRT
<213> ORGANISM: Artificial Sequence
<220> FEATURE:

<223> OTHER INFORMATION: Description of Artificial Sequence: Synthetic
peptide

<400> SEQUENCE: 170

Arg Arg Lys Arg
1

<210> SEQ ID NO 171
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 171

Arg Arg Lys Arg Val
1               5

<210> SEQ ID NO 172
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 172

Arg Arg Lys Arg Val Asn
1               5

<210> SEQ ID NO 173
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 173

Arg Arg Lys Arg Val Asn Thr Lys Arg Ser Ser
1               5                   10

<210> SEQ ID NO 174
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 174

Gln Lys Glu Lys
1

<210> SEQ ID NO 175
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 175

Gln Gln Lys Glu Lys
1               5

-continued

```
<210> SEQ ID NO 176
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Ser Gln Gln Lys Glu Lys
1               5
```

G-PROTEIN-COUPLED RECEPTOR INTERNAL SENSORS

CROSS-REFERENCE TO RELATED APPLICATIONS

This application is the U.S. National Stage Entry under § 371 of International Application No. PCT/US2017/062993, filed Nov. 22, 2017, which claims the benefit of U.S. Provisional Patent Application No. 62/426,173, filed on Nov. 23, 2016 and U.S. Provisional Patent Application No. 62/513,991, filed on Jun. 1, 2017, which are hereby incorporated herein by reference in their entireties for all purposes.

STATEMENT OF GOVERNMENTAL SUPPORT

This invention was made with government support under Grant Nos. DP2MH019427 and U01NS090604, awarded by the National Institutes of Health. The Government has certain rights in this invention.

REFERENCE TO A "SEQUENCE LISTING," A TABLE, OR A COMPUTER PROGRAM LISTING APPENDIX SUBMITTED ON A COMPACT DISK

The present application contains a Sequence Listing, which is being submitted via EFS-WEB on even date herewith. The Sequence Listing is submitted in a file entitle "Sequence Listing_052564_549N01US.txt," and is approximately 257 KB in size. This Sequence Listing is hereby incorporated by reference.

BACKGROUND

G-protein coupled receptors compose the largest family of membrane receptors in eukaryotes with more than 800 members and are involved in a variety of physiological processes. They are composed of 7-trasmembrane domains and relay an extracellular signal (i.e. light, hormone, neurotransmitter, peptide, small molecule ligand etc.) to intracellular signaling through a conformational change that triggers G-protein binding and affects a second messenger cascade. Recent crystallographic efforts have yielded important structural information for both the active and inactive state of ligand-activated GPCRs, the first of which was the Beta2AR, greatly improving our understanding of their activation mechanism [1-3]. Biopharmaceutical research has long focused on developing drugs targeting GPCRs, however these efforts have been doomed by a high failure rate, in part due to lack of tools to study drug-receptor interaction in intact living systems.

Molecular biosensors may be used in cultured cells or brain slice, or expressed in animals [4]. However, an ideal biosensor is genetically encoded and can be expressed in situ from a transgene. This allows targeting to defined cell populations by promoters and enhancers [5], conditional expression [6], and subcellular targeting with signal peptides and retention sequences [7]. Genetically encoded sensors typically employ either a single fluorescent protein or a FRET pair of donor and acceptor FPs as a reporter element. Currently available systems to study GPCR-drug interactions primarily rely on the principles of Forster Resonance Energy Transfer (FRET) or Bioluminescence Resonance Energy Transfer (BRET), between a donor and an acceptor inserted in two conformationally sensitive sites of a GPCR [8-10]. This system is bimolecular, as it necessitates a couple of fluorescence emitting molecules with partially overlapping excitation/emission spectrum to be genetically inserted into the GPCR (usually a combination of two fluorescent proteins (FPs), or one FP combined with either a peptide motif for specific dye labeling or luciferase), and therefore it consumes a large portion of the available spectrum for optical readouts. As yet another critical limitation of this system, FRET-based sensors typically afford very low signal-to-noise ratio (SNR) and dynamic range, and thus cannot be easily applied in living systems. The herein described sensors provide an improved method for single-wavelength fluorescent sensor development that allows easy generation of GPCR sensors with large SNR and dynamic range.

Fluorescent sensors based on circularly permuted single FPs (either green fluorescent protein or related FPs) have been engineered to sense small molecules so that these can be visualized directly with a change in fluorescence intensity of the chromophore [11]. Single-FP based indicators offer several appealing advantages, such as superior sensitivity, enhanced photostability, broader dynamic range and faster kinetics compared to FRET-based indicators. They are relatively small, thus relatively easier to be targeted to subcellular locations, such as spines and axonal terminals. The preserved spectrum bandwidth of single-FP indicators can allow for multiplex imaging or use alongside optogenetic effectors such as channel rhodopsin.

In systems employing fluorescent sensors based on circularly permuted single FPs, the conformation of the sensor controls the protonation state of its chromophore, and therefore its fluorescence intensity. The engineering process for these types of sensors can be streamlined and relies mostly on randomization of the linking regions between the conformational sensor (i.e. a bacterial Periplasmic Binding Protein) and a circularly permuted FP. This sensor design strategy has been able to yield sensors with 5-6 fold increases in GFP fluorescence in response to the stimulus and has encountered great applicability in living systems [12, 13]. Therefore, we demonstrate the design and creation of single-FP based sensors using GPCRs as a scaffold.

SUMMARY

In one aspect, provided is a G protein-coupled receptor (GPCR) comprising a sensor, e.g., a fluorescent sensor, integrated into the third intracellular loop of the G protein-coupled receptor. In varying embodiments, the sensor comprises the following polypeptide structure: L1-cpFP-L2, wherein:

(1) L1 comprises a peptide linker having LSS at the N-terminus and from 5 to 13 amino acid residues, wherein each amino acid residue can be any naturally occurring amino acid;

(2) cpFP comprises a circularly permuted fluorescent protein, wherein the circularly permuted N-terminus is positioned within beta strand seven of a non-permuted fluorescent protein; and (3) L2 comprises a peptide linker having DQL at the C-terminus and from 5 to 6 amino acid residues, wherein each amino acid residue can be any naturally occurring amino acid. In some embodiments, L1 comprises LSSX1X2 and L2 comprises X3X4DQL, wherein X1, X2, X3, X4 are independently any amino acid. In some embodiments, L1 comprises QLQKIDLSSX1X2 and L2 comprises X3X4DQL, wherein X1, X2, X3, X4 are independently any amino acid. In some embodiments, X1X2 is selected from the group consisting of leucine-isoleucine (LI), alanine-valine (AV), isoleucine-lysine (IK), serine-arginine (SR), lysine-valine (KV), leucine-alanine (LA), cysteine-proline (CP), glycine-methionine (GM), valine-arginine (VR), asparagine-valine (NV), arginine-valine (RV), arginine-glycine (RG), leucine-glutamate (LE), serine-glycine (SG), valine-aspartate (VD), alanine-phenylalanine (AF), threonine-aspartate (TD), methionine-arginine (MR), leucine-glycine (LG), arginine-glutamine (RQ), serine-tryptophan (SW), serine-glycine (SG), valine-aspartate (VD), leucine-glutamate (LE), alanine-phenylalanine (AF), serine-tryptophan (SW), arginine-glycine (RG), threonine-aspartate (TD), leucine-glycine (LG), arginine-glutamine (RQ), threonine-tyrosine (TY), leucine-leucine (LL), valine-leucine (VL), threonine-glutamine (TQ), valine-phenylalanine (VF), threonine-threonine (TT), leucine-valine (LV), valine-isoleucine (VI), valine-valine (VV), proline-valine (PV), glycine-valine (GV), serine-valine (SV), phenylalanine-valine (FV), cysteine-valine (CV), glutamate-valine (EV), glutamine-valine (QV), and lysine-valine (KV), arginine-tryptophan (RW), glycine-aspartate (GD), alanine-leucine (AL), proline-methionine (PM), glycine-arginine (GR), glycine-tyrosine (GY), isoleucine-cysteine (IC), and glycine-leucine (GL). In some embodiments, X3X4 is selected from the group consisting of asparagine-histidine (NH), threonine-arginine (TR), isoleucine-isoleucine (II), proline-proline (PP), leucine-phenylalanine (LF), valine-threonine (VT), glutamine-glycine (QG), alanine-leucine (AL), proline-arginine (PR), arginine-glycine (RG), threonine-leucine (TL), threonine-proline (TP), glycine-valine (GV), threonine-threonine (TT), cysteine-cysteine (CC), alanine-threonine (AT), leucine-proline (LP), tyrosine-proline (YP), tryptophan-proline (WP), serine-leucine (SL), glutamate-arginine (ER), methionine-cysteine (MC), methionine-histidine (MH), tryptophan-leucine (YL), leucine-serine (LS), arginine-proline (RP), lysine-proline (KP), tyrosine-proline (YP), tryptophan-proline (WP), serine-serine (SS), glycine-valine (GV), valine-serine (VS), glutamine-asparagine (QN), lysine-serine (KS), lysine-threonine (KT), lysine-histidine (KH), lysine-valine (KV), lysine-glutamine (KQ), lysine-arginine (KR), cysteine-proline (CP), alanine-proline (AP), serine-proline (SP), isoleucine-proline (IP), tyrosine-proline (YP), threonine-proline (TP), arginine-proline (RP), aspartate-histidine (DH), histidine-tyrosine (HY), glycine-glycine (GG), proline-histidine (PH), serine-threonine (ST), arginine-serine (RS), arginine-histidine (RH), and tryptophan-proline (WP). In some embodiments, X1X2 comprises alanine-valine (AV) and X3X4 comprises lysine-proline (KP); threonine-arginine (TR); aspartate-histidine (DH); threonine-threonine (TT); serine-serine (SS); glycine-valine (GV); cysteine-cysteine (CC); valine-serine (VS); glutamine-asparagine (QN); lysine-serine (KS); lysine-threonine (KT); lysine-histidine (KH); lysine-valine (KV); lysine-glutamine (KQ); lysine-arginine (KR); lysine-proline (KP); cysteine-proline (CP); alanine-proline (AP); serine-proline (SP); isoleucine-proline (IP); tyrosine-proline (YP); threonine-proline (TP); or arginine-proline (RP);

X1X2 comprises leucine-valine (LV) and X3X4 comprises threonine-arginine (TR), lysine-proline (KP) or valine-threonine (VT); X1X2 comprises arginine-valine (RV) and X3X4 comprises threonine-arginine (TR), lysine-proline (KP) or threonine-proline (TP); X1X2 comprises arginine-glycine (RG) and X3X4 comprises tyrosine-leucine (YL) or threonine-arginine (TR); X1X2 comprises serine-arginine (SR) and X3X4 comprises leucine-phenylalanine (LF) or proline-proline (PP); X1X2 comprises proline-methionine (PM) and X3X4 comprises proline-histidine (PH) or serine-serine (SS); X1X2 comprises valine-valine (VV) and X3X4 comprises threonine-arginine (TR) or lysine-proline (KP); X1X2 comprises leucine-isoleucine (LI) and X3X4 comprises threonine-arginine (TR); X1X2 comprises threonine-tyrosine (TY) and X3X4 comprises threonine-arginine (TR); X1X2 comprises isoleucine-lysine (IK) and X3X4 comprises isoleucine-isoleucine (II); X1X2 comprises cysteine-proline (CP) and X3X4 comprises alanine-leucine (AL); X1X2 comprises glycine-methionine (GM) and X3X4 comprises proline-arginine (PR); X1X2 comprises leucine-alanine (LA) and X3X4 comprises glutamine-glycine (QG); X1X2 comprises valine-arginine (VR) and X3X4 comprises arginine-glycine (RG); X1X2 comprises serine-glycine (SG) and X3X4 comprises tyrosine-proline (YP); X1X2 comprises valine-aspartate (VD) and X3X4 comprises tryptophan-proline (WP); X1X2 comprises leucine-glutamate (LE) and X3 X4 comprises leucine-proline (LP); X1X2 comprises alanine-phenylalanine (AF) and X3X4 comprises serine-leucine (SL); X1X2 comprises serine-tryptophan (SW) and X3X4 comprises arginine-proline (RP); X1X2 comprises threonine-aspartate (TD) and X3X4 comprises glutamate-arginine (ER); X1X2 comprises leucine-glycine (LG) and X3X4 comprises methionine-histidine (MH); X1X2 comprises arginine-glutamine (RQ) and X3X4 comprises leucine-serine (LS); X1X2 comprises methionine-arginine (MR) and X3X4 comprises methionine-cysteine (MC); X1X2 comprises leucine-leucine (LL) and X3X4 comprises threonine-arginine (TR); X1X2 comprises valine-leucine (VL) and X3X4 comprises threonine-arginine (TR); X1X2 comprises threonine-glutamine (TQ) and X3X4 comprises threonine-arginine (TR); X1X2 comprises valine-phenylalanine (VF) and X3X4 comprises threonine-arginine (TR); X1X2 comprises threonine-threonine (TT) and X3X4 comprises threonine-arginine (TR); X1X2 comprises valine-isoleucine (VI) and X3X4 comprises threonine-arginine (TR); X1X2 comprises proline-valine (PV) and X3X4 comprises lysine-proline (KP); X1X2 comprises glycine-valine (GV) and X3X4 comprises lysine-proline (KP); X1X2 comprises serine-valine (SV) and X3X4 comprises lysine-proline (KP); X1X2 comprises asparagine-valine (NV) and X3X4 comprises lysine-proline (KP); X1X2 comprises phenylalanine-valine (FV) and X3X4 comprises lysine-proline (KP); X1X2 comprises cysteine-valine (CV) and X3X4 comprises lysine-proline (KP); X1X2 comprises glutamate-valine (EV) and X3X4 comprises lysine-proline (KP); X1X2 comprises glutamine-valine (QV) and X3X4 comprises lysine-proline (KP); X1X2 comprises lysine-valine (KV) and X3X4 comprises lysine-proline (KP); X1X2 comprises arginine-tryptophan (RW) and X3X4 comprises histidine-tyrosine (HY); X1X2 comprises glycine-aspartate (GD) and X3X4 comprises glycine-glycine (GG); X1X2 comprises alanine-leucine (AL) and X3X4 comprises asparagine-histidine (NH); X1X2 comprises glycine-arginine (GR) and X3X4 comprises serine-threonine (ST); X1X2 comprises glycine-tyrosine (GY) and X3X4 comprises arginine-serine (RS); X1X2 comprises isoleucine-cysteine (IC) and X3X4 comprises arginine-histidine (RH); or X1X2 comprises glycine-leucine (GL) and X3X4 comprises tryptophan-proline (WP). In some embodiments, L1 comprises LSSLIX1 and L2 comprises X2NHDQL, wherein X1, X2 are independently any amino acid. In some embodiments, X1 is selected from the group consisting of I, W, V, L, F, P, N, Y and D; and X2 is selected from the group consisting of G, N, M, R T, S, K, L, Y, H, F, E, I and W. In some embodiments, X1 is I and X2 is N or S; X1 is W and X2 is M, T, F, E or I; X1 is V and X2 is R, Hor T; X1 is L and X2 is T; X1 is F and X2 is S; X1 is P and X2 is K or S; X1 is Y and X2 is S, L; or X1 is D and X2 is W. In some embodiments, the circularly permuted N-terminus of the cpFP is positioned within the motif YN(Y/F)(N/I)SHNV (SEQ ID NO:19) or WE(A/P/V)(S/L/N/T)(S/E/T)E(R/M/T/K)(M/L)(SEQ ID NO:20) of a non-permuted fluorescent protein. In some embodiments, the circularly permuted N-terminus is positioned at the amino acid residue corresponding to residue 7 of the amino acid motif YN(Y/F)(N/I) SHNV (SEQ ID NO:19) of a non-permuted green fluorescent protein. In some embodiments, the circularly permuted N-terminus is positioned at the amino acid residue corresponding to residue 3, 4, 5, 6 or 7 of the amino acid motif WE(A/P/V)(S/L/N/T)(S/E/T)E(R/M/T/K)(M/L)(SEQ ID NO: 20) of a non-permuted red-fluorescent protein. In some embodiments, the circularly permuted fluorescent protein is from a photo-convertible or photoactivable fluorescent protein. In some embodiments, the photo-convertible or photoactivable fluorescent protein is selected from the group consisting of paGFP, mCherry, mEos2, mRuby2, mRuby3, mClover3, mApple, mKate2, mMaple, mCardinal, mNeptune, far-red single-domain cyanbacteriochrome WP 016871037 and far-red single-domain cyanbacteriochrome anacy 2551g3. In some embodiments, the circularly permuted fluorescent protein is from a green fluorescent protein. In some embodiments, the circularly permuted fluorescent protein is from a fluorescent protein having at least about 90% sequence identity, e.g., at least about 91%, 92%, 93%, 94%, 95%, 96%, 97%, 98%, 99% or 100% sequence identity, to a non-permuted fluorescent protein selected from the group consisting of SEQ ID NOs: 1-14. In some embodiments, the circularly permuted fluorescent protein is from a green fluorescent protein having at least about 90% sequence identity, e.g., at least about 91%, 92%, 93%, 94%, 95%, 96%, 97%, 98%, 99% or 100% sequence identity, SEQ ID NO: 1, wherein the tyrosine at residue position 69 of SEQ ID NO: 1 is replaced with a tryptophan (Y69W) to generate a cyan fluorescent protein (CFP) sensor. In some embodiments, the circularly permuted fluorescent protein is from a green fluorescent protein having at least about 90% sequence identity, e.g., at least about 91%, 92%, 93%, 94%, 95%, 96%, 97%, 98%, 99% or 100% sequence identity, SEQ ID NO: 1, wherein the threonine at residue position 206 of SEQ ID NO: 1 is replaced with a tyrosine (T206Y) to generate a yellow fluorescent protein (YFP) sensor. In some embodiments, the circularly permuted fluorescent protein has at least about 90% sequence identity, e.g., at least about 91%, 92%, 93%, 94%, 95%, 96%, 97%, 98%, 99% or 100% sequence identity, to a circularly permuted fluorescent protein selected from the group consisting of SEQ ID NOs: 15-18. In some embodiments, the sensor is integrated into the third intracellular loop of the GPCR. In some embodiments, the GPCR is a class A type or alpha GPCR. In some embodiments, the GPCR is a Gs, Gi or Gq-coupled receptor. In some embodiments, the GPCR is selected from the group consisting of an adrenoceptor or adrenergic receptor, an opioid receptor, a 5-Hydroxytryptamine (5 HT) receptor, a dopamine receptor, a muscarinic acetylcholine receptor, an adenosine receptor, a glutamate metabotropic receptor, a gamma-aminobutyric acid (GABA) type B receptor, corticotropin-releasing factor (CRF) receptor, a tachykinin or neurokinin (NK) receptor, an angiotensin receptor, an apelin receptor, a bile acid receptor, a bombesin receptor, a bradykinin receptor, a cannabinoid receptor, a chemokine receptor, a cholecystokinin receptor, a complement peptide receptor, an endothelin receptor, a formylpeptide receptor, a free fatty acid receptor, a galanin receptor, a ghrelin receptor, a glycoprotein hormone, a gonadotrophin-releasing hormone receptor, a G protein-coupled estrogen receptor, an histamine receptor, a leukotriene receptor, a lysophospholipid (LPA) receptor, a lysophospholipid (SIP) receptor, a melanocortin receptor, a melatonin receptor, a neuropeptide receptor, a neurotensin receptor, an orexin receptor, a P2Y receptor, a prostanoid or prostaglandin receptor, somatostatin receptor, a tachykinin receptor, a thyrotropin-releasing hormone receptor, a urotensin receptor, and a vasopressin/oxytocin receptor. In some embodiments, the GPCR is selected from the group consisting of an ADRB1 (B1AR) adrenoceptor beta 1, an ADRB2 (B2AR) adrenoceptor beta 2, an adrenoceptor alpha 2A (ADRA2A), an ADORA1 (A1AR) adenosine A1 receptor, an ADORA2A (A2AR) adenosine A2a receptor, a mu (μ)-type opioid receptor (OPRM or MOR), a kappa (κ)-type opioid receptor (OPRK or KOR), a delta (δ)-type opioid receptor (OPRD or DOR), a Dopamine Receptor type-1 (DRD1); a Dopamine Receptor type-2 (DRD2); a Dopamine Receptor type-4 (DRD4); a Serotonin Receptor type-2A (5HT2A); a Serotonin Receptor type-2B (5HT2B), a MTNR1B (MT2) melatonin receptor 1B, a CNR1 (CB1) cannabinoid receptor 1, a histamine receptor H1 (HRH1), a neuropeptide Y receptor Y1 (NPY1R), a cholinergic receptor muscarinic 2 (CHRM2), a hypocretin (orexin) receptor 1 (HCRTR1), a tachykinin receptor 1 (TACR1)(a.k.a. neurokinin 1 receptor (NK1R)), a corticotropin releasing hormone receptor 1 (CRHR1), a glutamate metabotropic receptor 1 (GRM1), a gamma-aminobutyric acid (GABA) type B receptor subunit 1 (GABBR1), a Metabotropic Glutamate Receptor type-3 (MGLUR3); a Metabotropic Glutamate Receptor type-5 (MGLUR5); a Gamma-aminobutyric acid Receptor type-2 (GABAB1); a Gamma-aminobutyric acid Receptor type-2 (GABAB2); a Gonadotropin-Releasing Hormone Receptor (GNRHR); a Vasopressin Receptor type-1 (V1A); an Oxytocin Receptor (OTR); an Acetylcholine Muscarinic Receptor type-2 (M2R); an Histamine Receptor type-1 (H1R); a Tachykinin Receptor type-1 (NK1); a Tachykinin Receptor type-2 (NK2); a Tachykinin Receptor type-3 (NK3); a P2 purinoceptor type Y1 (P2Y1); an Angiotensin-II Receptor type-1 (AT1). In some embodiments, the GPCR is selected from the group consisting of ADRB1 (B1AR) adrenoceptor beta 1, ADRB2 (B2AR) adrenoceptor beta 2, ADORA1 (A1AR) adenosine A1 receptor, ADORA2A (A2AR) adenosine A2a receptor, a mu (μ)-type opioid receptor (OPRM or MOR), a kappa (κ)-type opioid receptor (OPRK or KOR), a dopamine receptor D1 (DRD1), a dopamine receptor D2 (DRD2), a dopamine receptor D4 (DRD4), a 5 hydroxy-tryptamine receptor 2A (5-HT2A), MTNR1B (MT2) melatonin receptor 1B. In some embodiments, the GPCR:

i) is a human dopamine receptor D1 (DRD1), and the N-terminus of the sensor abuts the amino acid sequence RIYRIAQK of the receptor and the C-terminus of the sensor abuts the amino acid sequence KRETKVLK of the receptor;

ii) is a human ADRB1 (B1AR) adrenoceptor beta 1 receptor, and the N-terminus of the sensor abuts the amino acid sequence RVFREAQK of the receptor and the C-terminus of the sensor abuts the amino acid sequence REQKALKT of the receptor;

iii) is a human ADRB2 (B2AR) adrenoceptor beta 2 receptor, and the N-terminus of the sensor abuts the amino acid sequence RVFQEAKR of the receptor and the C-terminus of the sensor abuts the amino acid sequence KEHKALKT of the receptor;

iv) is a human dopamine receptor D2 (DRD2), and the N-terminus of the sensor abuts the amino acid sequence IVLRRRRK of the receptor and the C-terminus of the sensor abuts the amino acid sequence QKEKKATQ of the receptor;

V is a human dopamine receptor D4 (DRD4), and the N-terminus of the sensor abuts the amino acid sequence RGLQRWEV of the receptor and the C-terminus of the sensor abuts the amino acid sequence GRERKAMR of the receptor;

vi) is a human kappa (κ)-type opioid receptor (OPRK or KOR), and the N-terminus of the sensor abuts the amino acid sequence LMILRLKS of the receptor and the C-terminus of the sensor abuts the amino acid sequence REKDRNLR of the receptor;

vii) is a human mu (μ)-type opioid receptor (OPRM or MOR), and the N-terminus of the sensor abuts the amino acid sequence LMILRLKS of the receptor and the C-terminus of the sensor abuts the amino acid sequence KEKDRNLR of the receptor;

viii) is a human ADORA2A (A2AR) adenosine A2a receptor, and the N-terminus of the sensor abuts the amino acid sequence RIYQIAKR of the receptor and the C-terminus of the sensor abuts the amino acid sequence REKRFTFV of the receptor;

ix) is a human MTNR1B (MT2) melatonin receptor 1B, and the N-terminus of the sensor abuts the amino acid sequence VLVLQARR of the receptor and the C-terminus of the sensor abuts the amino acid sequence KPSDLRSF of the receptor;

x) is a human 5 hydroxy-tryptamine receptor 2A (5-HT2A), and the N-terminus of the sensor abuts the amino acid sequence LTIKSLQK of the receptor and the C-terminus of the sensor abuts the amino acid sequence NEQKACKV of the receptor; or xi) is a human ADORA1 (A1AR) adenosine A1 receptor, and the N-terminus of the sensor abuts the amino acid sequence RVYVVAKR of the receptor and the C-terminus of the sensor abuts the amino acid sequence SREKKAAK of the receptor. In some embodiments, the receptor is mutated to be signaling incompetent or incapable. In some embodiments, the receptor is substantially isolated and/or purified and/or solubilized. In some embodiments, the GPCR comprises a beta2 adrenergic receptor having at least 90% sequence identity, e.g., at least about 91%, 92%, 93%, 94%, 95%, 96%, 97%, 98%, 99% or 100% sequence identity, to SEQ ID NO: 22 or SEQ ID NO:32. In some embodiments, one or more of amino acid residues S355 and S356 (residues 624-625 in SEQ ID NO: 22) are replaced with alanine residues. In some embodiments, X at amino acid residue 163 in SEQ ID NO: 22 or at residue 139 of SEQ ID NO: 32 is any amino acid or an amino acid selected from the group consisting of A, F, G, I, L, M, S, T and V. In some embodiments, the GPCR comprises a mu (μ)-type opioid receptor having at least 90% sequence identity, e.g., at least about 91%, 92%, 93%, 94%, 95%, 96%, 97%, 98%, 99% or 100% sequence identity, to SEQ ID NO: 24 or SEQ ID NO:37. In some embodiments, X at amino acid residue 199 in SEQ ID NO: 24 or at residue 175 of SEQ ID NO: 37 is any amino acid or an amino acid selected from the group consisting of A, F, G, I, L, M, S, T and V. In some embodiments, the GPCR comprises a dopamine receptor D1 (DRD1) having at least 90% sequence identity, e.g., at least about 91%, 92%, 93%, 94%, 95%, 96%, 97%, 98%, 99% or 100% sequence identity, to SEQ ID NO: 26 or SEQ ID NO:30. In some embodiments, X at amino acid residue 153 in SEQ ID NO: 26 or at residue 129 of SEQ ID NO: 30 is any amino acid or an amino acid selected from the group consisting of A, F, G, I, L, M, S, T and V. In some embodiments, the GPCR comprises a 5 hydroxy-tryptamine 2A (5-HT2A) receptor having at least 90% sequence identity, e.g., at least about 91%, 92%, 93%, 94%, 95%, 96%, 97%, 98%, 99% or 100% sequence identity, to SEQ ID NO: 28 or SEQ ID NO: 33. In some embodiments, X at amino acid residue 205 in SEQ ID NO: 28 or at residue 181 of SEQ ID NO:33 is any amino acid or an amino acid selected from the group consisting of A, F, G, I, L, M, S, T and V. In some embodiments, the GPCR comprises an adrenoceptor beta 1 (ADRB1) having at least 90% sequence identity, e.g., at least about 91%, 92%, 93%, 94%, 95%, 96%, 97%, 98%, 99% or 100% sequence identity, to SEQ ID NO:31. In some embodiments, X at amino acid residue 164 in SEQ ID NO: 31 is any amino acid or an amino acid selected from the group consisting of A, F, G, I, L, M, S, T and V. In some embodiments, the GPCR comprises an adenosine A2a receptor (ADORA2A) having at least 90% sequence identity, e.g., at least about 91%, 92%, 93%, 94%, 95%, 96%, 97%, 98%, 99% or 100% sequence identity, to SEQ ID NO: 34. In some embodiments, X at amino acid residue 110 in SEQ ID NO: 34 is any amino acid or an amino acid selected from the group consisting of A, F, G, I, L, M, S, T and V. In some embodiments, the GPCR comprises an adrenoceptor alpha 2A (ADRA2A) having at least 90% sequence identity, e.g., at least about 91%, 92%, 93%, 94%, 95%, 96%, 97%, 98%, 99% or 100% sequence identity, to SEQ ID NO: 35. In some embodiments, X at amino acid residue 139 in SEQ ID NO: 35 is any amino acid or an amino acid selected from the group consisting of A, F, G, I, L, M, S, T and V. In some embodiments, the GPCR comprises a kappa receptor delta 1 (OPRK1) having at least 90% sequence identity, e.g., at least about 91%, 92%, 93%, 94%, 95%, 96%, 97%, 98%, 99% or 100% sequence identity, to SEQ ID NO: 36. In some embodiments, X at amino acid residue 164 in SEQ ID NO: 36 is any amino acid or an amino acid selected from the group consisting of A, F, G, I, L, M, S, T and V. In some embodiments, the GPCR comprises an opioid receptor delta 1 (OPRD1) having at least 90% sequence identity, e.g., at least about 91%, 92%, 93%, 94%, 95%, 96%, 97%, 98%, 99% or 100% sequence identity, to SEQ ID NO: 38. In some embodiments, X at amino acid residue 154 in SEQ ID NO: 38 is any amino acid or an amino acid selected from the group consisting of A, F, G, I, L, M, S, T and V. In some embodiments, the GPCR comprises a melatonin receptor 1B (MTNR1B) having at least 90% sequence identity, e.g., at least about 91%, 92%, 93%, 94%, 95%, 96%, 97%, 98%, 99% or 100% sequence identity, to SEQ ID NO: 39. In some embodiments, X at amino acid residue 146 in SEQ ID NO: 39 is any amino acid or an amino acid selected from the group consisting of A, F, G, I, L, M, S, T and V. In some embodiments, the GPCR comprises a cannabinoid receptor type 1 (CNR1) having at least 90% sequence identity, e.g., at least about 91%, 92%, 93%, 94%, 95%, 96%, 97%, 98%, 99% or 100% sequence identity, to SEQ ID NO: 40. In some embodiments, X at amino acid residue 222 in SEQ ID NO: 40 is any amino acid or an amino acid selected from the group consisting of A, F, G, I, L, M, S, T and V. In some embodiments, the GPCR comprises a histamine receptor H1 (HRH1) having at least 90% sequence identity, e.g., at least about 91%, 92%, 93%, 94%, 95%, 96%, 97%, 98%, 99% or 100% sequence identity, to SEQ ID NO: 41. In some embodiments, X at amino acid residue 133 in SEQ ID NO: 41 is any amino acid or an amino acid selected from the group consisting of A, F, G, I, L, M, S, T and V. In some embodiments, the GPCR comprises a neuropeptide Y receptor Y1 (NPY1R) having at least 90% sequence identity, e.g., at least about 91%, 92%, 93%, 94%, 95%, 96%, 97%, 98%, 99% or 100% sequence identity, to SEQ ID NO: 42. In some embodiments, the GPCR comprises a muscarinic cholinergic receptor type 2 (CHRM2) having at least 90% sequence identity, e.g., at least about 91%, 92%, 93%, 94%, 95%, 96%, 97%, 98%, 99% or 100% sequence identity, to SEQ ID NO: 43. In some embodiments, X at amino acid residue 129 in SEQ ID NO: 43 is any amino acid or an amino acid selected from the group consisting of A, F, G, I, L, M, S, T and V. In some embodiments, the GPCR comprises a hypocretin (orexin) receptor 1 (HCRTR1) having at least 90% sequence identity, e.g., at least about 91%, 92%, 93%, 94%, 95%, 96%, 97%, 98%, 99% or 100% sequence identity, to SEQ ID NO: 44. In some embodiments, X at amino acid residue 152 in SEQ ID NO: 44 is any amino acid or an amino acid selected from the group consisting of A, F, G, I, L, M, S, T and V. In some embodiments, the GPCR comprises a dopamine receptor D2 (DRD2) having at least 90% sequence identity e.g., at least about 91%, 92%, 93%, 94%, 95%, 96%, 97%, 98%, 99% or 100% sequence identity, to SEQ ID NO: 46. In some embodiments, the GPCR comprises a dopamine receptor D4 (DRD4) having at least 90% sequence identity e.g., at least about 91%, 92%, 93%, 94%, 95%, 96%, 97%, 98%, 99% or 100% sequence identity, to SEQ ID NO: 48.

In a further aspect, provided is a nanodisc comprising the GPCR having a cpFP sensor integrated into its third intracellular loop, as described above and herein, as described above and herein. In a further aspect, provided is a solid support attached to one or more GPCR, or one or more nanodiscs, the GPCRs and nanodiscs being described above and herein. In some embodiments, the solid support is a bead or a microarray.

In a further aspect, provided is a polynucleotide encoding the GPCR having a cpFP sensor integrated into its third intracellular loop, as described above and herein, as described above and herein. Further provided is an expression cassette comprising the polynucleotide encoding the GPCR having an integrated sensor, as described above and herein. Further provided is a vector comprising the polynucleotide of encoding the GPCR having an integrated sensor, as described above and herein. In some embodiments, the vector is a plasmid vector or a viral vector. In some embodiments, the vector is a viral vector from a virus selected from the group consisting of a retrovirus, a lentivirus, an adeno virus, and an adeno-associated virus.

In another aspect, provided is cell comprising the GPCR having a cpFP sensor integrated into its third intracellular loop, as described above and herein, as described above and herein, e.g., integrated into the extracellular membrane of the cell. In another aspect, provided is cell comprising the polynucleotide encoding the GPCR, as described above and herein, e.g., integrated into the genome of the cell. In some embodiments, the cell is a mammalian cell. In some embodiments, the cell is an astrocyte or a neuronal cell. In some embodiments, the cell is an induced pluripotent stem cell (iPSC). In some embodiments, the cell is selected from a Chinese hamster ovary (CHO) cell, an HEK 293T cell and a HeLa cell.

In another aspect, provided is a transgenic animal comprising the GPCR having a cpFP sensor integrated into its third intracellular loop, as described above and herein. In some embodiments, the animal is selected from a mouse, a rat, a worm, a fly and a zebrafish. In some embodiments, the animal is a mouse, and the GPCR is expressed in the CNS tissues of the mouse. In some embodiments, the animal is a mouse, and the GPCR is expressed in the brain cortex of the mouse.

In a further aspect, provided is a kit comprising the GPCR having a cpFP sensor integrated into its third intracellular loop, as described above and herein, the solid support, the nanodisc, the polynucleotide, the expression cassette, the vector, the cell, and/or the transgenic animal, as described above and herein.

In another aspect, provided are methods of detecting binding of a ligand to a GPCR. In some embodiments, the methods comprise:

a) contacting the ligand with a GPCR, as described above and herein, under conditions sufficient for the ligand to bind to the GPCR; and
b) determining a change in an optics signal from the sensor integrated into the third intracellular loop of the GPCR, wherein a detectable change in fluorescence signal indicates binding of the ligand to the GPCR. In some embodiments, the optics signal is a linear optics signal. In some embodiments, the linear optics signal comprises fluorescence. In some embodiments, the change in fluorescence signal comprises a change in intensity of the fluorescence signal. In some embodiments, the change in fluorescence intensity is at least about 10% over, e.g., at least about 15%, 20%, 25%, 30%, 35%, 40%, or more, over baseline, in the absence of ligand binding. In some embodiments, the change in fluorescence signal comprises a change in color (spectrum or wavelength) of the fluorescence signal. In some embodiments, the optics signal is a non-linear optics signal. In some embodiments, the non-linear optics signal is selected from the group consisting of fiber optics, miniature fiber optics, fiber photometry, one photon imaging, two photon imaging, and three photon imaging. In some embodiments, a binding ligand further indicates activation of intracellular signaling from the GPCR. In some embodiments, the ligand is a suspected agonist of the GPCR. In some embodiments, the ligand is a suspected inverse agonist of the GPCR. In some embodiments, the ligand is a suspected antagonist of the GPCR. In some embodiments, the GPCR is in vitro. In some embodiments, the GPCR is in vivo.

In another aspect, provided are methods of screening for binding of a ligand to a GPCR. In some embodiments, the methods comprise:

a) contacting a plurality of members from a library of ligands with a plurality of GPCRs, as described above and herein, under conditions sufficient for the ligand members to bind to the GPCRs, wherein the plurality of GPCRs are arranged in an array of predetermined addressable locations; and b) determining a change in one or more optics signals from the sensor integrated into the third intracellular loop of the plurality GPCRs, wherein a detectable change in the one or more fluorescence signals indicates binding of one or more members of the library of ligands to at least one of the plurality GPCR. In some embodiments, the one or more optics signals comprise a linear optics signal. In some embodiments, the linear optics signal comprises fluorescence. In some embodiments, the one or more fluorescence signals fluoresce at the same wavelength. In some embodiments, the one or more fluorescence signals fluoresce at different wavelengths. In some embodiments, the change in fluorescence signal comprises a change in intensity of the fluorescence signal. In some embodiments, the change in fluorescence intensity is at least about 10% over, e.g., at least about 15%, 20%, 25%, 30%, 35%, 40%, or more, over baseline, in the absence of ligand binding. In some embodiments, the change in fluorescence signal comprises a change in color (spectrum or wavelength) of the fluorescence signal. In some embodiments, the optics signal is a non-linear optics signal. In some embodiments, the non-linear optics signal is selected from the group consisting of fiber optics, miniature fiber optics, fiber photometry, one photon imaging, two photon imaging, and three photon imaging. In some embodiments, a binding ligand further indicates activation of intracellular signaling from the GPCR. In some embodiments, two or more members of the plurality of GPCRs are different. In some embodiments, two or more members of the plurality of G-protein coupled receptors are a different type of GPCR. In some embodiments, two or more members of the plurality of G-protein coupled receptors are a different subtype of a GPCR. In some embodiments, two or more members of the plurality of GPCRs comprise a sensor that fluoresces at a different wavelength.

In a further aspect, further provided is a fluorescent sensor. In some embodiments, sensor comprises the following polypeptide structure: L1-cpFP-L2, wherein:

(1) L1 comprises a peptide linker having LSS at the N-terminus and from 5 to 13 amino acid residues, wherein each amino acid residue can be any naturally occurring amino acid;

(2) cpFP comprises a circularly permuted fluorescent protein, wherein the circularly permuted N-terminus is positioned within beta strand seven of a non-permuted fluorescent protein; and (3) L2 comprises a peptide linker having DQL at the C-terminus and from 5 to 6 amino acid residues, wherein each amino acid residue can be any naturally occurring amino acid. In some embodiments, L1 comprises LSSX1X2 and L2 comprises X3X4DQL, wherein X1, X2, X3, X4 are independently any amino acid. In some embodiments, wherein L1 comprises QLQKIDLSSX1X2 and L2 comprises X3X4DQL, wherein X1, X2, X3, X4 are independently any amino acid. In some embodiments, X1X2 is selected from the group consisting of leucine-isoleucine (LI), alanine-valine (AV), isoleucine-lysine (IK), serine-arginine (SR), lysine-valine (KV), leucine-alanine (LA), cysteine-proline (CP), glycine-methionine (GM), valine-arginine (VR), asparagine-valine (NV), arginine-valine (RV), arginine-glycine (RG), leucine-glutamate (LE), serine-glycine (SG), valine-aspartate (VD), alanine-phenylalanine (AF), threonine-aspartate (TD), methionine-arginine (MR), leucine-glycine (LG), arginine-glutamine (RQ), serine-tryptophan (SW), serine-glycine (SG), valine-aspartate (VD), leucine-glutamate (LE), alanine-phenylalanine (AF), serine-tryptophan (SW), arginine-glycine (RG), threonine-aspartate (TD), leucine-glycine (LG), arginine-glutamine (RQ), threonine-tyrosine (TY), leucine-leucine (LL), valine-leucine (VL), threonine-glutamine (TQ), valine-phenylalanine (VF), threonine-threonine (TT), leucine-valine (LV), valine-isoleucine (VI), valine-valine (VV), proline-valine (PV), glycine-valine (GV), serine-valine (SV), phenylalanine-valine (FV), cysteine-valine (CV), glutamate-valine (EV), glutamine-valine (QV), and lysine-valine (KV), arginine-tryptophan (RW), glycine-aspartate (GD), alanine-leucine (AL), proline-methionine (PM), glycine-arginine (GR), glycine-tyrosine (GY), isoleucine-cysteine (IC), and glycine-leucine (GL). In some embodiments, X3X4 is selected from the group consisting of asparagine-histidine (NH), threonine-arginine (TR), isoleucine-isoleucine (II), proline-proline (PP), leucine-phenylalanine (LF), valine-threonine (VT), glutamine-glycine (QG), alanine-leucine (AL), proline-arginine (PR), arginine-glycine (RG), threonine-leucine (TL), threonine-proline (TP), glycine-valine (GV), threonine-threonine (TT), cysteine-cysteine (CC), alanine-threonine (AT), leucine-proline (LP), tyrosine-proline (YP), tryptophan-proline (WP), serine-leucine (SL), glutamate-arginine (ER), methionine-cysteine (MC), methionine-histidine (MH), tryptophan-leucine (YL), leucine-serine (LS), arginine-proline (RP), lysine-proline (KP), tyrosine-proline (YP), tryptophan-proline (WP), serine-serine (SS), glycine-valine (GV), valine-serine (VS), glutamine-asparagine (QN), lysine-serine (KS), lysine-threonine (KT), lysine-histidine (KH), lysine-valine (KV), lysine-glutamine (KQ), lysine-arginine (KR), cysteine-proline (CP), alanine-proline (AP), serine-proline (SP), isoleucine-proline (IP), tyrosine-proline (YP), threonine-proline (TP), arginine-proline (RP), aspartate-histidine (DH), histidine-tyrosine (HY), glycine-glycine (GG), proline-histidine (PH), serine-threonine (ST), arginine-serine (RS), arginine-histidine (RH), and tryptophan-proline (WP). In some embodiments, X1X2 comprises alanine-valine (AV) and X3X4 comprises lysine-proline (KP); threonine-arginine (TR); aspartate-histidine (DH); threonine-threonine (TT); serine-serine (SS); glycine-valine (GV); cysteine-cysteine (CC); valine-serine (VS); glutamine-asparagine (QN); lysine-serine (KS); lysine-threonine (KT); lysine-histidine (KH); lysine-valine (KV); lysine-glutamine (KQ); lysine-arginine (KR); lysine-proline (KP); cysteine-proline (CP); alanine-proline (AP); serine-proline (SP); isoleucine-proline (IP); tyrosine-proline (YP); threonine-proline (TP); or arginine-proline (RP);

X1X2 comprises leucine-valine (LV) and X3X4 comprises threonine-arginine (TR), lysine-proline (KP) or valine-threonine (VT); X1X2 comprises arginine-valine (RV) and X3X4 comprises threonine-arginine (TR), lysine-proline (KP) or threonine-proline (TP); X1X2 comprises arginine-glycine (RG) and X3X4 comprises tyrosine-leucine (YL) or threonine-arginine (TR); X1X2 comprises serine-arginine (SR) and X3X4 comprises leucine-phenylalanine (LF) or proline-proline (PP); X1X2 comprises proline-methionine (PM) and X3X4 comprises proline-histidine (PH) or serine-serine (SS); X1X2 comprises valine-valine (VV) and X3X4 comprises threonine-arginine (TR) or lysine-proline (KP); X1X2 comprises leucine-isoleucine (LI) and X3X4 comprises threonine-arginine (TR); X1X2 comprises threonine-tyrosine (TY) and X3X4 comprises threonine-arginine (TR); X1X2 comprises isoleucine-lysine (IK) and X3X4 comprises isoleucine-isoleucine (II); X1X2 comprises cysteine-proline (CP) and X3X4 comprises alanine-leucine (AL); X1X2 comprises glycine-methionine (GM) and X3X4 comprises proline-arginine (PR); X1X2 comprises leucine-alanine (LA) and X3X4 comprises glutamine-glycine (QG); X1X2 comprises valine-arginine (VR) and X3X4 comprises arginine-glycine (RG); X1X2 comprises serine-glycine (SG) and X3X4 comprises tyrosine-proline (YP); X1X2 comprises valine-aspartate (VD) and X3X4 comprises tryptophan-proline (WP); X1X2 comprises leucine-glutamate (LE) and X3X4 comprises leucine-proline (LP); X1X2 comprises alanine-phenylalanine (AF) and X3X4 comprises serine-leucine (SL); X1X2 comprises serine-tryptophan (SW) and X3X4 comprises arginine-proline (RP); X1X2 comprises threonine-aspartate (TD) and X3X4 comprises glutamate-arginine (ER); X1X2 comprises leucine-glycine (LG) and X3X4 comprises methionine-histidine (MH); X1X2 comprises arginine-glutamine (RQ) and X3X4 comprises leucine-serine (LS); X1X2 comprises methionine-arginine (MR) and X3X4 comprises methionine-cysteine (MC); X1X2 comprises leucine-leucine (LL) and X3X4 comprises threonine-arginine (TR); X1X2 comprises valine-leucine (VL) and X3X4 comprises threonine-arginine (TR); X1X2 comprises threonine-glutamine (TQ) and X3X4 comprises threonine-arginine (TR); X1X2 comprises valine-phenylalanine (VF) and X3X4 comprises threonine-arginine (TR); X1X2 comprises threonine-threonine (TT) and X3X4 comprises threonine-arginine (TR); X1X2 comprises valine-isoleucine (VI) and X3X4 comprises threonine-arginine (TR); X1X2 comprises proline-valine (PV) and X3X4 comprises lysine-proline (KP); X1X2 comprises glycine-valine (GV) and X3X4 comprises lysine-proline (KP); X1X2 comprises serine-valine (SV) and X3X4 comprises lysine-proline (KP); X1X2 comprises asparagine-valine (NV) and X3X4 comprises lysine-proline (KP); X1X2 comprises phenylalanine-valine (FV) and X3X4 comprises lysine-proline (KP); X1X2 comprises cysteine-valine (CV) and X3X4 comprises lysine-proline (KP); X1X2 comprises glutamate-valine (EV) and X3X4 comprises lysine-proline (KP); X1X2 comprises glutamine-valine (QV) and X3X4 comprises lysine-proline (KP); X1X2 comprises lysine-valine (KV) and X3X4 comprises lysine-proline (KP); X1X2 comprises arginine-tryptophan (RW) and X3 X4 comprises histidine-tyrosine (HY); X1X2 comprises glycine-aspartate (GD) and X3X4 comprises glycine-glycine (GG); X1X2 comprises alanine-leucine (AL) and X3X4 comprises asparagine-histidine (NH); X1X2 comprises glycine-arginine (GR) and X3X4 comprises serine-threonine (ST); X1X2 comprises glycine-tyrosine (GY) and X3X4 comprises arginine-serine (RS); X1X2 comprises isoleucine-cysteine (IC) and X3X4 comprises arginine-histidine (RH); or X1X2 comprises glycine-leucine (GL) and X3X4 comprises tryptophan-proline (WP). In some embodiments, L1 comprises LSSLIX1 and L2 comprises X2NHDQL, wherein X1, X2 are independently any amino acid. In some embodiments, X1 is selected from the group consisting of I, W, V, L, F, P, N, Y and D; and X2 is selected from the group consisting of G, N, M, R T, S, K, L, Y, H, F, E, I and W. In some embodiments, X1 is I and X2 is Nor S; X1 is W and X2 is M, T, F, E or I; X1 is V and X2 is R, H or T; X1 is L and X2 is T; X1 is F and X2 is S; X1 is P and X2 is K or S; X1 is Y and X2 is S, L; or X1 is D and X2 is W. In some embodiments, the circularly permuted N-terminus is positioned within the motif YN(Y/F)(N/I)SHNV (SEQ ID NO:19) or WE(A/P/V)(S/L/N/T)(S/E/T)E(R/M/T/K)(M/L) (SEQ ID NO:20) of a non-permuted fluorescent protein. In some embodiments, the circularly permuted N-terminus is positioned at the amino acid residue corresponding to residue 7 of the amino acid motif YN(Y/F)(N/I)SHNV (SEQ ID NO:19) of a non-permuted green fluorescent protein. In some embodiments, the circularly permuted N-terminus is positioned at the amino acid residue corresponding to residue 3, 4, 5, 6 or 7 of the amino acid motif WE(A/P/V)(S/L/N/T)(S/E/T)E(R/M/T/K)(M/L)(SEQ ID NO:20) of a non-permuted red-fluorescent protein. In some embodiments, the circularly permuted fluorescent protein is from a photo-convertible or photoactivable fluorescent protein. In some embodiments, the photo-convertible or photoactivable fluorescent protein is selected from the group consisting of paGFP, mCherry, mEos2, mRuby2, mRuby3, mClover3, mApple, mKate2, mMaple, mCardinal, mNeptune, far-red single-domain cyanbacteriochrome WP_016871037 and far-red single-domain cyanbacteriochrome anacy 2551g3. In some embodiments, the circularly permuted fluorescent protein is from a green fluorescent protein. In some embodiments, the circularly permuted fluorescent protein is from a fluorescent protein having at least about 90% sequence identity, e.g., at least about 91%, 92%, 93%, 94%, 95%, 96%, 97%, 98%, 99% or 100% sequence identity, to a non-permuted fluorescent protein selected from the group consisting of SEQ ID NOs: 1-14. In some embodiments, the circularly permuted fluorescent protein is from a green fluorescent protein having at least about 90% sequence identity, e.g., at least about 91%, 92%, 93%, 94%, 95%, 96%, 97%, 98%, 99% or 100% sequence identity, SEQ ID NO: 1, wherein the tyrosine at residue position 69 of SEQ ID NO: 1 is replaced with a tryptophan (Y69W) to generate a cyan fluorescent protein (CFP) sensor. In some embodiments, the circularly permuted fluorescent protein is from a green fluorescent protein having at least about 90% sequence identity, e.g., at least about 91%, 92%, 93%, 94%, 95%, 96%, 97%, 98%, 99% or 100% sequence identity, SEQ ID NO: 1, wherein the threonine at residue position 206 of SEQ ID NO: 1 is replaced with a tyrosine (T206Y) to generate a yellow fluorescent protein (YFP) sensor.

In some embodiments, the circularly permuted fluorescent protein has at least about 90% sequence identity, e.g., at least about 91%, 92%, 93%, 94%, 95%, 96%, 97%, 98%, 99% or 100% sequence identity, to a circularly permuted fluorescent protein selected from the group consisting of SEQ ID NOs: 15-18. Further provided is a polynucleotide encoding the fluorescent sensor, as described above and herein.

Definitions

The terms "identical" or percent "identity," in the context of two or more nucleic acids or polypeptide sequences, refer to two or more sequences or subsequences that are the same or have a specified percentage of amino acid residues or nucleotides that are the same (i.e., share at least about 80% identity, for example, at least about 85%, 90%, 91%, 92%, 93%, 94%, 95%, 96%, 97%, 98%, 99% or 100% identity over a specified region to a reference sequence, e.g., any of SEQ ID NOs: 1-44, as described herein, when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Preferably, the identity exists over a region that is at least about 25 amino acids or nucleotides in length, for example, over a region that is 50, 100, 200, 300, 400 amino acids or nucleotides in length, or over the full-length of a reference sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins to fluorescent proteins, circularly permuted fluorescent proteins, and GPCR nucleic acids and proteins, the BLAST and BLAST 2.0 algorithms and the default parameters are used.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "isolated," and variants thereof when applied to a protein (e.g., a population of GPCRs having an integrated cpFP sensor), denotes that the protein is essentially free of other cellular components with which it is associated in the natural state. It is preferably in a homogeneous state. It can be in either a dry or aqueous solution, or solubilized. Purity and homogeneity are typically determined using known techniques, such as polyacrylamide gel electrophoresis or high performance liquid chromatography. A protein that is the predominant species present in a preparation is substantially purified.

The term "purified" denotes that a protein (e.g., a population of GPCRs having an integrated cpFP sensor) gives rise to essentially one band in an electrophoretic gel. Particularly, it means that the nucleic acid or protein is at least 80%, 85% or 90% pure, more preferably at least 95% pure, and most preferably at least 99% pure.

BRIEF DESCRIPTION OF THE DRAWINGS

FIGS. 6A-D illustrates characterization of Beta2AR with a cpGFP integrated into the third intracellular loop in neuronal cultures. Representative images before (A) and after (B) drug application (ISO, 10 μM) of DIV14 primary hippocampal neurons after 5 days of infection with a Lentivirus carrying a Synapsin promoter-driven Beta2AR with a cpGFP integrated into the third intracellular loop. C. ΔFF image obtained using a custom-made script on MatLab. D. Fluorescent signal trace during bath application of NE.

FIGS. 7A-D illustrate that Beta2AR with a cpGFP integrated into the third intracellular loop is signaling incompetent. Membrane relocalization of a conformationally-sensitive nanobody (Nb80) is used as an indication of Beta2AR activation. Wild-type Beta2AR with a GFP tag on it C-terminus is used as a control. Representative images before and after 10 μM drug application and fluorescence profiles are shown for Beta2AR-GFP in A and B, and for Beta2AR with a cpGFP integrated into the third intracellular loop in C and D, respectively.

FIGS. 8A-D illustrate an opioid sensor based on the Mu-opioid receptor. An opioid sensor was designed by inserting cpGFP into the Loop3 of the Mu-opioid receptor. A. Representative images of a HEK293T cell expressing the opioid sensor before and after addition of a specific Mu-opioid receptor agonist (DAMGO, 10 μM). B. Fluorescent signal trace upon addition of DAMGO, 10 μM. C. Titration curve upon addition of increasing concentrations of DAMGO (1 nm to 1 μM in 10-fold increases) and ligand washout. D. Drug/response curve of DAMGO for the opioid sensor indicates an apparent Kd of 25 nM.

FIG. 9 illustrates an alignment of fluorescent proteins of use in the present sensors. Legend: eGFP: enhanced green fluorescent protein (SEQ ID NO.: 128); eCFP: enhanced cyan fluorescent protein (SEQ ID NO.: 129); YFP: yellow fluorescent protein (SEQ ID NO.: 130); paGFP: photoactivable green fluorescent protein (SEQ ID NO.: 131); sfGFP: superfolder form of green fluorescent protein (SEQ ID NO.: 132); pamCherry: photoactivable monomeric cherry red fluorescent protein (SEQ ID NO.: 133); mKate: monomeric far-red fluorescent protein (SEQ ID NO.: 134); mEos2: green-to-red photoconvertible fluorescent protein (SEQ ID NO.: 135)

FIGS. 11A-E illustrate an alignment of the third intracellular loop from different G protein-coupled receptors. Legend: MGLUR3: Metabotropic Glutamate Receptor type-3 (SEQ ID NO.: 136); MGLUR5: Metabotropic Glutamate Receptor type-5 (SEQ ID NO.: 137); GABAB1: Gamma-aminobutyric acid Receptor type-2 (SEQ ID NO.: 138); GABAB2: Gamma-aminobutyric acid Receptor type-2 (SEQ ID NO.: 139); CB1: Cannabinoid Receptor type-1 (SEQ ID NO.: 140); GNRHR: Gonadotropin-Releasing Hormone Receptor (SEQ ID NO.: 141); VIA: Vasopressin Receptor type-1 (SEQ ID NO.: 142); OTR: Oxytocin Receptor (SEQ ID NO.: 143); A2A: Adenosine Receptor type-2 (SEQ ID NO.: 144); B2AR: Beta-2 Adrenergic Receptor (SEQ ID NO.: 145); DRD1: Dopamine Receptor type-1 (SEQ ID NO.: 146); M2R: Acetylcholine Muscarinic Receptor type-2 (SEQ ID NO.: 147); HIR: Histamine Receptor type-1 (SEQ ID NO.: 148); DRD2: Dopamine Receptor type-2 (SEQ ID NO.: 149); 5HT2A: Serotonin Receptor type-2A (SEQ ID NO.: 150); 5HT2B: Serotonin Receptor type-2B (SEQ ID NO.: 151); NK1: Tachykinin Receptor type-1 (SEQ ID NO.: 152); NK3: Tachykinin Receptor type-3 (SEQ ID NO.: 153); NK2: Tachykinin Receptor type-2 (SEQ ID NO.: 154); MTNR1B: Melatonin Receptor type-1B (SEQ ID NO.: 155); P2Y1: P2 purinoceptor type Y1 (SEQ ID NO.: 156); AT1: Angiotensin-II Receptor type-1 (SEQ ID NO.: 157); KOR1: Kappa Opioid Receptor type-1 (SEQ ID NO.: 158); MOR1: Mu Opioid Receptor type-1 (SEQ ID NO.: 159); and DOR1: Delta Opioid Receptor type-1 (SEQ ID NO.: 160).

FIGS. 12A-D illustrate an alignment of the third intracellular loop from different G protein-coupled receptors. Legend: MT2R: melatonin receptor type 1B (NCBI Reference Sequence: NP_005950.1, SEQ ID NO.: 161); KOR1: Kappa Opioid Receptor type-1 (GenBank: AAC50158.1, SEQ ID NO.: 162); 5HT2A: Serotonin Receptor type-2A (NCBI Reference Sequence: NP_000612.1, SEQ ID NO.: 163); A2AR: Alpha-2C Adrenergic Receptor (NCBI Reference Sequence: NP_000674.2, SEQ ID NO.: 164); B2AR: Beta-2 Adrenergic Receptor (GenBank: AAB82151.1, SEQ ID NO.: 165); and DRD1: Dopamine Receptor type-1 (GenBank: AAH96837.1, SEQ ID NO.: 166).

5HT2A: Serotonin Receptor type-2a (SEQ ID NO.: 33); A1AR: ADORA1, Adenosine A1 Receptor.

Figure 18:
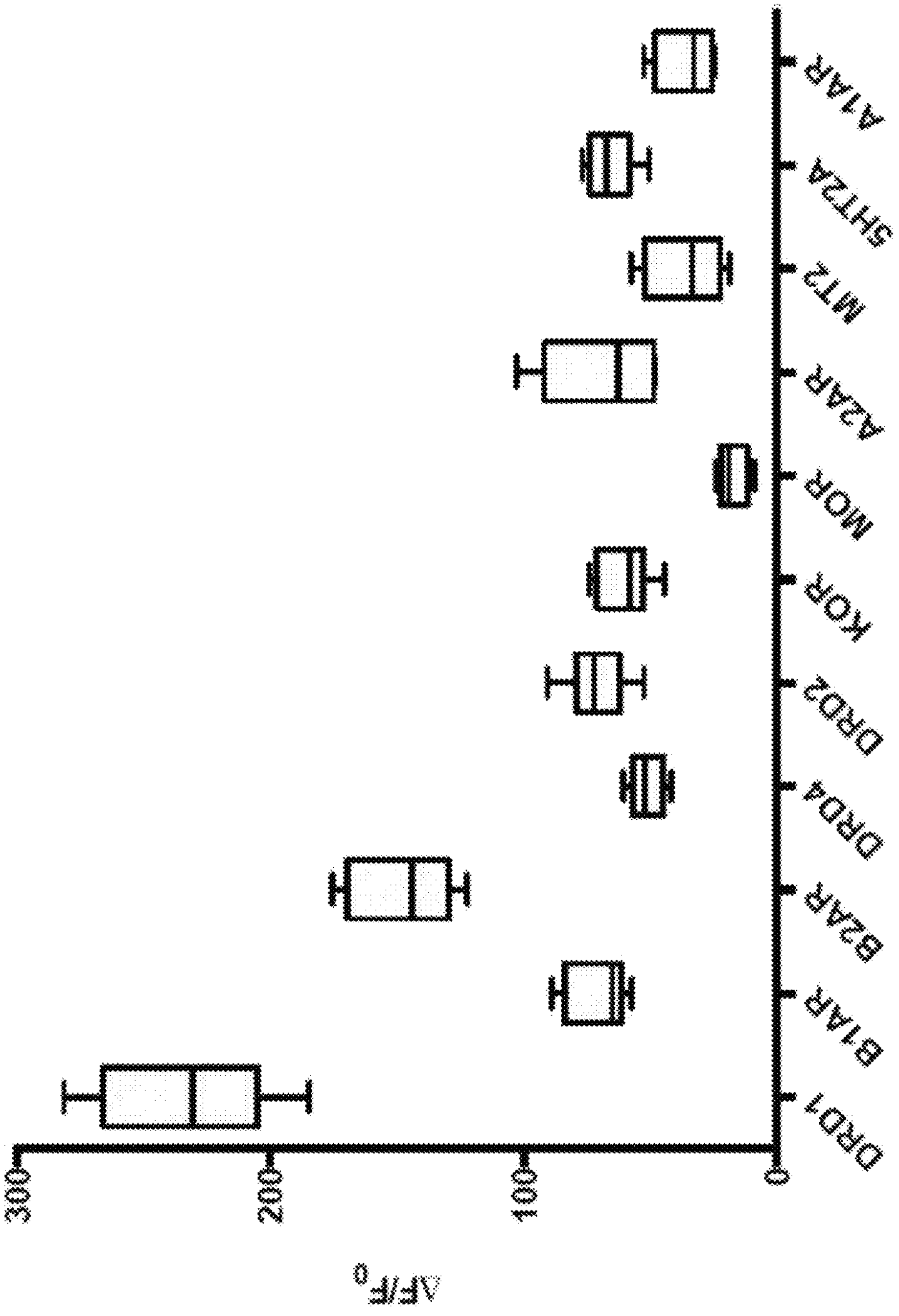

FIG. 18 illustrates graph describing the fluorescent response (fold-change, or DF/FO). The data are represented as Box and Whiskers view, with error bars being the standard error and the horizontal line inside the box being the median.

Figure 17:
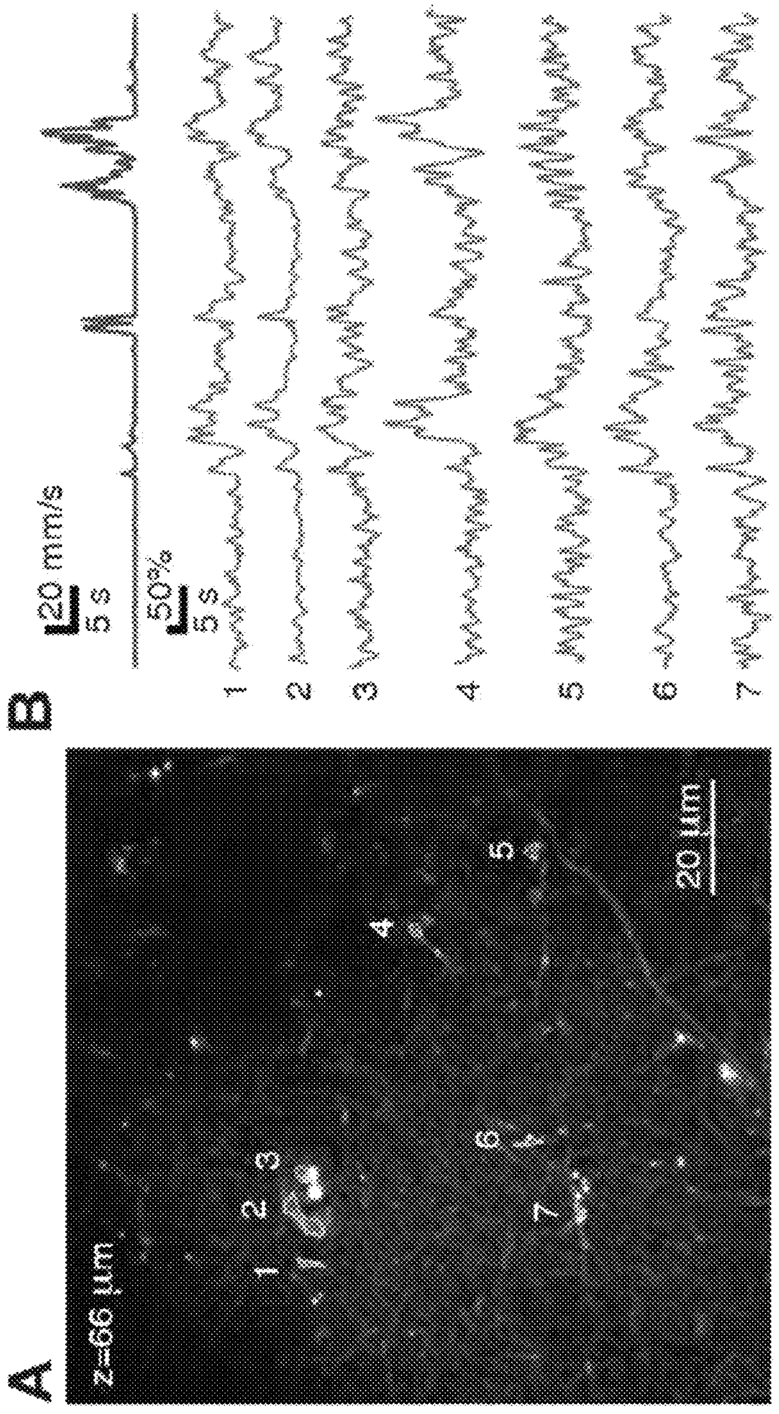
FIG. 17 illustrates Graphic description of universal module insertion sites into 11 example GPCR-sensors. Each raw contains from left to right: Abbreviated name of the GPCR used, sequence of the 8 amino acids preceding the universal module (in the direction from N-terminus to C-terminus), universal module, sequence of the 8 amino acids following the universal module. Legend: DRD1: Dopamine Receptor D1 (SEQ ID NO.: 30); B1AR: ADRB1, Adrenoreceptor Beta 1 (SEQ ID NO.: 31); B2AR: Beta-2 Adrenergic Receptor (SEQ ID NO.: 32); DRD2: Dopamine Receptor D2 (SEQ ID NO.: 46); DRD4: Dopamine Receptor D4 (SEQ ID NO.: 48); KOR: Kappa Opioid Receptor (SEQ ID NO.: 36); MOR: Mu Opioid Receptor (SEQ ID NO.: 37); A2AR: ADORA2A, Adenosine A2a Receptor (SEQ ID NO.: 34); MT2: MTNR1B, Melatonin Receptor 1B (SEQ ID NO.: 39)
Figure 19A:
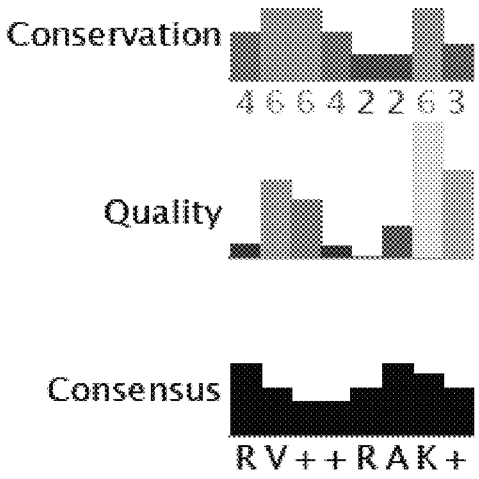
Figure 19B:
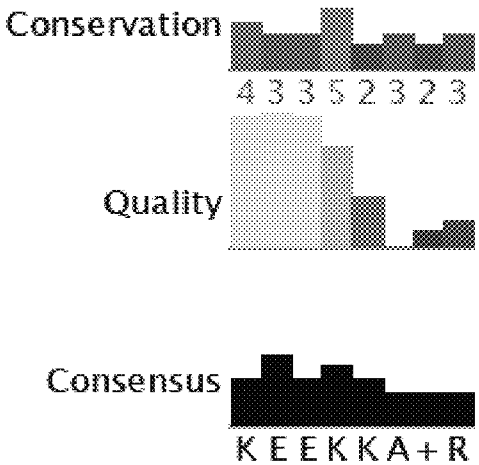

FIGS. 19A-B illustrate A. Alignment of the 8 amino acids comprising the GPCR sequence abutting the N-terminus of the sensor. B. Alignment of the 8 amino acids comprising the GPCR sequence abutting the C-terminus of the sensor. Alignments were done in Jalview Conservation. [ Same as FIG. 17**]

FIG. 20 illustrates results from screening a library of linker variants obtained by randomly mutating the X1X2X3X4 residues all at once. The first column from the left shows the fluorescence fold-change of each variant. The second column from the left shows the amino acid sequence of the X1X2 linker residues for each variant. The second column from the left shows the amino acid sequence of the X3X4 linker residues for each variant.

FIG. 21 illustrates results from screening a library of linker variants obtained by inserting a random amino acid after LI and NH parts of the universal module, to create an LIX1-cpGFP-NHX2 library. The first column from the left shows the fluorescence fold-change of each variant. The second column from the left shows the amino acid sequence of the LIX1 linker residues for each variant. The second column from the left shows the amino acid sequence of the NHX2 linker residues for each variant.

Figure 22:
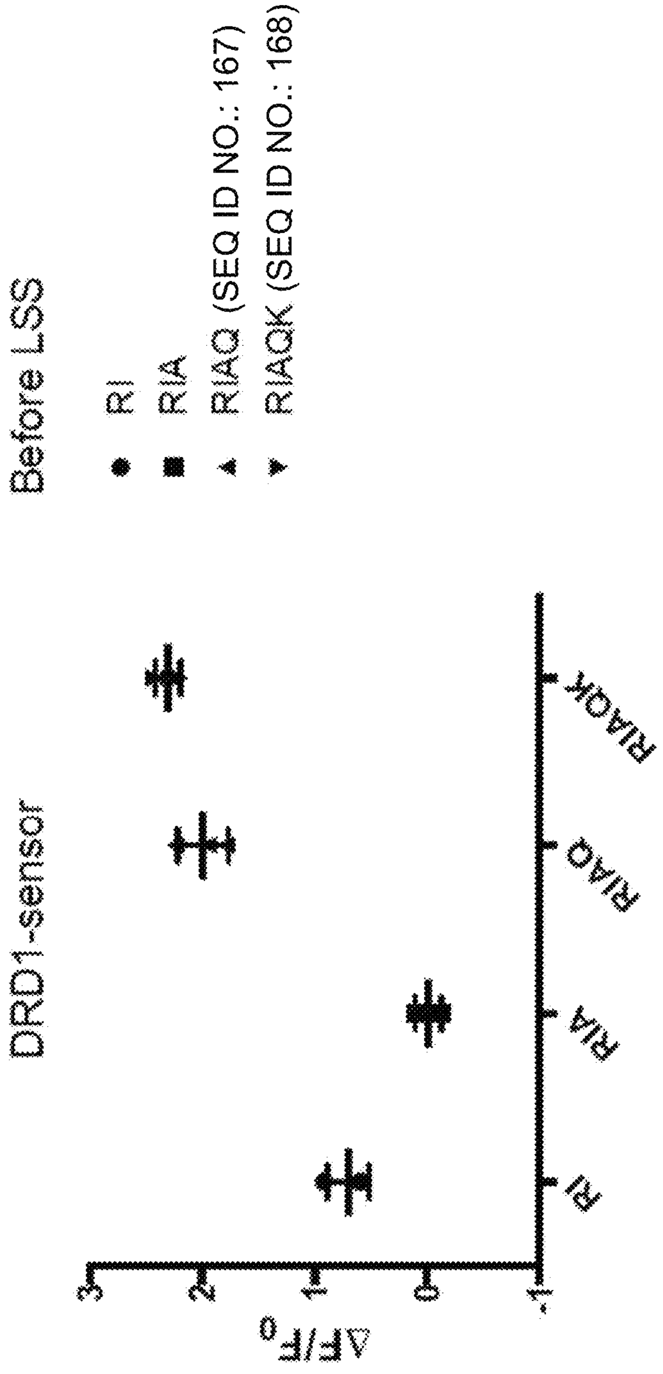

FIG. 22 illustrates graph showing the fluorescence fold-change response of DRD1-based dopamine sensor where the amino acid sequence of the GPCR prior to the beginning of the universal module has been sequentially deleted of 1, 2 and 3 amino acids. Legend: RI: DRD1 with sequential deletion of 3 amino acids; RIA: DRD1 with sequential deletion of 2 amino acids; RIAQ: DRD1 with sequential deletion of 1 amino acid (SEQ ID NO.: 167); RIAQK: DRD1 (SEQ ID NO.: 168).

Figure 23:
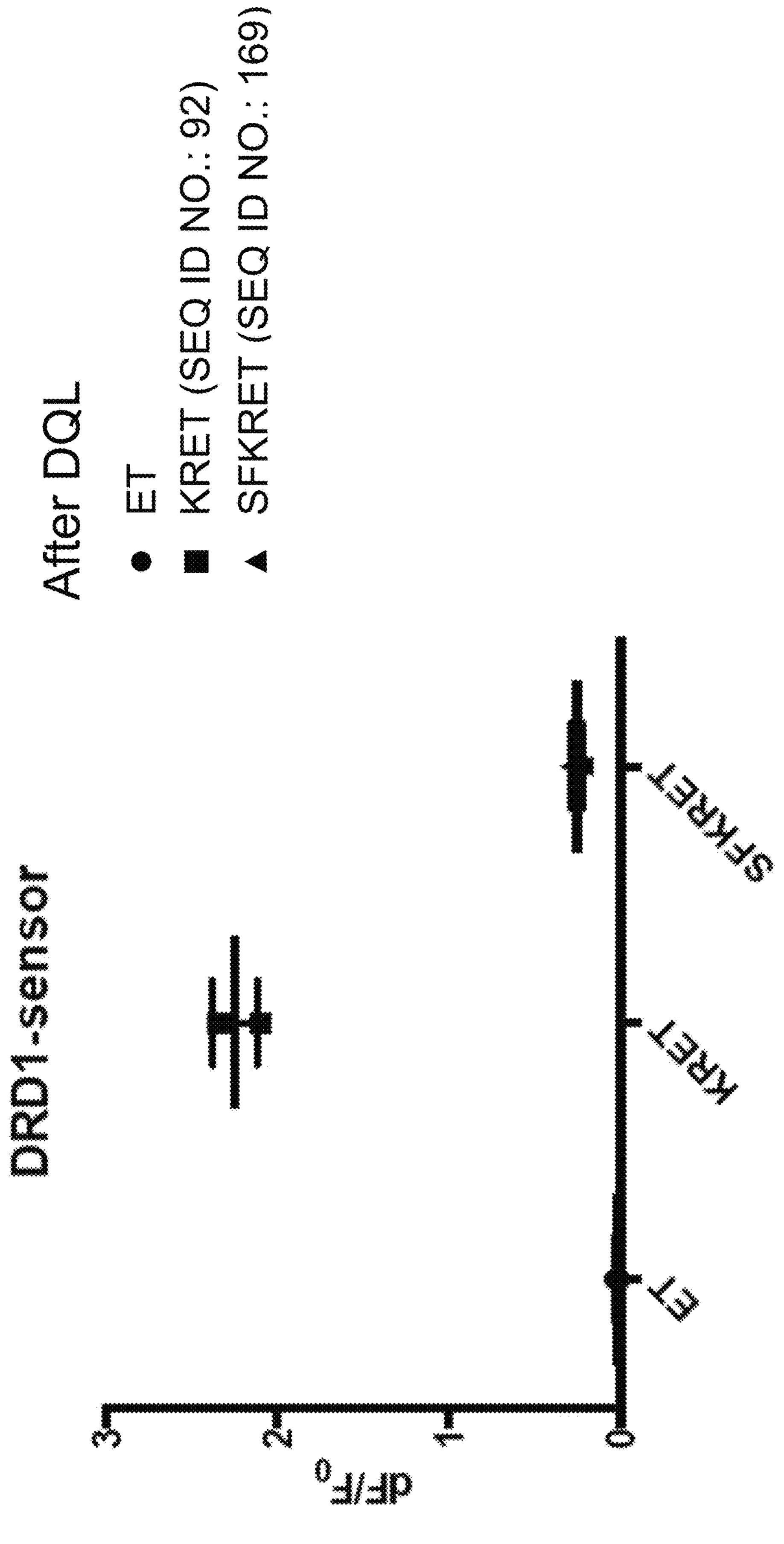

FIG. 23 illustrates graph showing the fluorescence fold-change response of DRD1-based dopamine sensor where the amino acid sequence of the GPCR after the end of the universal module has been added or deleted of 2 amino acids according to the DRD1 amino acid sequence. Legend: ET: DRD1 with deletion of 2 amino acids; KRET: DRD1 (SEQ ID NO.: 92); RIAQ: DRD1 with addition of 2 amino acids (SEQ ID NO.: 169).

Figure 24:
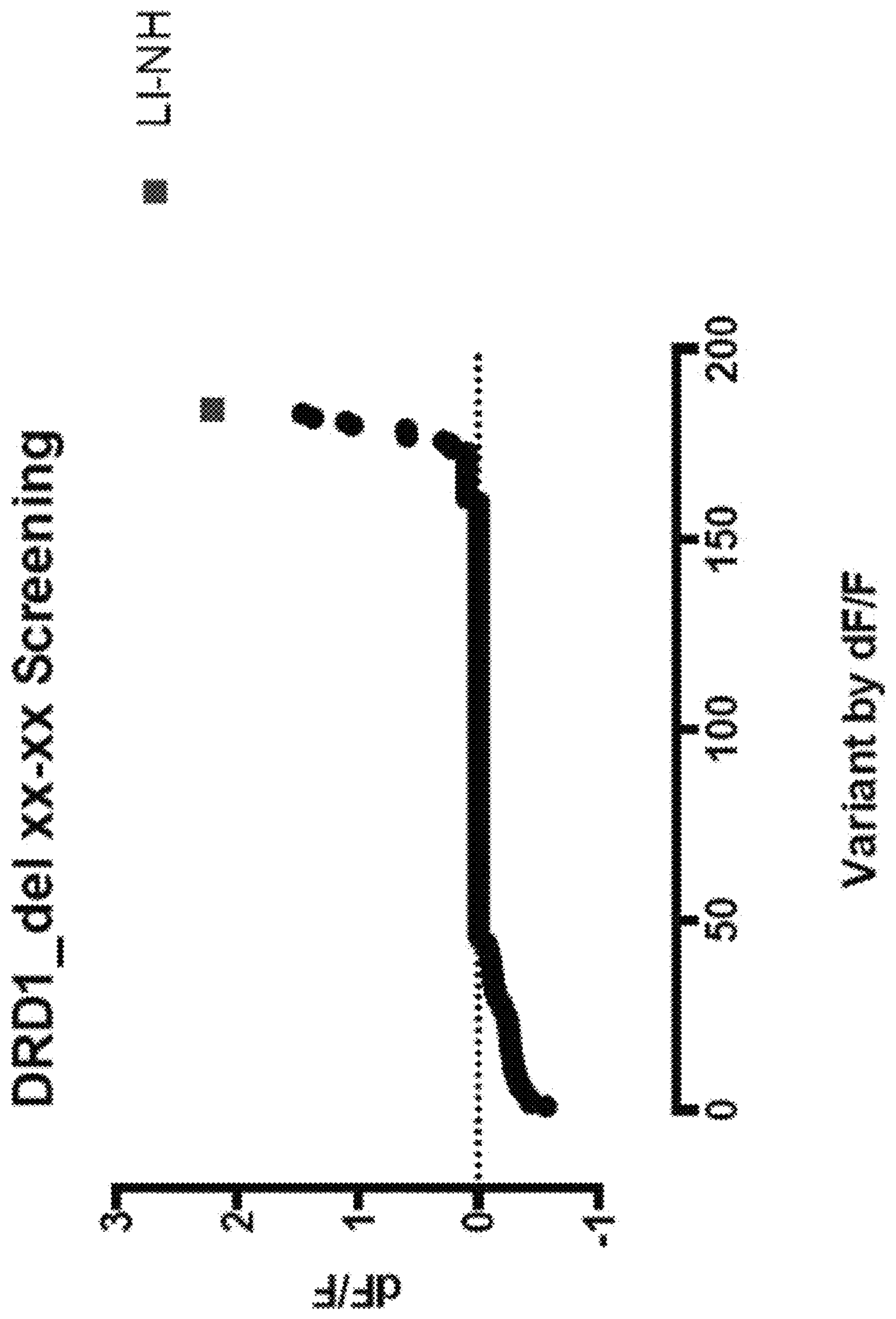

FIG. 24 illustrates graph showing the results from screening a library of DRD1-sensor linker variants obtained by randomly mutating the X1X2X3X4 residues replacing "LI" and "NH" all at once.

Figure 25:
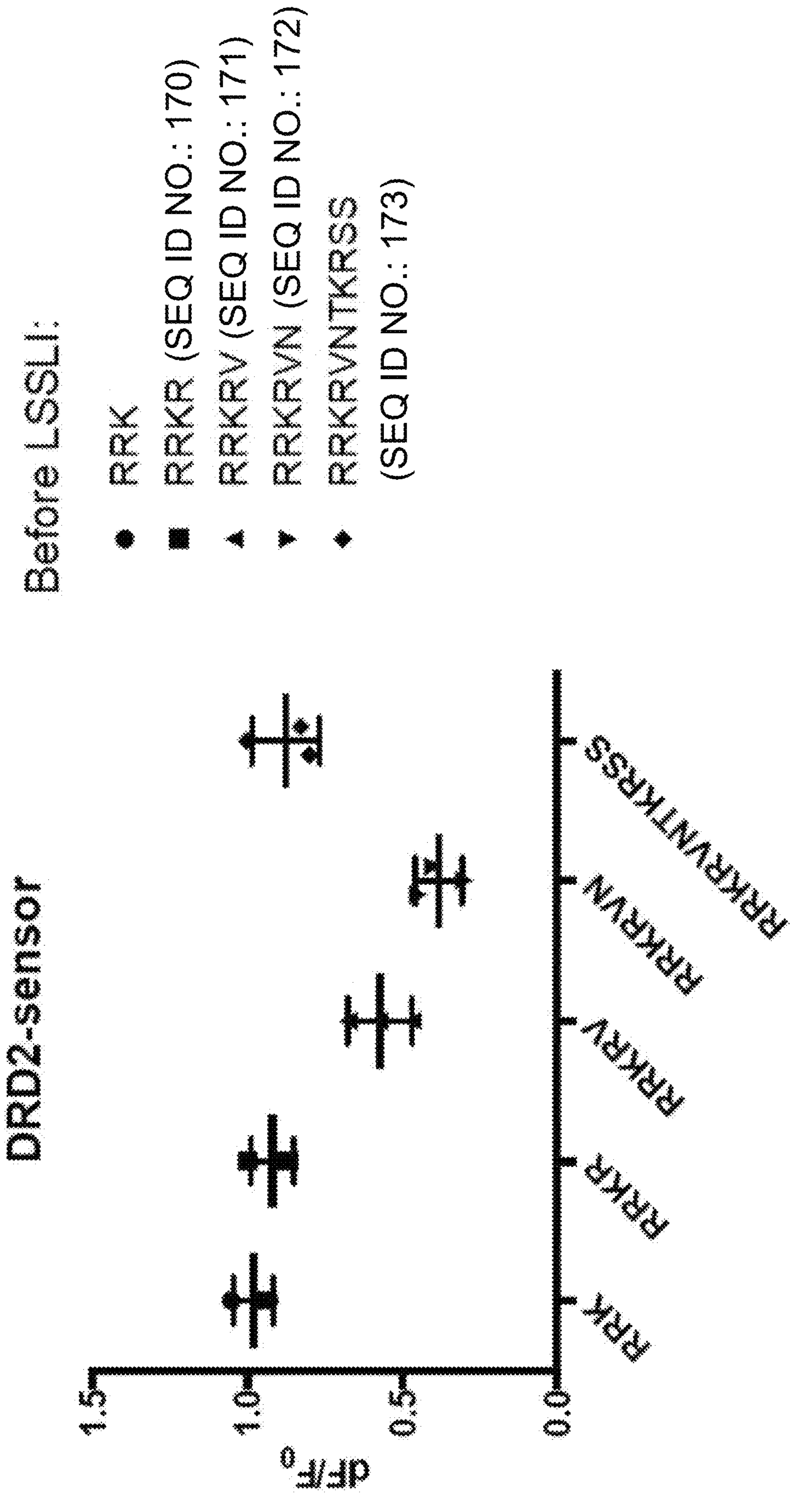

FIG. 25 illustrates graph showing the fluorescence fold-change response of DRD2-based dopamine sensor where after the amino acid sequence of the GPCR-sensor preceding the beginning of the universal module an insertion has been made of 1, 2, 3 and 8 amino acids, respectively, according to the DRD2 amino acid sequence. Legend: RRK: DRD2 with no insertion (SEQ ID NO.: 46); RRKR: DRD2 with insertion of 1 amino acid (SEQ ID NO.: 170; RRKRV: DRD2 with insertion of 2 amino acids (SEQ ID NO.: 171; RRKRVN: DRD2 with insertion of 3 amino acids (SEQ ID NO.: 172; RRKRVNTKRSS: DRD2 with insertion of 8 amino acids (SEQ ID NO.: 173.

Figure 26:
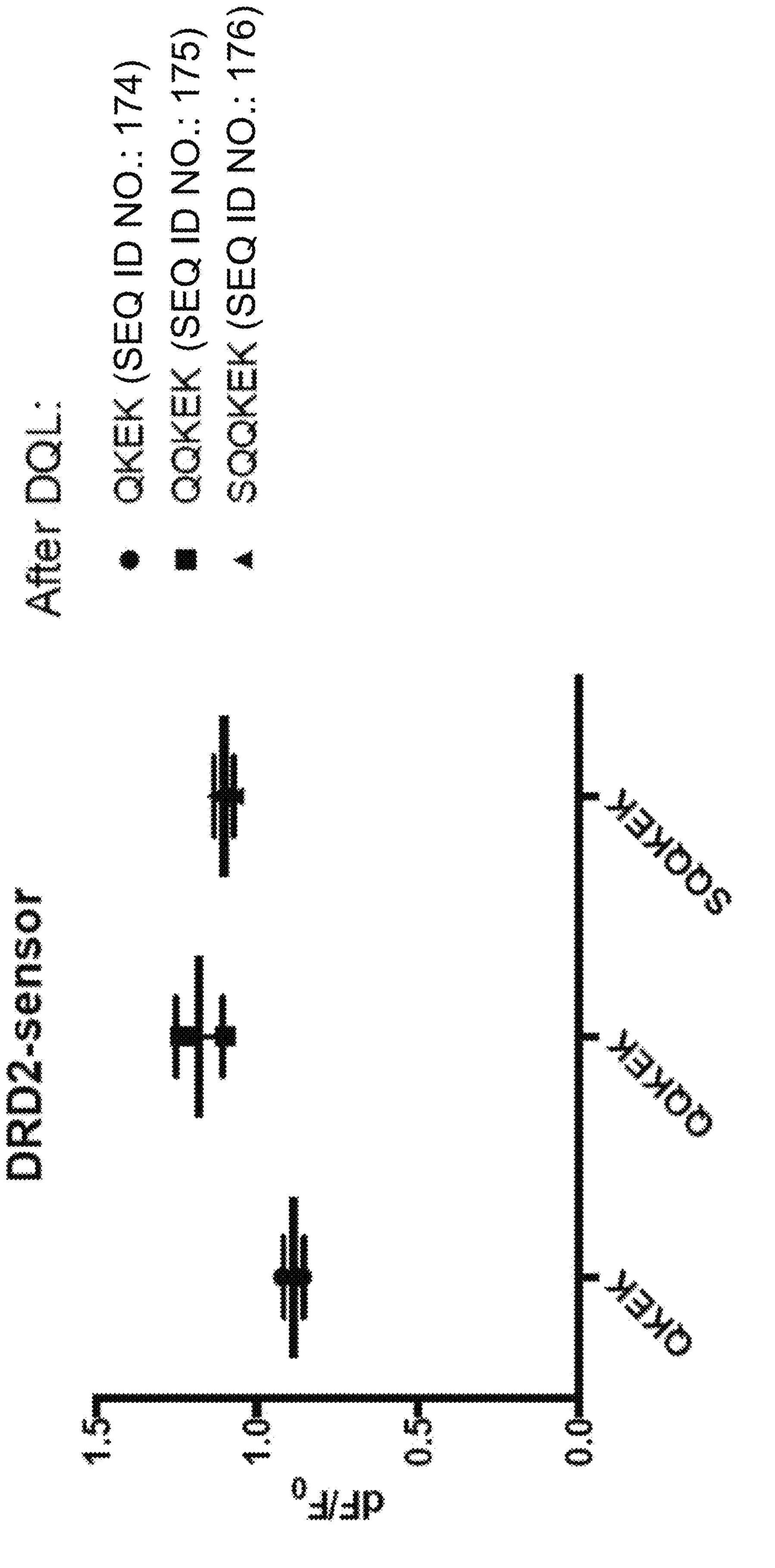

FIG. 26 illustrates graph showing the florescence fold-change response of DRD2-based dopamine sensor where after the amino acid sequence of the GPCR-sensor following the end of the universal module an insertion has been made of 1 and 2 amino acids, respectively, according to the DRD2 amino acid sequence. Legend: QKEK: DRD2 with no insertion (SEQ ID NO.: 46) and (SEQ ID NO: 174); QQKEK: DRD2 with insertion of 1 amino acid (SEQ ID NO.: 175; SQQKEK: DRD2 with insertion of 2 amino acids (SEQ ID NO.: 176.

DETAILED DESCRIPTION

1. Introduction

G-protein coupled receptors (GPCRs) are widely expressed in nervous systems and respond to a wide variety of ligands including hormones, neurotransmitters and neuromodulators. Drugs targeting members of this integral membrane protein superfamily represents the core of modern medicine. Here we developed a toolbox of optogenetic sensors for visualizing GPCR activation; the conformational dynamics triggered by ligand binding to the GPCR is monitored via ligand induced changes in fluorescence. This toolbox enables high-throughput cell-based screening, mapping neuromodulation networks in the brain and in vivo validation of potential therapeutics, which is expected to accelerate the discovery process of drugs for treating neurological disorders.

Using the prototype GPCR Beta2AR as a starting point, we inserted circular permuted green fluorescent protein (cpGFP) into the third intracellular loop region of the receptor to transform the ligand-induced conformational changes of Beta2AR into changes of fluorescence intensity of the GFP chromophore. A cell-based screening was then performed to determine the linker sequences between cpGFP and Beta2AR that maximize signal-to-noise ratio. Upon agonist binding (isoproterenol, ISO, 10 μM), we detected a 40% increase in fluorescence at the membrane of mammalian cells. The in situ affinity of this Beta2AR sensor is 1.2 nM for isoproterenol, 15 nM for epinephrine and 50 nM for norepinephrine, which is within the range of physiological relevance.

Accordingly, provided is a universal linker useful as an integrated sensor incorporated into the third intracellular loop of a G-protein-coupled receptor. In some embodiments, the universal linker has the structure of: LSSX1X2-cpGFP-X3X4DQL. In some embodiments, the universal linker has the structure of: QLQKIDLSSX1X2-cpGFP-X3X4DQL. We have demonstrated interchangeable utility of the universal GPCR integrated sensor in six structurally different and unrelated GPCRs: adrenoceptor beta 2 (ADRB2), mu (μ)-type opioid receptor (OPRM), kappa (κ)-type opioid receptor (OPRK), dopamine receptor D1 (DRD1), 5-hydroxytryptamine receptor 2A (HTR2A), and melatonin receptor type 1B (MTNR1B). Importantly, this group of GPCRs contains representative Gs, Gi and Gq-coupled receptors, demonstrating the universality of our approach. Upon insertion of the universal sensor, each of the six tested GPCRs was transformed into a sensor that showed positive fluorescence signal in response to the application of an agonist. Such an engineering approach is unprecedented and allows for rapid and efficient production of GPCR-sensors with applications in multiple scientific fields, from drug screening, to GPCR de-orphanization, to in vivo imaging of drug efficacy or dynamics of endogenous ligands.

The sensors described herein are capable of capturing conformational dynamics of G protein-coupled receptors, including Beta2AR, triggered by binding of a panel of full, partial and inverse agonists. Our illustrative Beta2AR sensor has been made signaling deficient by the following mutations: F139S, S355A/S356A, in order not to interfere with endogenous cellular signaling. A similar engineering approach was successfully employed to develop sensors for monitoring the activation of the μ-opioid receptor MOR-1, the Dopamine receptor D1 and the serotonin receptor 5-HT2A. The utility of these sensors can be implemented and further characterized in vivo, e.g., in the zebrafish brain and in the mouse spinal cord. Given the structural similarity of GPCRs, our sensor design strategy represents a universal scaffold that can be readily applied generally to many different GPCRs.

Cell-based high-throughput screening assays have been the workhorse fueling G-protein coupled receptors as one of the most studied classes of investigational drug targets. However, existing high-throughput cellular screening assays are based on measuring intracellular levels of downstream signaling molecules, such as calcium and cyclic adenosine monophosphate (cAMP), which only provide a downstream binary readout (on or off) of GPCR activation. In contrast, using an integrated GPCR sensor, as described herein, allows for direct imaging of GPCR ligand binding in living cells and animals with molecular specificity and subcellular resolution, providing a platform for high-throughput cell-based screening and validation of potential therapeutics in living animal disease models. Further, the integrated GPCR sensors described herein utilize a circularly permutated fluorescent protein, and therefore employ a single wavelength of fluorescent protein, which preserves the bandwidth to engineer multi-color palette of GPCR conformation sensors, enabling simultaneous imaging of multiple GPCRs. Moreover, when combined with optical measurement of other downstream signaling molecules such as calcium, cAMP and β-arrestin, the integrated GPCR sensors facilitate linking the conformation dynamics of GPCR with a specific downstream signaling branch, which further enhances the rigor of biased ligand detection. Additionally, the ability to detect ligand bias using the integrated sensors described herein furthers the understanding of structure-functional properties of drugs with allosteric and/or biased properties, which aids optimization for bias in addition to potency at the receptor, selectivity and pharmaceutical properties.

2. Fluorescent Sensors

Provided are fluorescent sensors designed to integrate into the third intracellular loop of a G protein-coupled receptor (GPCR). In some embodiments, the sensors comprise the following polypeptide structure: L1-cpFP-L2, wherein:

(1) L1 comprises a peptide linker having LSS at the N-terminus and from 5 to 13 amino acid residues, wherein each amino acid residue can be any naturally occurring amino acid;

(2) cpFP comprises a circularly permuted fluorescent protein, wherein the circularly permuted N-terminus is positioned within beta strand seven of a non-permuted fluorescent protein; and (3) L2 comprises a peptide linker having DQL at the C-terminus and from 5 to 6 amino acid residues, wherein each amino acid residue can be any naturally occurring amino acid.

Generally, the fluorescent sensors are integrated into a GPCR, e.g., into the third intracellular loop. The GPCR internal fluorescent sensors are polypeptides that can be produced using any method known in the art, including synthetic and recombinant methodologies. When produced recombinantly, the GPCR internal fluorescent sensor polypeptides can be expressed in eukaryotic or prokaryotic host cells.

a. Circularly Permuted Fluorescent Protein

Figure 10:
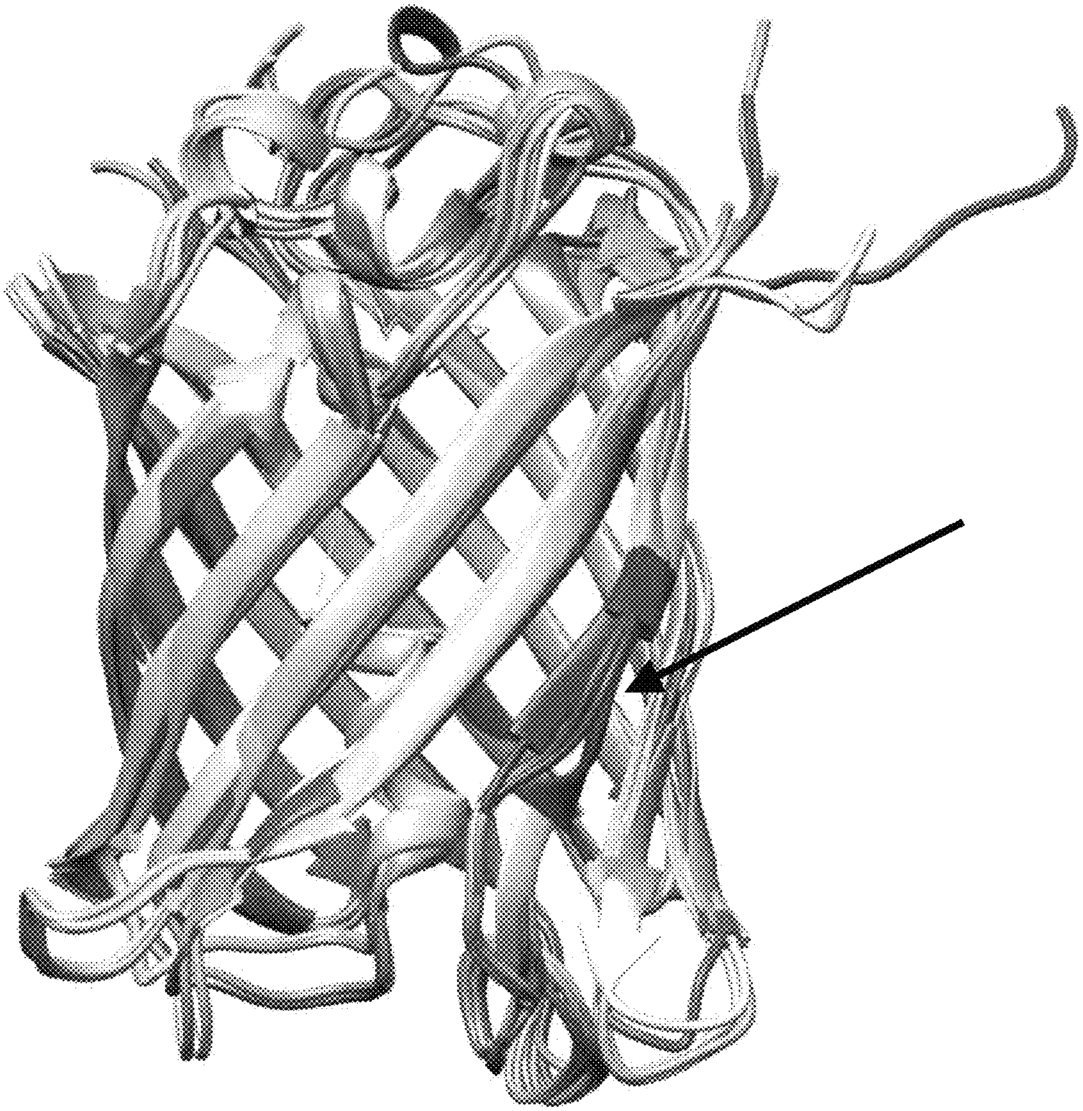
FIG. 10 illustrates an over-imposition of the PBD structures of illustrative fluorescent proteins useful in the present sensors (with the exclusion of the far-red single-domain cyanbacteriochromes for which no structure is available). The arrow indicates the sites of circular permutation of the various FPs.
Figure 13A:
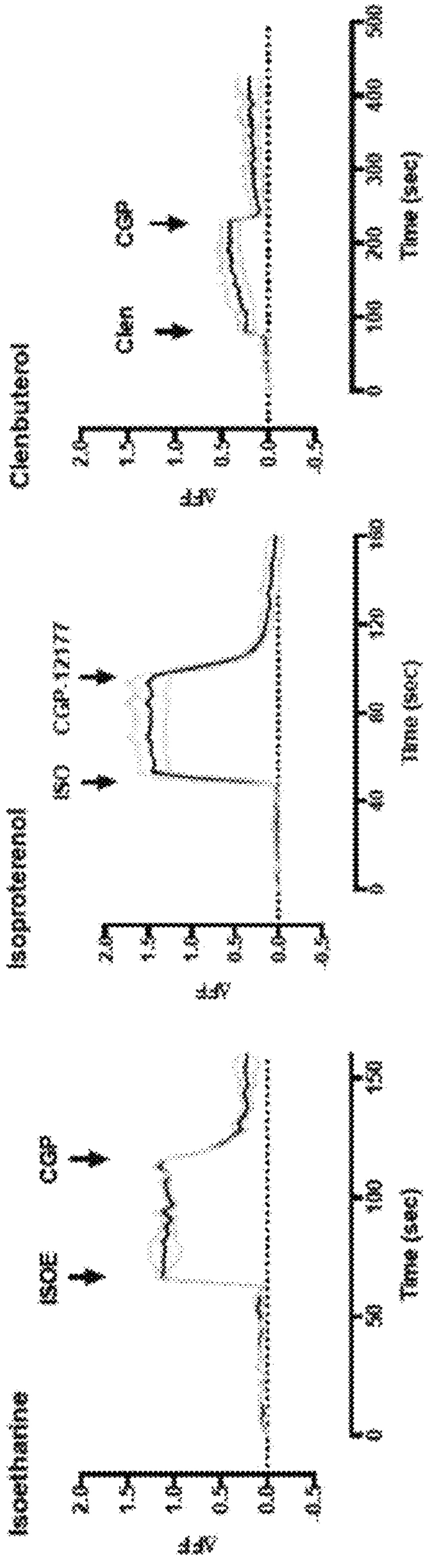
FIGS. 13A-D illustrate proof-of-principle experiment to show that a universal sensor (e.g., LSSLI-cpGFP-NHDQL or QLQKIDLSSLI-cpGFP-NHDQL) is capable of detecting the action of pharmacological drugs. (A-B) Screening of a panel of drugs using the b2AR with universal module 1 (e.g., QLQKIDLSSLI-cpGFP-NHDQL) in 293 cells and representative time-lapse curves are shown for each individual drug application. (C) a representative image of the HEK293t cells expressing the sensor shows good membrane expression. (D) a quantification of the maximal DF/F versus drug type. Both full agonists (isoetharine, isoproterenol), partial agonists (Salbutamol, Blenbuterol, Terbutaline), inverse agonist (CGP-12177) and antagonists (Alprenolol, Timolol) were used.
Figure 13B:
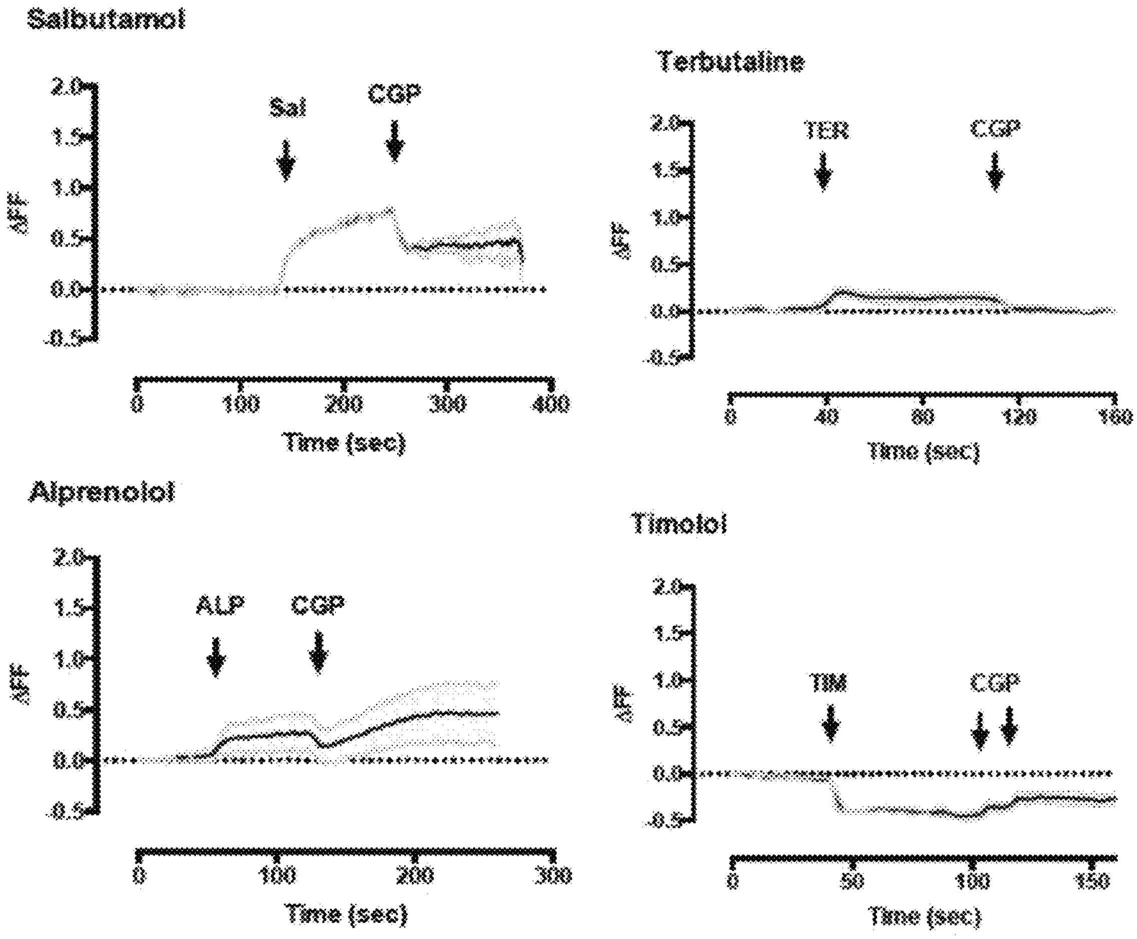
Figure 13C:
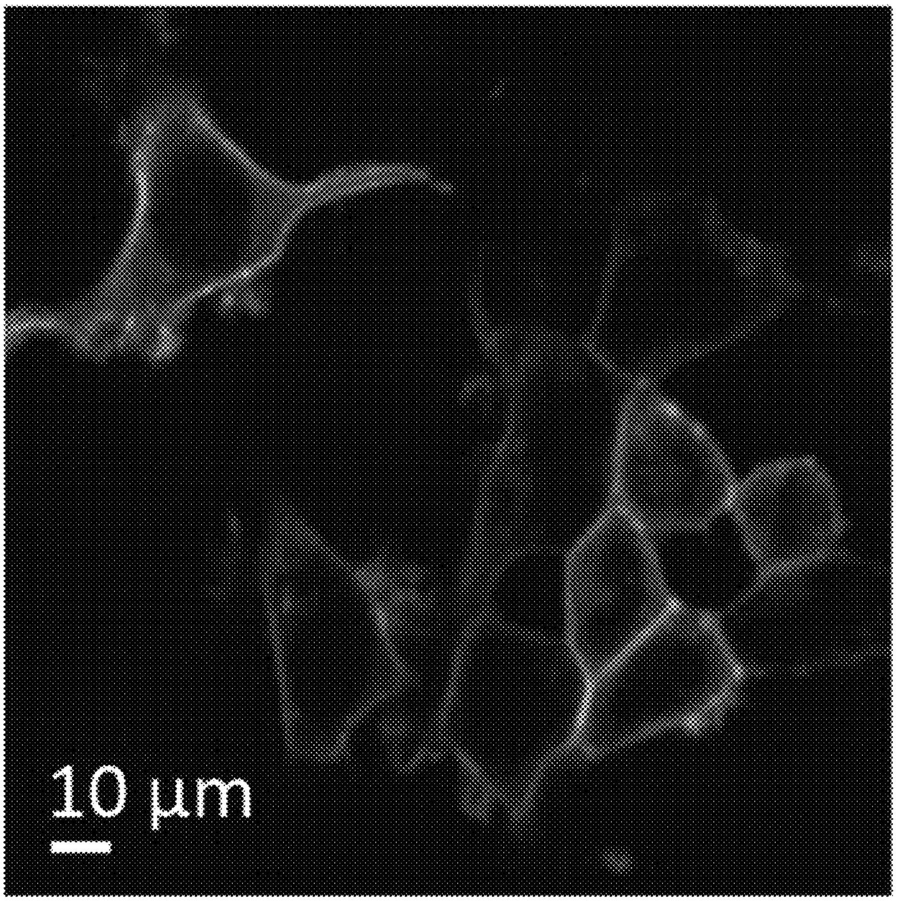
Figure 13D:
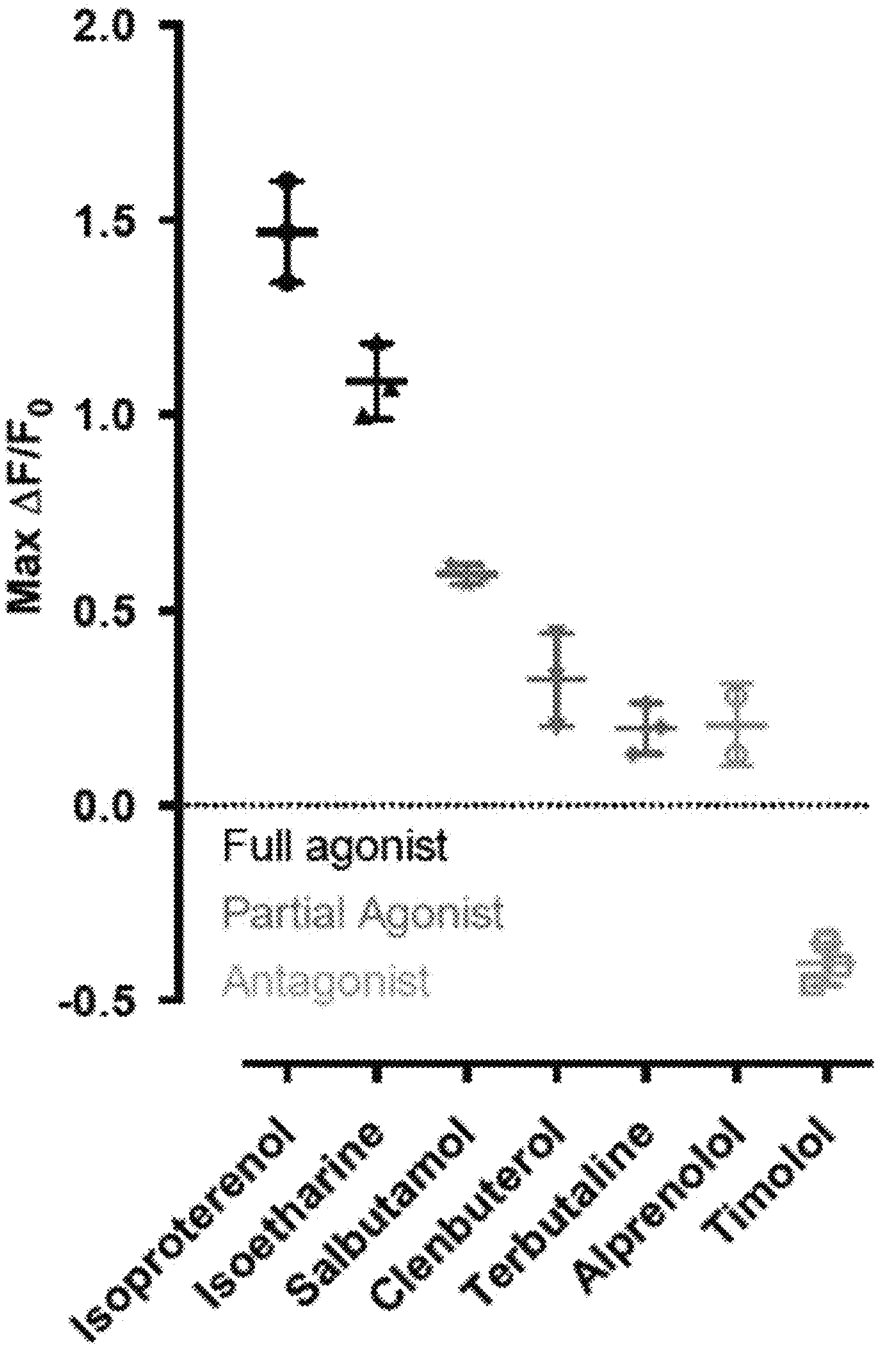

The circularly permuted fluorescent protein (cpFP) can be from any known fluorescent protein known in the art. In some embodiments, the circularly permuted protein is from a green fluorescent protein (GFP) or a red fluorescent protein (RFP), e.g., from mCherry, mEos2, mRuby2, mRuby3, mClover3, mApple, mKate2, mMaple, mCardinal, mNeptune, far-red single-domain cyanbacteriochrome WP_016871037 or far-red single-domain cyanbacteriochrome anacy 2551g3. Generally, the N-terminus of the circularly permuted is an amino acid residue within the seventh beta strand of the fluorescent protein in its non-circularly permuted form. This is depicted in FIG. 10. Within the seventh beta strand of the fluorescent protein, in some embodiments, the circularly permuted N-terminus of the cpFP is positioned within the motif YN(Y/F)(N/I)SHNV (SEQ ID NO:19), e.g., of a non-permuted green fluorescent protein, or within the motif WE(A/P/V)(S/L/N/T)(S/E/T)E (R/M/T/K)(M/L)(SEQ ID NO: 20) of a non-permuted red fluorescent protein. In some embodiments, the circularly permuted N-terminus is positioned at the amino acid residue corresponding to residue 7 (e.g., N) of the amino acid motif YN(Y/F)(N/I)SHNV (SEQ ID NO:19) of a non-permuted green fluorescent protein. In some embodiments, the circularly permuted N-terminus is positioned at the amino acid residue corresponding to residue 3 (e.g., (A/P/U/V/P)), 4 (e.g., (LSN)), 5 (e.g., S/T)), 6 (e.g., E) or 7 (e.g., R/M/K/T)) of the amino acid motif WE(A/P/V)(S/L/N/T)(S/E/T)E(R/M/T/K)(M/L)(SEQ ID NO:20) of a non-permuted red-fluorescent protein.

In some embodiments, the circularly permuted fluorescent protein is from a photo-convertible or photoactivable fluorescent protein. Numerous photo-convertible or photoactivable fluorescent proteins are known in the art, and their circularly permuted forms can be used in the present sensors. See, Rodriguez, et al., *Trends Biochem Sci.* (2016) November 1. pii: S0968-0004 (16) 30173-6; Ai, et al., *Nat Protoc.* 2014 April; 9 (4): 910-28; Kyndt, et al., *Photochem Photobiol Sci.* 2004 June; 3 (6): 519-30; Meyer, et al., *Photochem Photobiol Sci.* 2012 October; 11 (10): 1495-514. In some embodiments, the photo-convertible or photoactivable fluorescent protein is selected from the group consisting of photoactivable green fluorescent protein (paGFP; e.g., SEQ ID NO:4), mCherry (e.g., SEQ ID NOs: 6-7), mEos2 (e.g., SEQ ID NO: 11), mRuby2 (e.g., SEQ ID NO:9), mRuby3, mClover3, mApple (e.g., SEQ ID NO:8), mKate2 (e.g., SEQ ID NO:10), mMaple (SEQ ID NO:12), far-red single-domain cyanbacteriochrome WP_016871037 and far-red single-domain cyanbacteriochrome anacy 2551g3.

In some embodiments, the circularly permuted fluorescent protein is from a fluorescent protein having at least about 90% sequence identity, e.g., at least about 91%, 92%, 93%, 94%, 95%, 96%, 97%, 98%, 99% or 100% sequence identity, to a non-permuted fluorescent protein selected from the group consisting of SEQ ID NOs: 1-14. In some embodiments, the circularly permuted fluorescent protein is from a green fluorescent protein having at least about 90% sequence identity, e.g., at least about 91%, 92%, 93%, 94%, 95%, 96%, 97%, 98%, 99% or 100% sequence identity, to SEQ ID NO: 1, wherein the tyrosine at residue position 69 of SEQ ID NO:1 is replaced with a tryptophan (Y69W) to generate a cyan fluorescent protein (CFP) sensor. In some embodiments, the circularly permuted fluorescent protein is from a green fluorescent protein having at least about 90% sequence identity, e.g., at least about 91%, 92%, 93%, 94%, 95%, 96%, 97%, 98%, 99% or 100% sequence identity, to SEQ ID NO: 1, wherein the threonine at residue position 206 of SEQ ID NO:1 is replaced with a tyrosine (T206Y) to generate a yellow fluorescent protein (YFP) sensor. In some embodiments, the circularly permuted fluorescent protein has at least about 90% sequence identity, e.g., at least about 91%, 92%, 93%, 94%, 95%, 96%, 97%, 98%, 99% or 100% sequence identity, to a circularly permuted fluorescent protein selected from the group consisting of SEQ ID NOS: 15-18.

Numerous circularly permuted fluorescent proteins are described in the art, and may find use in the present fluorescent sensors. The choice of a particular circularly permuted fluorescent protein for use in a fluorescent protein sensor may depend on the desired emission spectrum for detection, and include, but is not limited to, circularly permuted fluorescent proteins with green, blue, cyan, yellow, orange, red, or far-red emissions. A number of circularly permuted fluorescent proteins are known and can be used in the present sensors. See, e.g., Pedelacq et al. (2006) *Nat. Biotechnol.* 24:79-88 for a description of circularly permuted superfolder GFP variant (cpsfGFP), Zhao et al. (2011) *Science* 333:1888-1891 for a description of circularly permuted mApple; Shui et al. (2011) *PLoS One;* 6 (5): e20505 for a description of circularly permuted variants of mApple and mKate; Carlson et al. (2010) *Protein Science* 19:1490-1499 for a description of circularly permuted red fluorescent proteins, Gautam et al. (2009) Front. Neuroeng. 2:14 for a description of circularly permuted variants of enhanced green fluorescent protein (EGFP) and mKate, Zhao et al. (2011) *Science* 333 (6051): 1888-1891 for a description of a circularly permuted variant of mApple; Liu et al. (2011) *Biochem. Biophys. Res. Commun.* 412 (1): 155-159 for a description of circularly permuted variants of Venus and Citrine, Li et al. (2008) *Photochem. Photobiol.* 84 (1): 111-119 for a description of circularly permuted variants of mCherry, and Perez-Jimenez et al. (2006) *J. Biol. Chem.* December 29; 281 (52): 40010-40014 for a description of circularly permuted variants of enhanced yellow fluorescent protein (EYFP). Further illustrative circularly permuted fluorescent proteins are described in e.g., Honda, et al., *PLoS One.* 2013 May 22;8 (5): e64597; Schwartzländer, et al., *Biochem J.* 2011 Aug. 1;437 (3): 381-7; Miyawaki, et al., *Adv Biochem Eng Biotechnol.* 2005; 95:1-15; Tantama, et al., *Prog Brain Res.* 2012; 196:235-63; Mizuno, et al., *J Am Chem Soc.* 2007 Sep. 19; 129 (37): 11378-83; Chiang, et al., *Biotechnol Lett.* 2006 April; 28 (7): 471-5; and in U.S. Patent Publication Nos. 2015/0132774; 2010/0021931; and 2008/0178309.

b. N-Terminal and C-Terminal Linkers

The G protein-coupled receptor (GPCR) internal fluorescent sensors have an N-terminal linker (L1) and a C-terminal linker (L2). In some embodiments, L1 comprises a peptide linker having from 2 to 13 amino acid residues, e.g., 2 to 3, 4, 5, 6, 7, 8, 9, 10, 11, 12 or 13 residues, wherein each amino acid residue can be any naturally occurring amino acid. In some embodiments, L2 comprises a peptide linker having from 2 to 5 amino acid residues, e.g., 2 to 3, 4 or 5 residues, wherein each amino acid residue can be any naturally occurring amino acid. In some embodiments, L1 and L2 are peptides that independently have 2, 3, 4, 5, or 6 amino acid residues. In some embodiments, L1 comprises LSSLI and L2 comprises NHDQL. In some embodiments, L1 comprises LSSX1X2 and L2 comprises X3X4DQL, wherein X1, X2, X3, X4 are independently any amino acid. In some embodiments, L1 comprises QLQKIDLSSX1X2 and L2 comprises X3X4DQL, wherein X1, X2, X3, X4 are independently any amino acid. In some embodiments, X1X2 is selected from the group consisting of leucine-isoleucine (LI), alanine-valine (AV), isoleucine-lysine (IK), serine-arginine (SR), lysine-valine (KV), leucine-alanine (LA), cysteine-proline (CP), glycine-methionine (GM), valine-arginine (VR), asparagine-valine (NV), arginine-valine (RV), arginine-glycine (RG), leucine-glutamate (LE), serine-glycine (SG), valine-aspartate (VD), alanine-phenylalanine (AF), threonine-aspartate (TD), methionine-arginine (MR), leucine-glycine (LG), arginine-glutamine (RQ), serine-tryptophan (SW), serine-glycine (SG), valine-aspartate (VD), leucine-glutamate (LE), alanine-phenylalanine (AF), serine-tryptophan (SW), arginine-glycine (RG), threonine-aspartate (TD), leucine-glycine (LG), arginine-glutamine (RQ), threonine-tyrosine (TY), leucine-leucine (LL), valine-leucine (VL), threonine-glutamine (TQ), valine-phenylalanine (VF), threonine-threonine (TT), leucine-valine (LV), valine-isoleucine (VI), valine-valine (VV), proline-valine (PV), glycine-valine (GV), serine-valine (SV), phenylalanine-valine (FV), cysteine-valine (CV), glutamate-valine (EV), glutamine-valine (QV), and lysine-valine (KV), arginine-tryptophan (RW), glycine-aspartate (GD), alanine-leucine (AL), proline-methionine (PM), glycine-arginine (GR), glycine-tyrosine (GY), isoleucine-cysteine (IC), and glycine-leucine (GL). In some embodiments, X3X4 is selected from the group consisting of asparagine-histidine (NH), threonine-arginine (TR), isoleucine-isoleucine (II), proline-proline (PP), leucine-phenylalanine (LF), valine-threonine (VT), glutamine-glycine (QG), alanine-leucine (AL), proline-arginine (PR), arginine-glycine (RG), threonine-leucine (TL), threonine-proline (TP), glycine-valine (GV), threonine-threonine (TT), cysteine-cysteine (CC), alanine-threonine (AT), leucine-proline (LP), tyrosine-proline (YP), tryptophan-proline (WP), serine-leucine (SL), glutamate-arginine (ER), methionine-cysteine (MC), methionine-histidine (MH), tryptophan-leucine (YL), leucine-serine (LS), arginine-proline (RP), lysine-proline (KP), tyrosine-proline (YP), tryptophan-proline (WP), serine-serine (SS), glycine-valine (GV), valine-serine (VS), glutamine-asparagine (QN), lysine-serine (KS), lysine-threonine (KT), lysine-histidine (KH), lysine-valine (KV), lysine-glutamine (KQ), lysine-arginine (KR), cysteine-proline (CP), alanine-proline (AP), serine-proline (SP), isoleucine-proline (IP), tyrosine-proline (YP), threonine-proline (TP), arginine-proline (RP), aspartate-histidine (DH), histidine-tyrosine (HY), glycine-glycine (GG), proline-histidine (PH), serine-threonine (ST), arginine-serine (RS), arginine-histidine (RH), and tryptophan-proline (WP). In some embodiments, X1X2 comprises alanine-valine (AV) and X3X4 comprises lysine-proline (KP); threonine-arginine (TR); aspartate-histidine (DH); threonine-threonine (TT); serine-serine (SS); glycine-valine (GV); cysteine-cysteine (CC); valine-serine (VS); glutamine-asparagine (QN); lysine-serine (KS); lysine-threonine (KT); lysine-histidine (KH); lysine-valine (KV); lysine-glutamine (KQ); lysine-arginine (KR); lysine-proline (KP); cysteine-proline (CP); alanine-proline (AP); serine-proline (SP); isoleucine-proline (IP); tyrosine-proline (YP); threonine-proline (TP); or arginine-proline (RP); X1X2 comprises leucine-valine (LV) and X3X4 comprises threonine-arginine (TR), lysine-proline (KP) or valine-threonine (VT); X1X2 comprises arginine-valine (RV) and X3X4 comprises threonine-arginine (TR), lysine-proline (KP) or threonine-proline (TP); X1X2 comprises arginine-glycine (RG) and X3X4 comprises tyrosine-leucine (YL) or threonine-arginine (TR); X1X2 comprises serine-arginine (SR) and X3X4 comprises leucine-phenylalanine (LF) or proline-proline (PP); X1X2 comprises proline-methionine (PM) and X3X4 comprises proline-histidine (PH) or serine-serine (SS); X1X2 comprises valine-valine (VV) and X3X4 comprises threonine-arginine (TR) or lysine-proline (KP); X1X2 comprises leucine-isoleucine (LI) and X3X4 comprises threonine-arginine (TR); X1X2 comprises threonine-tyrosine (TY) and X3X4 comprises threonine-arginine (TR); X1X2 comprises isoleucine-lysine (IK) and X3X4 comprises isoleucine-isoleucine (II); X1X2 comprises cysteine-proline (CP) and X3X4 comprises alanine-leucine (AL); X1X2 comprises glycine-methionine (GM) and X3X4 comprises proline-arginine (PR); X1X2 comprises leucine-alanine (LA) and X3X4 comprises glutamine-glycine (QG); X1X2 comprises valine-arginine (VR) and X3X4 comprises arginine-glycine (RG); X1X2 comprises serine-glycine (SG) and X3X4 comprises tyrosine-proline (YP); X1X2 comprises valine-aspartate (VD) and X3X4 comprises tryptophan-proline (WP); X1X2 comprises leucine-glutamate (LE) and X3X4 comprises leucine-proline (LP); X1X2 comprises alanine-phenylalanine (AF) and X3X4 comprises serine-leucine (SL); X1X2 comprises serine-tryptophan (SW) and X3X4 comprises arginine-proline (RP); X1X2 comprises threonine-aspartate (TD) and X3X4 comprises glutamate-arginine (ER); X1X2 comprises leucine-glycine (LG) and X3X4 comprises methionine-histidine (MH); X1X2 comprises arginine-glutamine (RQ) and X3X4 comprises leucine-serine (LS); X1X2 comprises methionine-arginine (MR) and X3X4 comprises methionine-cysteine (MC); X1X2 comprises leucine-leucine (LL) and X3X4 comprises threonine-arginine (TR); X1X2 comprises valine-leucine (VL) and X3X4 comprises threonine-arginine (TR); X1X2 comprises threonine-glutamine (TQ) and X3X4 comprises threonine-arginine (TR); X1X2 comprises valine-phenylalanine (VF) and X3X4 comprises threonine-arginine (TR); X1X2 comprises threonine-threonine (TT) and X3X4 comprises threonine-arginine (TR); X1X2 comprises valine-isoleucine (VI) and X3X4 comprises threonine-arginine (TR); X1X2 comprises proline-valine (PV) and X3X4 comprises lysine-proline (KP); X1X2 comprises glycine-valine (GV) and X3X4 comprises lysine-proline (KP); X1X2 comprises serine-valine (SV) and X3X4 comprises lysine-proline (KP); X1X2 comprises asparagine-valine (NV) and X3X4 comprises lysine-proline (KP); X1X2 comprises phenylalanine-valine (FV) and X3X4 comprises lysine-proline (KP); X1X2 comprises cysteine-valine (CV) and X3X4 comprises lysine-proline (KP); X1X2 comprises glutamate-valine (EV) and X3X4 comprises lysine-proline (KP); X1X2 comprises glutamine-valine (QV) and X3X4 comprises lysine-proline (KP); X1X2 comprises lysine-valine (KV) and X3X4 comprises lysine-proline (KP); X1X2 comprises arginine-tryptophan (RW) and X3X4 comprises histidine-tyrosine (HY); X1X2 comprises glycine-aspartate (GD) and X3X4 comprises glycine-glycine (GG); X1X2 comprises alanine-leucine (AL) and X3X4 comprises asparagine-histidine (NH); X1X2 comprises glycine-arginine (GR) and X3X4 comprises serine-threonine (ST); X1X2 comprises glycine-tyrosine (GY) and X3X4 comprises arginine-serine (RS); X1X2 comprises isoleucine-cysteine (IC) and X3X4 comprises arginine-histidine (RH); or X1X2 comprises glycine-leucine (GL) and X3X4 comprises tryptophan-proline (WP). In some embodiments, L1 comprises LSSLIX1 and L2 comprises X2NHDQL, wherein X1, X2 are independently any amino acid. In some embodiments, X1 is selected from the group consisting of I, W, V, L, F, P, N, Y and D; and X2 is selected from the group consisting of G, N, M, R T, S, K, L, Y, H, F, E, I and W. In some embodiments, X1 is I and X2 is N or S; X1 is W and X2 is M, T, F, E or I; X1 is V and X2 is R, H or T; X1 is L and X2 is T; X1 is F and X2 is S; X1 is P and X2 is K or S; X1 is Y and X2 is S, L; or X1 is D and X2 is W.

3. G Coupled Protein Receptors with Integrated Sensors

In some embodiments, the fluorescent sensors are incorporated or integrated into the third intracellular loop of a G protein-coupled receptor (GPCR). This can be readily accomplished employing recombinant techniques known in the art. Generally, any amino acid within the third loop region of a GPCR may serve as an insertion site for a cpFP (e.g., before or after, or as a replacement). In some embodiments, the cpFP sensor is inserted between two amino acid residues within the middle third of the third intracellular loop of a G protein-coupled receptor (GPCR). As necessary or appropriate, one, two, three, four, or more, amino acid residues within the third intracellular loop of the wild-type G protein-coupled receptor may be removed in order that the loop can accommodate the sensor. In some embodiments for inserting a cpFP into the third intracellular loop, the third intracellular loop and part of the sixth transmembrane sequence (TM6)(e.g., for a beta2 adrenergic receptor RQLQ—cpFP—CWLP) can be used as a module system to transfer to other GPCRs.

As is standard or customary in the art, the "third intracellular loop" or "third cytoplasmic loop" is with reference to N-terminus of the GPCR that is integrated into the extracellular membrane of a cell and refers to the third segment of a GPCR polypeptide that is located in the cytoplasmic or intracellular side of the extracellular membrane. It is phrase commonly used by those of skill in the art. See, e.g., Kubale, et al., *Int J Mol Sci*. (2016) July 19; 17 (7); Clayton, et al., *J Biol Chem*. (2014) November 28; 289 (48): 33663-75; Gómez-Moutón, et al., *Blood*. (2015) February 12; 125 (7): 1116-25; Terawaki, et al., *Biochem Biophys Res Commun*. 2015 Jul. 17-24;463 (1-2): 64-9; Gabl, et al., *PLoS One*. 2014 Oct. 10;9 (10): e109516; Fukunaga, et al., *Mol Neurobiol*. 2012 February; 45 (1): 144-52; Nakatsuma, et al., *Biophys J*. 2011 Apr. 20; 100 (8): 1874-82; Shioda, et al., *J Pharmacol Sci*. 2010; 114 (1): 25-31; Shpakov, et al., *Dokl Biochem Biophys*. 2010 March-April; 431:94-7; Takeuchi, et al., *J Neurochem*. 2004 June; 89 (6): 1498-507. The third intracellular loop of various G protein-coupled receptors (GPCRs) is identified in FIGS. 11A-E.

Accordingly, provided are G protein-coupled receptors comprising a cpFP sensor, as described above and herein, wherein the sensor is integrated into the third intracellular loop of the G protein-coupled receptor.

In some embodiments, the G protein-coupled receptor is a class A type or alpha G protein-coupled receptor. In some embodiments, the G protein-coupled receptor is selected from the group consisting of an adrenoceptor or adrenergic receptor, an opioid receptor, a 5-Hydroxytryptamine (5-HT) receptor, a dopamine receptor, a muscarinic acetylcholine receptor, an adenosine receptor, a glutamate metabotropic receptor, a gamma-aminobutyric acid (GABA) type B receptor, corticotropin-releasing factor (CRF) receptor, a tachykinin or neurokinin (NK) receptor, an angiotensin receptor, an apelin receptor, a bile acid receptor, a bombesin receptor, a bradykinin receptor, a cannabinoid receptor, a chemokine receptor, a cholecystokinin receptor, a complement peptide receptor, an endothelin receptor, a formylpeptide receptor, a free fatty acid receptor, a galanin receptor, a ghrelin receptor, a glycoprotein hormone, a gonadotrophin-releasing hormone receptor, a G protein-coupled estrogen receptor, an histamine receptor, a leukotriene receptor, a lysophospholipid (LPA) receptor, a lysophospholipid (S1P) receptor, a melanocortin receptor, a melatonin receptor, a neuropeptide receptor, a neurotensin receptor, an orexin receptor, a P2Y receptor, a prostanoid or prostaglandin receptor, somatostatin receptor, a tachykinin receptor, a thyrotropin-releasing hormone receptor, a urotensin receptor, and a vasopressin/oxytocin receptor. In some embodiments, the G protein-coupled receptor is selected from the group consisting of an adrenoceptor beta 1 (ADRB1), adrenoceptor beta 2 (ADRB2), adrenoceptor alpha 2A (ADRA2A), a mu (μ)-type opioid receptor (OPRM), a kappa (κ)-type opioid receptor (OPRK), a delta (δ)-type opioid receptor (OPRD), a dopamine receptor D1 (DRD1), a 5-hydroxy-tryptamine receptor 2A (5-HT2A), a melatonin receptor type 1B (MTNR1B), an adenosine A1 receptor (ADORA1), a cannabinoid receptor (type-1)(CNR1), a histamine receptor H1 (HRH1), a neuropeptide Y receptor Y1 (NPY1R), a cholinergic receptor muscarinic 2 (CHRM2), a hypocretin (orexin) receptor 1 (HCRTR1), a tachykinin receptor 1 (TACR1) (a.k.a. neurokinin 1 receptor (NK1R)), a corticotropin releasing hormone receptor 1 (CRHR1), a glutamate metabotropic receptor 1 (GRM1), and a gamma-aminobutyric acid (GABA) type B receptor subunit 1 (GABBR1). In some embodiments, the G protein-coupled receptor is selected from the group consisting of: Metabotropic Glutamate Receptor type-3 (MGLUR3); Metabotropic Glutamate Receptor type-5 (MGLUR5); Gamma-aminobutyric acid Receptor type-2 (GABAB1); Gamma-aminobutyric acid Receptor type-2 (GABAB2); Cannabinoid Receptor type-1 (CB1); Gonadotropin-Releasing Hormone Receptor (GNRHR); Vasopressin Receptor type-1 (VIA); Oxytocin Receptor (OTR); Adenosine Receptor type-2 (A2A); Beta-2 Adrenergic Receptor (B2AR); Dopamine Receptor type-1 (DRD1); Dopamine Receptor type-2 (DRD2); Acetylcholine Muscarinic Receptor type-2 (M2R); Histamine Receptor type-1 (H1R); Serotonin Receptor type-2A (5HT2A); Serotonin Receptor type-2B (5HT2B); Tachykinin Receptor type-1 (NK1); Tachykinin Receptor type-2 (NK2); Tachykinin Receptor type-3 (NK3); Melatonin Receptor type-1B (MTNR1B); P2 purinoceptor type Y1 (P2Y1); Angiotensin-II Receptor type-1 (AT1); Kappa Opioid Receptor type-1 (KOR1); Mu Opioid Receptor type-1 (MOR1); and Delta Opioid Receptor type-1 (DOR1).

In some embodiments, the receptor is mutated to be signaling incompetent or incapable. To prevent internalization and arrestin-dependent signaling for any GPCR, GRK6 phosphorylation sites can be replaced with alanine residues. The residue numbers and location of the G protein-coupled receptor kinase 6 (GRK6) residues vary between different GPCRs. On the Beta2AR, the GRK6 residues are SS355, 356 (residues 624-625 of SEQ ID NO: 22). Alternatively or additionally, G-protein dependent signaling can be prevented or inhibited by mutating a specific residue that is mostly conserved among many GPCRs. This residue corresponds to Phenylalanine (F) 139 (residue F163 of SEQ ID NO: 22) on the Beta2AR. This conserved residue that facilitates G protein dependent signaling varies from GPCR to GPCR, but the sequence alignment in FIG. 11 shows its correspondent residue on other GPCRs.

In some embodiments, the G protein-coupled receptor comprising an integrated cpFP sensor comprises a beta2 adrenergic receptor having at least 90% sequence identity, e.g., at least about 91%, 92%, 93%, 94%, 95%, 96%, 97%, 98%, 99% or 100% sequence identity, to SEQ ID NO: 22 or SEQ ID NO:32. In some embodiments, the sensor replaces one or more or all of amino acid residues QLQKIDKSEGRFHVQNLS (residues 253-270 of SEQ ID NO:22) and the carboxy-terminus of L2 abuts KEHK (residues 536-539 of SEQ ID NO:22). In some embodiments, the sensor replaces one or more or all of amino acid residues QLQKIDKSEGRFHVQNLS (residues 253-270 of SEQ ID NO:22) and the carboxy-terminus of L2 abuts FCLK (residues 533-536 of SEQ ID NO:22). In some embodiments, one or more of amino acid residues F139, S355 and S356 (residues 163 and 624-625 in SEQ ID NO: 22) of the beta2 adrenergic receptor are replaced with alanine residues to render the beta2 adrenergic receptor signaling incompetent. In some embodiments, X at amino acid residue 163 in SEQ ID NO: 22 or at residue 139 of SEQ ID NO:32 is any amino acid or an amino acid selected from the group consisting of A, F, G, I, L, M, S, T and V, particularly A. In some embodiments when the G protein-coupled receptor is a beta2 adrenergic receptor, the cpFP sensor is inserted into the third intracellular loop between residues AKRQ and LQKI, e.g., between residues 253 and 254 of SEQ ID NO:22. In some embodiments, the insertion sites of the cpGFP into a beta2 adrenergic receptor can be any amino acids in the region of KSEGRFHVQLSQVEQDGRTGHGL of the third loop. In some embodiments when the G protein-coupled receptor is a beta2 adrenergic receptor, the cpFP sensor is inserted into the third intracellular loop between residues QNLS and AEVK, e.g., between residues 270 and 271 of SEQ ID NO:22. In some embodiments when the G protein-coupled receptor is a beta2 adrenergic receptor, the cpFP sensor is inserted into the third intracellular loop between residues EAKR and QLQK, e.g., between residues 252 and 253 of SEQ ID NO:22. In some embodiments when the G protein-coupled receptor is a beta2 adrenergic receptor, the cpFP sensor is inserted into the third intracellular loop between residues KRQL and QKID, e.g., between residues 254 and 255 of SEQ ID NO:22. In some embodiments when the G protein-coupled receptor is a beta2 adrenergic receptor, L1 of the cpFP sensor is alanine-valine (AV) and L2 of the cpFP sensor is threonine-arginine (TR) or lysine-proline (KP).

In some embodiments, the G protein-coupled receptor comprising an integrated cpFP sensor comprises a mu (μ)-type opioid receptor having at least 90% sequence identity, e.g., at least about 91%, 92%, 93%, 94%, 95%, 96%, 97%, 98%, 99% or 100% sequence identity, to SEQ ID NO:24 or SEQ ID NO:37. In some embodiments, amino acid residue V199 (residue 199 in SEQ ID NO: 24) of the mu (μ)-type opioid receptor is replaced with an alanine residue to render the mu (μ)-type opioid receptor signaling incompetent. In some embodiments, X at amino acid residue 199 in SEQ ID NO: 24 or at residue 175 of SEQ ID NO: 37 is any amino acid or an amino acid selected from the group consisting of A, F, G, I, L, M, S, T and V, particularly A. In some embodiments when the G protein-coupled receptor is a mu (μ)-type opioid receptor, the cpFP sensor is inserted into the third intracellular loop between residues RMLS and GS, e.g., between residues 292 and 293 of SEQ ID NO:24. In some embodiments when the G protein-coupled receptor is a mu (μ)-type opioid receptor, L1 of the cpFP sensor is isoleucine-lysine (IK) and L2 of the cpFP sensor is isoleucine-isoleucine (II).

In some embodiments, the G protein-coupled receptor comprising an integrated cpFP sensor comprises a dopamine receptor D1 (DRD1) having at least 90% sequence identity, e.g., at least about 91%, 92%, 93%, 94%, 95%, 96%, 97%, 98%, 99% or 100% sequence identity, to SEQ ID NO: 26 or SEQ ID NO:30. In some embodiments, the N-terminus of L1 abuts IAQK (residues 244-247 of SEQ ID NO:26), the C-terminus of L2 abuts KRET (residues 534-537 of SEQ ID NO:26), the sensor replacing residues 248 to 533 of SEQ ID NO:26. In some embodiments, amino acid residue F129 (residue 153 in SEQ ID NO: 26 or residue 129 of SEQ ID NO:30) of the dopamine receptor D1 (DRD1) is replaced with an alanine residue to render the dopamine receptor D1 (DRD1) signaling incompetent. In some embodiments, X at amino acid residue 153 in SEQ ID NO: 26 or at residue 129 of SEQ ID NO:30 is any amino acid or an amino acid selected from the group consisting of A, F, G, I, L, M, S, T and V, particularly A. In some embodiments when the G protein-coupled receptor is a dopamine receptor D1 (DRD1), the cpFP sensor is inserted into the third intracellular loop between residues AKNC and QTTT, e.g., between residues 265 and 266 of SEQ ID NO:21. In some embodiments when the G protein-coupled receptor is a dopamine receptor D1 (DRD1), L1 of the cpFP sensor is serine-arginine (SR) and L2 of the cpFP sensor is proline-proline (PP).

In some embodiments, the G protein-coupled receptor comprising an integrated cpFP sensor comprises a 5 hydroxy-tryptamine 2A (5-HT2A) receptor having at least 90% sequence identity, e.g., at least about 91%, 92%, 93%, 94%, 95%, 96%, 97%, 98%, 99% or 100% sequence identity, to SEQ ID NO: 28 or SEQ ID NO:33. In some embodiments, the N-terminus of LI abuts SLQK (residues 284-287 of SEQ ID NO:28), the C-terminus of L2 abuts NEQK (residues 586-589 of SEQ ID NO:28), the sensor replacing residues 288 to 585 of SEQ ID NO: 28. In some embodiments, amino acid residue I181 (residue 205 in SEQ ID NO: 28) of the 5-hydroxy-tryptamine 2A (5-HT2A) receptor is replaced with an alanine residue to render the 5-hydroxy-tryptamine 2A (5-HT2A) receptor signaling incompetent. In some embodiments, X at amino acid residue 205 in SEQ ID NO: 28 or at residue 181 of SEQ ID NO: 33 is any amino acid or an amino acid selected from the group consisting of A, F, G, I, L, M, S, T and V, particularly A. In some embodiments when the G protein-coupled receptor is a 5-hydroxy-tryptamine 2A (5-HT2A) receptor, the cpFP sensor is inserted into the third intracellular loop between residues TRAK and LASF, e.g., between residues 301 and 302 of SEQ ID NO:23. In some embodiments when the G protein-coupled receptor is a 5-hydroxy-tryptamine 2A (5-HT2A) receptor, L1 of the cpFP sensor is serine-arginine (SR) and L2 of the cpFP sensor is leucine-phenylalanine (LF).

In some embodiments, the G protein-coupled receptor comprising an integrated cpFP sensor comprises an adrenoceptor beta 1 (ADRB1) having at least 90% sequence identity, e.g., at least about 91%, 92%, 93%, 94%, 95%, 96%, 97%, 98%, 99% or 100% sequence identity, to SEQ ID NO:31. In some embodiments, X at amino acid residue 164 in SEQ ID NO: 31 is any amino acid or an amino acid selected from the group consisting of A, F, G, I, L, M, S, T and V, particularly A. In some embodiments, the G protein-coupled receptor comprising an integrated cpFP sensor comprises an adenosine A2a receptor (ADORA2A) having at least 90% sequence identity, e.g., at least about 91%, 92%, 93%, 94%, 95%, 96%, 97%, 98%, 99% or 100% sequence identity, to SEQ ID NO: 34. In some embodiments, X at amino acid residue 110 in SEQ ID NO: 34 is any amino acid or an amino acid selected from the group consisting of A, F, G, I, L, M, S, T and V, particularly A. In some embodiments, the G protein-coupled receptor comprising an integrated cpFP sensor comprises an adrenoceptor alpha 2A (ADRA2A) having at least 90% sequence identity, e.g., at least about 91%, 92%, 93%, 94%, 95%, 96%, 97%, 98%, 99% or 100% sequence identity, to SEQ ID NO: 35. In some embodiments, X at amino acid residue 139 in SEQ ID NO: 35 is any amino acid or an amino acid selected from the group consisting of A, F, G, I, L, M, S, T and V, particularly A. In some embodiments, the G protein coupled-receptor comprising an integrated cpFP sensor comprises a kappa receptor delta 1 (OPRK1) having at least 90% sequence identity, e.g., at least about 91%, 92%, 93%, 94%, 95%, 96%, 97%, 98%, 99% or 100% sequence identity, to SEQ ID NO: 36. In some embodiments, X at amino acid residue 164 in SEQ ID NO: 36 is any amino acid or an amino acid selected from the group consisting of A, F, G, I, L, M, S, T and V, particularly A. In some embodiments, the G protein-coupled receptor comprising an integrated cpFP sensor comprises an opioid receptor delta 1 (OPRD1) having at least 90% sequence identity, e.g., at least about 91%, 92%, 93%, 94%, 95%, 96%, 97%, 98%, 99% or 100% sequence identity, to SEQ ID NO: 38. In some embodiments, X at amino acid residue 154 in SEQ ID NO: 38 is any amino acid or an amino acid selected from the group consisting of A, F, G, I, L, M, S, T and V, particularly A. In some embodiments, the G protein couple receptor comprising an integrated cpFP sensor comprises a melatonin receptor 1B (MTNR1B) having at least 90% sequence identity, e.g., at least about 91%, 92%, 93%, 94%, 95%, 96%, 97%, 98%, 99% or 100% sequence identity, to SEQ ID NO: 39. In some embodiments, X at amino acid residue 146 in SEQ ID NO: 39 is any amino acid or an amino acid selected from the group consisting of A, F, G, I, L, M, S, T and V, particularly A. In some embodiments, the G protein-coupled receptor comprising an integrated cpFP sensor comprises a cannabinoid receptor type 1 (CNR1) having at least 90% sequence identity, e.g., at least about 91%, 92%, 93%, 94%, 95%, 96%, 97%, 98%, 99% or 100% sequence identity, to SEQ ID NO: 40. In some embodiments, X at amino acid residue 222 in SEQ ID NO: 40 is any amino acid or an amino acid selected from the group consisting of A, F, G, I, L, M, S, T and V, particularly A. In some embodiments, the G protein-coupled receptor comprising an integrated cpFP sensor comprises a histamine receptor H1 (HRH1) having at least 90% sequence identity, e.g., at least about 91%, 92%, 93%, 94%, 95%, 96%, 97%, 98%, 99% or 100% sequence identity, to SEQ ID NO: 41. In some embodiments, X at amino acid residue 133 in SEQ ID NO: 41 is any amino acid or an amino acid selected from the group consisting of A, F, G, I, L, M, S, T and V, particularly A. In some embodiments, the G protein-coupled receptor comprising an integrated cpFP sensor comprises a neuropeptide Y receptor Y1 (NPY1R) having at least 90% sequence identity, e.g., at least about 91%, 92%, 93%, 94%, 95%, 96%, 97%, 98%, 99% or 100% sequence identity, to SEQ ID NO: 42. In some embodiments, the G protein-coupled receptor comprising an integrated cpFP sensor comprises a muscarinic cholinergic receptor type 2 (CHRM2) having at least 90% sequence identity, e.g., at least about 91%, 92%, 93%, 94%, 95%, 96%, 97%, 98%, 99% or 100% sequence identity, to SEQ ID NO: 43. In some embodiments, X at amino acid residue 129 in SEQ ID NO: 43 is any amino acid or an amino acid selected from the group consisting of A, F, G, I, L, M, S, T and V, particularly A. In some embodiments, the G protein-coupled receptor comprising an integrated cpFP sensor comprises a hypocretin (orexin) receptor 1 (HCRTR1) having at least 90% sequence identity, e.g., at least about 91%, 92%, 93%, 94%, 95%, 96%, 97%, 98%, 99% or 100% sequence identity, to SEQ ID NO: 44. In some embodiments, X at amino acid residue 152 in SEQ ID NO: 44 is any amino acid or an amino acid selected from the group consisting of A, F, G, I, L, M, S, T and V, particularly A.

4. Production of Circularly Permuted Fluorescent Protein Sensors and GPCRs with an Integrated cpFP Sensor Fluorescent protein sensors can be produced in any number of ways, all of which are well known in the art. In one embodiment, the fluorescent protein sensors are generated using recombinant techniques. One of skill in the art can readily determine nucleotide sequences that encode the desired polypeptides using standard methodology and the teachings herein. Oligonucleotide probes can be devised based on the known sequences and used to probe genomic or cDNA libraries. The sequences can then be further isolated using standard techniques and, e.g., restriction enzymes employed to truncate the gene at desired portions of the full-length sequence. Similarly, sequences of interest can be isolated directly from cells and tissues containing the same, using known techniques, such as phenol extraction and the sequence further manipulated to produce the desired truncations. See, e.g., Green and Sambrook, Molecular Cloning: A Laboratory Manual (Fourth Edition), 2012, Cold Spring Harbor Laboratory Press and Ausubel, et al., eds. Current Protocols in Molecular Biology, 1987-2016, John Wiley & Sons (onlinelibrary.wiley.com/book/10.1002/0471142727), for a description of techniques used to obtain, isolate and manipulate nucleic acids. In some embodiments, Circular Polymerase Extension Cloning (CPEC) can be used to insert a polynucleotide encoding a cpFP sensor into a polynucleotide encoding a GPCR. See, e.g., Quan, et al., *Nat Protoc,* 2011. 6 (2): p. 242-51.

The sequences encoding polypeptides can also be produced synthetically, for example, based on the known sequences. The nucleotide sequence can be designed with the appropriate codons for the particular amino acid sequence desired. The complete sequence is generally assembled from overlapping oligonucleotides prepared by standard methods and assembled into a complete coding sequence. See, e.g., Edge (1981) Nature 292:756; Nambair et al. (1984) Science 223:1299; Jay et al. (1984) J. Biol. Chem. 259:6311; Stemmer et al. (1995) Gene 164:49-53.

Recombinant techniques are readily used to clone sequences encoding polypeptides useful in the present fluorescent protein sensors that can then be mutagenized in vitro by the replacement of the appropriate base pair(s) to result in the codon for the desired amino acid. Such a change can include as little as one base pair, effecting a change in a single amino acid, or can encompass several base pair changes. Alternatively, the mutations can be effected using a mismatched primer that hybridizes to the parent nucleotide sequence (generally cDNA corresponding to the RNA sequence), at a temperature below the melting temperature of the mismatched duplex. The primer can be made specific by keeping primer length and base composition within relatively narrow limits and by keeping the mutant base centrally located. See, e.g., Innis et al, (1990) PCR Applications: Protocols for Functional Genomics; Zoller and Smith, Methods Enzymol. (1983) 100:468. Primer extension is effected using DNA polymerase, the product cloned and clones containing the mutated DNA, derived by segregation of the primer extended strand, selected. Selection can be accomplished using the mutant primer as a hybridization probe. The technique is also applicable for generating multiple point mutations. See, e.g., Dalbie-McFarland et al. Proc. Natl. Acad. Sci. USA (1982) 79:6409.

Once coding sequences have been isolated and/or synthesized, they can be cloned into any suitable vector or replicon for expression. As will be apparent from the teachings herein, a wide variety of vectors encoding modified polypeptides can be generated by creating expression constructs which operably link, in various combinations, polynucleotides encoding polypeptides having deletions or mutations therein.

Numerous cloning vectors are known to those of skill in the art, and the selection of an appropriate cloning vector is a matter of choice. Examples of recombinant DNA vectors for cloning and host cells which they can transform include the bacteriophage.lamda. (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (*Bacillus*), pIJ61 (*Streptomyces*), pUC6 (*Streptomyces*), YIp5 (*Saccharomyces*), YCp19 (*Saccharomyces*) and bovine papilloma virus (mammalian cells). See, generally, Green and Sambrook, supra; and Ausubel, supra.

Insect cell expression systems, such as baculovirus systems, can also be used and are known to those of skill in the art and described in, e.g., Summers and Smith, Texas Agricultural Experiment Station Bulletin No. 1555 (1987). Materials and methods for baculovirus/insect cell expression systems are commercially available in kit form from, inter alia, Invitrogen, San Diego Calif. ("MaxBac" kit).

Plant expression systems can also be used to produce the fluorescent protein sensors described herein. Generally, such systems use virus-based vectors to transfect plant cells with heterologous genes. For a description of such systems see, e.g., Porta et al., Mol. Biotech. (1996) 5:209-221; and Hackland et al., Arch. Virol. (1994) 139:1-22.

Viral systems, such as a vaccinia based infection/transfection system, as described in Tomei et al., J. Virol. (1993) 67:4017-4026 and Selby et al., *J. Gen. Virol.* (1993) 74:1103-1113, will also find use. In this system, cells are first transfected in vitro with a vaccinia virus recombinant that encodes the bacteriophage T7 RNA polymerase. This polymerase displays exquisite specificity in that it only transcribes templates bearing T7 promoters. Following infection, cells are transfected with the DNA of interest, driven by a T7 promoter. The polymerase expressed in the cytoplasm from the vaccinia virus recombinant transcribes the transfected DNA into RNA that is then translated into protein by the host translational machinery. The method provides for high level, transient, cytoplasmic production of large quantities of RNA and its translation product(s). Other viral systems that find use include adenovirus, adeno-associated virus, lentivirus and retrovirus.

The gene can be placed under the control of a promoter, ribosome binding site (for bacterial expression) and, optionally, an operator (collectively referred to herein as "control" elements), so that the DNA sequence encoding the desired polypeptide is transcribed into RNA in the host cell transformed by a vector containing this expression construction. The coding sequence may or may not contain a signal peptide or leader sequence. Both the naturally occurring signal peptides and heterologous sequences can be used. Leader sequences can be removed by the host in post-translational processing. See, e.g., U.S. Pat. Nos. 4,431,739; 4,425,437; 4,338,397. Such sequences include, but are not limited to, the TPA leader, as well as the honey bee mellitin signal sequence.

Other regulatory sequences may also be desirable which allow for regulation of expression of the protein sequences relative to the growth of the host cell. Such regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

The control sequences and other regulatory sequences may be ligated to the coding sequence prior to insertion into a vector. Alternatively, the coding sequence can be cloned directly into an expression vector that already contains the control sequences and an appropriate restriction site.

In some cases it may be necessary to modify the coding sequence so that it may be attached to the control sequences with the appropriate orientation; i.e., to maintain the proper reading frame. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, generally, Green and Sambrook, supra; and Ausubel, supra.

The expression vector is then used to transform an appropriate host cell. A number of mammalian cell lines are known in the art and include immortalized cell lines available from the American Type Culture Collection (ATCC), such as, but not limited to, Chinese hamster ovary (CHO) cells, HeLa cells, HEK 293T cells, baby hamster kidney (BHK) cells, monkey kidney cells (COS), human hepatocellular carcinoma cells (e.g., Hep G2), Vero293 cells, as well as others. Similarly, bacterial hosts such as *E. coli*, *Bacillus subtilis*, and *Streptococcus* spp., will find use with the present expression constructs. Yeast hosts useful include inter alia, *Saccharomyces cerevisiae, Candida albicans, Candida maltosa, Hansenula polymorphs, Kluyveromyces fragilis, Kluyveromyces lactis, Pichia guillerimondii, Pichia pastoris, Schizosaccharomyces pombe* and *Yarrowia lipolytica*. Insect cells for use with baculovirus expression vectors include, inter alia, *Aedes aegypti, Autographa californica, Bombyx mori, Drosophila melanogaster, Spodoptera frugiperda*, and *Trichoplusia ni*.

Depending on the expression system and host selected, the fluorescent protein sensors are produced by growing host cells transformed by an expression vector described above under conditions whereby the protein of interest is expressed. The selection of the appropriate growth conditions is within the skill of the art.

5. Polynucleotides, Expression Cassettes, Vectors

Accordingly, provided are polynucleotides that encode the cpFP sensors, as described above and herein. In some embodiments, the polynucleotide encodes a cpFP sensor (L1-cpFP-L2), wherein the circularly permuted fluorescent protein has at least about 90% sequence identity, e.g., at least about 91%, 92%, 93%, 94%, 95%, 96%, 97%, 98%, 99% or 100% sequence identity, to a circularly permuted fluorescent protein selected from the group consisting of SEQ ID NOS: 15-18 (e.g., cpGFP, cpmRuby2, cpmApple and cpmEos2). In some embodiments, the polynucleotide encodes a cpFP sensor (L1-cpFP-L2), wherein the polynucleotide encoding the circularly permuted fluorescent protein has at least about 90% sequence identity, e.g., at least about 91%, 92%, 93%, 94%, 95%, 96%, 97%, 98%, 99% or 100% sequence identity, to SEQ ID NO: 29 (a cpGFP).

Further provided are polynucleotides encoding a GPCR comprising a cpFP sensor integrated into its third intracellular loop. In some embodiments, the polynucleotide encodes a beta2 adrenergic receptor comprising an integrated cpFP sensor, the protein having at least 90% sequence identity, e.g., at least about 91%, 92%, 93%, 94%, 95%, 96%, 97%, 98%, 99% or 100% sequence identity, to SEQ ID NO: 22. In some embodiments, the polynucleotide encodes a beta2 adrenergic receptor comprising an integrated cpFP sensor, the polynucleotide having at least 90% sequence identity, e.g., at least about 91%, 92%, 93%, 94%, 95%, 96%, 97%, 98%, 99% or 100% sequence identity, to SEQ ID NO: 16. In some embodiments, the polynucleotide encodes a mu (μ)-type opioid receptor comprising an integrated cpFP sensor, the protein having at least 90% sequence identity, e.g., at least about 91%, 92%, 93%, 94%, 95%, 96%, 97%, 98%, 99% or 100% sequence identity, to SEQ ID NO: 24. In some embodiments, the polynucleotide encodes a mu (μ)-type opioid receptor comprising an integrated cpFP sensor, the polynucleotide having at least 90% sequence identity, e.g., at least about 91%, 92%, 93%, 94%, 95%, 96%, 97%, 98%, 99% or 100% sequence identity, to SEQ ID NO: 18. In some embodiments, the polynucleotide encodes a dopamine receptor D1 (DRD1) comprising an integrated cpFP sensor, the protein having at least 90% sequence identity, e.g., at least about 91%, 92%, 93%, 94%, 95%, 96%, 97%, 98%, 99% or 100% sequence identity, to SEQ ID NO: 26. In some embodiments, the polynucleotide encodes a dopamine receptor D1 (DRD1) comprising an integrated cpFP sensor, the protein having at least 90% sequence identity, e.g., at least about 91%, 92%, 93%, 94%, 95%, 96%, 97%, 98%, 99% or 100% sequence identity, to SEQ ID NO: 20. In some embodiments, the polynucleotide encodes a 5 hydroxy-tryptamine 2A (5-HT2A) receptor comprising an integrated cpFP sensor, the protein having at least 90% sequence identity, e.g., at least about 91%, 92%, 93%, 94%, 95%, 96%, 97%, 98%, 99% or 100% sequence identity, to SEQ ID NO: 28. In some embodiments, the polynucleotide encodes a 5 hydroxy-tryptamine 2A (5-HT2A) receptor comprising an integrated cpFP sensor, the polynucleotide having at least 90% sequence identity, e.g., at least about 91%, 92%, 93%, 94%, 95%, 96%, 97%, 98%, 99% or 100% sequence identity, to SEQ ID NO: 22.

Further provided are expression cassettes comprising the polynucleotides encoding the cpFP sensors or GPCRs comprising a cpFP sensor integrated into its third intracellular loop, as described above and herein. The expression cassettes comprise a promoter operably linked to and capable of driving the expression of the cpFP sensor or GPCR comprising a cpFP sensor integrated into its third intracellular loop. In some embodiments, the promoters can promote expression in a prokaryotic or a eukaryotic cell, e.g., a mammalian cell, a fish cell. In some embodiments, the promoter is constitutive or inducible. In some embodiments, the promoter is organ or tissue specific. In some embodiments, the expression cassettes comprise a synapsin, CAG (composed of: (C) the cytomegalovirus (CMV) early enhancer element; (A) the promoter, the first exon and the first intron of chicken beta-actin gene; (G) the splice acceptor of the rabbit beta-globin gene), cytomegalovirus (CMV), glial fibrillary acidic protein (GFAP), Calcium/calmodulin-dependent protein kinase II (CaMKII) or Cre-dependent promoter (e.g., such as FLEX-rev) operably linked to and driving the expression a polynucleotide encoding a GPCR comprising a cpFP sensor integrated into its third intracellular loop, to direct expression in neurons. Subcellular targeting of GPCR comprising cpGFP is also possible using genetic strategy or intrabodies.

Further provided are plasmid and viral vectors comprising the polynucleotides encoding the cpFP sensors or GPCRs comprising a cpFP sensor integrated into its third intracellular loop, as described above and herein. Viral vectors of use include lentiviral vectors, adenoviral vectors, adeno-associated viral vectors, retroviral vectors and vaccinia viral vectors.

6. Cells

Further provided are cells comprising the polynucleotides encoding the cpFP sensors or GPCRs comprising a cpFP sensor integrated into its third intracellular loop, as described above and herein. In some embodiments, the polynucleotides encoding the cpFP sensors or GPCRs comprising a cpFP sensor integrated into its third intracellular loop may be episomal or integrated into the genome of the cell. In some embodiments, the host cells are prokaryotic or eukaryotic. Illustrative eukaryotic cells include without limitation mammalian cells (e.g., Chinese hamster ovary (CHO) cells, HeLa cells, HEK 293T cells, baby hamster kidney (BHK) cells, monkey kidney cells (COS), human hepatocellular carcinoma cells (e.g., Hep G2), Vero293 cells) fish cells (e.g., zebra fish cells) and insect cells.

In addition, GPCRs having an integrated cpFP sensor can be expressed in iPSC-derived cells or primary cells, such as dissociated neuronal culture. For example, in some embodiments with patient iPSC-derived brain cells (e.g., neurons and astrocytes), can be transformed with a polynucleotide encoding a GPCR having an integrated cpFP sensor. GPCRs comprising a cpFP sensor can be used for evaluating mechanistic action of neuropharmacological drugs.

In certain embodiments, the GPCRs having an integrated cpFP sensor can be wholly or partially purified and/or solubilized from the host cell, using methodologies for wholly or partially purifying and/or solubilizing the wild-type GPCRs known in the art. In some embodiments, the GPCRs having an integrated cpFP sensor are produced as partially or substantially purified nanodiscs solubilized-proteins. The method of solubilizing membrane proteins on nanodiscs has been well-established, especially in large scale production of GPCRs for crystallization purposes. Production of nanodisc-solubilized GPCR is described, e.g., in Manglik, et al. "Crystal structure of the μ-opioid receptor bound to a morphinan antagonist" *Nature*. (2012) 485 (7398): 321-6. Nanodiscs attached to membrane proteins are further described, e.g., in Parker, et al., *Biochemistry* (2014) 53 (9): 1511-20; Bertram, et al., *Langmuir* (2015) 31 (30): 8386-91; and Ma, et al., *Anal Chem*. (2016) 88 (4): 2375-9. Nanodiscs are reviewed in, e.g., Viegas, et al., *Biol Chem*. (2016) 397 (12): 1335-1354; Malhotra, et al., *Biotechnol Genet Eng Rev*. (2014) 30 (1-2): 79-93; Schuler, et al., *Methods Mol Biol*. (2013) 974:415-33; and Inagaki, et al., *Methods*. (2013) 59 (3): 287-300. Among many advantages, substantially purified (and solubilized) sensor proteins can have a long shelf life, e.g., of about 1-2 months (when refrigerated and stored properly) and can be immobilized onto a chip (e.g., a nanodisc) for the production of diagnostics or similar devices to be used, e.g., in clinical medicine, sport medicine or for a variety of other applications. In some embodiments, nanodisc-immobilized and solubilized GPCRs having an integrated cpFP sensor can be substantially purified and delivered to live cells and tissues to monitor the local drug effect.

7. Transgenic Animals

Further provided are transgenic animals comprising one or more G Coupled-Protein Receptors (GPCRs) comprising a cpFP sensor integrated into its third intracellular loop, as described above and herein. In some embodiments, the transgenic animal is a mouse, a rat, a worm, a fly or a zebrafish. Depending on the promoter or promoters driving the expression of the G Coupled-Protein Receptors (GPCRs) comprising a cpFP sensor integrated into its third intracellular loop, the GPCR may be expressed only in select tissues or organs, or may be inducible. In some embodiments, a polynucleotide encoding a GPCRs having an integrated a cpFP sensor can be integrated into any locus in the genome of a non-human animal, e.g., via CRISPR/Cas9 or equivalent techniques. As described above and herein, the GPCR transgenes may be altered such that the expressed GPCR is signaling incompetent. In certain embodiments, a polynucleotide encoding a G Coupled-Protein Receptors (GPCRs) comprising a cpFP sensor integrated into its third intracellular loop is administered to a non-human animal in a viral vector.

Methods for making transgenic mice are known in the art, and described, e.g., in Behringer and Gertsenstein, "Manipulating the Mouse Embryo: A Laboratory Manual," Fourth edition, 2013, Cold Spring Harbor Laboratory Press; Pinkert, "Transgenic Animal Technology, Third Edition: A Laboratory Handbook," 2014, Elsevier; Hofker and Van Deursen, "Transgenic Mouse Methods and Protocols (Methods in Molecular Biology)," 2011, Humana Press.

Methods for making transgenic rats are known in the art, and described, e.g., in Li, et al., "Efficient Production of Fluorescent Transgenic Rats using the piggyBac Transposon," *Sci Rep*. 2016 Sep. 14; 6:33225. doi: 10.1038/srep33225 (PMID: 27624004); Kawamata, et al., "Gene-manipulated embryonic stem cells for rat transgenesis," Cell Mol Life Sci. 2011 June; 68 (11): 1911-5; Pradhan, et al., "An Efficient Method for Generation of Transgenic Rats Avoiding Embryo Manipulation," Mol Ther Nucleic Acids. 2016 Mar. 8;5: e293; Kanatsu-Shinohara, et al., "Production of transgenic rats via lentiviral transduction and xenogeneic transplantation of spermatogonial stem cells," *Biol Reprod*. 2008 December; 79 (6): 1121-8.

Methods for making transgenic zebrafish are known in the art, and described, e.g., in Kimura, et al., "Efficient generation of knock-in transgenic zebrafish carrying reporter/driver genes by CRISPR/Cas9-mediated genome engineering," Nature *Scientific Reports* 4, Article number: 6545 (2014); Allende, "Transgenic Zebrafish Production," 2001, John Wiley & Sons, Ltd.; Bernardos and Raymond, "GFAP transgenic zebrafish," *Gene Expression Patterns*, (2006) 6 (8): 1007-1013; Clark, et al., "Transgenic zebrafish using transposable elements," *Methods Cell Biol*. 2011; 104:137-49; Lin, "Transgenic zebrafish," in Developmental Biology Protocols: Volume II, Volume 136 of the series Methods in Molecular Biology™ pp 375-383, 2000, Humana Press.

Methods for making transgenic worms (e.g., *Caenorhabditis elegans*) are known in the art, and described, e.g., in Praitis, et al., Methods in Cell Biology (2011) 106:159-185; Hochbaum, et al., "Generation of Transgenic *C. elegans* by Biolistic Transformation," J Vis Exp. 2010; (42): 2090, video at jove.com/video/2090/generation-of-transgenic-c-elegans-by-biolistic-transformation; Berkowitz, et al., "Generation of Stable Transgenic *C. elegans* Using Microinjection," J Vis Exp. 2008 Aug. 15; (18). pii: 833, video at jove.com/video/833/generation-of-stable-transgenic-c-elegans-using-microinjection; and Wu, et al., *Curr Alzheimer Res*. (2005) 2 (1): 37-45. Additionally, Knudra Transgenics provides services for creating transgenic *C. elegans* (knudra.com).

Methods for making transgenic flies (e.g., *Drosophila*) are known in the art, and described, e.g., in Fujioka, et al., "Production of Transgenic *Drosophila*," in Developmental Biology Protocols: Volume II, Volume 136 of the series Methods in Molecular Biology™ pp 353-363; Fish, et al, *Nat Protoc*. (2007) 2 (10): 2325-31; Jenett, et al., *Cell Rep*. (2012) 2 (4): 991-1001; and at the Transgenic Fly Virtual Lab (hhmi.org/biointeractive/transgenic-fly-virtual-lab). Further, Genetics Services, Inc. provides services for creating transgenic *Drosophila* (geneticservices.com/injection/*drosophila*-injections/).

In addition, virus encoding the GPCR having an integrated cpFP can also be injected into a transgenic mammal (e.g., rodents such as mice and rats) for transient, local expression followed by live imaging. UAS-GAL4 systems can also be used for specific expression of GPCR having an integrated cpFP into other animals, including worms, flies and zebrafish. See, e.g., DeVorkin, et al., *Cold Spring Harb Protoc.* (2014) 2014 (9): 967-72 (*Drosophila*); Jeibmann, et al., Int J Mol Sci (2009)(*Drosophila*); Halpern, et al., Zebrafish. 2008 Summer; 5 (2): 97-110 (zebrafish); Scheer, et al., *Mechanisms of Development* (1999) 80 (2): 153-158 (zebrafish); Auer, et al., *Nature Protocols* (2014) 9:2823-2840 (zebrafish).

8. Methods of Determining G Coupled-Protein Receptor (GPCR) Activation

The G Coupled-Protein Receptors (GPCRs) having a fluorescent sensor integrated into their third intracellular loop are useful to detect binding (and activation or inactivation) of ligands (e.g. agonists, inverse agonist and antagonists), in both in vitro and in vivo model systems. Accordingly, provided are methods of detecting binding of a ligand to a G protein-coupled receptor. In some embodiments, the methods comprise:

a) contacting the ligand with a GPCR, as described above and herein, under conditions sufficient for the ligand to bind to the GPCR; and b) determining a change, e.g., increase or decrease, in an optics signal from the sensor integrated into the third intracellular loop of the GPCR, wherein a detectable change in fluorescence signal indicates binding of the ligand to the GPCR. In some embodiments, the optics signal is a linear optics signal. In some embodiments, the linear optics signal comprises fluorescence. In some embodiments, the change, e.g., increase or decrease, in fluorescence signal comprises a change in intensity of the fluorescence signal. In some embodiments, the change, e.g., increase or decrease, in fluorescence intensity is at least about 10% over, e.g., at least about 15%, 20%, 25%, 30%, 35%, 40%, or more, over baseline, in the absence of ligand binding. In some embodiments, the change in fluorescence signal comprises a change in color (spectrum or wavelength) of the fluorescence signal. In some embodiments, the optics signal is a non-linear optics signal. In some embodiments, the non-linear optics signal is selected from the group consisting of fiber optics, miniature fiber optics, fiber photometry, one photon imaging, two photon imaging, and three photon imaging. The use of non-linear optics in biological imaging is known in the art and can find use in the present methods. Fiber optic fluorescence imaging is described in Flusberg, et al., *Nat Methods.* 2005 December; 2 (12): 941-50. Further illustrative publications relating to the use of non-linear optics in biological imaging include without limitation Javadi, et al, *Nat Commun.* (2015) 6:8655; Qian, et al., *Adv Mater.* (2015) 27 (14): 2332-9; Kirmani, et al., *Science.* (2014) 343 (6166): 58-61; Kierdaszuk, *J Fluoresc.* (2013) 23 (2): 339-47; Ware, Biotechniques. (2014) 57 (5): 237-9; Mandal, et al., *ACS Nano.* (2015) 9 (5): 4796-805; Guo, et al., *Biomed Opt Express.* (2015) 6 (10): 3919-31; Miyamoto, et al., *Neurosci Res.* (2016) 103:1-9.

In some embodiments, a binding ligand further indicates activation of intracellular signaling from the GPCR. In some embodiments, the ligand is a suspected agonist of the GPCR. In some embodiments, the ligand is a suspected inverse agonist of the GPCR. In some embodiments, the ligand is a suspected antagonist of the GPCR. In some embodiments, the GPCR is in vitro, e.g., integrated into the extracellular membrane of a cell. In some embodiments, the GPCR is in vivo, e.g., expressed in a transgenic animal. In some embodiments, the GPCRs are altered to be signaling incompetent, as described above and herein.

In certain embodiments, the in vitro binding detection methods can be performed by measuring the fluorescence intensity of host cells expressing the G Coupled-Protein Receptors (GPCRs) having a fluorescent sensor integrated into their third intracellular loop employing microscopy, e.g., using a perfusion chamber to efficiently wash cultured cells in an isotonic buffer. For performing the methods in vivo, the one or more ligands suspected or known to be an agonist, inverse agonist or antagonist of the GPCR.

9. Methods of Library Screening

The G Coupled-Protein Receptors (GPCRs) having a fluorescent sensor integrated into their third intracellular loop are further useful for screening of a plurality of ligands that are suspected agonists, inverse agonist and antagonists of the GPCR, particularly in in vitro model systems. Accordingly, provided are methods of screening for binding of a ligand to a G protein-coupled receptor and/or activation of a GPCR by a ligand. The methods can be performed for high throughput screening. In some embodiments, the methods comprise: a) contacting a plurality of members from a library of ligands with a plurality of GPCRs, as described above and herein, under conditions sufficient for the ligand members to bind to the GPCRs, wherein the plurality of GPCRs are arranged in an array of predetermined addressable locations; and b) determining a change, e.g., increase or decrease, in one or more optics signals from the sensor integrated into the third intracellular loop of the plurality GPCRs, wherein a detectable change in the one or more fluorescence signals indicates binding of one or more members of the library of ligands to at least one of the plurality GPCR.

In some embodiments, the one or more optics signals comprise a linear optics signal. In some embodiments, the linear optics signal comprises fluorescence. In some embodiments, the one or more fluorescence signals fluoresce at the same wavelength. In some embodiments, the one or more fluorescence signals fluoresce at different wavelengths. In some embodiments, the change in fluorescence signal comprises a change, e.g., increase or decrease, in intensity of the fluorescence signal. In some embodiments, the change, e.g., increase or decrease, in fluorescence intensity is at least about 10% over, e.g., at least about 15%, 20%, 25%, 30%, 35%, 40%, or more, over baseline, in the absence of ligand binding. In some embodiments, the change in fluorescence signal comprises a change in color (spectrum or wavelength) of the fluorescence signal. In some embodiments, the optics signal is a non-linear optics signal. In some embodiments, the non-linear optics signal is selected from the group consisting of fiber optics, miniature fiber optics, fiber photometry, one photon imaging, two photon imaging, and three photon imaging. In some embodiments, a binding ligand further indicates activation of intracellular signaling from the GPCR. In some embodiments, two or more members of the plurality of GPCRs are different. In some embodiments, two or more members of the plurality of G-protein coupled receptors are a different type of GPCR. In some embodiments, two or more members of the plurality of G-protein coupled receptors are a different subtype of a GPCR. In some embodiments, two or more members of the plurality of GPCRs comprise a sensor that fluoresces at a different wavelength.

In some embodiments, the one or more fluorescence signals fluoresce at the same wavelength. In some embodiments, the one or more fluorescence signals fluoresce at different wavelengths. In some embodiments, the change in fluorescence signal comprises a change in intensity of the fluorescence signal. In some embodiments, the change in fluorescence intensity is at least about 10% over baseline, e.g., at least about 15%, 20%, 25%, 30%, 35%, 40%, or more, in the absence of ligand binding. In some embodiments, the change in fluorescence signal comprises a change in color (spectrum or wavelength) of the fluorescence signal. In some embodiments, the change in fluorescence signal comprises both a change in intensity and a change in color (spectrum or wavelength) of the fluorescence signal. In some embodiments, a binding ligand further indicates activation of intracellular signaling from the G protein-coupled receptor. In some embodiments, two or more members of the plurality of G protein-coupled receptors are different. In some embodiments, two or more members of the plurality of G-protein coupled receptors are a different type of G protein-coupled receptor. In some embodiments, two or more members of the plurality of G-protein coupled receptors are a different subtype of a G protein-coupled receptor. In some embodiments, two or more members of the plurality of G-protein coupled receptors comprise a sensor that fluoresces at a different wavelength. In some embodiments, the plurality of ligands comprises suspected or known agonists of the G protein-coupled receptor. In some embodiments, the plurality of ligands comprises suspected or known inverse agonists of the G protein-coupled receptor. In some embodiments, the plurality of ligands comprises suspected or known antagonists of the G protein-coupled receptor. In some embodiments, the GPCRs are altered to be signaling incompetent, as described above and herein. In some embodiments, the screening methods are performed in a multiwell plate.

10. Kits

Provided are kits comprising one or more circularly permuted fluorescent protein sensors as described above and herein, e.g., in polynucleotide form, e.g., in a vector such as a plasmid or viral vector, suitable to integrate into a G Coupled-Protein Receptor (GPCR). Further provided are kits comprising one or more G Coupled-Protein Receptors (GPCRs) having a circularly permuted fluorescent protein sensor integrated into its third intracellular loop as described above and herein, e.g., in polypeptide and/or polynucleotide form. When provided in polynucleotide form, the polynucleotides may be lyophilized. In some embodiments, the kits comprise expression cassettes, plasmid vectors, viral vectors or cells comprising a polynucleotide encoding a G Coupled-Protein Receptor (GPCR) having a circularly permuted fluorescent protein sensor integrated into its third intracellular loop, as described above and herein. In kits comprising cells, the cells may be suspended in a glycerol solution and frozen. The kits may further comprise buffers, reagents, and instructions for use. In some embodiments, the kits comprise one or more transgenic animals having a transgene for expressing a G Coupled-Protein Receptor (GPCR) with a cpFP sensor integrated into its third intracellular loop, as described above and herein.

EXAMPLES

The following examples are offered to illustrate, but not to limit the claimed invention.

Example 1

An Optogenetic Platform For Monitoring G Coupled-Protein Receptor (GPCR) Activation Materials and Methods:

Computational analysis. PyRosetta3 was used to extract every Phi dihedral angles for each residue from the active and inactive structure of Beta-2 Adrenergic receptor (PDB: 3POG and 2RHl respectively). The difference of phi angles was plotted along the residue sequence to identify the most dramatic change of phi angles between active and inactive state.

Molecular cloning. Codon optimized geneblocks were ordered from Integrated DNA Technologies (IDT) for each of the following GPCRs: Beta-2 Adrenergic Receptor (Beta2AR), Mu-type Opioid Receptor-1 (MOR-1), Dopamine Receptor D1 (DRD1) and Serotonin Receptor-2A (5-HT2A). Briefly, the geneblocks contained the following in order from the beginning: Hind-III site, hemagglutinin secretion motif, flag tag, the full length human GPCR coding sequence (with the exception of DRD1 for which the sequence corresponding to amino acids 1-377 was used), Not-I cut site. In the case of the DRD1 sensor, an ER export motif (FCENEV) was added at the C-terminus to aid surface expression. The geneblocks were cloned into pEGFP_N1, a plasmid carrying a CMV promoter, using the Hind-III and Not-I sites. To linearize the vector for CPEC we used the following primers:

Beta2AR vector:

```
FWD (SEQ ID NO: 100):
5'-GTCAGTTTTTACGTTCCTCTGGTTATTATG G-3',

REV (SEQ ID NO: 101):
5'-CATGATAATTCCAAGCGTCTTCAGCG-3';
```

mu-type opioid receptor, MOR-1 vector:

```
FWD (SEQ ID NO: 102):
5'-GGCAGCAAGGAGAAGGACCGC-3',

REV (SEQ ID NO: 103):
5'-ACTGAGCATTCGAACTGATTTGAGCC-3';
```

DRD1 vector:

```
FWD (SEQ ID NO: 104):
5'-CAGACCACCACAGGTAATGGAAAGCCTG-3',

REV (SEQ ID NO: 105):
5'-GCAATTCTTGGCGTGGACTGCTGC-3';
```

5-HT2A vector:

```
FWD (SEQ ID NO: 106):
5'-CTTGCCAGCTTCTCATTCCTTCCCC-3',

REV (SEQ ID NO: 107):
5'-TTTGGCCCGAGTGCCGAGGTC-3'.
```

To create a library of insert variants with randomized linkers cpGFP was amplified from a GCaMP6 template using the following primers:

Beta2AR cpGFP insert library:

```
FWD (SEQ ID NO: 108):
5'-GGACGCTTTCATGTGCAGAATCTTTCANNKNNKAACGTCTATATCAA

GGCCGACAAGCA-3',

REV (SEQ ID NO: 109):
5'-CTGTGCGTCCGTCCTGTTCAACTTGMNNMNNGTTGTACTCCAGCTTG

TGCCCCAG-3';
```

MOR-1 cpGFP insert library: FWD (SEQ ID NO:

```
FWD (SEQ ID NO: 110):
5'-TTGGAAGCGGAAACTGCTCCTCTGCCANNKNNKaacGTCTATATCAA

GGCCGAC-3',

REV (SEQ ID NO: 111):
5'-GCGGCCGCTGTACATCAGGTTGTCAMNNMNNGTTGTACTCCAGCTTG

TG-3';
```

DRD1 cpGFP insert library:

```
FWD (SEQ ID NO: 112):
5'-GCAGCAGTCCACGCCAAGAATTGCNNKNNKAACGTCTATATCAAGGC

CGACAAGC-3',

REV (SEQ ID NO: 113)
5'-CAGGCTTTCCATTACCTGTGGTGGTCTGMNNMNNGTTGTACTCCAGC

TTGTGCCCCAG-3';
```

5-HT2A cpGFP insert library:

```
FWD (SEQ ID NO: 114):
5'-GACCTCGGCACTCGGGCCAAANNKNNKAACGTCTATATCAAGGCCGA

CAAGCAG-3',

REV (SEQ ID NO: 115):
5'-GGGGAAGGAATGAGAAGCTGGCAAGMNNMNNGTTGTACTCCAGCTTG

TGCCCCAGGATG-3'.
```

With reference to the above-described primers, N means any nucleic acid base; K means either C or T; M means either C or A.

Cell culture, confocal imaging and quantification. For sensor screening, HEK293T cells (ATCC #1573) were cultured at 37° C. either on glass-bottomed 3.5 cm dishes (Mattek) or on glass-bottomed 12-well plates (Fisher Scientific) in the presence of DMEM supplemented with 10% Fetal Bovine Serum and 100 U/ml Penicillin/Streptomycin (all from Life Technologies). Cells were transfected at 60% confluency using Effectene reagent (Qiagen).

For sensor characterization, primary hippocampal neurons were freshly isolated according to a previously published protocol and co-cultured with astrocytes in Neurobasal medium with 2% 50x B27, 1% 100x glutamax, 5% FBS and 0.01% gentamicin (10 mg/mL)(all reagents from Life Technologies). After 5-7 days in vitro fluorodexoyuridine (FUdR) is added to cultures to inhibit mitotic growth of glia. Neuronal cultures were prepared on glass-bottomed dishes (Matteks) coated with Poly-Ornithine/Laminine (20 µg/ml and 5 µg/ml respectively). Neurons were infected at DIV7 and imaged at DIV14-20 using a 40X oil-based objective on an inverted Zeiss Observer LSN710 confocal microscope with 488/513 ex/em wavelengths. Cells were washed immediately prior to imaging using HBSS (Life Technologies) buffer supplemented with 1 mM $CaCl_2$) and MgCl2. The sensor performance was analyzed as fluorescence signal change (AFF) after the addition of the Beta2AR agonist isoproterenol diluted in HBSS (10 M). During drug titrations, a dual buffer gravity-driven perfusion system was used to exchange buffers between different drug concentrations. To determine AFF, ROIs were selected at the cell membrane signal was extracted using Fiji. For drug/response curves, data were plotted and fit using a One Phase Association curve on GraphPad Prism.

Results:

Sensor Design and Screening

Figure 1:
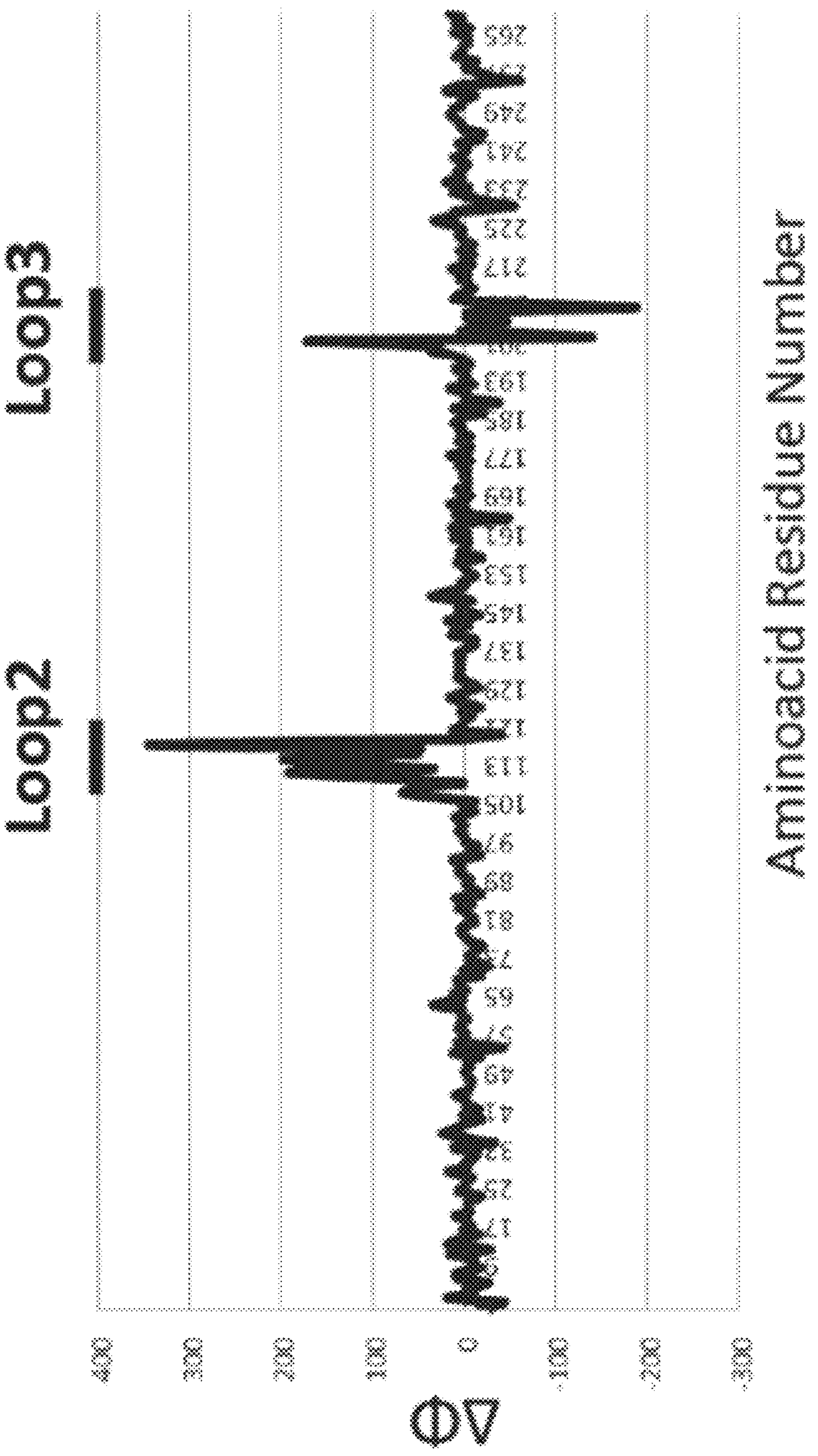
FIG. 1 illustrates computationally-guided design of cpGFP insertion site into Beta2AR. Graph indicating amino acid by amino acid changes in the torsion angle of the polypeptide chain of Beta2AR between active and inactive state. The torsion angle describes rotations of the polypeptide backbone around the bonds between nitrogen atom and the alpha-carbon. The numbering on the X axis corresponds to the amino acid numbers on the full-length human Beta2AR protein sequence (GenBank Accession Number: AAB82150.1).
Figure 2:
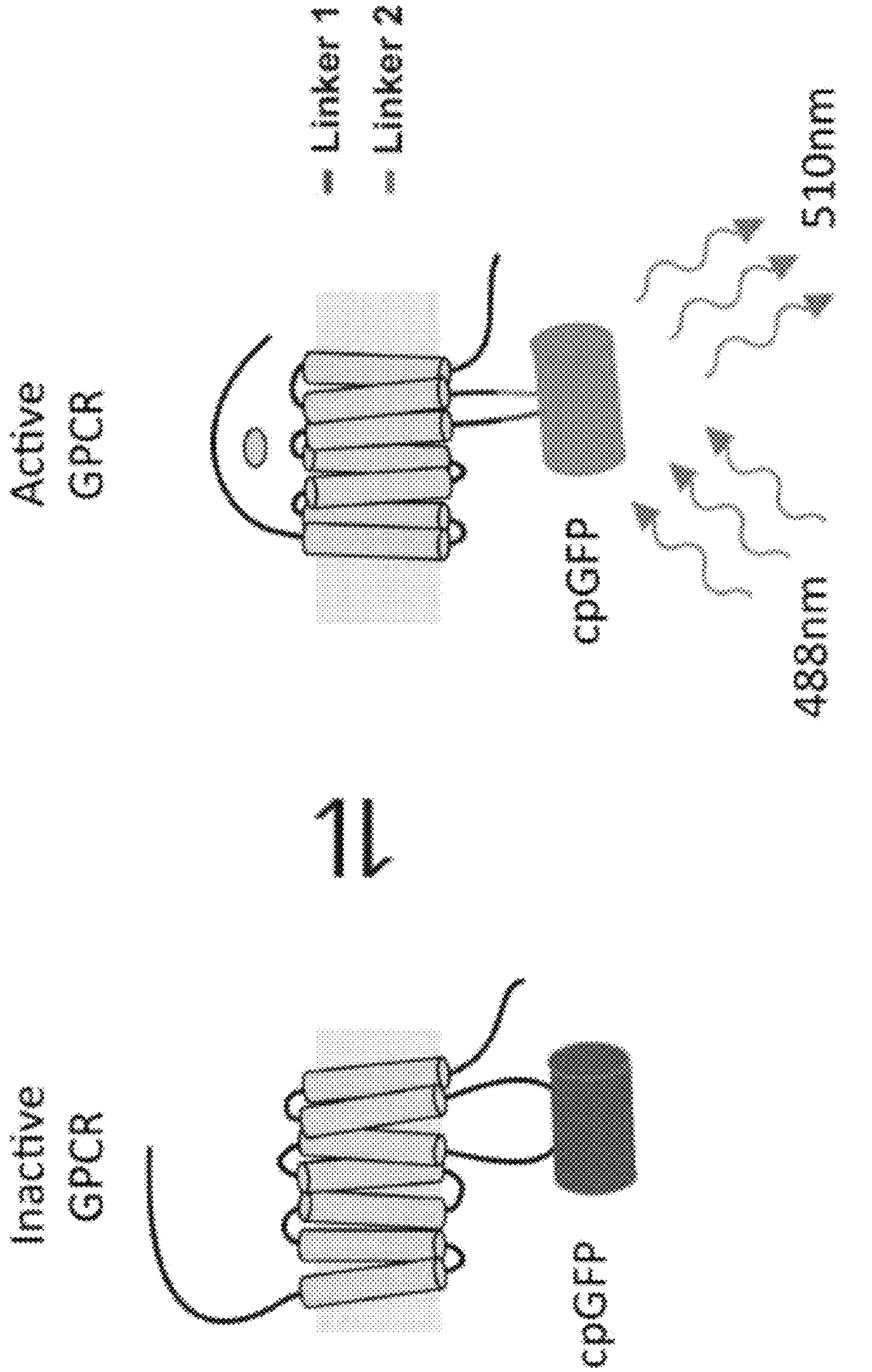
FIG. 2 illustrates the design of a circularly permuted green fluorescent protein (cpGFP) sensor integrated into the third intracellular loop of the beta2 adrenergic receptor (Beta2AR). A circularly-permuted GFP is inserted in the intracellular Loop3 of the Beta2AR and is connected to the GPCR via two linker regions (highlighted as Linker 1 in red and Linker 2 in blue). Agonist induced conformational activation of the receptor triggers a reversible increase in cpGFP fluorescence (excitation λ 488 nm, emission λ 510 nm).

Computationally-guided design of optimal insertion site of cpGFP into Beta2AR. In general, a protein-based biosensor consists of at least a recognition element and a reporter element. Here we choose circular permuted GFP as a reporter element. When properly inserted to the recognition element (i.e. GPCRs), ligand binding induces conformational adjustments of the receptor, which will result in changes in the chromophore environment, thus transforming the ligand-binding event into a fluorescence change. As a prototype to test our sensor design strategy, we chose the Beta2AR, a well-studied GPCR for which a wealth of structural information is available [3]. Using PyRosetta we compared the active and inactive structures of Beta2 AR and extracted the Phi torsion angle values for each residue of the structure (FIG. 1). This approach highlighted Loop2 and Loop3 of Beta2AR as the regions that undergo the most dramatic conformational changes during receptor activation. This is in line with the structural information of the two transmembrane domains (TM5, TM6) adjacent to the third intracellular loop (Loop3) undergo an outward movement during the activation process [2, 14]. We therefore chose to insert circularly permuted GFP (cpGFP) within the third intracellular loop of Beta2AR (see FIG. 2).

To identify the best position for cpGFP insertion within the Loop3 multiple insertion modalities were tested, comprising both different insertion sites and deletions of part of the Loop3 sequence (Table 1). Circular Polymerase Extension Cloning (CPEC) was used to insert cpGFP into the GPCR (for details about this technique see [15]). Briefly primers were designed to PCR a cpGFP insert from GCaMP6 (including original linker sequences: LE-LP) containing overhangs that overlap with the chosen Beta2AR insertion site sequence. Primers were also designed to open the Beta2AR-containing vector DNA. Finally the two products were DpnI digested and mixed together for CPEC. The different sensor variants were separately transfected using Effectene transfection reagent (Qiagen) onto HEK293T cells cultured in 12-well glass bottomed plates. After 24 hours of expression, cells were imaged using a confocal microscope at 488 nm excitation and 513 nm emission wavelengths. During time lapse, images were continuously taken approximately every 2 seconds. Fluorescence at the cell membrane was monitored upon addition of saturating concentration of the Beta2AR full agonist isoproterenol (ISO, 10 µM). ROIs were manually selected using Fiji. The dynamic range of the sensor variants (AFF) was calculated as the fractional difference of the fluorescence change over baseline fluorescence. The largest change in fluorescence was achieved when the complete sequence of Loop3 was maintained while cpGFP was inserted between amino acids S246 and Q247 ($\Delta F/F=-35\%$).

TABLE 1

| Variant Name | Amino Acid Residues positions in SEQ ID NO: 165 | Insertion Site | DFF |
|---|---|---|---|
| Beta2AR V1 | 226-233 | AKRQ-LQKI | −26% |
| Beta2AR V2 | 243-250 | QNLS-QVEQ | −35% |
| Beta2AR V3 | 225-228 - [residues 229-266 deleted]-267-270 | EAKR-deleted-KEHK | −13% |
| Beta2AR V4 | 227-230 - [residues 231-263 deleted]-264-267 | KRQL-deleted-FCLK | −11% |

Table 1 shows a list of the tested modalities of cpGFP insertion into the intracellular Loop3 of the Beta2AR and the corresponding ΔFFs. The residues indicated in the insertion site represent the 4 amino acid residues before and after cpGFP insertion (which occurs where the-symbol is). In two variants, a portion of the Beta2AR Loop3 (originally contained between the shown amino acids) was deleted.

In situ high-throughput screening for optimizing the dynamic range of Beta2AR with a cpGFP integrated into the third intracellular loop. Through engineering GCaMP and iGluSnFR, we learned that both linker regions between Beta2AR and cpGFP are critical for a sensor's dynamics and kinetics. Therefore, we created 6 different types of linker libraries by randomizing the first and last 2-amino acids of the cpGFP (using NNK and MNN codons in our cpGFP forward and reverse primers respectively, XX-NV;-XX). In addition, rationale design of linker sequences was also employed. We set up a cell-based high-throughput screening method measuring changes in fluorescence in the absence and presence of agonists. The linkers of lead variants showing best AF/F from a library of ~200 variants were sequenced and are shown in Table 2. In particular, we identified a variant (linker 1 sequence: AV; linker 2 sequence: TR) with a strong increase in fluorescence intensity upon activation and high photostability (defined as a fluorescence decay of less than 10% while illuminated in its active state at 1% laser power for ten minutes), turning our construct from negative to positive sensor (ΔFF=+40%). The dynamic range of Beta2AR with a cpGFP integrated into the third intracellular loop can be increased (or decreased) by employing rational design and direct evolution.

TABLES 2A-G

L1 and L2 Linkers

TABLE 2A

| XX-XX Library | | |
|---|---|---|
| Positive ΔFF | Linker 1 (L1) | Linker 2 (L2) |
| 6% | CP | AL |
| 10% | NV | TL |
| 15% | GM | PR |
| 16% | RV | TP |
| 23% | LA | QG |
| 30% | VR | RG |
| 35% | KV | VT |
| 40% | AV | TR |

TABLE 2B

| XX-XX Library | | |
|---|---|---|
| Negative ΔFF | Linker 1 (L1) | Linker 2 (L2) |
| −40% | SG | YP |
| −40% | VD | WP |
| −35% | LE | LP |
| −33% | AF | SL |
| −32% | SW | RP |
| −30% | RG | YL |
| −29% | TD | ER |
| −28% | LG | MH |
| −25% | RQ | LS |
| −10% | MR | MC |

TABLE 2C

| XX-TR Library | | |
|---|---|---|
| ΔFF | Linker 1 (L1) | Linker 2 (L2) |
| −40% | TY | TR |
| −40% | LL | TR |
| −30% | VL | TR |
| −28% | TQ | TR |
| −20% | VF | TR |
| −5% | TT | TR |
| 15% | LV | TR |
| 20% | LI | TR |
| 20% | RV | TR |
| 30% | VI | TR |
| 40% | VV | TR |
| 55% | RG | TR |

TABLE 2D

| AV-XX Library | | |
|---|---|---|
| ΔFF | Linker 1 (L1) | Linker 2 (L2) |
| 10% | AV | TT |
| 18% | AV | AT |
| 22% | AV | SS |
| 25% | AV | GV |
| 25% | AV | CC |
| 33% | AV | VS |
| 50% | AV | QN |

TABLE 2E

| AV-KX Library | | |
|---|---|---|
| ΔFF | Linker 1 (L1) | Linker 2 (L2) |
| 25% | AV | KS |
| 40% | AV | KT |
| 40% | AV | KH |
| 40% | AV | KV |
| 40% | AV | KQ |
| 60% | AV | KR |
| 80% | AV | KP |

TABLE 2F

| AV-XP Library | | |
|---|---|---|
| ΔFF | Linker 1 (L1) | Linker 2 (L2) |
| 10% | AV | CP |
| 10% | AV | AP |
| 15% | AV | SP |

TABLE 2F-continued

| AV-XP Library | | |
|---|---|---|
| ΔFF | Linker 1 (L1) | Linker 2 (L2) |
| 20% | AV | IP |
| 20% | AV | YP |
| 25% | AV | TP |
| 40% | AV | RP |

TABLE 2G

| XV-KP Library | | |
|---|---|---|
| ΔFF | Linker 1 (L1) | Linker 2 (L2) |
| 0% | PV | KP |
| 25% | GV | KP |
| 30% | LV | KP |
| 40% | SV | KP |
| 40% | NV | KP |
| 50% | FV | KP |

TABLE 2G

| XV-KP Library | | |
|---|---|---|
| ΔFF | Linker 1 (L1) | Linker 2 (L2) |
| 50% | CV | KP |
| 50% | VV | KP |
| 50% | EV | KP |
| 50% | QV | KP |
| 60% | KV | KP |
| 70% | RV | KP |

Tables 2A-B list different linker variants flanking the N- and C-termini of the integrated circularly permuted fluorescent protein, separated in two groups: positive variants (which show positive fluorescent signal change, AFF) and the negative variants (which show a negative AFF). Variant (linkers AV-TR) were further characterized, as shown in Tables 2C-D. For each variant the AFF value, the amino acid sequence for both Linker 1 and Linker 2 and the photobleaching properties are shown. No photobleaching is defined as a fluorescence decay of less than 10% while the sensor expressed on cells is illuminated in its active state at 1% laser power for ten minutes.

Figure 3A:
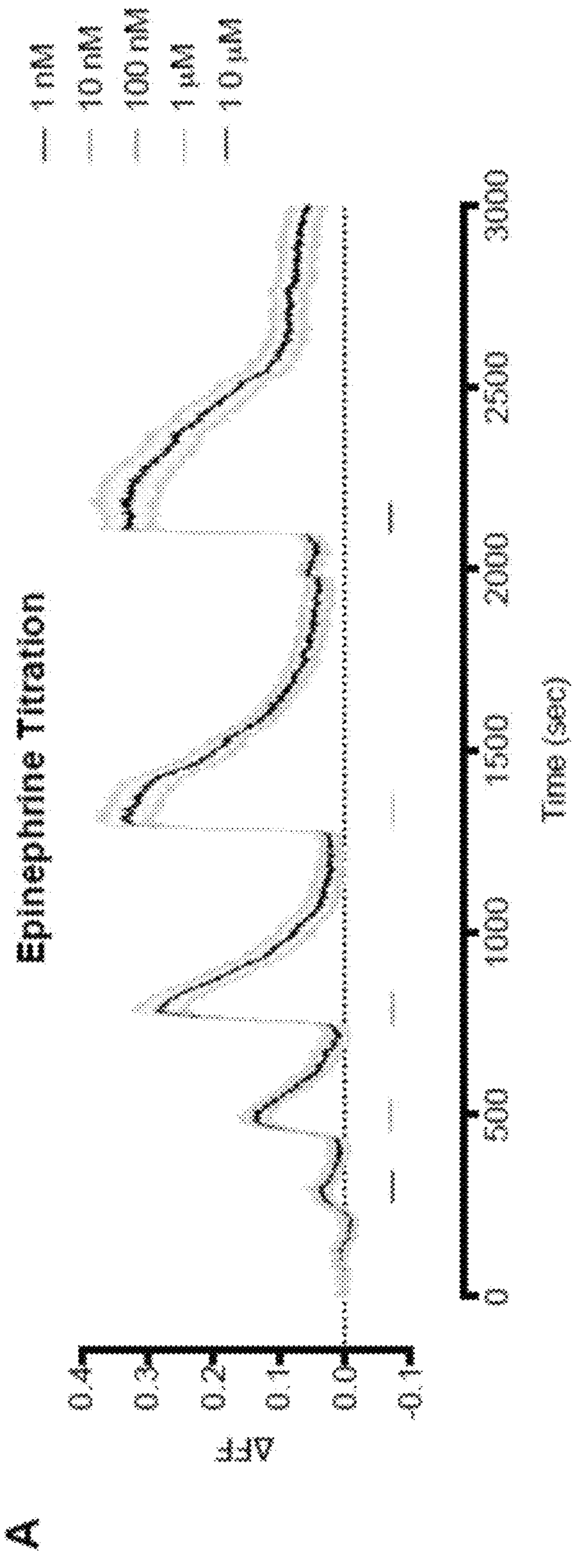
FIGS. 3A-C illustrate full-agonist titrations on a cpGFP sensor integrated into the third intracellular loop of the Beta2AR. Titrations of three different Beta2AR full-agonists (A, epinephrine, EPI; B, norepinephrine, NE; C, isoproterenol, ISO) were performed on HEK293T cells expressing Beta2AR with a cpGFP integrated into the third intracellular loop using a constant perfusion chamber with buffer exchange. Images of the cells were taken on a confocal microscope every 4 seconds and analyzed on Fiji using manually drawn ROIs. n=3 ROIs per trace.
Figure 3B:
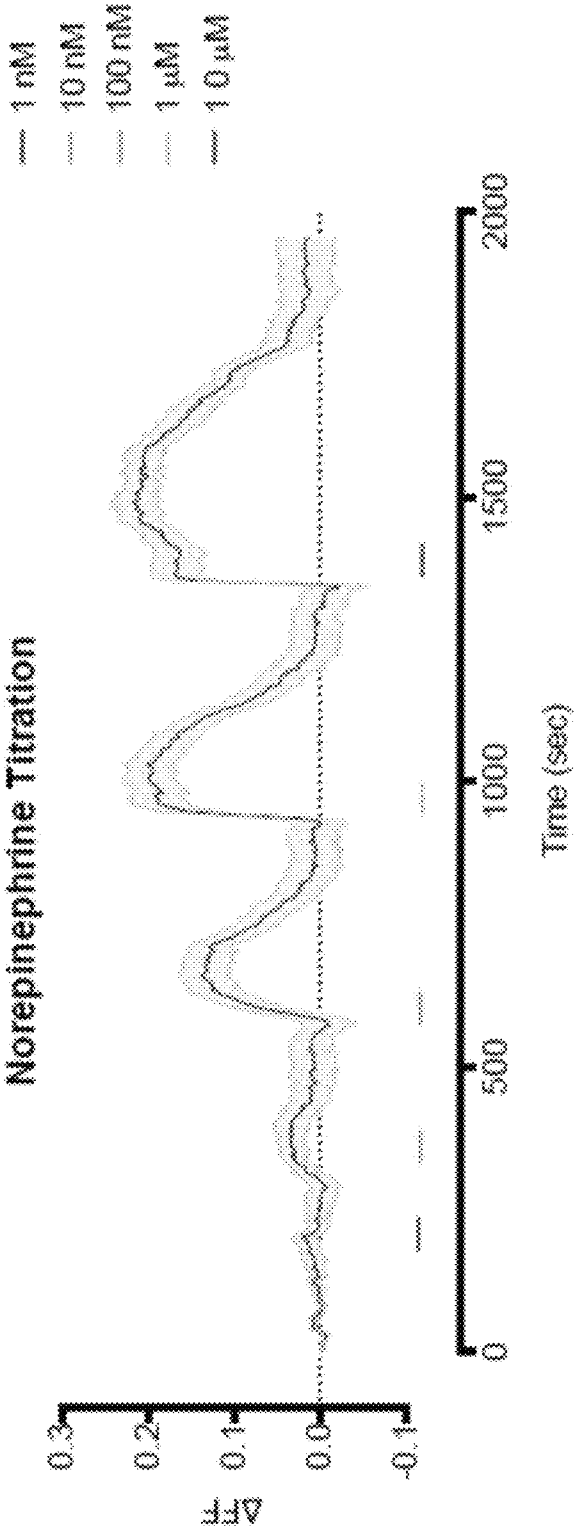
Figure 3C:
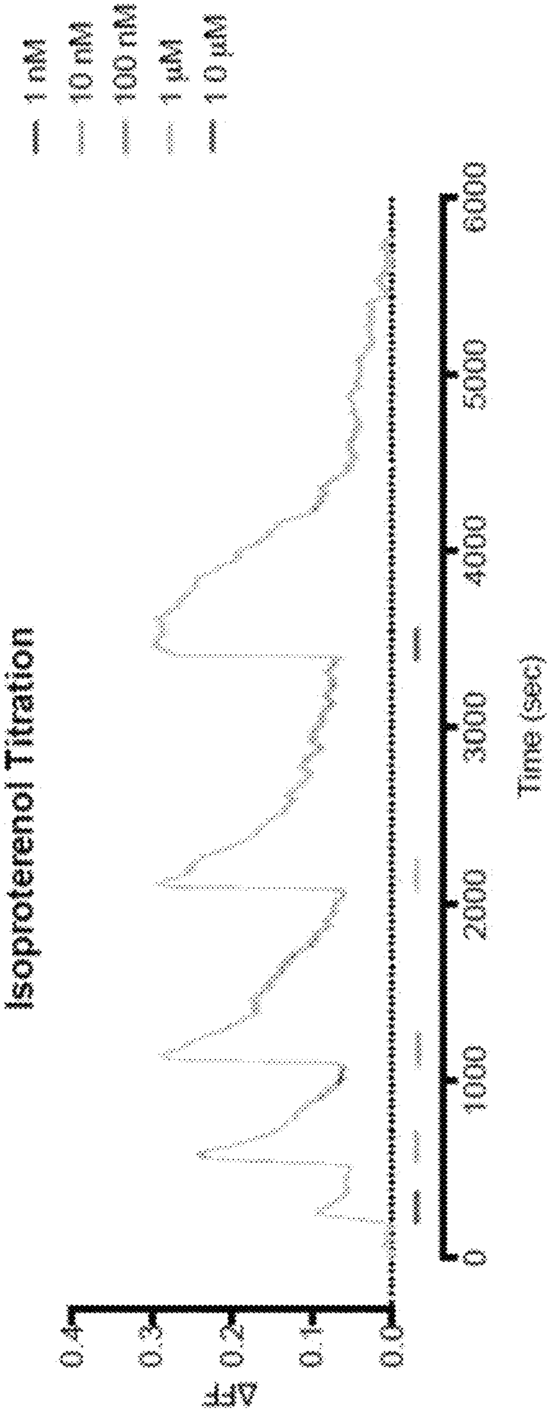
Figure 4A:
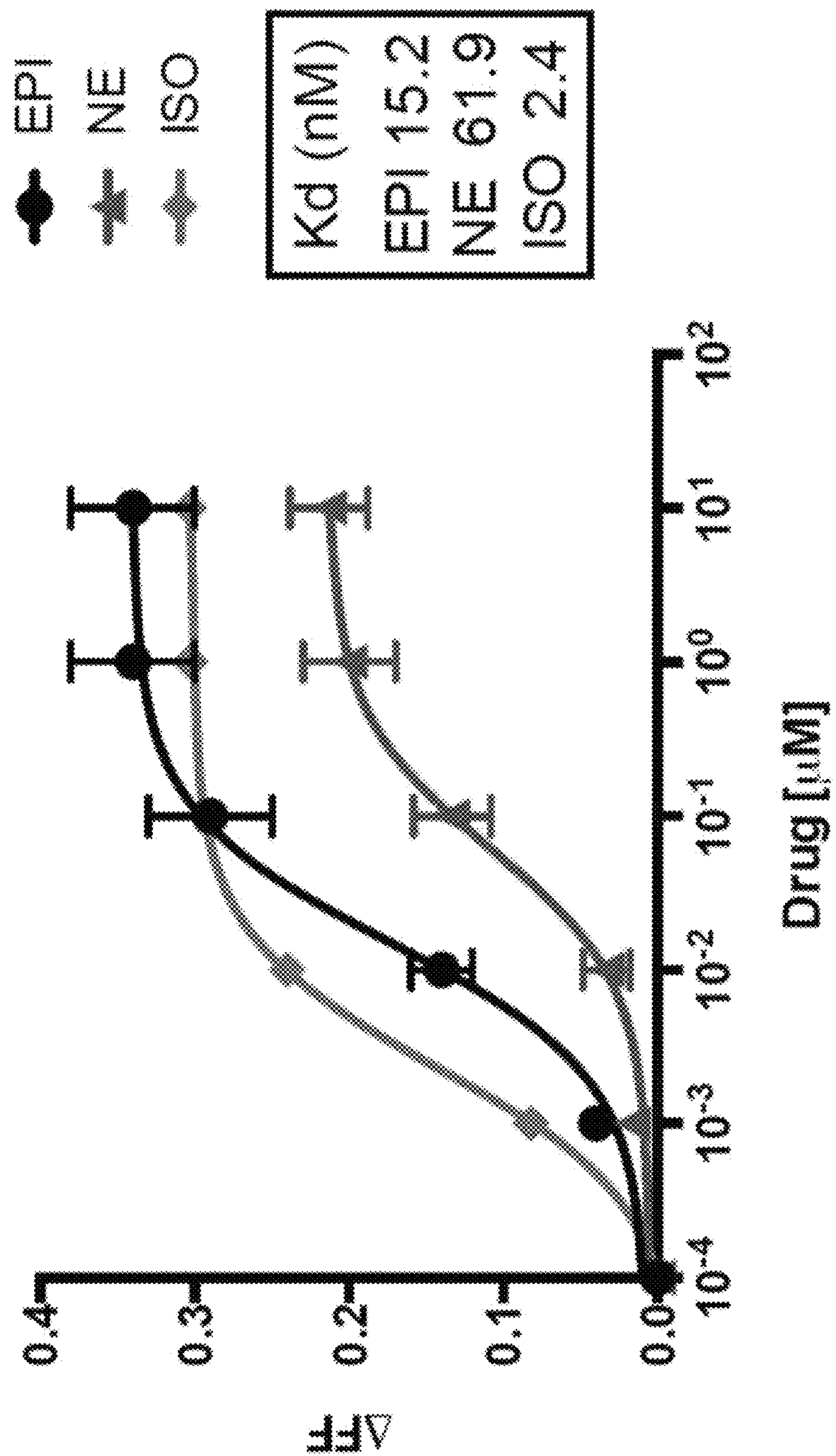
FIGS. 4A-B illustrate affinity and specificity characterization of a cpGFP sensor integrated into the third intracellular loop of the Beta2AR. A. Drug/response curves for the three different full-agonists tested on Beta2AR with a cpGFP integrated into the third intracellular loop. The curves were fit with a one-site total binding curve using GraphPad Prism 6 software. B. Fluorescence trace of Beta2AR with a cpGFP integrated into the third intracellular loop expressed on HEK293T cells during bath application of non-Beta2AR ligands (Serotonin (SER) and Dopamine (DA)) followed by application of the Beta2AR agonist ISO and successive inhibitory competition using a higher concentration (50 μM) of the Beta2AR inverse agonist CGP-12177.
Figure 4B:
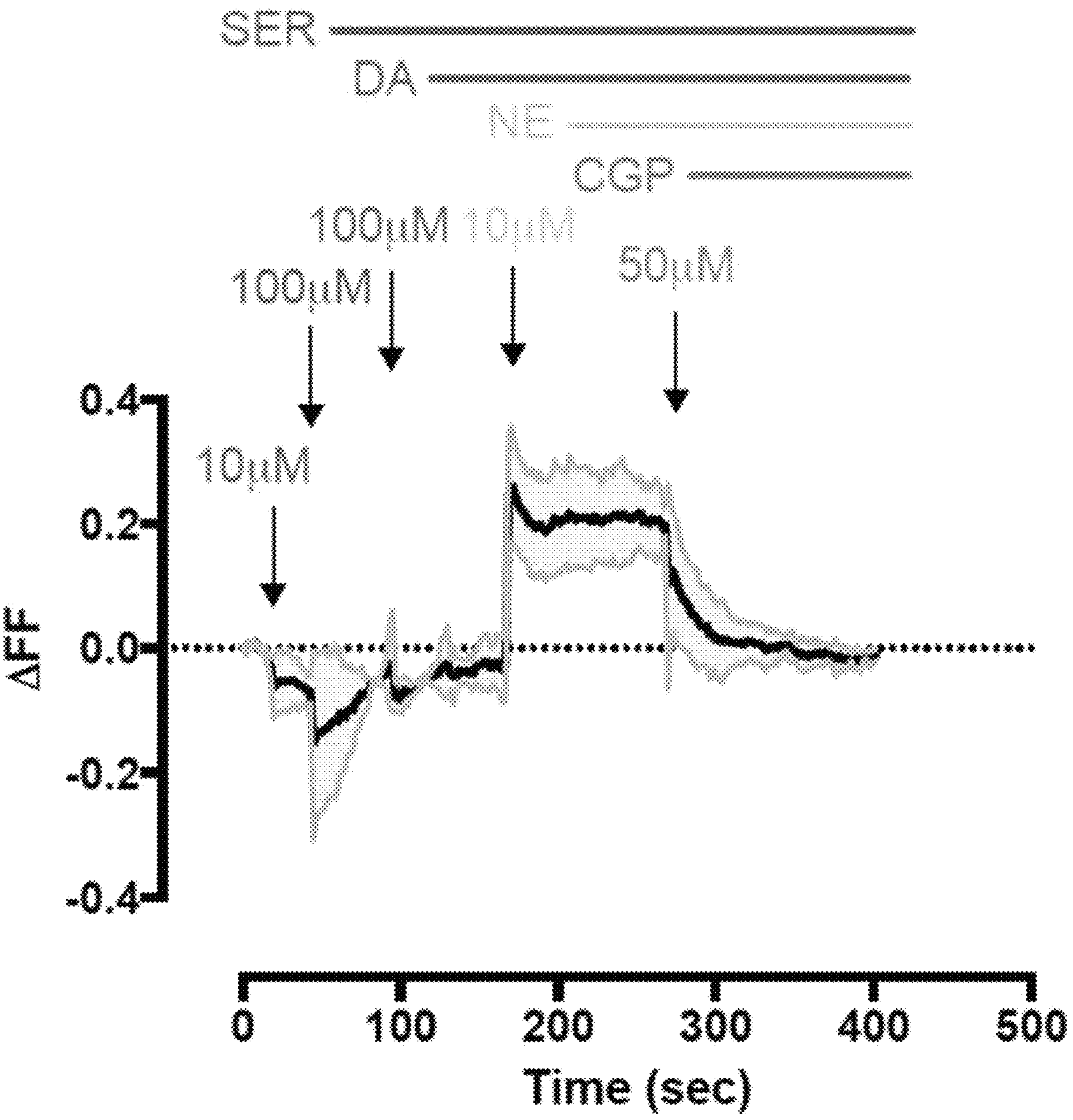
Figure 5A:
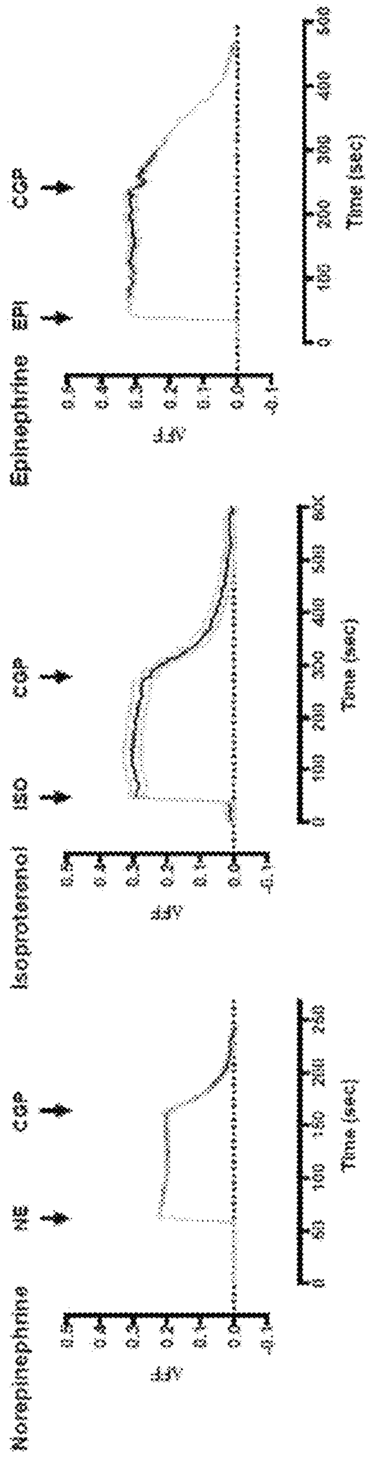
FIGS. 5A-D illustrate that Beta2AR with a cpGFP integrated into the third intracellular loop can distinguish different classes of ligands. Fluorescence trace of Beta2AR with a cpGFP integrated into the third intracellular loop in response to three different agonists (one full agonist: Norepinephrine, followed by inverse agonist competition, and two partial agonists: Terbutaline and Dobutamine) applied under identical conditions but in three separate experiments.
Figure 5B:
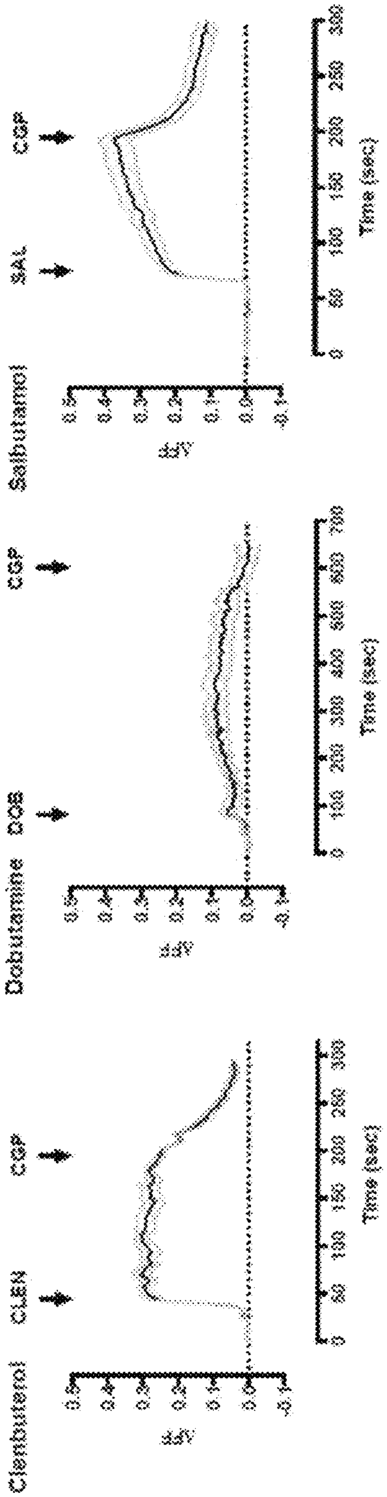
Figure 5C:
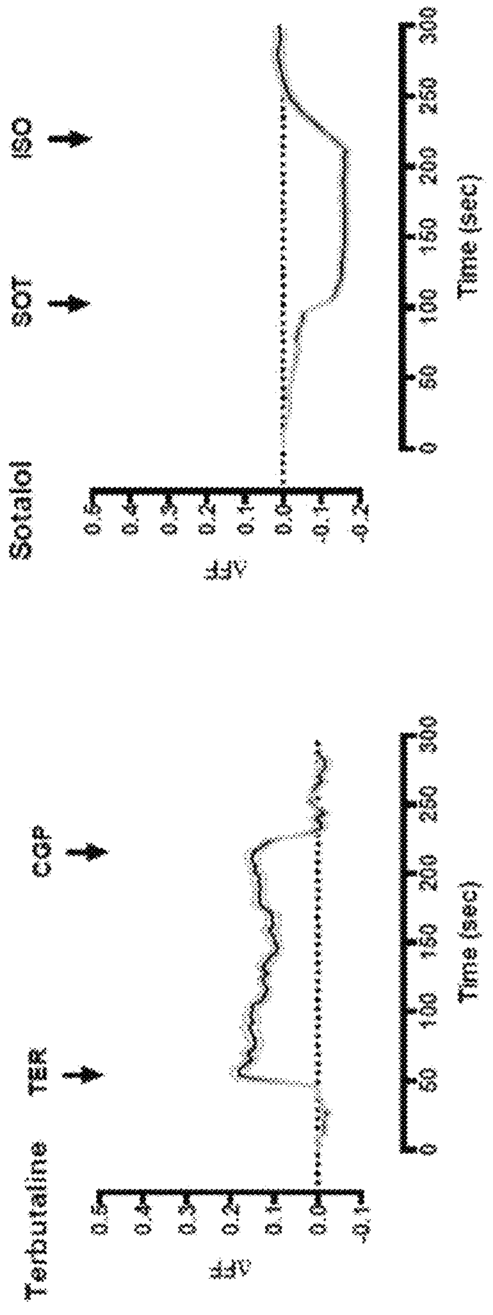
Figure 5D:
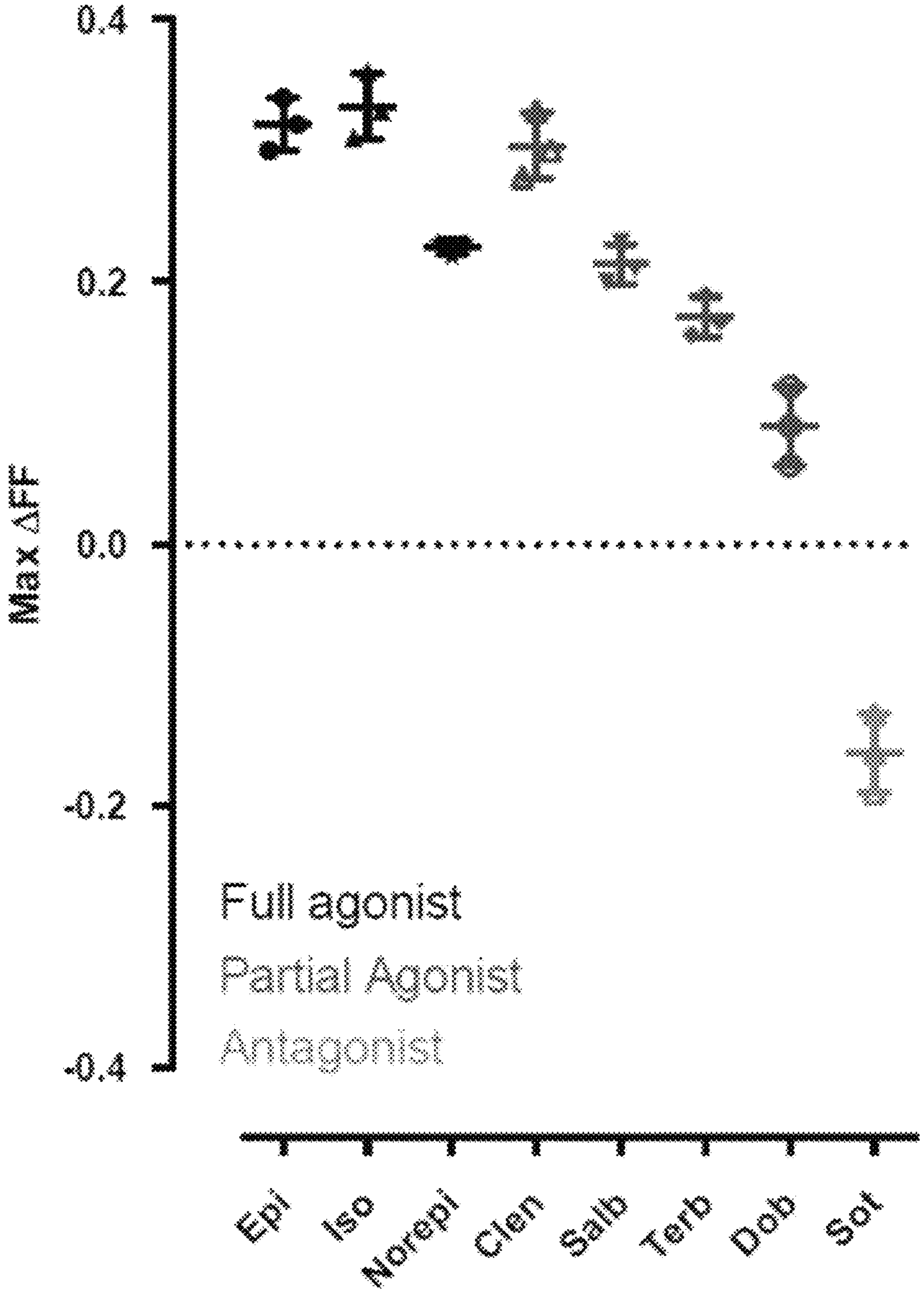

Calibrate affinity, specificity and dynamic range of Beta2AR with a cpGFP integrated into the third intracellular loop in mammalian 293 cells. We next set out to determine the specificity and sensitivity of Beta2AR with a cpGFP integrated into the third intracellular loop (driven by CMV promoter) by measuring the fluorescence of HEK293 cells with confocal microscopy, using a perfusion chamber to efficiently wash cultured cells in Hank's balanced salt solution (HBSS)-agonists solutions. A series of agonist solutions ranging from 1 nM to 10 μM were made, covering three full agonists (isoproterenol (ISO), epinephrine (EPI) and norepinephrine (NE))(FIG. 3). The in situ affinity and response linearity of the sensors were determined to see whether it fits the range expected to be physiologically relevant for measuring neuromodulator release. To determine the specificity, a series of other neurotransmitters including dopamine and serotonin, were used for titration. To determine the kinetics, we either washed out the agonists using HBSS or used a published concentration (50 μM) of a Beta2AR inverse agonist (CGP-12177), known to counteract the effects of saturating full agonist in cell cultures [16]. The in situ Kd of the sensor for isoproterenol, epinephrine and norepinephrine are 1.2 nM, 15 nM and 50 nM respectively, whose ratios are in line with the known affinities of these drugs for the Beta2AR (FIG. 4A). We further characterized the kinetics of drug-sensor interaction by determining the time constants (11/2) of association and dissociation for the three different full agonists tested (Table 3). In addition, we did not detect any specific response of the sensor when incubated with 50 μM Serotonin and Dopamine (two drugs that should not activate Beta2AR)(FIG. 4B). The apparent decrease in fluorescence during Serotonin application is non-specific and due to the fluorescence quenching properties of the drug itself (i.e. it can be seen also when applying Serotonin onto control GFP expressing cells). These results suggest that Beta2AR with a cpGFP integrated into the third intracellular loop is capable to detect physiologically relevant changes of neuromodulator with high signal-to-noise ratio and specificity.

TABLE 3

| | τ½ON (seconds) | τ½OFF (seconds) | Kd (nM) |
|---|---|---|---|
| EPI | 17.1 | 235.34 | 15 |
| NE | 29.62 | 106.91 | 50 |
| ISO | 17.6' | 368.03 | 1.2 |

Table 3 shows the time constants of association (11/2 ON) and dissociation (11/2 OFF) as well as the affinity values (Kd) of the three different full agonists tested on Beta2AR with a cpGFP integrated into the third intracellular loop. The time constants were calculated by interpolating the titration curve values under saturating conditions (1 μM drug) to determine the y value corresponding to the half-time of the association or dissociation phase respectively: y= (X1-X0)/2. The affinity values were calculated by fitting the respective drug/response curves with a one-site total binding fit curve using GraphPad Prism 6.

Determining the conformational dynamics of Beta2AR in response to drugs using Beta2AR with a cpGFP integrated into the third intracellular loop. A G protein-coupled receptor with a cpFP integrated into the third intracellular loop represents a new method to visualize the conformational dynamics of GPCR in the presence and absence of drugs. It remains less understood at the molecular level how drugs stimulate the signaling activity of a GPCR at different potency. Visualizing the structural rearrangement of GPCR triggered by binding of ligands in real-time will aid in screening and design of new GPCR-targeted drugs with tailored pharmacological efficacy. We thus tested the utility of Beta2AR with a cpGFP integrated into the third intracellular loop in reporting conformation dynamics of Beta2AR triggered by different classes of agonists. We compared the structural rearrangement of Beta2AR in response to a panel of drugs, including 3 full agonists 4 partial agonists and an antagonist (FIG. 5). Interestingly, we observed a drug-specific fluorescent response using Beta2AR with a cpGFP integrated into the third intracellular loop, with the full-agonists being able to activate the sensor's fluorescence change to fully, while the partial agonists performed less than the full agonists and to various degrees. Of particular interest we observed a decrease in fluorescence using the antagonist Sotalol, which indicated that the true dynamic range of Beta2AR with a cpGFP integrated into the third intracellular loop is even larger than what was characterized using full agonists (FIG. 5). The different responses of the sensor to unrelated partial agonists indicate that our sensor is capable of distinguishing among different conformational states or structural rearrangement of the receptor triggered by different drugs and highlight the versatility of its use in drug screenings. We thus conclude that our sensor can be used as a tool for testing affinity, specificity, to predict the pharmacological action of different drugs targeting GPCR, especially orphan GPCRs, to reveal more subtle molecular mechanisms underlying GPCR activation, and to unveil new opportunities for the development of more selective clinical therapies, such as biased ligands.

Characterization of Beta2AR sensors in dissociated neuronal culture and in vivo in zebrafish and mouse brain. Neuroscience faces two great interrelated challenges: to develop better therapeutic neural drugs, and to alleviate the damage done by addictive drugs. To address these, it is desirable to better understand the mechanisms of action of existing drugs, at the level of molecular and cell biology, so that the field can exploit this knowledge to design even better therapeutic reagents. GPCRs are target of a series of drugs including antidepressants, antipsychotics, opiates and neuroprotective drugs. A G protein-coupled receptor with a cpFP integrated into the third intracellular loop represents a novel toolbox to do so and we therefore characterize the sensor's performance in living neurons.

To characterize the expression of the sensor in neurons, Beta2AR with a cpGFP integrated into the third intracellular loop was sub-cloned into an HIV-based lentiviral vector under the control of the synapsin promoter. Primary hippocampal neurons were cultured in the presence of astrocytes on glass-bottomed dishes (Matteks) coated with Poly-Ornithine/Laminine (20 μg/ml and 5 μg/ml respectively). Neurons were infected at DIV7 and imaged at DIV14-20. As an advantage of using the synapsin promoter, the expression of the sensor is restricted to neurons. Although quite dim, seven days post-infection neurons clearly showed visible fluorescence at the plasma membrane, indicating that the sensor expresses, folds and inserts into the membrane properly. Upon application of a saturating dose of the agonist ISO (10 μM) we observed a 25% increase in fluorescence intensity (FIG. 6). The DFF in neurons appears lower than what was observed in HEK293T cells due to the lower expression levels of the sensor itself.

The superior signal-to-noise ratio of a G protein-coupled receptor with a cpFP integrated into the third intracellular loop permits mapping spatiotemporal dynamics of neuromodulators and neural drugs in living brain. In order to prove that our sensor can achieve such goal, we chose to test it in the nervous system of two different vertebrate model organisms: the zebrafish and the mouse. Our current work is focused on testing the utility of our sensors in detecting the spatial action and effective concentrations of pharmacological drugs in brain with single cell and single synapse in vivo.

Design of a signaling-incompetent G protein-coupled receptor with a cpFP integrated into the third intracellular loop sensor. To be suitable for in vivo expression an ideal sensor should not alter or interfere with endogenous cellular signaling. GPCRs are known to activate cellular signaling through both G-protein and β-Arrestin-dependent pathways [18]. Structural studies have highlighted one particular well conserved residue on GPCRs (F139 for the Beta2AR) that plays a critical role in mediating the interaction with G proteins. In addition, phosphorylation of two G-protein coupled receptor kinase-6 (GRK6) sites on the Beta2AR C-terminus (S355, S356) is known to be a critical determinant for β-Arrestin recruitment and signaling. To eliminate the possibility of our sensor interfering with endogenous cellular signaling, we mutated both F139 and S355, S366 residues to Alanine in our sensor. Importantly the mutations we introduced in our sensor have no effect on either sensor brightness or response to agonist. We compared mutated Beta2AR with a cpGFP integrated into the third intracellular loop with wild-type Beta2AR for the ability to recruit G-proteins upon activation using an established assay that measures membrane recruitment of Nb80 in HEK293T cells [16]. The results confirmed that our mutated sensor cannot recruit Nb80 upon activation (FIG. 7 A-D). We further confirmed lack of G-protein dependent signaling in our mutated sensor (using a TYG/TSG mutation to abolish chromophore of cpGFP) by measuring intracellular production of the second messenger cAMP upon receptor activation using a luciferase based assay. For those applications in which the sensor's signaling must be completely abolished, we propose to use a different set of mutations (Beta2ART68F, Y132G, Y219A, or Beta2ARTYY), which are known to completely abolish cAMP production by the Beta2AR [20]; however those mutations may affect surface expression of the GPCR. To test that our mutated Beta2AR with a cpGFP integrated into the third intracellular loop does not interfere with β-Arrestin signaling, we tested it for internalization, a well-known β-Arrestin-dependent phenomenon that occurs rapidly after GPCR activation and that shifts its signaling to endosomes [16, 21, 22]. To test for internalization, we compared our mutated Beta2AR with a cpGFP integrated into the third intracellular loop to GFP-labeled wildtype Beta2AR using total-internal reflection (TIRF) microscopy and confirmed that the sensor does not undergo internalization. Taken together, these data prove that our mutated sensor does not interfere with cellular signaling and is thus suitable for in vivo applications.

Multiplex imaging. The preserved spectrum bandwidth of single-FP indicators can allow for multiplex imaging with other optogenetic sensors including calcium, and cAMP or use alongside optogenetic effectors such as channel rhodopsin. We have also expanded the color-spectrum of GPCR based sensor, which allow multiplex imaging of activation of different types of GPCR simultaneously.

Figure 8A:
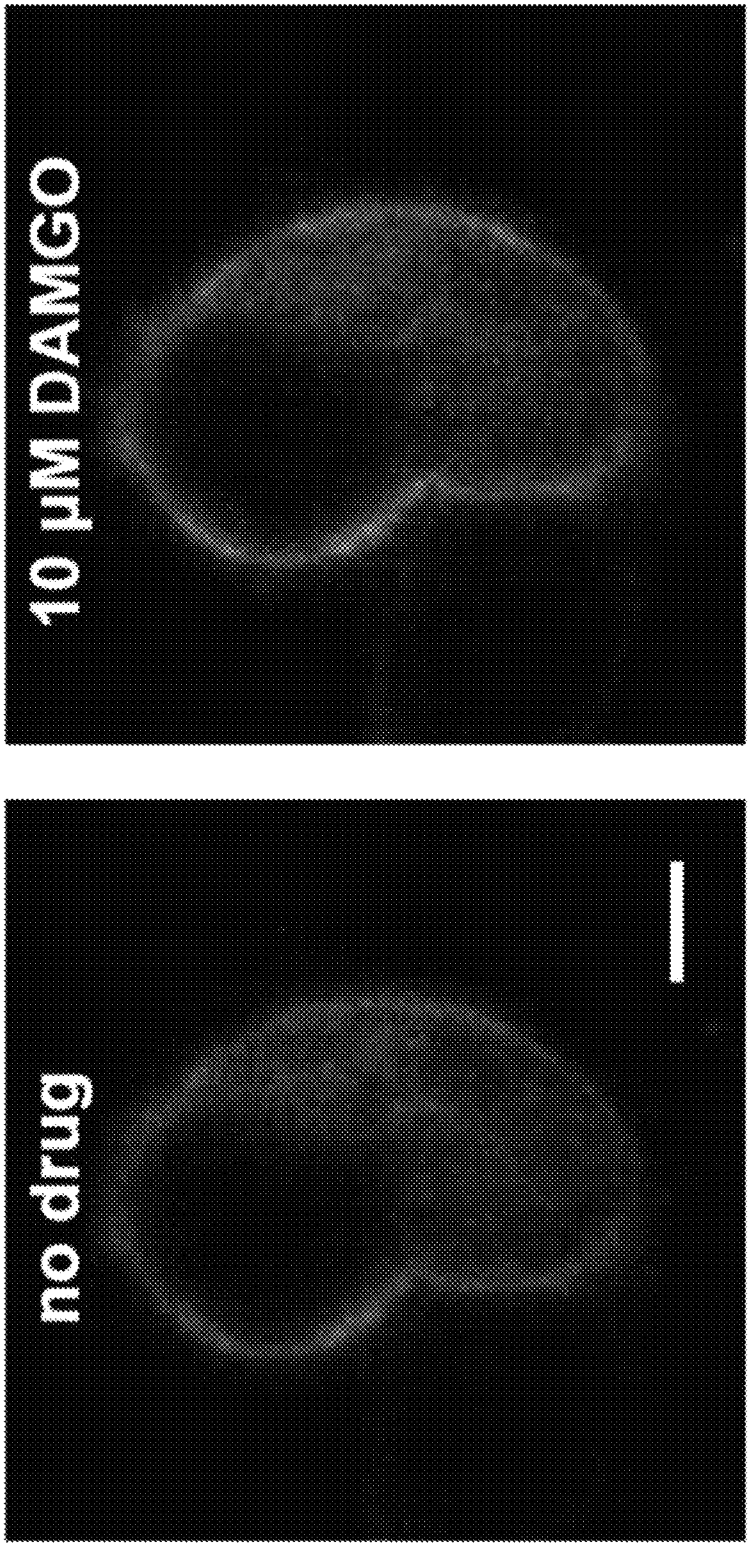

Towards engineering circularly permuted fluorescent protein sensors for other types of GPCRs. A similar sensor design strategy can be extend to other GPCRs, for example, μ-opioid receptor 1 (MOR-1), dopamine receptor D1 (DRD1), 5-Hydroxytryptamine (5-HT) receptor. We have already obtained a MOR-1 sensor variant that displays 25% positive ΔF/F in response to 10 μM DAMGO (FIG. 8).

REFERENCES

1. Tautermann, C. S., GPCR structures in drug design, emerging opportunities with new structures. Bioorg Med Chem Lett, 2014. 24 (17): p. 4073-9.
2. Dror, R. O., D. H. Arlow, P. Maragakis, T. J. Mildorf, A. C. Pan, H. Xu, D. W. Borhani, and D. E. Shaw, Activation mechanism of the beta2-adrenergic receptor. Proc Natl Acad Sci USA, 2011. 108 (46): p. 18684-9.
3. Shonberg, J., R. C. Kling, P. Gmeiner, and S. Lober, GPCR crystal structures: Medicinal chemistry in the pocket. Bioorg Med Chem, 2015. 23 (14): p. 3880-906.
4. Dulla, C., H. Tani, S. Okumoto, W. B. Frommer, R. J. Reimer, and J. R. Huguenard, Imaging of glutamate in brain slices using FRET sensors. J Neurosci Methods, 2008. 168 (2): p. 306-19.
5. Feng, G., R. H. Mellor, M. Bernstein, C. Keller-Peck, Q. T. Nguyen, M. Wallace, J. M. Nerbonne, J. W. Lichtman, and J. R. Sanes, Imaging neuronal subsets in transgenic mice expressing multiple spectral variants of GFP. Neuron, 2000. 28 (1): p. 41-51.

6. Hasan, M. T., R. W. Friedrich, T. Euler, M. E. Larkum, G. Giese, M. Both, J. Duebel, J. Waters, H. Bujard, O. Griesbeck, R. Y. Tsien, T. Nagai, A. Miyawaki, and W. Denk, Functional fluorescent Ca2+ indicator proteins in transgenic mice under TET control. PLoS Biol, 2004. 2 (6): p. e163.
7. Fehr, M., S. Lalonde, D. W. Ehrhardt, and W. B. Frommer, Live imaging of glucose homeostasis in nuclei of COS-7 cells. J Fluoresc, 2004. 14 (5): p. 603-9.
8. Hoffmann, C., G. Gaietta, M. Bunemann, S. R. Adams, S. Oberdorff-Maass, B. Behr, J. P. Vilardaga, R. Y. Tsien, M. H. Ellisman, and M. J. Lohse, A FLASH-based FRET approach to determine G protein-coupled receptor activation in living cells. Nat Methods, 2005. 2 (3): p. 171-6.
9. Salahpour, A., S. Espinoza, B. Masri, V. Lam, L. S. Barak, and R. R. Gainetdinov, BRET biosensors to study GPCR biology, pharmacology, and signal transduction. Front Endocrinol (Lausanne), 2012. 3: p. 105.
10. Vilardaga, J. P., M. Bunemann, C. Krasel, M. Castro, and M. J. Lohse, Measurement of the millisecond activation switch of G protein-coupled receptors in living cells. Nat Biotechnol, 2003. 21 (7): p. 807-12.
11. Baird, G. S., D. A. Zacharias, and R. Y. Tsien, Circular permutation and receptor insertion within green fluorescent proteins. Proc Natl Acad Sci USA, 1999. 96 (20): p. 11241-6.
12. Chen, T. W., T. J. Wardill, Y. Sun, S. R. Pulver, S. L. Renninger, A. Baohan, E. R. Schreiter, R. A. Kerr, M. B. Orger, V. Jayaraman, L. L. Looger, K. Svoboda, and D. S. Kim, Ultrasensitive fluorescent proteins for imaging neuronal activity. Nature, 2013. 499 (7458): p. 295-300.
13. Tian, L., S. A. Hires, T. Mao, D. Huber, M. E. Chiappe, S. H. Chalasani, L. Petreanu, J. Akerboom, S. A. Mckinney, E. R. Schreiter, C. I. Bargmann, V. Jayaraman, K. Svoboda, and L. L. Looger, Imaging neural activity in worms, flies and mice with improved GCaMP calcium indicators. Nat Methods, 2009. 6 (12): p. 875-81.
14. Rasmussen, S. G., H. J. Choi, J. J. Fung, E. Pardon, P. Casarosa, P. S. Chae, B. T. Devree, D. M. Rosenbaum, F. S. Thian, T. S. Kobilka, A. Schnapp, I. Konetzki, R. K. Sunahara, S. H. Gellman, A. Pautsch, et al., Structure of a nanobody-stabilized active state of the beta (2) adrenoceptor. Nature, 2011. 469 (7329): p. 175-80.
15. Quan, J. and J. Tian, Circular polymerase extension cloning for high-throughput cloning of complex and combinatorial DNA libraries. Nat Protoc, 2011. 6 (2): p. 242-51.
16. Irannejad, R., J. C. Tomshine, J. R. Tomshine, M. Chevalier, J. P. Mahoney, J. Steyaert, S. G. Rasmussen, R. K. Sunahara, H. El-Samad, B. Huang, and M. von Zastrow, Conformational biosensors reveal GPCR signalling from endosomes. Nature, 2013. 495 (7442): p. 534-8.
17. Chung, F. Z., C. D. Wang, P. C. Potter, J. C. Venter, and C. M. Fraser, Site-directed mutagenesis and continuous expression of human beta-adrenergic receptors. Identification of a conserved aspartate residue involved in agonist binding and receptor activation. J Biol Chem, 1988. 263 (9): p. 4052-5.
18. Lohse, M. J. and K. P. Hofmann, Spatial and Temporal Aspects of Signaling by G-Protein-Coupled Receptors. Mol Pharmacol, 2015. 88 (3): p. 572-8.
19. Heim, R., D. C. Prasher, and R. Y. Tsien, Wavelength mutations and posttranslational autoxidation of green fluorescent protein. Proc Natl Acad Sci USA, 1994. 91 (26): p. 12501-4.
20. Shenoy, S. K., M. T. Drake, C. D. Nelson, D. A. Houtz, K. Xiao, S. Madabushi, E. Reiter, R. T. Premont, O. Lichtarge, and R. J. Lefkowitz, beta-arrestin-dependent, G protein independent ERK1/2 activation by the beta2 adrenergic receptor. J Biol Chem, 2006. 281 (2): p. 1261-73.
21. Vilardaga, J. P., F. G. Jean-Alphonse, and T. J. Gardella, Endosomal generation of CAMP in GPCR signaling. Nat Chem Biol, 2014. 10 (9): p. 700-6.
22. Lohse, M. J. and D. Calebiro, Cell biology: Receptor signals come in waves. Nature, 2013. 495 (7442): p. 457-8.

Example 2

Discovering A Universal Module For GPCR Sensor Engineering

This example describes the additional sequences for linkers L1 and L2 in the circularly permuted fluorescent protein sensors, including linker sequences that allow for the construction of a universal GPCR sensor, that can be integrated into the third intracellular loop of any GPCR. Importantly, the prototype GPCRs we tested belong to each of the three different GPCR types available: Gs-coupled (B2AR, DRD1), Gq-coupled (MT2R, 5HT2A) and Gi-coupled (A2AR, KOR). In addition, our prototype sensors show the applicability of our universal module to GPCRs that bind ligands of different nature: monoamines for B2AR, A2AR, DRD1, MT2R, 5HT2A and neuropeptides for KOR. The data are consistent with the conclusion that the identified universal cpFP sensor modules described herein can be integrated into and successfully used to evaluate signaling of all GPCR types.

We have identified minimal sequences for LI and L2 for the construction of a universal linker that could be inserted into the third loop of GPCRs generally to readily produce a positive sensor.

Universal cpFP sensor module 1: L1 contains the 11 amino acids QLQKIDLSSX1X2 and L2 contains the 5 amino acids X3X4DQL. In some embodiments, X1X2 can be amino acid LI (Leucine-Isoleucine) and X3X4 can be NH (Asparagine-Histidine). In a particular embodiment, universal module 1 is QLQKIDLSSLI-cpGFP-NHDQL.

Universal cpFP sensor module 2: L1 contains the 5 amino acids LSSX1X2 and L2 contains the 5 amino acids X3X4DQL. In some embodiments, X1X2 can be amino acid LI (Leucine-Isoleucine) and X3X4 can be NH (Asparagine-Histidine). In a particular embodiment, universal module 2 is LSSLI-cpGFP-NHDQL.

In some embodiments, universal cpFP sensor modules can be inserted into or can replace the third loop of any GPCR. As proof of principle, we demonstrated that this universal module can inserted into or replace the third loop of MT2R: melatonin receptor type 1B (NCBI Reference Sequence: NP_005950.1); KOR1: Kappa Opioid Receptor type-1 (GenBank: AAC50158.1); 5HT2A: Serotonin Receptor type-2A (NCBI Reference Sequence: NP_000612.1); A2AR: Alpha-2C Adrenergic Receptor (NCBI Reference Sequence: NP_000674.2); B2AR: Beta-2 Adrenergic Receptor (GenBank: AAB82151.1); and DRD1: Dopamine Receptor type-1 (GenBank: AAH96837.1) to transform these GPCRs into sensors that give a positive fluorescent signal in response to ligand binding. See, FIG. 14).

Figure 14:
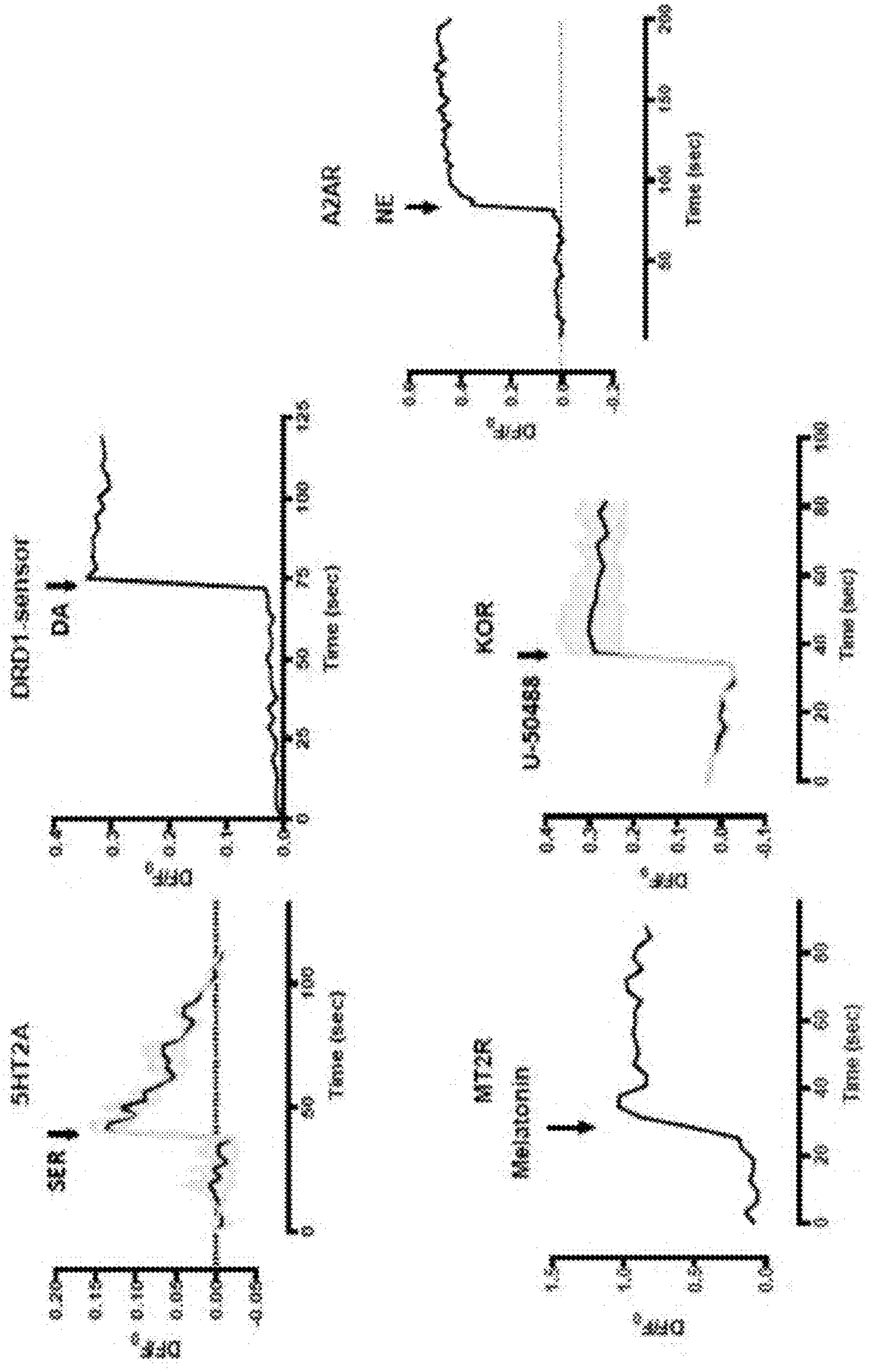
FIG. 14 illustrates representative time-lapse curves for each of the GPCR sensors developed with universal module 1. Agonist application is indicated by an arrow in each graph.

FIG. 14 demonstrates that the universal module 1 can be inserted into EAKR-deleted third intracellular loop residues-KEHK of B2AR to obtain a sensor with 150% ΔF/F in response to 10 μM norepinephrine (NE). See, e.g., FIG. 12. We fully characterized this B2AR variant with a panel of different B2AR drugs, including full, partial and inverse agonists as well as antagonists. See, FIG. 13.

Universal module 1 can be used to replace the whole third intracellular loop of GPCRs to produce positive sensors to various degrees of ΔF/F out of all the GPCR tested, including 5HT2A, DRD1, MT2R, KOR and A2AR, confirming the development of a universal cpFP sensor that can be integrated into or replace the third cellular loop of any GPCR (FIG. 14).

Figure 15:
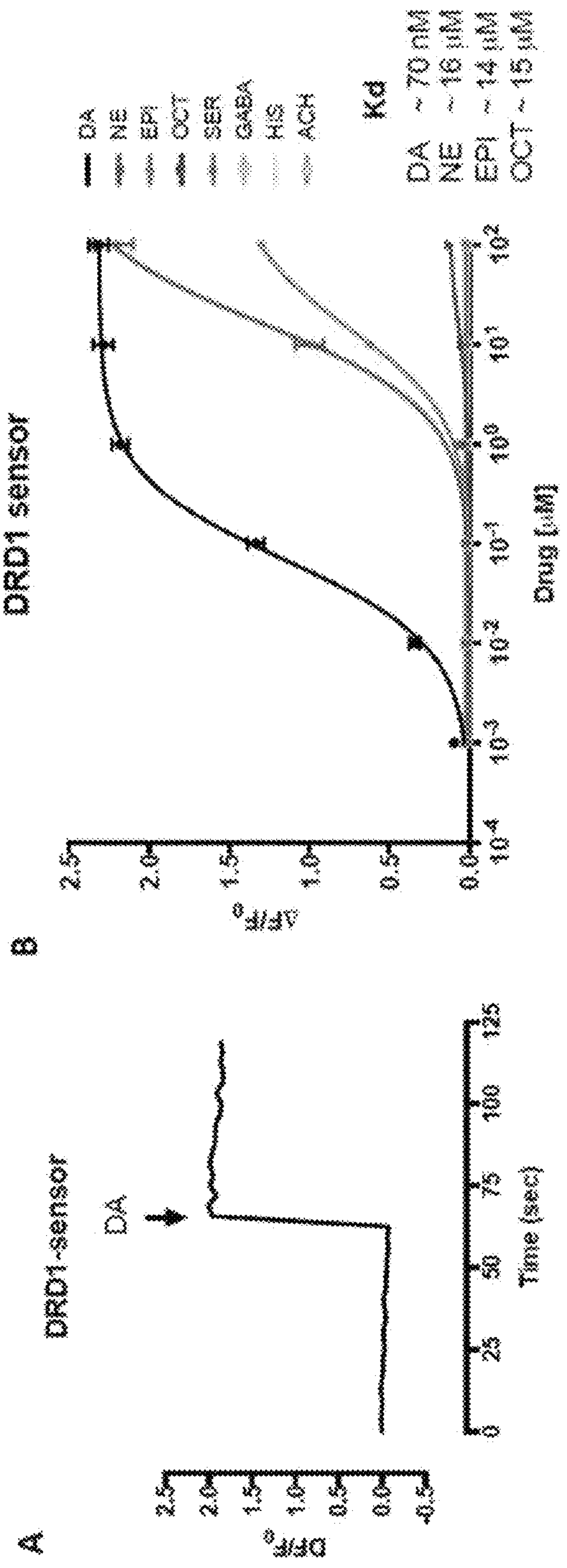
FIGS. 15A-E provide representative time-lapse curves for each of the GPCR sensors developed with universal module 2 (e.g., LSSLI-cpGFP-NHDQL)(A, C, D, E). Agonist application is indicated by an arrow in each graph. (B) In situ titration of the dopamine DRD1-based sensor with apparent Kd of ~70 nM, while other non-selective ligands (norepinephrine, epinephrine) can only trigger a similar response with ~200-fold lower affinity (~16, 14 μM, respectively).

Universal module 2 can be inserted into EAKR-deleted third intracellular loop residues-KEHK of B2AR (100% ΔF/F) or replace the third intracellular loop of DRD1 (IAQK-deleted third intracellular loop residues-KRET) to make a sensor that responds with ~230% ΔF/F to dopamine; into SLQK-deleted third intracellular loop residues-NEQK of 5HT2A receptor to make a sensor that responds with ~30% to serotonin; into RLKS-deleted third intracellular loop residues-REKD of KOR to make a sensor that responds with ~40% to the kappa-opioid agonist U-50488 (FIG. 15).

More precisely, the sequences flanking the deletion site are summarized as follows and depicted in FIG. 12:

A2AR: IAKR-deleted third intracellular loop residues-REKR

MT2R: QARR-deleted third intracellular loop residues-KPSD

DRD1: IAQK-deleted third intracellular loop residues-KRET

5HT2A: SLQK-deleted third intracellular loop residues-NEQK

KOR: RLKS-deleted third intracellular loop residues-REKD

For B2AR, in some embodiments, the universal cpFP sensor modules can be inserted into QLQKIDKSEGRFHVQNLS-deleted third intracellular loop residues-KEHK where L1-cpGFP-L2 can replace any part of QLQKIDKSEGRFHVQNLS. In some embodiments, the universal cpFP sensor modules can be inserted into QLQKIDKSEGRFHVQNLS-deleted-FCLK where L1-cpGFP-L2 can replace any part of QLQKIDKSEGRFHVQNLS.

Generally, in determining the location where to delete residues of the GPCR third intracellular loop, we consider the degree of sequence homology to the original B2AR deletion site (EAKR-deleted third intracellular loop residues-KEHK). Depending on the GPCR sequence, we select as starting point for the Loop deletion a position between 0 and +2 residues from the last positively charged amino acid residue (reading the sequence N-terminal to C-terminal) in the sequence that aligns with B2AR sequence EAKR. To precisely determine the end of the deletion, we select a position between 0 and −3 amino acids (reading the sequence N-terminal to C-terminal) away from the first charged amino acid (reading the sequence left to right) in the region that aligns with the B2AR sequence KEHK.

Example 3

Determining the Conformational Dynamics of B2AR in the Brain of Behaving Mice.

Figure 16:
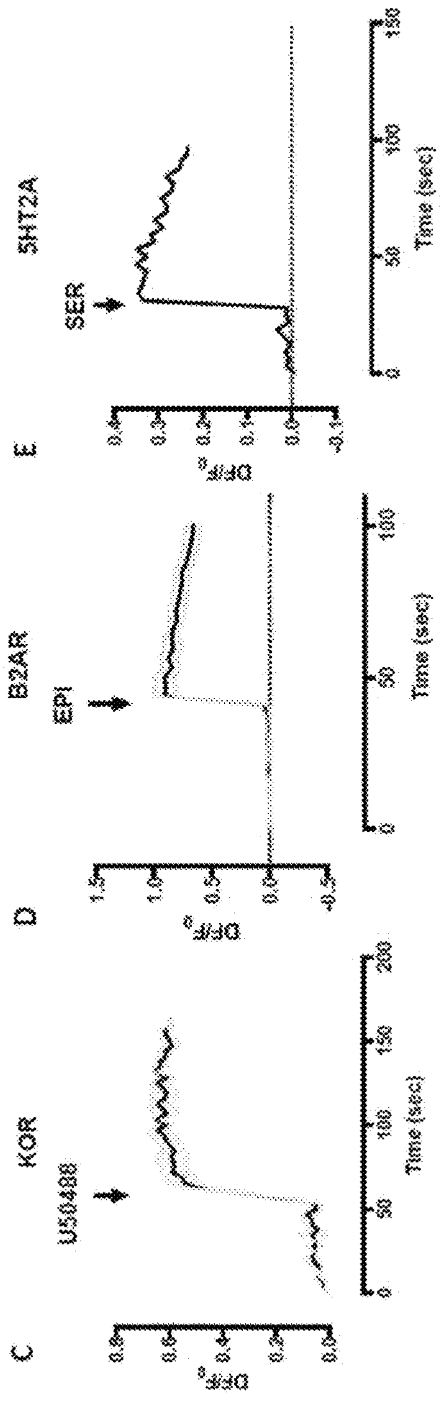
FIGS. 16A-B illustrate measuring GPCR activation in the living brain. B2AR-sensor signals (pink traces in B corresponding to yellow ROIs in A) measured in the cortex of a mouse reported endogenous norepinephrine release triggered by running on a spherical treadmill. Running speed is indicated in the top blue trace and correlates with signal peaks.

We sought to test the utility of B2AR conformational sensor in response to endogenous cortical norepinephrine (NE) release triggered by running in mice. After introducing the genetically-encoded sensors in the mouse motor cortex with the use of an adeno-associated virus (AAV) we could observe for the first time spontaneous norepinephrine release that correlated well with the running activity of the mice (See FIG. 16 in collaboration with Axel Nimmerjahn, Salk Institute). This affirmatively demonstrates that our sensors are capable not only to enabling breakthrough discoveries, but also to visualize the presence and dynamics of a GPCR ligand in a previously inaccessible system (living brain tissue).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

INFORMAL SEQUENCE LISTING amino acid sequence of enhanced green fluorescent protein (eGFP) - circular permutation cleavage motif in seventh beta sheet underlined;
GenBank Accession No. AFA52654.1 GI: 375332228

Sequence ID No: 1

```
msrvskgeel ftgvvpilve ldgdvnghkf svsgegegda tygkltlkfi cttgklpvpw

ptlvttltyg vqcfsrypdh mkqhdffksa mpegyvqert iffkddgnyk traevkfegd

tlvnrielkg idfkedgnil ghkleynyns hnvyimadkq kngikvnfki rhniedgsvq

ladhyqqntp igdgpvllpd nhylstqsal skdpnekrdh mvllefvtaa gitlgmdely

k
```

Y69W - Substitute tyrosine at position 69 to tryptophan to create cyan fluorescent protein (CFP)
T206Y - Substitute threonine at position 206 to tyrosine to create yellow fluorescent protein (YFP)

-continued

| INFORMAL SEQUENCE LISTING |
|---|
| amino acid sequence of enhanced cyan fluorescent protein (eCFP) - circular permutation cleavage motif in seventh beta sheet underlined; GenBank Accession No. ABN59503.1 GI: 125976354 |
| Sequence ID No: 2 |
| mvskgeelft gvvpilveld gdvnghkfsv sgegegdaty gkltlkfict tgklpvpwpt |
| lvttltwgvq cfsrypdhmk qhdffksamp egyvqertif fkddgnyktr aevkfegdtl |
| vnrielkgid fkedgnilgh kleynyishn vyitadkqkn gikanfkirh niedgsvqla |
| dhyqqntpig dgpvllpdnh ylstqsalsk dpnekrdhmv llefvtaagi tlgmdelyk |
| amino acid sequence of yellow fluorescent protein (YFP) - circular permutation cleavage motif in seventh beta sheet underlined; GenBank Accession No. AFI26426.1 GI: 384875628 |
| Sequence ID No: 3 |
| mvskgeelft gvvpilveld gdvnghkfsv sgegegdaty gkltlkfict tgklpvpwpt |
| lvttfgyglq cfarypdhmk lhdffksamp egyvqertif fkddgnyktr aevkfegdtl |
| vnrielkgid fkedgnilgh kleynynshn vyimadkqkn gikvnfkirh niedgsvqla |
| dhyqqntpig dgpvllpdnh ylsyqsalsk dpnekrdhmv llefvtaagi tlgmdelyk |
| amino acid sequence of Photoactivatable green fluorescent protein (paGFP) (from Patterson, G. H.; Lippincott-Schwartz, J. Science 2002, 297, 1873-1877); circular permutation cleavage motif in seventh beta sheet underlined; |
| Sequence ID No: 4 |
| mvskgeelftgvvpilveldgdvnghkfsvsgegegdatygkltlkficttgklpvpwptlvt |
| tfsygvqcfsrypdhmkqhdffksampegyvqertiffkddgnyktraevkfegdtlvnriel |
| kgidfkedgnilghkleynynshnvyimadkqkngikanfkirhniedgsvqladhyqqntpi |
| gdgpvllpdnhylshqsalskdpnekrdhmvllefvtaagitlgmdelyk |
| amino acid sequence of superfolder form of the green fluorescent protein (sfGFP) (from Pédelacq J. D., Nat Biotechnol 2006 January; 24(1): 79-88); circular permutation cleavage motif in seventh beta sheet underlined; |
| Sequence ID No: 5 |
| mskgeelftgvvpilveldgdvnghkfsvrgegegdatngkltlkficttgklpvpwptlvtt |
| ltygvqcfsrypdhmkrhdffksampegyvqertisfkddgtyktraevkfegdtlvnrielk |
| gidfkedgnilghkleynfnshnvyitadkqkngikanfkirhnvedgsvqladhyqqntpig |
| dgpvllpdnhylstqsvlskdpnekrdhmvllefvtaagithgmdelyk |
| amino acid sequence of monomeric cherry red fluorescent protein (mCherry) - circular permutation cleavage motif in seventh beta sheet underlined; GenBank Accession No. ANO45948.1 GI: 1041520567 |
| Sequence ID No: 6 |
| mvskgeednm aiikefmrfk vhmegsvngh efeiegegeg rpyegtqtak lkvtkggplp |
| fawdilspqf mygskayvkh padipdylkl sfpegfkwer vmnfedggvv tvtqdsslqd |
| gefiykvklr gtnfpsdgpv mqkktmgwea ssermypedg alkgeikqrl klkdgghyda |
| evkttykakk pvqlpgaynv nikldditshn edytiveqye raegrhst |
| amino acid sequence of Photoactivatable monomeric cherry red fluorescent protein (PAmCherry-1) (from Suback F. V. et al., Nature Methods 6, 153-159 (2009); circular permutation cleavage motif in seventh beta sheet underlined; |
| Sequence ID No: 7 |
| mvskgeednmaiikefmrfkvhmegsvnghvfeiegegegrpyegtqtaklkvtkggplpftw |
| dilspqfmygsnayvkhpadipdyfklsfpegfkwervmkfedggvvtvtqdsslqdgefiyk |

-continued

| INFORMAL SEQUENCE LISTING |
|---|

vklrgtnfpsdgpvmqkktmgwealsermypedgalkgevkprvklkdgghydaevkttykak kpvqlpgaynvnrklditshnedytiveqyeraegrhstggmdelyk amino acid sequence of monomeric red fluorescent protein (mApple) - circular permutation cleavage motif in seventh beta sheet underlined; GenBank Accession No. AEM37572.1 GI: 343458870

Sequence ID No: 8 mvskgeennm aiikefmrfk vhmegsvngh efeiegegeg rpyeafqtak lkvtkggplp fawdilspqf mygskvyikh padipdyfkl sfpegfrwer vmnfedggii hvnqdsslqd gvfiykvklr gtnfpsdgpv mqkktmgwea seermypedg alkseikkrl klkdgghyaa evkttykakk pvqlpgayiv diklldivshn edytiveqye raegrhstgg mdelyk amino acid sequence of monomeric red fluorescent protein (mRuby2) - circular permutation cleavage motif in seventh beta sheet underlined; GenBank Accession No. AKE14366.1 GI: 810222672

Sequence ID No: 9 mvskgeelik enmrmkvvme gsvnghqfkc tgegegnpym gtqtmrikvi eggplpfafd ilatsfmygs rtfikypkgi pdffkqsfpe gftwervtry edggvvtvmq dtsledgclv yhvqvrgvnf psngpvmqkk tkgwepntem mypadgglrg ythmalkvdg gghlscsfvt tyrskktvgn ikmpgihavd hrlerleesd nemfvvqreh avakfaglgg gmdelyk amino acid sequence Monomeric Far-Red Fluorescent Protein (mKate2) (from Shcherbo D. et al., Biochem J. 2009 418(3): 567-74); circular permutation cleavage motif in seventh beta sheet underlined;

Sequence ID No: 10 mvselikenmhmklymegtvnnhhfkctsegegkpyegtqtmrikaveggplpfafdilatsf mygsktfinhtqgipdffkqsfpegftwervttyedggvltatqdtslqdgcliynvkirgvn fpsngpvmqkktlgweastetlypadgglegradmalklvggghlicnlkttyrskkpaknlk mpgvyyvdrrlerikeadketyveghevavarycdlpsklghr amino acid sequence of green-to-red photoconvertible fluorescent protein mEos2 - GenBank Accession No. ACN37844.1 GI: 224037249; circular permutation cleavage motif in seventh beta sheet underlined;

Sequence ID No: 11 msaikpdmki klrmegnvng hhfvidgdgt gkpfegkqsm dlevkeggpl pfafdiltta fhygnrvfak ypdnigdyfk qsfpkgyswe rsltfedggi ciarnditme gdtfynkvrf ygtnfpangp vmqkktlkwe pstekmyvrd gvltgdihma lllegnahyr cdfrttykak ekgvklpgyh fvdhcieils hdkdynkvkl yehavahsgl pdnarr amino acid sequence of mMaple; from McEvoy, et al., PLoS One. 2012; 7(12): e51314; circular permutation cleavage motif in seventh beta sheet underlined;

SEQ ID No: 12 mvskgeetimsvikpdmkiklrmegnvnghafviegegsgkpfegiqtidlevkegaplpfay dilttafhygnrvftkypedipdyfkqsfpegyswersmtyedggiciatnditmeedsfink ihfkgtnfppngpvmqkrtvgwevstekmyvrdgvlkgdvkmklllkggshyrcdfrttykvk qkavklpdyhfvdhrieilshdkdynkvklyehavarnstdsmdelyk amino acid sequence of far-red fluorescent protein mCardinal; GenBank: AHL19967.1, from Chu, et al., *Nat. Methods* (2014) 11(5): 572-578; circular permutation cleavage motif in seventh beta sheet underlined;

SEQ ID No: 13 mvskgeelik enmhmklyme gtvnnhhfkc ttegegkpye gtqtqrikvv eggplpfafd ilatcfmygs ktfinhtqgi pdffkqsfpe gftwervtty edggvltvtq dtslqdgcli -continued

| INFORMAL SEQUENCE LISTING |
| --- |

ynvklrgvnf psngpvmqkk tlgweattet lypadggleg rcdmalklvg gghlhcnlkt tyrskkpakn lkmpgvyfvd rrlerikead netyveqhev avarycdlps klghklngmd elyk amino acid sequence of mNeptune; GenBank: CBH32884.1, from Lin, et al., *Chem. Biol.* (2009) 16(11): 1169-1179; circular permutation cleavage motif in seventh beta sheet underlined;

SEQ ID No: 14 mvskgeelik enmhmklyme gtvnnhhfkc tsegegkpye gtqtgrikvv eggplpfafd ilatcfmygs ktfinhtqgi pdffkqsfpe gftwervtty edggvltatq dtslqdgcli ynvkirgvnf psngpvmqkk tlgweastet lypadggleg rcdmalklvg gghlicnlkt tyrskkpakn lkmpgvyfvd rrlerikead netyveqhev avarycdlps klghklngmd elyk amino acid sequence of circularly permuted green fluorescent protein; N-terminus at residue 148 in eGFP (SEQ ID NO: 1); GGTGGS linker connecting C-terminus to N terminus underlined;

SEQ ID No: 15 n v y i k a d k q k n g i k a n f k i r h n i e d g g v q l a y h y q q n t p i g d g p v l l p d n h y l s v q s k l s k d p n e k r d h m v l l e f v t a a g i t l g m d e l y k g g t g g s m v s k g e e l f t g v v p i l v e l d g d v n g h k f s v s g e g e g d a t y g k l t l k f i c t t g k l p v p w p t l v t t l t y g v q c f s r y p d h m k q h d f f k s a m p e g y i q e r t i f f k d d g n y k

V55Y: Substitute threonine at position 55 to tyrosine to create yellow fluorescent protein (cpYFP)
Y136W: Substitute tyrosine at position 136 to tryptophan to create cyan fluorescent protein (cpCFP)

amino acid sequence of circularly permuted mRuby2; N-terminus at residue 147 in mRuby2 (SEQ ID NO: 9); GGTGGS linker connecting C-terminus to N terminus underlined (from Akerboom J et al., *Front Mol Neurosci.*, 2013 6: 2)

SEQ ID No: 16

NTEMMYPADGGLRGYTHMALKVDGGGHLSCSFVTTYRSKKTVGNIKMPGIHYVSHRLERLEES

DNEMFVVQREHAVAKFVGLGGGGGTGGSMNSLIKENMRMKVVLEGSVNGHQFKCTGEGEGNPY

MGTQTMRIKVIEGGPLPFAFDILATSFMSRTFIKYPKGIPDFFKQSFPEGFTWERVTRYEDGG

VITVMQDTSLEDGCLVYHAQVRGVNFPSNGAVMQKKTKGWEPTRDQLT amino acid sequence of circularly permuted mApple; GGTGGS linker connecting C-terminus to N terminus underlined (from Zhao Y. et al., *Science*, 2011 333(6051): 1888-1891)

SEQ ID No: 17

VVSERMYPEDGALKSEIKKGLRLKDGGHYAAEVKTTYKAKKPVQLPGAYIVDIKLDIVSHNED

YTIVEQCERAEGRHSTGGMDELYKGGTGGSLVSKGEEDNMAIIKEFMRFKVHMEGSVNGHEFE

IEGEGEGRPYEAFQTAKLKVTKGGPLPFAWDILSPQFMSKAYIKHPADIPDYFKLSFPEGERW

ERVMNFEDGGIIHVNQDSSLQDGVFIYKVKLRGTNFPPDGPVMQKKTMGWEA

-continued

INFORMAL SEQUENCE LISTING amino acid sequence of circularly permuted mEos2; GGTGGS linker connecting C-terminus to N terminus underlined (from Fosque B. F. et al., *Science* 2015 347(6223): 755-60)

SEQ ID No: 18

LECEKMYVRDGVLTGDIHMALLLEGNAHYRCDFRTTYKAKEKGVKLPGYHFVDHCIEILSHDK

DYNKVKLYEHAVAHSGLPDNARRGGTGGSMVSAIKPDMKIKLRMEGNVNGHHFVIDGDGTGKP

YEGKQTMDLEVKEGGPLPFAFDILTTAFHNRVFVKYPDNIQDYFKQSFPKGYSWERSMTFEDG

GICYARNDITMEGDTFYNKVRFYGTNFPANGPVMQKKTLKW motif in beta strand seven of fluorescent protein (e.g., green fluorescent protein, cyan fluorescent protein, yellow fluorescent protein)

SEQ ID NO: 19

YN(Y/F)(N/I)SHNV motif in beta strand seven of a red fluorescent protein (e.g., mCherry, mRuby2, mRuby3, mApple, mKate2, mEos2, mMaple, mCardinal, mNeptune)

SEQ ID NO: 20

WE(A/P/V)(S/L/N/T)(S/E/T)E R/M/T/K)(M/L)

nucleic acid sequence of GFP sensor integrated into third intracellular loop of beta2 adrenergic receptor SEQ ID No: 21 atgaagacgatcatcgccctgagctacatcttctgcctggtgttc*gccgactacaaggacgat*

*gatgacgcc*atggggcagccaggtaatggctctgcgttcttgttggccccgaacaggagccat gctcccgaccatgacgtcacccaacagagagatgaggtctgggtagtaggcatgggtattgtc atgtctctgatagtcttggcaatcgtgtttggaaatgtgctcgttatcacggcaatagctaag tttgagcgacttcaaacggtaacaaattatttcataacatctctcgcgtgtgcagatctcgta atgggactcgctgtggtcccctttggcgcggcccatatcctgatgaagatgtggacttttggt aatttctggtgtgaattttggaccagcatagatgtactctgtgttacagcttcaattgaaact ctctgtgtgatagccgttgatcgctatttcgccattacgtcccctgccaagtatcaatcattg cttaccaagaataaagcccgagtaataattctcatggtgtggatcgtaagcgggctcacatct tttttgccgattcagatgcactggtatagagcaacgcaccaagaagccataaactgctacgca aatgaaacttgctgtgacttctttacaaatcaggcttacgctattgcctcttcaatagtcagt ttttacgttcctctggttattatggtgtttgtatactcacgggtattccaggaggctaagcgg cagctccagaaaatagacaagagtgagggacgctttcatgtgcagaatctttca*GCCGTC*AAC

GTCTATATCAAGGCCGACAAGCAGAAGAACGGCATCAAGGCGAACTTCAAGATCCGCCACAAC

ATCGAGGACGGCGGCGTGCAGCTCGCCTACCACTACCAGCAGAACACCCCCATCGGCGACGGC

CCCGTGCTGCTGCCCGACAACCACTACCTGAGCGTGCAGTCCAAACTTTCGAAAGACCCCAAC

GAGAAGCGCGATCACATGGTCCTGCTGGAGTTCGTGACCGCCGCCGGGATCACTCTCGGCATG

GACGAGCTGTACAAGGGCGGTACCGGAGGGAGCATGGTGAGCAAGGGCGAGGAGCTGTTCACC

GGGGTGGTGCCCATCCTGGTCGAGCTGGACGGCGACGTAAACGGCCACAAGTTCAGCGTGTCC

GGCGAGGGTGAGGGCGATGCCACCTACGGCAAGCTGACCCTGAAGTTCATCTGCACCACCGGC

AAGCTGCCCGTGCCCTGGCCCACCCTCGTGACCACCCTGACCTACGGCGTGCAGTGCTTCAGC

CGCTACCCCGACCACATGAAGCAGCACGACTTCTTCAAGTCCGCCATGCCCGAAGGCTACATC

CAGGAGCGCACCATCTTCTTCAAGGACGACGGCAACTACAAGACCCGCgccgaggtgaagttc gagggcgacaccctggtgaaccgcatcgagctgaagggcatcgacttcaaggaggacggcaac atcctggggcacaagctggagtacaacaccagacaagttgaacaggacggacgcacaggtcat -continued

INFORMAL SEQUENCE LISTING ggcctcaggaggagttctaagttctgcttgaaggagcacaaagcgctgaagacgcttggaatt atcatggggacgtttactctctgctggcttcctttcttcatagtaaacattgttcacgtaatc caagacaatctgattcgaaaggaggtgtatattctcctcaattggattgggtacgtaaacagc ggatttaatcctcttatctattgccgaagccctgatttccgcatagcctttcaggaactgctt tgtcttcgccgaagcagccttaaagcgtacggaaatggttacgctgcaaatgggaatacaggc gagcaaagcgggtatcacgtcgagcaagagaaggagaacaaacttctgtgcgaagacctgcct ggcacggaagatttgtcggacaccaagggacggtaccgagtgacaatatcgacagtcaaggc cgaaactgctcaactaatgattcactcctgtag Feature Annotations for SEQ ID NO: 21

| Residue numbers | Formatting | Feature definition |
|---|---|---|
| 1-45 | Underlined | Secretory sequence (from Hemagglutinin) |
| 46-72 | Italics | Flag-tag (non essential to sensor function) |
| 487-489 and 1870-1875 | Bold and double underline | Mutations from wild-type B2AR sequence to generate signaling-incompetent sensor; F139A and SS355-356AA |
| 811-1434 | CAPITALS | circularly permuted GFP (cpGFP) (including nucleic acids encoding alanine-valine (AV) linker at 3' end and threonine-arginine (TR) linker at 5' end of cpGFP) |
| 811-816 and 1429-1434 | ITALIC CAPITALS | alanine-valine (AV) linker at 3' end and threonine-arginine (TR) linker at 5' end of cpGFP |

amino acid sequence of GFP sensor integrated into third intracellular loop of beta2 adrenergic receptor SEQ ID No: 22 m k t i i a l s y i f c l v f *a d y k d d d d a* m g q p g n g s a f l l a p n r s h a p d h d v t q q r d e v w v v g m g i v m s l i v l a i v f g n v l v i t a i a k f e r l q t v t n y f i t s l a c a d l v m g l a v v p f g a a h i l m k m w t f g n f w c e f w t s i d v l c v t a s i e t l c v i a v d r y f a i t s p x k y q s l l t k n k a r v i i l m v w i v s g l t s f l p i q m h w y r a t h q e a i n c y a n e t c c d f f t n q a y a i a s s i v s f y v p l v i m v f v y s r v f *g e a k r g l q k*

*i d k s e g r f h v q n l s* A V N V Y I K A D K Q K N G I K A N

F K I R H N I E D G G V Q L A Y H Y Q Q N T P I G D G P V L L P

D N H Y L S V Q S K L S K D P N E K R D H M V L L E F V T A A G

I T L G M D E L Y K G G T G G S M V S K G E E L F T G V V P I L

V E L D G D V N G H K F S V S G E G E G D A T Y G K L T L K F I

C T T G K L P V P W P T L V T T L T Y G V Q C F S R Y P D H M K

Q H D F F K S A M P E G Y I Q E R T I F F K D D G N Y K *T R a e*

*v k f e g d t l v n r i e l k g i d f k e d g n i l g h k l e y*

*n t r q v e q d g r t g h g l r r s s k f c l k e h* k a l k t l g i i m g t f t l c w l p f f i v n i v h v i q d n l i r k e v

-continued

| INFORMAL SEQUENCE LISTING |
|---|
| y i l l n w i g y v n s g f n p l i y c r s p d f r i a f q e l |
| l c l r r s s l k a y g n g y **a a** n g n t g e q s g y h v e q e |
| k e n k l l c e d l p g t e d f v g h q q g t v p s d n i d s q g |
| r n c s t n d s l l stop |

Feature Annotations for SEQ ID NO: 22

| Residue numbers | Formatting | Feature definition |
|---|---|---|
| 1-15 | Underlined | Secretory sequence (from Hemagglutinin) |
| 16-24 | Italics | Flag-tag (non essential to sensor function) |
| 163 | Bold and double underline | X is any amino acid or an amino acid selected from the group consisting of F, A, G, V, I, L, M, S, T |
| 163 and 624-625 | Bold and double underline | Mutations from wild-type B2AR sequence to generate signaling-incompetent sensor; F139A and SS355-356AA |
| 248-270 and 479-538 | Underline and italics | Third intracellular loop, split by integration of sensor |
| 271-478 | CAPITALS | circularly permuted GFP (cpGFP) (including alanine-valine (AV) linker at N-terminus and threonine-arginine (TR) linker at C-terminus of cpGFP) |
| 271-272 and 477-478 | ITALIC CAPITALS | alanine-valine (AV) linker at N-terminus and threonine-arginine (TR) linker at C-terminus of cpGFP |

nucleic acid sequence of GFP sensor integrated into third intracellular loop of µ-type opioid receptor SEQ ID No: 23 atgaagacgatcatcgccctgagctacatcttctgcctggtgttc*gccgactacaaggacgat*

*gatgacgcc*atggatagtagcgctgcgcctaccaacgcgtcaaactgcaccgatgctcttgcg tactcctcctgctccccggcacctagtcccggttcttgggtcaatttgtcccatctggacgga aacctctctgatccctgtgggcctaacaggacggacctcggtgggagggactccctttgcccg ccgaccggatctccgtccatgataacggccattacaattatggcgttgtatagcatcgtatgc gttgtaggtctttttgggaatttcctggtgatgtacgtcatcgtcaggtacacaaagatgaaa acagctactaacatttatatatttaacctggcgctcgcggacgctctcgcaacgtcaacgctc ccgtttcagtccgtgaattatctcatgggtacttggcctttcggaacaatactgtgtaaaatt gttataagcatagattattataatatgttcacgtccatcttcacactctgcacaatgtctgtg gataggtacattgctgtatgtcacccagctaaggcgcttgactttagaactccacgcaatgca aagattataaatgtgtgcaactggatcttgtcctctgcaatagggcttcctgtgatgttcatg gcgactactaagtacagacagggcagcatagattgcacactcaccttctcacacccaacttgg tactgggaaaatctgctcaagatctgcgtcttcattttttgcttttatcatgccagtattgata atcacggtctgttacgggttgatgattttgcggctcaaatcagttcgaatgctcagt*ATCAAA*

AACGTCTATATCAAGGCCGACAAGCAGAAGAACGGCATCAAGGCGAACTTCAAGATCCGCCAC

AACATCGAGGACGGCGGCGTGCAGCTCGCCTACCACTACCAGCAGAACACCCCCATCGGCGAC

GGCCCCGTGCTGCTGCCCGACAACCACTACCTGAGCGTGCAGTCCAAACTTTCGAAAGACCCC

AACGAGAAGCGCGATCACATGGTCCTGCTGGAGTTCGTGACCGCCGCCGGGATCACTCTCGGC

ATGGACGAGCTGTACAAGGGCGGTACCGGAGGGAGCATGGTGAGCAAGGGCGAGGAGCTGTTC

ACCGGGGTGGTGCCCATCCTGGTCGAGCTGGACGGCGACGTAAACGGCCACAAGTTCAGCGTG

-continued

INFORMAL SEQUENCE LISTING

TCCGGCGAGGGTGAGGGCGATGCCACCTACGGCAAGCTGACCCTGAAGTTCATCTGCACCACC

GGCAAGCTGCCCGTGCCCTGGCCCACCCTCGTGACCACCCTGACCTACGGCGTGCAGTGCTTC

AGCCGCTACCCCGACCACATGAAGCAGCACGACTTCTTCAAGTCCGCCATGCCCGAAGGCTAC

ATCCAGGAGCGCACCATCTTCTTCAAGGACGACGGCAACTACAAGACCCGCGCCGAGGTGAAG

TTCGAGGGCGACACCCTGGTGAACCGCATCGAGCTGAAGGGCATCGACTTCAAGGAGGACGGC

AACATCCTGGGGCACAAGCTGGAGTACAAC*ATTATC*ggcagcaaggagaaggaccgcaacctc agaaggataacgagaatggtgctggtcgtagtggcggttttcattgtttgttggacgccaata cacatatacgtgattataaaggctctggtgacaattcccgaaacaacgtttcagacggtctct tggcatttctgtattgcattggggtacactaattcctgccttaatcctgtattgtacgccttt ctggatgaaaactttaaaagatgtttccgcgagttctgcataccgaccagcagcaacattgaa caacaaaactccacgcgcatacggcaaaatactagggatcacccgtccactgcgaatactgta gaccgaacgaaccatcagttggagaatttggaagcggaaactgctcctctgccatga Feature Annotations for SEQ ID NO: 23

| Residue numbers | Formatting | Feature definition |
|---|---|---|
| 1-45 | Underlined | Secretory sequence (from Hemagglutinin) |
| 46-72 | Italics | Flag-tag (non essential to sensor function) |
| 595-597 | Bold and double underline | V199A mutation from wild-type μ-type opioid receptor signaling incompetent |
| 877-1611 | CAPITALS | circularly permuted GFP (cpGFP) (including nucleic acids encoding isoleucine-lysine (IK) linker at 3' end and isoleucine-isoleucine (II) linker at 5' end of cpGFP) |
| 877-882 and 1606-1611 | ITALIC CAPITALS | isoleucine-lysine (IK) linker at 3' end and isoleucine-isoleucine (II) linker at 5' end of cpGFP |

amino acid sequence of GFP sensor integrated
into third intracellular loop of μ-type opioid receptor SEQ ID No: 24 mktiialsyifclvf*adykdddda*mdssaaptnasnctdalaysscspapspgswvnlshldg nlsdpcgpnrtdlggrdslcpptgspsmitaitimalysivcvvglfgnflvmyvivrytkmk tatniyifnlaladalatstlpfqsvnylmgtwpfgtilckivisidyynmftsiftlctmsv dryiavchpxkaldfrtprnakiinvonwilssaiglpvmfmattkyrqgsidctltfshptw ywenllkicvfifafimpvliitvcyglmilrlksv*rmlsIK*NVYIKADKQKNGIKANFKIRH

NIEDGGVQLAYHYQQNTPIGDGPVLLPDNHYLSVQSKLSKDPNEKRDHMVLLEFVTAAGITLG

MDELYKGGTGGSMVSKGEELFTGVVPILVELDGDVNGHKFSVSGEGEGDATYGKLTLKFICTT

GKLPVPWPTLVTTLTYGVQCFSRYPDHMKQHDFFKSAMPEGYIQERTIFFKDDGNYKTRAEVK

FEGDTLVNRIELKGIDFKEDGNILGHKLEYN*IIgs*kekdrnlrritrmvlvvvavfivcwtpi hiyviikalvtipettfqtvswhfcialgytnsclnpvlyafldenfkrcfrefciptssnie qqnstrirqntrdhpstantvdrtnhqlenleaetaplp- -continued

INFORMAL SEQUENCE LISTING

Feature Annotations for SEQ ID NO: 24

| Residue numbers | Formatting | Feature definition |
|---|---|---|
| 1-15 | Underlined | Secretory sequence (from Hemagglutinin) |
| 16-24 | Italics | Flag-tag (non essential to sensor function) |
| 199 | Bold and double underline | X is any amino acid or an amino acid selected from the group consisting of F, A, G, V, I, L, M, S, T |
| 289-292 and 538-539 | Underline and italics | Third intracellular loop, split by integration of sensor |
| 293-537 | CAPITALS | circularly permuted GFP (cpGFP) (including isoleucine-lysine (IK) linker at N-terminus and isoleucine-isoleucine (II) linker at C-terminus of cpGFP) |
| 293-294 and 536-537 | ITALIC CAPITALS | isoleucine-lysine (IK) linker at N-terminus and isoleucine-isoleucine (II) linker at C-terminus of cpGFP |

nucleic acid sequence of GFP sensor integrated into third intracellular loop of dopamine receptor D1 (DRD1)

SEQ ID No: 25 atgaagacgatcatcgccctgagctacatcttctgcctggtgttc*gccgactacaaggacgat*

*gatgacgcc*atgaggactctgaacacctctgccatggacgggactgggctggtggtggagagg gacttctctgttcgtatcctcactgcctgtttcctgtcgctgctcatcctgtccacgctcctg gggaacacgctggtctgtgctgccgttatcaggttccgacacctgcggtccaaggtgaccaac ttctttgtcatctccttggctgtgtcagatctcttggtggccgtcctggtcatgccctggaag gcagtggctgagattgctggcttctggccctttgggtccttctgtaacatctgggtggccttt gacatcatgtgctccactgcatccatcctcaacctctgtgtgatcagcgtggacaggtattgg gctatctccagccctgcccggtatgagagaaagatgacccccaaggcagccttcatcctgatc agtgtggcatggaccttgtctgtactcatctccttcatcccagtgcagctcagctggcacaag gcaaaacccacaagcccctctgatggaaatgccacttccctggctgagaccatagacaactgt gactccagcctcagcaggacatatgccatctcatcctctgtaatcagcttttacatccctgtg gccatcatgattgtcacctacaccaggatctacaggattgctcagaaacaaatacggcgcatt gcggccttggagagggcagcagtccacgccaagaattgc*TCTCGG*AACGTGTATATCAAGGCT

GATAAACAAAAGAATGGTATCAAAGCTAATTTCAAAATCCGCCACAATATCGAAGATGGCGGC

GTCCAGCTCGCTTATCATTATCAGCAGAATACACCTATCGGTGACGGGCCGGTGCTTTTGCCT

GATAACCATTACCTGAGTGTTCAAAGTAAACTGAGCAAGGATCCAAATGAAAAAAGGGACCAC

ATGGTGCTTCTCGAATTTGTAACGGCTGCAGGCATTACTCTCGGGATGGACGAACTTTACAAA

GGAGGGACCGGAGGCAGCATGGTGTCCAAGGGGGAGGAACTTTTCACTGGCGTCGTGCCGATA

CTCGTCGAACTCGATGGAGATGTTAATGGACACAAATTTTCAGTCAGTGGCGAAGGGGAAGGG

GATGCTACTTACGGGAAACTCACACTGAAGTTTATTTGTACGACAGGCAAACTCCCGGTACCT

TGGCCGACCTTGGTGACCACGTTGACGTATGGAGTACAGTGCTTCTCCAGGTACCCGGACCAC

ATGAAGCAACATGACTTTTTCAAAAGCGCTATGCCCGAGGGCTACATTCAAGAACGGACTATT

TTCTTTAAGGACGATGGAAACTATAAAACCAGAGCTGAGGTGAAATTCGAGGGTGACACTCTT

GTAAACCGGATAGAACTCAAAGGTATAGATTTCAAAGAAGACGGAAACATCTTGGGGCATAAA

CTCGAGTATAAT*CCTCCT*cagaccaccacaggtaatggaaagcctgtcgaatgttctcaaccg

-continued

INFORMAL SEQUENCE LISTING gaaagttcttttaagatgtccttcaaaagagaaactaaagtcctgaagactctgtcggtgatc atgggtgtgtttgtgtgctgttggctacctttcttcatcttgaactgcattttgcccttctgt gggtctggggagacgcagcccttctgcattgattccaacacctttgacgtgtttgtgtggttt gggtgggctaattcatccttgaaccccatcatttatgcctttaatgctgattttcggaaggca ttttcaaccctcttaggatgctacagactttgccctgcgacgaataatgccatagagacggtg agtatcaataacaatggggccgcgatgttttccagccatcatgagcca*ttctgctacgagaat*

*gaagtc*tga

Feature Annotations for SEQ ID NO: 25

| Residue numbers | Formatting | Feature definition |
|---|---|---|
| 1-45 | Underlined | Secretory sequence (from Hemagglutinin) |
| 46-72 | Italics | Flag-tag (non essential to sensor function) |
| 457-459 | Bold and double underline | F129A mutation from wild-type DRD1 sequence to generate signaling-incompetent sensor |
| 796-1530 | CAPITALS | circularly permuted GFP (cpGFP) (including nucleic acids encoding serine-arginine (SR) linker at 3' end and proline-proline (PP) linker at 5' end of cpGFP) |
| 796-801 and 1525-1530 | ITALIC CAPITALS | serine-arginine (SR) linker at 3' end and proline-proline (PP) linker at 5' end of cpGFP |
| 1939-1959 | italic and underlined | Endoplasmic Reticulum Export Sequence |

amino acid sequence of GFP sensor integrated into third intracellular loop of dopamine receptor D1 (DRD1)

SEQ ID No: 26 mktiialsyifclvf*adykdddda*mrtlntsamdgtglvverdfsvriltacflsllilstll gntlvcaavirfrhlrskvtnffvislavsdllvavlvmpwkavaeiagfwpfgsfcniwvaf dimcstasilnlcvisvdrywaisspxryerkmtpkaafilisvawtlsvlisfipvqlswhk akptspsdgnatslaetidncdsslsrtyaisssvisfyipvaimivtytriyria*gkqirri*

*aaleraavhakncSR*NVYIKADKQKNGIKANFKIRHNIEDGGVQLAYHYQQNTPIGDGPVLLP

DNHYLSVQSKLSKDPNEKRDHMVLLEFVTAAGITLGMDELYKGGTGGSMVSKGEELFTGVVPI

LVELDGDVNGHKFSVSGEGEGDATYGKLTLKFICTTGKLPVPWPTLVTTLTYGVQCFSRYPDH

MKQHDFFKSAMPEGYIQERTIFFKDDGNYKTRAEVKFEGDTLVNRIELKGIDFKEDGNILGHK

LEYN*PPqtttgngkpvecsqpessfkmsfkretk*vlktlsvimgvfvccwlpffilncilpfc gsgetqpfcidsntfdvfvwfgwansslnpiiyafnadfrkafstllgcyrlcpatnnaietv sinnngaamfsshhep*fcyenev*-

Feature Annotations for SEQ ID NO: 26

| Residue numbers | Formatting | Feature definition |
|---|---|---|
| 1-15 | Underlined | Secretory sequence (from Hemagglutinin) |
| 16-24 | Italics | Flag-tag (non essential to sensor function) |
| 153 | Bold and double underline | X is any amino acid or an amino acid selected from the group consisting of F, A, G, V, I, L, M, S, T |
| 246-265 and 511-538 | italic and underlined | Third intracellular loop, split by integration of sensor |

-continued

| INFORMAL SEQUENCE LISTING | | |
|---|---|---|
| 266-510 | CAPITALS | circularly permuted GFP (cpGFP) (including serine-arginine (SR) linker at N-terminus and proline-proline (PP) linker at C-terminus of cpGFP) |
| 266-267 and 509-510 | ITALIC CAPITALS | serine-arginine (SR) linker at N-terminus and proline-proline (PP) linker at C-terminus of cpGFP |
| 647-653 | italic and underlined | Endoplasmic Reticulum Export Sequence |

nucleic acid sequence of GFP sensor integrated into third intracellular loop of 5-Hydroxytryptamine 2A (5-HT2A) receptor SEQ ID No: 27 atgaagacgatcatcgccctgagctacatcttctgcctggtgttc*gccgactacaaggacgat*

*gatgacgcc*atggacatactttgtgaagagaatacttcactctcttctactactaactctctt atgcaactgaacgatgatacccgattgtactcaaacgacttcaattccggcgaagcgaacacc agtgacgcattcaactggactgtcgattctgaaaacagaactaatctgtcatgcgagggttgt cttagtccctcttgtctcagcctgttgcacctccaggaaaagaactggtcagcactgctcact gcggtagtgataatactcactattgctggcaatattctcgtaattatggcagtctccttggag aagaaactccaaaacgccacaaattattttcttatgagccttgccatcgcagatatgctcttg ggatttttggtgatgcctgtgagtatgctcacgatactgtatggatatcgctggcctctgccg tctaaactttgcgctgtgtggatttacttggatgtcctttttttcaactgcgagtattatgcat ctttgcgccattagtcttgataggtatgtggctatccaaaatcctgcccaccattcccgcttt aatagtagaactaaggcttttctgaaaataatagcagtgtggaccatatctgtcggcataagc atgcctatccccgtatttggacttcaagatgactcaaaggtattcaaagaagggtcatgtctg ctggccgatgacaatttcgtgcttattggatccttcgtcagtttcttcattcctttgacaatc atggtgattacctactttcttacgattaaatctttgcaaaaggaggctactctgtgcgtcagc gacctcggcactcgggccaaa*TCTCGG*AACGTCTATATCAAGGCCGACAAGCAGAAGAACGGC

ATCAAGGCGAACTTCAAGATCCGCCACAACATCGAGGACGGCGGCGTGCAGCTCGCCTACCAC

TACCAGCAGAACACCCCCATCGGCGACGGCCCCGTGCTGCTGCCCGACAACCACTACCTGAGC

GTGCAGTCCAAACTTTCGAAAGACCCCAACGAGAAGCGCGATCACATGGTCCTGCTGGAGTTC

GTGACCGCCGCCGGGATCACTCTCGGCATGGACGAGCTGTACAAGGGCGGTACCGGAGGGAGC

ATGGTGAGCAAGGGCGAGGAGCTGTTCACCGGGGTGGTGCCCATCCTGGTCGAGCTGGACGGC

GACGTAAACGGCCACAAGTTCAGCGTGTCCGGCGAGGGTGAGGGCGATGCCACCTACGGCAAG

CTGACCCTGAAGTTCATCTGCACCACCGGCAAGCTGCCCGTGCCCTGGCCCACCCTCGTGACC

ACCCTGACCTACGGCGTGCAGTGCTTCAGCCGCTACCCCGACCACATGAAGCAGCACGACTTC

TTCAAGTCCGCCATGCCCGAAGGCTACATCCAGGAGCGCACCATCTTCTTCAAGGACGACGGC

AACTACAAGACCCGCGCCGAGGTGAAGTTCGAGGGCGACACCCTGGTGAACCGCATCGAGCTG

AAGGGCATCGACTTCAAGGAGGACGGCAACATCCTGGGGCACAAGCTGGAGTACAAC*CTTTTC* cttgccagcttctcattccttccccagtcctctctttccagtgagaaacttttccaacgatcc atacatagggagccgggtagttatacaggacggcggacgatgcaatcaattagtaatgagcaa aaggcttgtaaggtactcggcatagtcttctttctgtttgtggtgatgtggtgtcccttcttt ataacgaatatcatggcagtgatctgcaaggaatcatgcaatgaggatgtgatcggggcactt ctgaacgttttcgtgtggatagggtatctgtcaagtgctgtgaacccactggtctataccttg tttaataagacataccgctcagccttttcacggtatattcaatgtcagtataaggaaaacaag -continued

INFORMAL SEQUENCE LISTING aaacctctgcaacttattcttgtgaacactatccctgccctggcttataagtcatcacagttg cagatgggccagaaaaaaaattccaagcaggacgcgaagacaacagacaacgattgtagtatg gttgccctcggcaagcagcacagtgaagaagcgagcaaagacaatagtgatggcgtaaacgaa aaagtcagttgtgtataa Feature Annotations for SEQ ID NO: 27

| Residue numbers | Formatting | Feature definition |
|---|---|---|
| 1-45 | Underlined | Secretory sequence (from Hemagglutinin) |
| 46-72 | Italics | Flag-tag (non essential to sensor function) |
| 613-615 | Bold and double underline | I181A mutation from wild-type 5HT-2A sequence to generate signaling-incompetent sensor |
| 904-1638 | CAPITALS | circularly permuted GFP (cpGFP) (including nucleic acids encoding serine-arginine (SR) linker at 3' end and leucine-phenylalanine (LF) linker at 5' end of cpGFP) |
| 904-909 and 1633-1638 | ITALIC CAPITALS | serine-arginine (SR) linker at 3' end and leucine-phenylalanine (LF) linker at 5' end of cpGFP |

amino acid sequence of GFP sensor integrated into third intracellular loop of 5-Hydroxytryptamine 2A (5-HT2A) receptor SEQ ID No: 28 mktiialsyifclvf*adykdddda*mdilceentslssttnslmqlnddtrlysndfnsgeant sdafnwtvdsenrtnlscegclspsclsllhlqeknwsalltavviiltiagnilvimavsle kklqnatnyflmslaiadmllgflvmpvsmltilygyrwplpsklcavwiyldvlfstasimh lcaisldryvaiqnpxhhsrinsrtkaflkiiavwtisvgismpipvfglqddskvfkegscl laddnfvligsfvsffipltimvityfltiksl*gkeatlcvsdlgtrakSR*NVYIKADKQKNG

IKANFKIRHNIEDGGVQLAYHYQQNTPIGDGPVLLPDNHYLSVQSKLSKDPNEKRDHMVLLEF

VTAAGITLGMDELYKGGTGGSMVSKGEELFTGVVPILVELDGDVNGHKFSVSGEGEGDATYGK

LTLKFICTTGKLPVPWPTLVTTLTYGVQCFSRYPDHMKQHDFFKSAMPEGYIQERTIFFKDDG

NYKTRAEVKFEGDTLVNRIELKGIDFKEDGNILGHKLEYN*LFlasfsflpqsslsseklfqrs*

*ihrepgsytgrrtmqsisneqk*ackvlgivfflfvvmwcpffitnimavickescnedvigal lnvfvwigylssavnplvytlfnktyrsafsryiqcqykenkkplqlilvntipalaykssql qmgqkknskqdakttdndcsmvalgkqhseeaskdnsdgvnekvscv- Feature Annotations for SEQ ID NO: 28

| Residue numbers | Formatting | Feature definition |
|---|---|---|
| 1-15 | Underlined | Secretory sequence (from Hemagglutinin) |
| 16-24 | Italics | Flag-tag (non essential to sensor function) |
| 205 | Bold and double underline | X is any amino acid or an amino acid selected from the group consisting of F, A, G, V, I, L, M, S, T |

-continued

| INFORMAL SEQUENCE LISTING | | |
|---|---|---|
| 286-301 and 547-589 | italic and underlined | Third intracellular loop, split by integration of sensor |
| 302-546 | CAPITALS | circularly permuted GFP (cpGFP) (including serine-arginine (SR) linker at N-terminus and leucine-phenylalanine (LF) linker at C-terminus of cpGFP) |
| 302-303 and 545-546 | ITALIC CAPITALS | serine-arginine (SR) linker at N-terminus and leucine-phenylalanine (LF) linker at C-terminus of cpGFP |

nucleic acid sequence of circularly permuted green fluorescent protein

SEQ ID No: 29

AACGTCTATATCAAGGCCGACAAGCAGAAGAACGGCATCAAGGCGAACTTCAAGATCCGCCAC

AACATCGAGGACGGCGGCGTGCAGCTCGCCTACCACTACCAGCAGAACACCCCCATCGGCGAC

GGCCCCGTGCTGCTGCCCGACAACCACTACCTGAGCGTGCAGTCCAAACTTTCGAAAGACCCC

AACGAGAAGCGCGATCACATGGTCCTGCTGGAGTTCGTGACCGCCGCCGGGATCACTCTCGGC

ATGGACGAGCTGTACAAGGGCGGTACCGGAGGGAGCATGGTGAGCAAGGGCGAGGAGCTGTTC

ACCGGGGTGGTGCCCATCCTGGTCGAGCTGGACGGCGACGTAAACGGCCACAAGTTCAGCGTG

TCCGGCGAGGGTGAGGGCGATGCCACCTACGGCAAGCTGACCCTGAAGTTCATCTGCACCACC

GGCAAGCTGCCCGTGCCCTGGCCCACCCTCGTGACCACCCTGACCTACGGCGTGCAGTGCTTC

AGCCGCTACCCCGACCACATGAAGCAGCACGACTTCTTCAAGTCCGCCATGCCCGAAGGCTAC

ATCCAGGAGCGCACCATCTTCTTCAAGGACGACGGCAACTACAA(G/C)

Dopamine Receptor D1 (DRD1) containing cpFP sensor replacing all or part of 3rd intracellular loop

SEQ ID NO: 30

MRTLNTSAMDGTGLVVERDESVRILTACFLSLLILSTLLGNTLVCAAVIRFRHLRSKVTNFFV

ISLAVSDLLVAVLVMPWKAVAEIAGFWPFGSFCNIWVAFDIMCSTASILNLCVISVDRYWAIS

SP*X*RYERKMTPKAAFILISVAWTLSVLISFIPVQLSWHKAKPTSPSDGNATSLAETIDNCDSS

LSRTYAISSSVISFYIPVAIMIVTYTRIYRIAQK<u>QLQKIDLSSLI</u>nvyikadkqkngikanfk irhniedggvqlayhyqqntpigdgpvllpdnhylsvqsklskdpnekrdhmvllefvtaagi tlgmdelykggtggsmvskgeelftgvvpilveldgdvnghkfsvsgegegdatygkltlkfi cttgklpvpwptlvttltygvqcfsrypdhmkqhdffksampegyiqertiffkddgnyktra evkfegdtlvnrielkgidfkedgnilghkleyn<u>NHDQL</u>KRETKVLKTLSVIMGVFVCCWLPF

FILNCILPFCGSGETQPFCIDSNTFDVFVWFGWANSSLNPIIYAFNADFRKAFSTLLGCYRLC

PATNNAIETVSINNNGAAMFSSHHEPRGSISKECNLVYLIPHAVGSSEDLKKEEAAGIARPLE

KLSPALSVILDYDTDVS[L/M]EKIQPITQNGQHPT*

| Feature Annotations for SEQ ID NO: 30 | | |
|---|---|---|
| Residue numbers | Formatting | Feature definition |
| 129 | Bold and italic | X is any amino acid or an amino acid selected from the group consisting of F, A, G, V, I, L, M, S, T |
| 224-234 | Bold and underlined | Optional long linker at N-terminus of cpFP |
| 230-234 | Bold and underlined | Optional short linker at N-terminus of cpFP |

-continued

INFORMAL SEQUENCE LISTING

| | | |
|---|---|---|
| 235-475 | Lower case | cpGFP or any other cpFP described herein |
| 476-480 | Bold and underlined | Linker at C-terminus of cpFP |

adrenoceptor beta 1 (ADRB1, ADRB1R, B1AR, BETA1AR) containing cpFP sensor replacing all or part of 3rd intracellular loop

SEQ ID NO: 31

MGAGVLVLGASEPGNLSSAAPLPDGAATAARLLVPASPPASLLPPASESPEPLSQQWTAGMGL

LMALIVLLIVAGNVLVIVAIAKTPRLQTLTNLFIMSLASADLVMGLLVVPFGATIVVWGRWEY

GSFFCELWTSVDVLCVTASIETLCVIALDRYLAITSP*X*RYQSLLTRARARGLVCTVWAISALV

SELPILMHWWRAESDEARRCYNDPKCCDFVTNRAYAIASSVVSFYVPLCIMAFVYLRVFREAQ

KQLQKIDLSSLInvyikadkqkngikanfkirhniedggvqlayhyqqntpigdgpvllpdnh ylsvqsklskdpnekrdhmvllefvtaagitlgmdelykggtggsmvskgeelftgvvpilve ldgdvnghkfsvsgegegdatygkltlkficttgklpvpwptlvttltygvqcfsrypdhmkq hdffksampegyiqertiffkddgnyktraevkfegdtlvnrielkgidfkedgnilghkley nNHDQLREQKALKTLGIIMGVFTLCWLPFFLANVVKAFHRELVPDRLFVFFNWLGYANSAFNP

IIYCRSPDFRKAFQGLLCCARRAARRRHATHGDRPRASGCLARPGPPPSPGAASDDDDDDVVG

ATPPARLLEPWAGCNGGAAADSDSSLDEPCRPGFASESKV*

Feature Annotations for SEQ ID NO: 31

| Residue numbers | Formatting | Feature definition |
|---|---|---|
| 164 | Bold and italic | X is any amino acid or an amino acid selected from the group consisting of F, A, G, V, I, L, M, S, T |
| 254-264 | Bold and underlined | Optional long linker at N-terminus of cpFP |
| 260-264 | Bold and underlined | Optional short linker at N-terminus of cpFP |
| 265-505 | Lower case | cpGFP or any other cpFP described herein |
| 506-510 | Bold and underlined | Linker at C-terminus of cpFP |

adrenoceptor beta 2 (ADRB2, B2AR; ADRB2R; BETA2AR) containing cpFP sensor replacing all or part of 3rd intracellular loop

SEQ ID NO: 32

MGQPGNGSAFLLAPNRSHAPDHDVTQQRDEVWVVGMGIVMSLIVLAIVFGNVLVITAIAKFER

LQTVTNYFITSLACADLVMGLAVVPFGAAHILMKMWTFGNFWCEFWTSIDVLCVTASIETLCV

IAVDRYFAITSP*X*KYQSLLTKNKARVIILMVWIVSGLTSFLPIQMHWYRATHQEAINCYANET

CCDFFTNQAYAIASSIVSFYVPLVIMVFVYSRVFQEAKRQLQKIDLSSLInvyikadkqkngi kanfkirhniedggvqlayhyqqntpigdgpvllpdnhylsvqsklskdpnekrdhmvllefv taagitlgmdelykggtggsmvskgeelftgvvpilveldgdvnghkfsvsgegegdatygkl tlkficttgklpvpwptlvttltygvqcfsrypdhmkqhdffksampegyiqertiffkddgn yktraevkfegdtlvnrielkgidfkedgnilghkleynNHDQLKEHKALKTLGIIMGTFTLC

WLPFFIVNIVHVIQDNLIRKEVYILLNWIGYVNSGFNPLIYCRSPDFRIAFQELLCLRRSRYP

NVRPNNGYIYNAHSWQSENREQSKGSSGDSDHAEGNLAKEECLSADKTDSNGNCSKAQMRVL*

-continued

INFORMAL SEQUENCE LISTING

Feature Annotations for SEQ ID NO: 32

| Residue numbers | Formatting | Feature definition |
|---|---|---|
| 139 | Bold and italic | X is any amino acid or an amino acid selected from the group consisting of F, A, G, V, I, L, M, S, T |
| 229-239 | Bold and underlined | Optional long linker at N-terminus of cpFP |
| 235-239 | Bold and underlined | Optional short linker at N-terminus of cpFP |
| 240-480 | Lower case | cpGFP or any other cpFP described herein |
| 481-485 | Bold and underlined | Linker at C-terminus of cpFP |

5-hydroxytryptamine receptor 2A (HTR2A, 5-HT2A) containing cpFP sensor replacing all or part of 3rd intracellular loop

SEQ ID NO: 33

MDILCEENTSLSSTINSLMQLNDDTRLYSNDFNSGEANTSDAFNWTVDSENRTNLSCEGCLSP

SCLSLLHLQEKNWSALLTAVVIILTIAGNILVIMAVSLEKKLQNATNYFLMSLAIADMLLGEL

VMPVSMLTILYGYRWPLPSKLCAVWIYLDVLFSTASIMHLCAISLDRYVAIQNP*X*HHSRFNSR

TKAFLKIIAVWTISVGISMPIPVFGLQDDSKVFKEGSCLLADDNFVLIGSFVSFFIPLTIMVI

TYFLTIKSLQKQLQKIDLSSLInvyikadkqkngikanfkirhniedggvqlayhyqqntpig dgpvllpdnhylsvqsklskdpnekrdhmvllefvtaagitlgmdelykggtggsmvskgeel ftgvvpilveldgdvnghkfsvsgegegdatygkltlkficttgklpvpwptlvttltygvqc fsrypdhmkqhdffksampegyiqertiffkddgnyktraevkfegdtlvnrielkgidfked gnilghkleynNHDQLNEQKACKVLGIVFFLFVVMWCPFFITNIMAVICKESCNEDVIGALLN

VFVWIGYLSSAVNPLVYTLFNKTYRSAFSRYIQCQYKENKKPLQLILVNTIPALAYKSSQLQM

GQKKNSKQDAKTTDNDCSMVALGKQHSEEASKDNSDGVNEKVSCV*

Feature Annotations for SEQ ID NO: 33

| Residue numbers | Formatting | Feature definition |
|---|---|---|
| 181 | Bold and italic | X is any amino acid or an amino acid selected from the group consisting of F, A, G, V, I, L, M, S, T |
| 264-274 | Bold and underlined | Optional long linker at N-terminus of cpFP |
| 270-274 | Bold and underlined | Optional short linker at N-terminus of cpFP |
| 275-515 | Lower case | cpGFP or any other cpFP described herein |
| 516-520 | Bold and underlined | Linker at C-terminus of cpFP |

adenosine A2a receptor (ADORA2A, A2aR) containing cpFP sensor replacing all or part of 3rd intracellular loop

SEQ ID NO: 34

MPIMGSSVYITVELAIAVLAILGNVLVCWAVWLNSNLQNVTNYFVVSLAAADIAVGVLAIPFA

ITISTGFCAACHGCLFIACFVLVLTQSSIFSLLAIAIDRYIAIRIP*X*RYNGLVTGTRAKGIIA

ICWVLSFAIGLTPMLGWNNCGQPKEGKNHSQGCGEGQVACLFEDVVPMNYMVYFNFFACVLVP

LLLMLGVYLRIFLAARRQLQKIDLSSLInvyikadkqkngikanfkirhniedggvqlayhyq qntpigdgpvllpdnhylsvqsklskdpnekrdhmvllefvtaagitlgmdelykggtggsmv skgeelftgvvpilveldgdvnghkfsvsgegegdatygkltlkficttgklpvpwptlvttl tygvqcfsrypdhmkqhdffksampegyiqertiffkddgnyktraevkfegdtlvnrielkg idfkedgnilghkleynNHDQLKEVHAAKSLAIIVGLFALCWLPLHIINCFTFFCPDCSHAPL -continued

INFORMAL SEQUENCE LISTING

WLMYLAIVLSHINSVVNPFIYAYRIREFRQTFRKIIRSHVLRQQEPFKAAGTSARVLAAHGSD

GEQVSLRLNGHPPGVWANGSAPHPERRPNGYALGLVSGGSAQESQGNTGLPDVELLSHELKGV

CPEPPGLDDPLAQDGAGVS*

Feature Annotations for SEQ ID NO: 34

| Residue numbers | Formatting | Feature definition |
|---|---|---|
| 110 | Bold and italic | X is any amino acid or an amino acid selected from the group consisting of F, A, G, V, I, L, M, S, T |
| 207-217 | Bold and underlined | Optional long linker at N-terminus of cpFP |
| 213-217 | Bold and underlined | Optional short linker at N-terminus of cpFP |
| 218-458 | Lower case | cpGFP or any other cpFP described herein |
| 459-463 | Bold and underlined | Linker at C-terminus of cpFP |

adrenoceptor alpha 2A (ADRA2A, ADRA2 ; ADRAR; ADRA2R) containing cpFP sensor replacing all or part of 3rd intracellular loop

SEQ ID NO: 35

MGSLQPDAGNASWNGTEAPGGGARATPYSLQVTLTLVCLAGLLMLLTVFGNVLVIIAVFTSRA

LKAPQNLFLVSLASADILVATLVIPFSLANEVMGYWYFGKAWCEIYLALDVLFCTSSIVHLCA

ISLDRYWSITQA*X*EYNLKRTPRRIKAIIITVWVISAVISFPPLISIEKKGGGGGPQPAEPRCE

INDQKWYVISSCIGSFFAPCLIMILVYVRIYQIAKRQLQKIDLSSLInvyikadkqkngikan fkirhniedggvqlayhyqqntpigdgpvllpdnhylsvqsklskdpnekrdhmvllefvtaa gitlgmdelykggtggsmvskgeelftgvvpilveldgdvnghkfsvsgegegdatygkltlk ficttgklpvpwptlvttltygvqcfsrypdhmkqhdffksampegyiqertiffkddgnykt raevkfegdtlvnrielkgidfkedgnilghkleynNHDQLREKRFTFVLAVVIGVFVVCWFP

FFFTYTLTAVGCSVPRTLFKFFFWFGYCNSSLNPVIYTIFNHDFRRAFKKILCRGDRKRIV*

Feature Annotations for SEQ ID NO: 35

| Residue numbers | Formatting | Feature definition |
|---|---|---|
| 139 | Bold and italic | X is any amino acid or an amino acid selected from the group consisting of F, A, G, V, I, L, M, S, T |
| 226-236 | Bold and underlined | Optional long linker at N-terminus of cpFP |
| 232-236 | Bold and underlined | Optional short linker at N-terminus of cpFP |
| 237-477 | Lower case | cpGFP or any other cpFP described herein |
| 476-482 | Bold and underlined | Linker at C-terminus of cpFP |

opioid receptor kappa 1 (OPRK1, KOR1) containing cpFP sensor replacing all or part of 3rd intracellular loop

SEQ ID NO: 36

MDSPIQIFRGEPGPTCAPSACLPPNSSAWFPGWAEPDSNGSAGSEDAQLEPAHISPAIPVIIT

AVYSVVFVVGLVGNSLVMFVIIRYTKMKTATNIYIFNLALADALVTTTMPFQSTVYLMNSWPF

GDVLCKIVISIDYYNMFTSIFTLTMMSVDRYIAVCHP*X*KALDFRTPLKAKIINICIWLLSSSV

GISAIVLGGTKVREDVDVIECSLQFPDDDYSWWDLEMKICVFIFAFVIPVLIIIVCYTLMILR

LKSQLQKIDLSSLInvyikadkqkngikanfkirhniedggvqlayhyqqntpigdgpvllpd nhylsvqsklskdpnekrdhmvllefvtaagitlgmdelykggtggsmvskgeelftgvvpil -continued

INFORMAL SEQUENCE LISTING veldgdvnghkfsvsgegegdatygkltlkficttgklpvpwptlvttltygvqcfsrypdhm kqhdffksampegyiqertiffkddgnyktraevkfegdtlvnrielkgidfkedgnilghkl eynNHDQLREKDRNLRRITRLVLVVVAVFVVCWTPIHIFILVEALGSTSHSTAALAAYYFCIA

LGYTNAALNPILYAFLDENFKRCFRDFCFPLKMRMERQATARVRNTVQDPAYLRDIDGMNKPV

Feature Annotations for SEQ ID NO: 36

| Residue numbers | Formatting | Feature definition |
|---|---|---|
| 164 | Bold and italic | X is any amino acid or an amino acid selected from the group consisting of F, A, G, V, I, L, M, S, T |
| 256-266 | Bold and underlined | Optional long linker at N-terminus of cpFP |
| 262-266 | Bold and underlined | Optional short linker at N-terminus of cpFP |
| 267-507 | Lower case | cpGFP or any other cpFP described herein |
| 508-512 | Bold and underlined | Linker at C-terminus of cpFP |

opioid receptor mu 1 (OPRM1, MOR1) containing
cpFP sensor replacing all or part of 3rd intracellular loop
SEQ ID NO: 37

MDSSAAPTNASNCTDALAYSSCSPAPSPGSWVNLSHLDGNLSDPCGPNRTDLGGRDSLCPPTG

SPSMITAITIMALYSIVCVVGLFGNFLVMYVIVRYTKMKTATNIYIFNLALADALATSTLPFQ

SVNYLMGTWPFGTILCKIVISIDYYNMFTSIFTLCTMSVDRYIAVCHP*X*KALDFRTPRNAKII

NVCNWILSSAIGLPVMFMATTKYRQGSIDCTLTFSHPTWYWENLLKICVFIFAFIMPVLIITV

CYGLMILRLKSQLQKIDLSSLInvyikadkqkngikanfkirhniedggvqlayhyqqntpig dgpvllpdnhylsvqsklskdpnekrdhmvllefvtaagitlgmdelykggtggsmvskgeel ftgvvpilveldgdvnghkfsvsgegegdatygkltlkficttgklpvpwptlvttltygvqc fsrypdhmkqhdffksampegyiqertiffkddgnyktraevkfegdtlvnrielkgidfked gnilghkleynNHDQLKEKDRNLRRITRMVLVVVAVFIVCWTPIHIYVIIKALVTIPETTFQT

VSWHFCIALGYTNSCLNPVLYAFLDENFKRCFREFCIPTSSNIEQQNSTRIRQNTRDHPSTAN

TVDRTNHQLENLEAETAPLP*

Feature Annotations for SEQ ID NO: 37

| Residue numbers | Formatting | Feature definition |
|---|---|---|
| 175 | Bold and italic | X is any amino acid or an amino acid selected from the group consisting of F, A, G, V, I, L, M, S, T |
| 264-274 | Bold and underlined | Optional long linker at N-terminus of cpFP |
| 270-274 | Bold and underlined | Optional short linker at N-terminus of cpFP |
| 275-515 | Lower case | cpGFP or any other cpFP described herein |
| 516-520 | Bold and underlined | Linker at C-terminus of cpFP |

opioid receptor delta 1 (OPRD1, DOR1) containing
cpFP sensor replacing all or part of 3rd intracellular loop
SEQ ID NO: 38

MEPAPSAGAELQPPLFANASDAYPSACPSAGANASGPPGARSASSLALAIAITALYSAVCAVG

LLGNVLVMFGIVRYTKMKTATNIYIFNLALADALATSTLPFQSAKYLMETWPFGELLCKAVLS

IDYYNMFTSIFTATMMSVDRYIAVCHP*X*KALDERTPAKAKLINICIWVLASGVGVPIMVMAVT

RPRDGAVVCMLQFPSPSWYWDTVTKICVFLFAFVVPILIITVCYGLMLLRLRSQLQKIDLSSL

-continued

INFORMAL SEQUENCE LISTING

<u>I</u>nvyikadkqkngikanfkirhniedggvqlayhyqqntpigdgpvllpdnhylsvqsklskd pnekrdhmvllefvtaagitlgmdelykggtggsmvskgeelftgvvpilveldgdvnghkfs vsgegegdatygkltlkficttgklpvpwptlvttltygvqcfsrypdhmkqhdffksampeg yiqertiffkddgnyktraevkfegdtlvnrielkgidfkedgnilghkleyn<u>NHDQL</u>KEKDR

SLRRITRMVLVVVGAFVVCWAPIHIFVIVWTLVDIDRRDPLVVAALHLCIALGYANSSLNPVL

YAFLDENFKRCFRQLCRA*

Feature Annotations for SEQ ID NO: 38

| Residue numbers | Formatting | Feature definition |
|---|---|---|
| 154 | Bold and italic | X is any amino acid or an amino acid selected from the group consisting of F, A, G, V, I, L, M, S, T |
| 243-253 | Bold and underlined | Optional long linker at N-terminus of cpFP |
| 249-253 | Bold and underlined | Optional short linker at N-terminus of cpFP |
| 254-494 | Lower case | cpGFP or any other cpFP described herein |
| 495-499 | Bold and underlined | Linker at C-terminus of cpFP |

melatonin receptor 1B (MTNR1B, MT2R) containing cpFP sensor replacing all or part of 3rd intracellular loop

SEQ ID NO: 39

MSENGSFANCCEAGGWAVRPGWSGAGSARPSRTPRPPWVAPALSAVLIVTTAVDVVGNLLVIL

SVLRNRKLRNAGNLFLVSLALADLVVAFYPYPLILVAIFYDGWALGEEHCKASAFVMGLSVIG

SVFNITAIAINRYCYICHS*X*AYHRIYRRWHTPLHICLIWLLTVVALLPNFFVGSLEYDPRIYS

CTFIQTASTQYTAAVVVIHFLLPIAVVSFCYLRIWVLVLQARR<u>QLQKIDLSSLI</u>nvyikadkq kngikanfkirhniedggvqlayhyqqntpigdgpvllpdnhylsvqsklskdpnekrdhmvl lefvtaagitlgmdelykggtggsmvskgeelftgvvpilveldgdvnghkfsvsgegegdat ygkltlkficttgklpvpwptlvttltygvqcfsrypdhmkqhdffksampegyiqertiffk ddgnyktraevkfegdtlvnrielkgidfkedgnilghkleyn<u>NHDQL</u>KPSDLRSFLTMFVVF

VIFAICWAPLNCIGLAVAINPQEMAPQIPEGLFVTSYLLAYFNSCLNAIVYGLLNQNFRREYK

RILLALWNPRHCIQDASKGSHAEGLQSPAPPIIGVQHQADAL*

Feature Annotations for SEQ ID NO: 39

| Residue numbers | Formatting | Feature definition |
|---|---|---|
| 146 | Bold and italic | X is any amino acid or an amino acid selected from the group consisting of F, A, G, V, I, L, M, S, T |
| 233-243 | Bold and underlined | Optional long linker at N-terminus of cpFP |
| 239-243 | Bold and underlined | Optional short linker at N-terminus of cpFP |
| 244-484 | Lower case | cpGFP or any other cpFP described herein |
| 485-489 | Bold and underlined | Linker at C-terminus of cpFP |

Cannabinoid Receptor (type-1) (CNR1, CB1; CNR; CB-R; CB1A; CB1R; CANN6; CB1K5) containing cpFP sensor replacing all or part of 3rd intracellular loop

SEQ ID NO: 40

MKSILDGLADTTERTITTDLLYVGSNDIQYEDIKGDMASKLGYFPQKFPLTSFRGSPFQEKMT

AGDNPQLVPADQVNITEFYNKSLSSFKENEENIQCGENFMDIECFMVLNPSQQLAIAVLSLTL

-continued

| INFORMAL SEQUENCE LISTING |
|---|

GTFTVLENLLVLCVILHSRSLRCRPSYHFIGSLAVADLLGSVIFVYSFIDFHVFHRKDSRNVF

LFKLGGVTASFTASVGSLFLTAIDRYISIHRP*X*AYKRIVTRPKAVVAFCLMWTIAIVIAVLPL

LGWNCEKLQSVCSDIFPHIDETYLMFWIGVTSVLLLFIVYAYMYILWKAHSHAVRMIQRQLQK

IDLSSLInvyikadkqkngikanfkirhniedggvqlayhyqqntpigdgpvllpdnhylsvq sklskdpnekrdhmvllefvtaagitlgmdelykggtggsmvskgeelftgvvpilveldgdv nghkfsvsgegegdatygkltlkficttgklpvpwptlvttltygvqcfsrypdhmkqhdffk sampegyiqertiffkddgnyktraevkfegdtlvnrielkgidfkedgnilghkleynNHDQ

LRMDIRLAKTLVLILVVLIICWGPLLAIMVYDVFGKMNKLIKTVFAFCSMLCLLNSTVNPIIY

ALRSKDLRHAFRSMFPSCEGTAQPLDNSMGDSDCLHKHANNAASVHRAAESCIKSTVKIAKV*

Feature Annotations for SEQ ID NO: 40

| Residue numbers | Formatting | Feature definition |
|---|---|---|
| 222 | Bold and italic | X is any amino acid or an amino acid selected from the group consisting of F, A, G, V, I, L, M, S, T |
| 312-322 | Bold and underlined | Optional long linker at N-terminus of cpFP |
| 318-322 | Bold and underlined | Optional short linker at N-terminus of cpFP |
| 323-563 | Lower case | cpGFP or any other cpFP described herein |
| 564-568 | Bold and underlined | Linker at C-terminus of cpFP |

histamine receptor H1 (HRH1, H1R; H1-R; HH1R; hisH1) containing cpFP sensor replacing all or part of 3rd intracellular loop

SEQ ID NO: 41

MSLPNSSCLLEDKMCEGNKTTMASPQLMPLVVVLSTICLVTVGLNLLVLYAVRSERKLHTVGN

LYIVSLSVADLIVGAVVMPMNILYLLMSKWSLGRPLCLFWLSMDYVASTASIFSVFILCIDRY

RSVQQP*X*RYLKYRIKTRASATILGAWFLSFLWVIPILGWNHFMQQTSVRREDKCETDFYDVTW

FKVMTAIINFYLPTLLMLWFYAKIYKAVRQLQKIDLSSLInvyikadkqkngikanfkirhni edggvqlayhyqqntpigdgpvllpdnhylsvqsklskdpnekrdhmvllefvtaagitlgmd elykggtggsmvskgeelftgvvpilveldgdvnghkfsvsgegegdatygkltlkficttgk lpvpwptlvttltygvqcfsrypdhmkqhdffksampegyiqertiffkddgnyktraevkfe gdtlvnrielkgidfkedgnilghkleynNHDQLRERKAAKQLGFIMAAFILCWIPYFIFFMV

IAFCKNCCNEHLHMFTIWLGYINSTLNPLIYPLCNENFKKTFKRILHIRS*

Feature Annotations for SEQ ID NO: 41

| Residue numbers | Formatting | Feature definition |
|---|---|---|
| 133 | Bold and italic | X is any amino acid or an amino acid selected from the group consisting of F, A, G, V, I, L, M, S, T |
| 219-229 | Bold and underlined | Optional long linker at N-terminus of cpFP |
| 225-229 | Bold and underlined | Optional short linker at N-terminus of cpFP |

-continued

INFORMAL SEQUENCE LISTING

| | | |
|---|---|---|
| 230-470 | Lower case | cpGFP or any other cpFP described herein |
| 471-475 | Bold and underlined | Linker at C-terminus of cpFP |

neuropeptide Y receptor Y1 (NPY1R, NPYR; NPY1-R) containing cpFP sensor replacing all or part of 3rd intracellular loop

SEQ ID NO: 42

MNSTLFSQVENHSVHSNFSEKNAQLLAFENDDCHLPLAMIFTLALAYGAVIILGVSGNLALII

IILKQKEMRNVINILIVNLSFSDLLVAIMCLPFTFVYTLMDHWVFGEAMCKLNPFVQCVSITV

SIFSLVLIAVERHQLIINPRGWRPNNRHAYVGIAVIWVLAVASSLPFLIYQVMTDEPFQNVTL

DAYKDKYVCFDQFPSDSHRLSYTTLLLVLQYFGPLCFIFICYFKIYIRLKRRQLQKIDLSSLI nvyikadkqkngikanfkirhniedggvqlayhyqqntpigdgpvllpdnhylsvqsklskdp nekrdhmvllefvtaagitlgmdelykggtggsmvskgeelftgvvpilveldgdvnghkfsv sgegegdatygkltlkficttgklpvpwptlvttltygvqcfsrypdhmkqhdffksampegy iqertiffkddgnyktraevkfegdtlvnrielkgidfkedgnilghkleynNHDQLSETKRI

NIMLLSIVVAFAVCWLPLTIFNTVFDWNHQIIATCNHNLLFLLCHLTAMISTCVNPIFYGFLN

KNFQRDLQFFFNFCDFRSRDDDYETIAMSTMHTDVSKTSLKQASPVAFKKINNNDDNEKI

Feature Annotations for SEQ ID NO: 42

| Residue numbers | Formatting | Feature definition |
|---|---|---|
| 242-252 | Bold and underlined | Optional long linker at N-terminus of cpFP |
| 248-252 | Bold and underlined | Optional short linker at N-terminus of cpFP |
| 253-493 | Lower case | cpGFP or any other cpFP described herein |
| 494-498 | Bold and underlined | Linker at C-terminus of cpFP |

cholinergic receptor muscarinic 2 (CHRM2, HM2) containing cpFP sensor replacing all or part of 3rd intracellular loop

SEQ ID NO: 43

MNNSTNSSNNSLALTSPYKTFEVVFIVLVAGSLSLVTIIGNILVMVSIKVNRHLQTVNNYFLF

SLACADLIIGVFSMNLYTLYTVIGYWPLGPVVCDLWLALDYVVSNASVMNLLIISFDRYFCVT

KP*X*TYPVKRTTKMAGMMIAAAWVLSFILWAPAILFWQFIVGVRTVEDGECYIQFFSNAAVTFG

TAIAAFYLPVIIMTVLYWHISRASKSQLQKIDLSSLInvyikadkqkngikanfkirhniedg gvqlayhyqqntpigdgpvllpdnhylsvqsklskdpnekrdhmvllefvtaagitlgmdely kggtggsmvskgeelftgvvpilveldgdvnghkfsvsgegegdatygkltlkficttgklpv pwptlvttltygvqcfsrypdhmkqhdffksampegyiqertiffkddgnyktraevkfegdt lvnrielkgidfkedgnilghkleynNHDQLREKKVTRTILAILLAFIITWAPYNVMVLINTF

CAPCIPNTVWTIGYWLCYINSTINPACYALCNATFKKTFKHLLMCHYKNIGATR

Feature Annotations for SEQ ID NO: 43

| Residue numbers | Formatting | Feature definition |
|---|---|---|
| 129 | Bold and italic | X is any amino acid or an amino acid selected from the group consisting of F, A, G, V, I, L, M, S, T |
| 216-226 | Bold and underlined | Optional long linker at N-terminus of cpFP |

-continued

| INFORMAL SEQUENCE LISTING | | |
|---|---|---|
| 222-226 | Bold and underlined | Optional short linker at N-terminus of cpFP |
| 227-467 | Lower case | cpGFP or any other cpFP described herein |
| 468-472 | Bold and underlined | Linker at C-terminus of cpFP |

hypocretin (orexin) receptor 1 (HCRTR1, OX1R) containing cpFP sensor replacing all or part of 3rd intracellular loop

SEQ ID NO: 44

MEPSATPGAQMGVPPGSREPSPVPPDYEDEFLRYLWRDYLYPKQYEWVLIAAYVAVFVVALVG

NTLVCLAVWRNHHMRTVTNYFIVNLSLADVLVTAICLPASLLVDITESWLFGHALCKVIPYLQ

AVSVSVAVLTLSFIALDRWYAICHP*X*LFKSTARRARGSILGIWAVSLAIMVPQAAVMECSSVL

PELANRTRLFSVCDERWADDLYPKIYHSCFFIVTYLAPLGLMAMAYFQIFRKLWGRQLQKIDL

SSLInvyikadkqkngikanfkirhniedggvqlayhyqqntpigdgpvllpdnhylsvqskl skdpnekrdhmvllefvtaagitlgmdelykggtggsmvskgeelftgvvpilveldgdvngh kfsvsgegegdatygkltlkficttgklpvpwptlvttltygvqcfsrypdhmkqhdffksam pegyiqertiffkddgnyktraevkfegdtlvnrielkgidfkedgnilghkleynNHDQLRA

RRKTAKMLMVVLLVFALCYLPISVLNVLKRVFGMFRQASDREAVYACFTFSHWLVYANSAANP

IIYNFLSGKFREQFKAAFSCCLPGLGPCGSLKAPSPRSSASHKSLSLQSRCSISKISEHVVLT

SVTTVLP

Feature Annotations for SEQ ID NO: 44

| Residue numbers | Formatting | Feature definition |
|---|---|---|
| 152 | Bold and italic | X is any amino acid or an amino acid selected from the group consisting of F, A, G, V, I, L, M, S, T |
| 246-256 | Bold and underlined | Optional long linker at N-terminus of cpFP |
| 252-256 | Bold and underlined | Optional short linker at N-terminus of cpFP |
| 257-497 | Lower case | cpGFP or any other cpFP described herein |
| 498-502 | Bold and underlined | Linker at C-terminus of cpFP |

nucleic acid sequence of Dopamine Receptor D2 (DRD2) containing cpFP sensor replacing all or part of 3rd intracellular loop SEQ ID No: 45

ATGGACCCCCTTAACCTCTCATGGTACGACGATGATCTTGAGAGGCAGAACTGGTCCCGACCA

TTCAATGGGTCTGATGGTAAGGCTGACCGGCCTCATTACAATTATTATGCGACCCTGCTTACT

CTTCTTATCGCTGTGATCGTATTCGGCAACGTCTTGGTTTGCATGGCAGTCTCTAGGGAAAAA

GCGCTCCAGACGACAACTAATTACTTGATTGTGAGTCTGGCTGTAGCTGACTTGCTTGTGGCG

ACCCTGGTGATGCCATGGGTCGTATACTTGGAAGTCGTTGGCGAGTGGAAGTTTTCTAGGATT

CATTGCGACATATTTGTAACTCTGGACGTAATGATGTGTACTGCTTCCATTTTGAACCTCTGC

GCTATATCCATTGACAGGTACACGGCGGTTGCTATGCCGATGCTTTATAATACCCGGTATTCA

AGCAAAAGGCGAGTAACTGTGATGATAAGCATTGTATGGGTGCTCAGTTTCACAATTAGCTGC

CCTCTGCTCTTCGGCCTTAACAACGCGGATCAAAATGAATGCATCATCGCAAACCCGGCTTTT

GTGGTTTATAGCAGCATTGTTAGCTTCTATGTGCCATTCATAGTTACGCTCCTTGTTTATATA

AAAATTTATATCGTGCTTAGGCGCCGCCGAAAACGAGTTAACACCAAGCGGAGCAGCCTGAGC

TCActcattAATGTATATATCAAAGCTGATAAGCAAAAAAACGGTATCAAGGCTAATTTTAAG

ATCAGACATAATATAGAGGATGGAGGCGTTCAACTGGCCTACCACTACCAGCAAAACACGCCG

-continued

| INFORMAL SEQUENCE LISTING |
|---|

ATCGGGGATGGGCCAGTACTTCTGCCAGATAACCATTATCTCTCAGTTCAAAGCAAACTCTCT

AAGGACCCTAATGAGAAACGAGATCATATGGTTCTGCTCGAATTCGTTACAGCCGCCGGTATC

ACACTTGGGATGGACGAGTTGTATAAGGGTGGAACAGGAGGGTCAATGGTAAGCAAAGGCGAG

GAGCTGTTTACGGGGGTCGTCCCGATACTTGTTGAACTCGACGGCGATGTCAACGGGCACAAA

TTCTCAGTGAGTGGCGAGGGGGAAGGAGACGCCACTTATGGAAAACTGACATTGAAATTCATA

TGTACGACTGGGAAGTTGCCTGTGCCTTGGCCTACGCTCGTTACTACACTTACTTACGGGGTA

CAGTGTTTCAGTAGGTATCCAGATCACATGAAACAGCACGATTTTTTCAAGAGTGCAATGCCG

GAAGGATATATACAAGAAAGAACTATTTTCTTTAAAGATGACGGCAACTATAAAACGCGAGCA

GAGGTGAAGTTTGAGGGCGATACCTTGGTTAATAGGATCGAACTCAAAGGCATAGACTTCAAA

GAAGACGGAAACATTCTGGGTCACAAACTGGAATACAACaatcatGACCAACTGCAGAAGGAA

AAGAAGGCCACGCAAATGTTGGCAATCGTGCTCGGCGTGTTCATAATCTGCTGGCTTCCATTT

TTTATAACGCATATATTGAACATACACTGTGATTGCAATATTCCACCAGTCCTGTATAGTGCG

TTTACGTGGTTGGGTTATGTGAATTCTGCGGTTAACCCGATCATTTACACCACGTTCAACATA

GAATTCCGAAAGGCATTCCTCAAAATATTGCATTGTTAG amino acid sequence of Dopamine Receptor D2 (DRD2) containing cpFP sensor replacing all or part of 3rd intracellular loop

SEQ ID NO: 46

MDPLNLSWYDDDLERQNWSRPFNGSDGKADRPHYNYYATLLTLLIAVIVFGNVLVCMAVSREK

ALQTTTNYLIVSLAVADLLVATLVMPWVVYLEVVGEWKFSRIHCDIFVTLDVMMCTASILNLC

AISIDRYTAVAMP*X*LYNTRYSSKRRVTVMISIVWVLSFTISCPLLFGLNNADQNECIIANPAF

VVYSSIVSFYVPFIVTLLVYIKIYIVLRRRRKLSSLInvyikadkqkngikanfkirhniedg gvqlayhyqqntpigdgpvllpdnhylsvqsklskdpnekrdhmvllefvtaagitlgmdely kggtggsmvskgeelftgvvpilveldgdvnghkfsvsgegegdatygkltlkficttgklpv pwptlvttltygvqcfsrypdhmkqhdffksampegyiqertiffkddgnyktraevkfegdt lvnrielkgidfkedgnilghkleynNHDQLQKEKKATQMLAIVLGVFIICWLPFFITHILNI

HCDCNIPPVLYSAFTWLGYVNSAVNPIIYTTFNIEFRKAFLKILHC*

| Feature Annotations for SEQ ID NO: 46 | | |
|---|---|---|
| Residue numbers | Formatting | Feature definition |
| 140 | Bold and italic | X is any amino acid or an amino acid selected from the group consisting of F, A, G, V, I, L, M, S, T |
| 222-226 | Bold and underlined | linker at N-terminus of cpFP |
| 235-475 | Lower case | cpGFP or any other cpFP described herein |
| 476-480 | Bold and underlined | Linker at C-terminus of cpFP |

nucleic acid sequence of Dopamine Receptor D4 (DRD4) containing cpFP sensor replacing all or part of 3rd intracellular loop SEQ ID No: 47

ATGGGGAACAGATCCACTGCAGATGCAGACGGTCTTCTCGCAGGCCGGGGACCTGCTGCCGGA

GCGAGCGCTGGGGCTTCCGCAGGTCTTGCTGGGCAGGGGGCCGCGGCCTTGGTTGGAGGCGTT

TTGCTTATAGGGGCCGTTCTTGCTGGCAATAGTTTGGTATGTGTTTCAGTTGCGACAGAGCGC

GCACTTCAGACGCCGACTAACTCCTTTATAGTGAGTTTGGCTGCTGCAGATCTCTTGTTGGCA

-continued

INFORMAL SEQUENCE LISTING

TTGTTGGTACTCCCACTGTTCGTTTATTCAGAAGTACAGGGTGGCGCATGGCTCCTGTCACCC

AGGTTGTGTGATGCCTTGATGGCCATGGATGTTATGCTGTGTACCGCTTCTATCTTTAACCTT

TGTGCTATCAGTGTTGACAGATTCGTCGCGGTCGCGGTCCCTCTGAGGTATAACCGGCAAGGA

GGCAGCAGGAGGCAACTGCTGCTGATCGGCGCAACTTGGCTCCTCTCCGCAGCAGTGGCCGCG

CCTGTTCTGTGTGGTCTCAACGACGTTCGCGGCAGAGACCCGGCTGTATGTCGCCTCGAGGAT

AGAGATTATGTCGTATACTCAAGTGTGTGTTCCTTTTTTCTTCCTTGCCCACTGATGCTTCTG

TTGTATTGGGCTACCTTTAGAGGACTGCAACGCTGGGAAGTCCTGAGCTCActcattAATGTA

TATATCAAAGCTGATAAGCAAAAAAACGGTATCAAGGCTAATTTTAAGATCAGACATAATATA

GAGGATGGAGGCGTTCAACTGGCCTACCACTACCAGCAAAACACGCCGATCGGGGATGGGCCA

GTACTTCTGCCAGATAACCATTATCTCTCAGTTCAAAGCAAACTCTCTAAGGACCCTAATGAG

AAACGAGATCATATGGTTCTGCTCGAATTCGTTACAGCCGCCGGTATCACACTTGGGATGGAC

GAGTTGTATAAGGGTGGAACAGGAGGGTCAATGGTAAGCAAAGGCGAGGAGCTGTTTACGGGG

GTCGTCCCGATACTTGTTGAACTCGACGGCGATGTCAACGGGCACAAATTCTCAGTGAGTGGC

GAGGGGGAAGGAGACGCCACTTATGGAAAACTGACATTGAAATTCATATGTACGACTGGGAAG

TTGCCTGTGCCTTGGCCTACGCTCGTTACTACACTTACTTACGGGGTACAGTGTTTCAGTAGG

TATCCAGATCACATGAAACAGCACGATTTTTTCAAGAGTGCAATGCCGGAAGGATATATACAA

GAAAGAACTATTTTCTTTAAAGATGACGGCAACTATAAAACGCGAGCAGAGGTGAAGTTTGAG

GGCGATACCTTGGTTAATAGGATCGAACTCAAAGGCATAGACTTCAAAGAAGACGGAAACATT

CTGGGTCACAAACTGGAATACAACaatcatGACCAACTGGGCCGCGAACGGAAAGCCATGCGA

GTTTTGCCGGTGGTAGTAGGGGCATTCCTTCTTTGTTGGACCCCTTTTTTTGTGGTGCATATA

ACGCAGGCTCTGTGCCCGGCCTGTTCTGTCCCACCCCGCCTCGTGTCAGCTGTCACTTGGTTG

GGTTACGTAAACTCAGCCCTCAATCCAGTTATCTATACGGTTTTCAATGCCGAGTTCAGGAAT

GTTTTTAGGAAGGCCCTTAGAGCCTGTTGTTAG amino acid sequence of Dopamine Receptor D4 (DRD4) containing cpFP sensor replacing all or part of 3rd intracellular loop

SEQ ID NO: 48

MGNRSTADADGLLAGRGPAAGASAGASAGLAGQGAAALVGGVLLIGAVLAGNSLVCVSVATER

ALQTPTNSFIVSLAAADLLLALLVLPLFVYSEVQGGAWLLSPRLCDALMAMDVMLCTASIFNL

CAISVDRFVAVAVP*X*RYNRQGGSRRQLLLIGATWLLSAAVAAPVLCGLNDVRGRDPAVCRLED

RDYVVYSSVCSFFLPCPLMLLLYWATFRGLQRWEVLSSLInvyikadkqkngikanfkirhni edggvqlayhyqqntpigdgpvllpdnhylsvqsklskdpnekrdhmvllefvtaagitlgmd elykggtggsmvskgeelftgvvpilveldgdvnghkfsvsgegegdatygkltlkficttgk lpvpwptlvttltygvqcfsrypdhmkqhdffksampegyiqertiffkddgnyktraevkfe gdtlvnrielkgidfkedgnilghkleynNHDQLGRERKAMRVLPVVVGAFLLCWTPFFVVHI

TQALCPACSVPPRLVSAVTWLGYVNSALNPVIYTVFNAEFRNVFRKALRACC*

Feature Annotations for SEQ ID NO: 48

| Residue numbers | Formatting | Feature definition |
|---|---|---|
| 141 | Bold and italic | X is any amino acid or an amino acid selected from the group consisting of F, A, G, V, I, L, M, S, T |

-continued

| INFORMAL SEQUENCE LISTING | | |
|---|---|---|
| 225-229 | Bold and underlined | linker at N-terminus of cpFP |
| 230-470 | Lower case | cpGFP or any other cpFP described herein |
| 471-475 | Bold and underlined | Linker at C-terminus of cpFP |

What is claimed is:

1. A class A type G protein-coupled receptor (GPCR) comprising a fluorescent sensor, the sensor comprising the following polypeptide structure:

L1-cpFP-L2, wherein:

(1) L1 comprises a peptide linker LSSLI (SEQ ID NO:73);

(2) cpFP comprises a circularly permuted beta barrel fluorescent protein, wherein the circularly permuted N-terminus is positioned within beta strand seven of a non-permuted beta barrel fluorescent protein; and (3) L2 comprises a peptide linker NHDQL (SEQ ID NO:74), and wherein the GPC rises SEQ ID NO. 165;

wherein the circularly permuted fluorescent protein is from a fluorescent protein having at least 90% sequence identity to a non-permuted fluorescent protein selected from the group consisting of SEQ ID NO's: 1-14 or wherein the circularly permuted fluorescent protein has at least 90% sequence identity to a circularly permuted fluorescent protein selected from the group consisting of SEQ ID NOs: 15-18;

wherein the insertion site for the sensor is located in the third intracellular loop of SEQ ID NO: 165;

wherein the insertion site in the GPCR for the sensor is located after amino acid residue 228 of SEQ ID NO: 165; and wherein the insertion site for the sensor is located between Q229 and L230, is located between S246 and Q247, replaces the amino acid residues between R228 and K267, or replaces the amino acid residues between L230 and F264.

2. The GPCR of claim 1, wherein L1 comprises QLQKIDLSSLI (SEQ ID NO: 75).

3. The GPCR of claim 1, wherein the circularly permuted fluorescent protein is from a fluorescent protein having at least 90% sequence identity to a non-permuted fluorescent protein selected from the group consisting of SEQ ID NOs: 1-14.

4. The GPCR of claim 1, wherein the circularly permuted fluorescent protein has at least 90% sequence identity to a circularly permuted fluorescent protein selected from the group consisting of SEQ ID NOs: 15-18.

5. A polynucleotide encoding the GPCR of claim 1.

6. An expression cassette comprising the polynucleotide of claim 5.

7. A vector comprising the polynucleotide of claim 5.

8. A cell comprising the GPCR of claim 1.

9. A transgenic animal comprising the GPCR of claim 1.

10. A method of detecting binding of a ligand to a GPCR, comprising:

a) contacting the ligand with a GPCR of claim 1 under conditions sufficient for the ligand to bind to the GPCR; and b) determining a change in an optics signal from the sensor integrated into the third intracellular loop of the GPCR, wherein a detectable change in fluorescence signal indicates binding of the ligand to the GPCR.

11. A method of screening for binding of a ligand to a GPCR, comprising:

a) contacting a plurality of members from a library of ligands with a plurality of GPCRs under conditions sufficient for the ligand members to bind to the GPCRs, wherein the plurality of GPCRs are arranged in an array of predetermined addressable locations, wherein each GPCR in the plurality of GPCRs is independently a GPCR of claim 1; and b) determining a change in one or more optics signals from the sensor integrated into the third intracellular loop of the plurality GPCRs, wherein a detectable change in the one or more fluorescence signals indicates binding of one or more members of the library of ligands to at least one QPCR of the plurality of GPCRs.

12. A class A type G protein-coupled receptor (GPCR) comprising a fluorescent sensor, the sensor comprising the following polypeptide structure:

L1-cpFP-L2, wherein:

(1) L1 comprises a peptide linker LSSLI (SEQ ID NO:73);

(2) cpFP comprises a circularly permuted beta barrel fluorescent protein, wherein the circularly permuted N-terminus is positioned within beta strand seven of a non-permuted beta barrel fluorescent protein; and (3) L2 comprises a peptide linker NHDQL (SEQ ID NO:74), and wherein the GPCR is a GPCR selected from the group consisting of ADRB1 (B1AR) adrenoceptor beta 1, ADORA1 (A1AR) adenosine A1 receptor, ADORA2A (A2AR) adenosine A2a receptor, a mu ($\mu$)-type opioid receptor (MOR), a kappa ($\eta$)-type opioid receptor (KOR), a dopamine receptor type-1 (DRD1), a dopamine receptor type-2 (DRD2), a dopamine receptor type-4 (DRD4), a 5-hydroxy-tryptamine receptor 2A (5-HT2A), and MTNR1B (MT2) melatonin receptor 1B;

wherein the circularly permuted fluorescent protein is from a fluorescent protein having at least 90% sequence identity to a non-permuted fluorescent protein selected from the group consisting of SEQ ID NO's: 1-14 or wherein the circularly permuted fluorescent protein selected from the group consisting of SEQ ID NOs: 15-18;

wherein the insertion site for the sensor replaces the third intracellular loop of the GPCR; and wherein:

i) when the GPCR is DRD1 then the insertion site for the sensor replaces the amino acid residues of the receptor between RIYRIAQK (SEQ ID NO:52) and KRETKVLK (SEQ ID NO:53) where the N-terminus of the sensor abuts the amino acid sequence of RIYRIAQK (SEQ ID NO:52) of the receptor and the C-terminus of the sensor abuts the amino acid sequence KRETKVLK (SEQ ID NO:53) of the receptor;

ii) when the GPCR is B1AR then the insertion site for the sensor replaces the amino acid residues of the receptor between RVFREAQK (SEQ ID NO:54) and REQKALKT (SEQ ID NO:55) where the N-terminus of the sensor abuts the amino acid sequence of RVFREAQK (SEQ ID NO: 54) of the receptor and the C-terminus of the sensor abuts the amino acid sequence REQKALKT (SEQ ID NO:55) of the receptor;

iii) when the GPCR is DRD2 then the insertion site for the sensor replaces the amino acid residues of the receptor between IVLRRRRK (SEQ ID NO:58) and QKEKKATQ (SEQ ID NO:59) where the N-terminus of the sensor abuts the amino acid sequence of IVLRRRRK (SEQ ID NO: 58) of the receptor and the C-terminus of the sensor abuts the amino acid sequence QKEKKATQ (SEQ ID NO:59) of the receptor;

iv) when the GPCR is DRD4 then the insertion site for the sensor replaces the amino acid residues of the receptor between RGLQRWEV (SEQ ID NO:60) and GRERKAMR (SEQ ID NO:61) where the N-terminus of the sensor abuts the amino acid sequence of RGLQRWEV (SEQ ID NO: 60) of the receptor and the C-terminus of the sensor abuts the amino acid sequence GRERKAMR (SEQ ID NO:61) of the receptor;

v) when the GPCR is KOR then the insertion site for the sensor replaces the amino acid residues of the receptor between LMILRLKS (SEQ ID NO:62) and REKDRNLR (SEQ ID NO:63) where the N-terminus of the sensor abuts the amino acid sequence of LMILRLKS (SEQ ID NO:62) of the receptor and the C-terminus of the sensor abuts the amino acid sequence REKDRNLR (SEQ ID NO:63) of the receptor;

vi) when the GPCR is MOR then the insertion site for the sensor replaces the amino acid residues of the receptor between LMILRLKS (SEQ ID NO:62) and KEKDRNLR (SEQ ID NO:64) where the N-terminus of the sensor abuts the amino acid sequence of LMILRLKS (SEQ ID NO:62) of the receptor and the C-terminus of the sensor abuts the amino acid sequence KEKDRNLR (SEQ ID NO:64) of the receptor;

vii) when the GPCR is A2AR then the insertion site for the sensor replaces the amino acid residues of the receptor between RIYQIAKR (SEQ ID NO:65) and REKRFTFV (SEQ ID NO:66) where the N-terminus of the sensor abuts the amino acid sequence of RIYQIAKR (SEQ ID NO:65) of the receptor and the C-terminus of the sensor abuts the amino acid sequence REKRFTFV (SEQ ID NO:66) of the receptor;

viii) when the GPCR is MT2 then the insertion site for the sensor replaces the amino acid residues of the receptor between VLVLQARR (SEQ ID NO:67) and KPSDLRSF (SEQ ID NO:68) where the N-terminus of the sensor abuts the amino acid sequence of VLVLQARR (SEQ ID NO: 67) of the receptor and the C-terminus of the sensor abuts the amino acid sequence KPSDLRSF (SEQ ID NO:68) of the receptor;

ix) when the GPCR is 5-HT2A then the insertion site for the sensor replaces the amino acid residues of the receptor between LTIKSLOK (SEQ ID NO:69) and NEQKACKV (SEQ ID NO:70) where the N-terminus of the sensor abuts the amino acid sequence of LTIKSLOK (SEQ ID NO:69) of the receptor and the C-terminus of the sensor abuts the amino acid sequence NEQKACKV (SEQ ID NO:70) of the receptor;

x) when the GPCR is A1AR then the insertion site for the sensor replaces the amino acid residues of the receptor between RVYVVAKR (SEQ ID NO:71) and SREKKAAK (SEQ ID NO:72) where the N-terminus of the sensor abuts the amino acid sequence of RVYVVAKR (SEQ ID NO: 71) of the receptor and the C-terminus of the sensor abuts the amino acid sequence SREKKAAK (SEQ ID NO:72) of the receptor.

13. A method of detecting binding of a ligand to a GPCR, comprising:

a) contacting the ligand with a GPCR of claim 12 under conditions sufficient for the ligand to bind to the GPCR; and b) determining a change in an optics signal from the sensor integrated into the third intracellular loop of the GPCR, wherein a detectable change in fluorescence signal indicates binding of the ligand to the GPCR.

14. A method of screening for binding of a ligand to a GPCR, comprising:

a) contacting a plurality of members from a library of ligands with a plurality of GPCRs under conditions sufficient for the ligand members to bind to the GPCRs, wherein the plurality of GPCRs are arranged in an array of predetermined addressable locations, wherein each GPCR in the plurality of GPCRs is independently a GPCR of claim 12; and b) determining a change in one or more optics signals from the sensor integrated into the third intracellular loop of the plurality GPCRs, wherein a detectable change in the one or more fluorescence signals indicates binding of one or more members of the library of ligands to at least one GPCR of the plurality of GPCRs.

* * * * *